United States Patent
Avgerinos et al.

(10) Patent No.: US 11,884,740 B1
(45) Date of Patent: *Jan. 30, 2024

(54) ANTI-CD20 ANTIBODY COMPOSITIONS

(71) Applicants: TG Therapeutics, Inc., New York, NY (US); Laboratoire Francais Du Fractionnement Et Des Biotechnologies, Les Ulis (FR)

(72) Inventors: George Costas Avgerinos, Sudbury, MA (US); Patrick Michael Hossler, Westborough, MA (US); Jill A. Myers, Brookline, MA (US); Yune Z. Kunes, Cambridge, MA (US)

(73) Assignees: TG Therapeutics, Inc., New York, NY (US); Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,407

(22) Filed: Aug. 22, 2022

Related U.S. Application Data

(60) Provisional application No. 63/347,852, filed on Jun. 1, 2022.

(51) Int. Cl.
C07K 16/28 (2006.01)
A61K 39/395 (2006.01)

(52) U.S. Cl.
CPC ...... C07K 16/2887 (2013.01); A61K 39/3955 (2013.01); C07K 2317/732 (2013.01); C07K 2317/734 (2013.01)

(58) Field of Classification Search
CPC .............................. A61K 39/395; C07K 16/28
See application file for complete search history.

(56) References Cited

U.S. PATENT DOCUMENTS

| | | | |
|---|---|---|---|
| 5,736,137 | A | 4/1998 | Anderson et al. |
| 6,326,469 | B1 | 12/2001 | Ullrich et al. |
| 7,514,444 | B2 | 4/2009 | Honigberg et al. |
| 7,713,524 | B2 | 5/2010 | Bourel et al. |
| 7,931,895 | B2 | 4/2011 | Beliard et al. |
| 8,088,309 | B2 | 1/2012 | Yu et al. |
| 8,088,781 | B2 | 1/2012 | Honigberg et al. |
| 8,697,711 | B2 | 4/2014 | Honigberg et al. |
| 8,703,780 | B2 | 4/2014 | Honigberg et al. |
| 9,150,579 | B2 | 10/2015 | Vakkalanka |
| 9,234,045 | B2 | 1/2016 | deRomeuf et al. |
| 9,475,818 | B2 | 10/2016 | Vakkalanka |
| 9,669,033 | B2 | 6/2017 | Vakkalanka |
| 9,694,071 | B2 | 7/2017 | Weiss et al. |
| 9,873,745 | B2 | 1/2018 | deRomeuf et al. |
| 9,951,077 | B2 | 4/2018 | Liu et al. |
| 10,072,013 | B2 | 9/2018 | Vakkalanka |
| 10,272,083 | B2 | 4/2019 | Hamdy |
| 10,966,977 | B2 | 4/2021 | Weiss et al. |
| 2005/0271652 | A1 | 12/2005 | de Romeuf et al. |
| 2009/0053233 | A1 | 2/2009 | de Romeuf |
| 2011/0118257 | A1 | 5/2011 | Muthuppalaniappan et al. |
| 2012/0100133 | A1 | 4/2012 | Fisson et al. |
| 2014/0011819 | A1 | 1/2014 | Vakkalanka |
| 2015/0252108 | A1 | 9/2015 | Washburn et al. |
| 2015/0267261 | A1 | 9/2015 | Byrd et al. |
| 2015/0290317 | A1 | 10/2015 | Weiss et al. |
| 2016/0038495 | A1 | 2/2016 | Kuo et al. |
| 2017/0121336 | A1 | 5/2017 | Vakkalanka |
| 2017/0304441 | A1 | 10/2017 | Weiss et al. |
| 2019/0175592 | A1 | 6/2019 | Weiss et al. |
| 2020/0323981 | A1 | 10/2020 | Weiss et al. |

FOREIGN PATENT DOCUMENTS

| | | |
|---|---|---|
| EP | 1985633 | 10/2008 |
| EP | 2000541 | 12/2008 |
| JP | 2006-080746 | 3/2006 |
| JP | 2010-525037 A | 7/2010 |
| JP | 2012-510976 A | 5/2012 |
| JP | 2015-191426 | 11/2015 |
| WO | WO 2004/056312 | 7/2004 |
| WO | WO 2006/064121 | 6/2006 |
| WO | WO 2010/014595 | 2/2010 |
| WO | WO 2011/055215 | 5/2011 |
| WO | WO 2013/021279 | 2/2013 |
| WO | WO 2014/006572 | 1/2014 |
| WO | WO 2014/035698 | 3/2014 |
| WO | WO 2014/071125 | 5/2014 |
| WO | WO 2014/165280 | 10/2015 |
| WO | WO 2015/181728 | 12/2015 |
| WO | WO 2016/024021 | 2/2016 |
| WO | WO 2016/024232 | 2/2016 |
| WO | WO 2016/032197 | 3/2016 |

(Continued)

OTHER PUBLICATIONS clinicaltrials.gov, "Study to Assess the Efficacy and Safety of Ublituximab in Participants with Relapsing Forms of Multiple Sclerosis (RMS) (Ultimate 1)," dated Dec. 6, 2021, retrieved Apr. 18, 2023 from URL <clinicaltrials.gov/ct2/show/study/NCT03277261>, 9 pages.
TG Therapeutics, "Phase III: UbliTuximab in Multiple Sclerosis Treatment Effects (Ultimate 1 Study), NCT03277261, protocol version 5.0," dated Sep. 4, 2020, 143 pages.
Polman et al., "Diagnostic criteria for multiple sclerosis: 2010 revisions to the McDonald criteria," Annals of Neurology, Feb. 2011, 69(2):292-302.
Akinleye et al., "Ibrutinib and novel BTK inhibitors in clinical development," Journal of Hematology & Oncology, Dec. 2013, 6(1): 1-9.
atcc.org, "U266B1, ATCC TIB-196," retrieved Sep. 9, 2022 from URL <https://www.atcc.org/products/tib-196>.
Babiker et al., "Ublituximab for the treatment of CD20 positive B-cell malignancies," Expert Opinion on Investigational Drugs, Apr. 3, 2018, 27(4):407-12.

(Continued)

Primary Examiner — Xiaozhen Xie
(74) Attorney, Agent, or Firm — Fish & Richardson P.C.

(57) ABSTRACT

Provided herein are populations of anti-CD20 antibody proteins with specified ranges of post-translational modifications. Also provided are methods of using and methods of making such populations of anti-CD20 antibody proteins.

15 Claims, 17 Drawing Sheets

Specification includes a Sequence Listing.

(56) References Cited

FOREIGN PATENT DOCUMENTS

WO    WO 2018/223004    12/2018

OTHER PUBLICATIONS

Baritaki et al., "The anti-CD20 mAb LFB-R603 interrupts the dysregulated NF-κB/Snail/RKIP/PTEN resistance loop in B-NHL cells: role in sensitization to TRAIL apoptosis," International Journal of Oncology, Jun. 1, 2011, 38(6): 1683-94.

Barun et al., "Treatment of multiple sclerosis with anti-CD20 antibodies," Clinical Immunology, Jan. 1, 2012, 142(1):31-7.

Bearss et al., "Design, optimization, and biological evaluation of potent irreversible inhibitors of BTK kinase," Cancer Research, Apr. 15, 2011, 71(8 Supp):2788 (abstract), 4 pages.

Bellon et al., Comparison of Cell lysis mediated by LFB-R603 with that mediated by ofatumumab against cells expressing low levels of CD20, 53rd ASH Annual Meeting, Dec. 13, 2011, retrieved Sep. 12, 2022 from URL <https://tgtherapeutics.com/ASH2011Poster3913.pdf>, 1 page.

Bezombes et al., "Direct Effect of Rituximab in B-Cell-Derived Lymphoid Neoplasias: Mechanism, Regulation, and Perspectives Direct Effect of Rituximab," Molecular Cancer Research, Nov. 1, 2011, 9(11): 1435-42.

Bingham et al., "Over one hundred solvates of sulfathiazole Electronic supplementary information (ESI) available: solvates and adducts of sulfathiazole, See http://www.rsc. org/suppdata/cc/b0/b009540k," Chemical Communications, Mar. 2001, (7):603-4.

Binnerts, M. E. et al., "Abstract C186: SNS-062 is a potent noncovalent BTK inhibitor with comparable activity against wild type BTK and BTK with an acquired resistance mutation," AACR-NCI-EORTC International Conference: Molecular Targets and Cancer Therapeutics, Nov. 5-9, 2015, Boston, MA, dated Dec. 1, 2015, 14(12 supp 2), 5 pages.

Birg et al., "Expression of the FMS/KIT-like gene FLT3 in human acute leukemias of the myeloid and lymphoid lineages," Blood, Nov. 1992, 80:2584-2593.

Burris et al., "Activity of TGR-1202, a novel once-daily PI3Kδ inhibitor, in patients with relapsed or refractory hematologic malignancies," Abstract 2513, 2014 ASCO Annual Meeting, Journal of Clinical Oncology, May 20, 2014, 32(15 supp), 4 pages.

Burris et al., "Long-term follow-up of the PI3Kδ inhibitor TGR-1202 to demonstrate a differentiated safety profile and high response rates in CLL and NHL: Integrated-analysis of TGR-1202 monotherapy and combined with ublituximab," Abstract 7512, 2016 ASCO Annual Meeting I, Journal of Clinical Oncology, May 20, 2022, 34(15 supp), 4 pages.

Burris et al., "TGR-1202, a novel once daily PI3Kδ inhibitor, demonstrates clinical activity with a favorable safety profile, lacking hepatotoxicity, in patients with chronic lymphocytic leukemia and B-cell lymphoma," Blood, Nov. 14, 2014, 124(21): 1984 (abstract).

Burris et al., "Umbralisib, a novel PI3Kδ and casein kinase-1ε inhibitor, in relapsed or refractory chronic lymphocytic leukaemia and lymphoma: an open-label, phase 1, dose-escalation, first-in-human study," The Lancet Oncology, Apr. 1, 2018, 19(4):486-96.

Burris et al., "Updated findings of a first-in-human, phase I study of margetuximab (M), an Fc-optimized chimeric monoclonal antibody (MAb), in patients (pts) with HER2-positive advanced solid tumors," Journal of Clinical Oncology, May 20, 2015, 33(15), 4 pages.

Burris et al., "Long-term follow-up of the PI3K delta inhibitor TGR-1202 demonstrates a differentiated safety profile and high response rates in CLL and NHL: Integrated-analysis of TGR-1202 monotherapy and combined with ublituximab," American Society of Clinical Oncology Annual Meeting (ASCO), Abstract #7512, Jun. 3-7, 2016, 1 page.

Byrd et al., "Ibrutinib versus ofatumumab in previously treated chronic lymphoid leukemia," New England Journal of Medicine, Jul. 17, 2014, 371(3):213, 18 pages.

CAS No. 439574-61-5, "N-(5-((5-(4-Acetylpiperazine-1-carbonyl)-4-methoxy-2-methylphenyl)thio)thiazol-2-yl)-4-(((3-methylbutan-2-yl)amino)methyl)benzamide," retrieved Sep. 7, 2022 from URL <https://www.chemicalbook.com/ChemicalProductProperty_EN_CB32514618.htm>, 2 pages.

Chang et al., "PCI-45292, a novel Btk Inhibitor with optimized pharmaceutical properties, demonstrates potent activities in mouse models of arthritis," Arthritis Rheum, Nov. 6-11, 2010, Atlanta, GA, 62(Suppl 10), Abstract 286, 1 page.

Cheson et al., "Revised response criteria for malignant lymphoma," Journal of Clinical Oncology, Feb. 10, 2007, 25(5):579-86.

cinicaltrials.gov, "Phase III: UbLiTuximab in Multiple Sclerosis Treatment Effects (Ultimate II Study)," Sep. 4, 2020, retrieved Sep. 1, 2022 from URL <https://clinicaltrials.gov/ProvidedDocs/48/NCT03277248/Prot_000.pdf>, 144 pages.

CN Office Action in Chinese Appln. No. 201380069143.1, dated Oct. 15, 2018, 12 pages (with English translation).

CN Office Action in Chinese Appln. No. 201910562572.1, dated Dec. 30, 2020, 9 pages (with English translation).

Cotchett et al., "Comparison of the efficacy and safety of anti-CD20 B cells depleting drugs in multiple sclerosis," Multiple Sclerosis and Related Disorders, Apr. 1, 2021, 49:102787.

D'Cruz et al., "Novel Bruton's tyrosine kinase inhibitors currently in development," OncoTargets and Therapy, Mar. 2013, 6:161-76.

Davids et al., "TGR-1202 in combination with ibrutinib in patients with relapsed or refractory CLL or MCL: preliminary results of a multicenter phase I/Ib study," Blood, Jan. 1, 2016, 128(22):641, 18 pages.

De Romeuf et al., "Chronic lymphocytic leukaemia cells are efficiently killed by an anti-CD20 monoclonal antibody selected for improved engagement of FcγRIIIA/CD16," British Journal of Haematology, Mar. 2008, 140(6):635-43.

Dearden, "B-and T-cell prolymphocytic leukemia: antibody approaches," Hematology 2010, the American Society of Hematology Education Program Book, Dec. 8, 2012, 2012(1):645-51.

Demarest et al., "Emerging antibody combinations in oncology," Mabs, Jul. 1, 2011, 3(4):338-51.

Deng et al., "Novel PI3K Inhibitors Demonstrated Marked Cytotoxicity in T Cell Lymphoma Models, Caused Apoptosis and Were Synergistic with A Novel Anti-CD20 Monoclonal Antibody Ublituximab in B Cell Lymphoma Models," Abstract 3725, Blood, Nov. 16, 2012, 120(21), 4 pages.

Deng et al., "Novel PI3K Inhibitors Demonstrated Marked Cytotoxicity of T Cell Lymphoma Models, Caused Apoptosis and Were Synergistic with the Novel Anti-CD20 Monoclonal Antibody Ublituximab in Models of B Cell Lymphoma," Poster Presentation at ASH Annual Meeting, Dec. 8-11, 2012, 1 page.

Deng, "A phase I dose-escalation trial of ublituximab (TG-1101), a novel anti-CD20 monoclonal antibody (mAb), for rituximab relapsed/refractory B-cell lymphoma patients," Journal of Clinical Oncology, Abstract No. 8575, May 20, 2013, 31(15 supp), 4 pages.

Ding et al., "Irreversible dual inhibitory mode: the novel Btk inhibitor PLS-123 demonstrates promising anti-tumor activity in human B-cell lymphoma," Oncotarget, Jun. 6, 2015, 6(17): 15122-36.

EP European Search Report in European Appln. No. 16185090.4, dated Dec. 20, 2016, 10 pages.

EP European Search Report in European Appln. No. 20175073.4, dated Oct. 12, 2020, 9 pages.

EP Extended Search Report in European Appln. No. 17803731.3, dated Nov. 28, 2019, 9 pages.

EP Office Action in European Appln. No. 13792152.4, dated Nov. 15, 2016, 8 pages.

EP Office Action in European Appln. No. 16185090.4, dated Jun. 4, 2018, 6 pages.

EP Office Action in European Appln. No. 3463318.3, dated Feb. 15, 2022, 7 pages.

Evans et al., "Abstract# 2868: Thymidine Kinase 1, a molecular target for immunotherapy is overexpressed in the plasma membrane of lymphoma cells," 100th AACR Annual Meeting, Apr. 18-22, 2009, Denver, CO, Cancer Research, May 1, 2009, 69(9_Supplement):2868, 4 pages.

(56) References Cited

OTHER PUBLICATIONS

Forero-Torres et al., "Abstract CT056: Preliminary safety, efficacy, and pharmacodynamics of a highly selective PI3Kδ inhibitor, INCB050465, in patients with previously treated B-cell malignancies," Cancer Research, Jul. 15, 2016, 76(14_Supplement):CT056, 4 pages.

Fowler et al., "Safety and activity of the chemotherapy-free triplet of ublituximab, TGR-1202, and ibrutinib in relapsed B-cell malignancies.," Abstract 8501, 2015 ASCO Annual Meeting I, Journal of Clinical Oncology, May 20, 2015, 33(15 supp), 4 pages.

Fox et al., "A phase 2 multicenter study of ublituximab, a novel glycoengineered anti-CD20 monoclonal antibody, in patients with relapsing forms of multiple sclerosis," Multiple Sclerosis Journal, Mar. 2021, 27(3):420-9.

GenBank Accession No. NP_000052, "tyrosine-protein kinase BTK isoform 1 [*Homo sapiens*]," dated Jan. 5, 2016, 4 pages.

Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood, The Journal of the American Society of Hematology, Jun. 15, 2008, 111(12):5446-56.

Honigberg et al., "The Bruton tyrosine kinase inhibitor PCI-32765 blocks B-cell activation and is efficacious in models of autoimmune disease and B-cell malignancy," Proceedings of the National Academy of Sciences, Jul. 20, 2010, 107(29):13075-80.

ir.tgtherapeutics.com, TG Therapeutics, Inc. Announces Poster Presentation for Ublituximab (TGTX-1101) at the 7th International! Workshop on Waldenstrom's Macroglobulinemia, Ublituximab Demonstrates Greater Antibody-Dependent Cellular Cytotoxicity (ADCC) Than Rituximab (Rituxan(R)) in Waldenstrom's Macroglobulinemia Patient Blood Samples, Aug. 24, 2012, retrieved Oct. 21, 2022 from URL <https://ir.tgtherapeutics.com/static-files/55033a31-62fd-41be-bee5-15fa0c0b51a1>, 2 pages.

Irie et al., "Abstract A273: TAS-5567, a highly potent and selective inhibitor of SYK kinase, demonstrated antitumor activity in diffuse large B-cell lymphoma (DLBCL) cells in vitro and in vivo," Molecular Cancer Therapeutics, Nov. 2013, 12(11 Supp), 5 pages.

Jazirehi et al., "Rituximab (anti-CD20) selectively modifies Bcl-xL and apoptosis protease activating factor-1 (Apaf-1) expression and sensitizes human non-Hodgkin's lymphoma B cell lines to paclitaxel-induced apoptosis," Molecular Cancer Therapeutics, Nov. 2003, 2(11):1183-93.

JP Japanese Office Action in Japanese Appln. No. 2015-540798, dated Jul. 3, 2018, 4 pages (with English translation).

JP Japanese Office Action in Japanese Appln. No. 2015-540798, dated Jun. 27, 2017, 13 pages (with English translation).

JP Japanese Office Action in Japanese Appln. No. 2015-540798, dated Mar. 20, 2018, 6 pages (with English translation).

Kawagishi et al., "Abstract A274: Novel SYK inhibitors have demonstrated potent antiproliferative effects in both ABC-and GCB-DLBCL cell lines via suppression of multiple pathways downstream of the B-cell receptor," Molecular Cancer Therapeutics, Nov. 2013, 12(11 Supp), 5 pages.

Klein et al., "Epitope interactions of monoclonal antibodies targeting CD20 and their relationship to functional properties," MAbs, Jan. 1, 2013, 5(1):22-33.

Kolibaba et al., "Ublituximab (TG-1101), a novel glycoengineered anti-CD20 monoclonal antibody, in combination with ibrutinib is highly active in patients with relapsed and/or refractory mantle cell lymphoma Results of a phase II trial," Blood, Dec. 3, 2015, 126(23):3980, 3 pages.

Kozaki et al., "Abstract 857: Development of a Bruton's tyrosine kinase (Btk) inhibitor—ONO-WG-307, a potential treatment for B-cell malignancies," Cancer Research, Apr. 15, 2012, 72(8 Supp), 4 pages.

KR Office Action in Korean Appln. No. 2015-7014678, dated Jun. 18, 2020, 13 pages (with English translation).

Lanasa et al., "First-in-human study of AMG 319, a highly selective, small molecule inhibitor of PI3Kδ, in adult patients with relapsed or refractory lymphoid malignancies," Blood, Nov. 15, 2013, 122(21):678, 3 pages.

Li et al., "The characteristics of 62 cases of CD20-positive multiple myeloma," Zhonghua xue ye xue za zhi= Zhonghua Xueyexue Zazhi, Jan. 1, 2015, 36(1):44-8 (with English Abstract).

Lim et al., "Anti-CD20 monoclonal antibodies: historical and future perspectives," Haematologica, Jan. 2010, 95(1):135.

Lin et al., "Selective Itk inhibitors block T-cell activation and murine lung inflammation," Biochemistry, Aug. 31, 2004, 43(34):11056-62.

Lovett-Racke et al., "B cell depletion with ublituximab reshapes the T cell profile in multiple sclerosis patients," Journal of Neuroimmunology, Jul. 15, 2019, 332: 187-97.

Lunning et al., "Ublituximab and umbralisib in relapsed/refractory B-cell non-Hodgkin lymphoma and chronic lymphocytic leukemia," Blood, Nov. 21, 2019, 134(21): 1811-20.

Miller et al., "Ublituximab (TGTX-1101), A Novel Anti-CD20 Monoclonal Antibody (mAb), Demonstrates Activity in Rituximab-Sensitive and Rituximab-resistant B Non-Hodgkin Lymphoma (B-NHL) Pre-Clinical In vitro and in Vivo models," (abstract 2756), Blood, Nov. 16, 2012, 120(21), 6 pages.

Moreno et al., "Abstract CT157: Clinical pharmacokinetics and pharmacodynamics of ME-401, an oral, potent and selective inhibitor of phosphatidylinositol 3-kinase P110δ, following single ascending dose administration to healthy volunteers," Cancer Research, Jul. 15, 2016, 76(14 Supp), 4 pages.

Nastoupil et al. Oral Presentations, Abstracts, A90, Hematological Oncology, Special Issue: 13-ICML, 13th International Conference on Malignant Lymphoma, Pallazzo dei Congressie, Lugano, Switzerland, 17-20, Jun. 9, 2015, 33(supp 1), 81 pages.

Nastoupil et al., "Chemo-Free Triplet Combination of TGR-1202 Ublituximab and Ibrutnib is Well Tolerated and Highly Active in Patients with Advanced CLL and NHL," Hematological Oncology, Jun. 2017, 35:112-3.

Nastoupil et al., "The chemotherapy-free triplet of Ublituximab, TGR-1202, and ibrutinib is safe and highly active in relapsed B-cell malignancies," Hematol Oncol, 2015, 33:156-7.

Nastoupil et al., "Tolerability and activity of chemo-free triplet combination of TGR-1202, ublituximab, and ibrutinib in patients with advanced CLL and NHL," Abstract 7511, 2017 ASCO Annual Meeting I, Journal of Clinical Oncology, May 30, 2017, 35:7511, 4 pages.

Nastoupil et al., "Tolerability and activity of ublituximab, umbralisib, and ibrutinib in patients with chronic lymphocytic leukaemia and non-Hodgkin lymphoma: a phase 1 dose escalation and expansion trial," The Lancet Haematology, Feb. 1, 2019, 6(2):e100, 10 pages.

O'Brien et al., "Duvelisib (IPI-145), a PI3K-δ, γ inhibitor, is clinically active in patients with relapsed/refractory chronic lymphocytic leukemia," Blood, Nov. 14, 2014, 124(21):3334, 26 pages.

O'Connor et al., "A phase I trial of ublituximab (TG-1101), a novel glycoengineered anti-CD20 monoclonal antibody (mAb) in B-cell non-Hodgkin lymphoma patients with prior exposure to rituximab," Abstract 8524, Journal of Clinical Oncology, May 20, 2014, 32:5s, 4 pages.

O'Connor et al., "TGR-1202, a novel once daily PI3K-delta inhibitor, demonstrates clinical activity with a favorable safety profile in patients with CLL and B-cell lymphoma," Abstract 4154, Blood, Dec. 3, 2015, 126(23), 4 pages.

Oken et al., "Toxicity and response criteria of the Eastern Cooperative Oncology Group," American Journal of Clinical Oncology, Dec. 1, 1982, 5(6):649-56.

Pan et al., "Discovery of selective irreversible inhibitors for Bruton's tyrosine kinase," ChemMedChem: Chemistry Enabling Drug Discovery, Jan. 15, 2007, 2(1):58-61.

PCT International Preliminary Report on Patentability in International Appln. No. PCT/JP2018/027895, dated Jan. 28, 2020, 5 pages.

PCT International Preliminary Report on Patentability in International Appln. No. PCT/US2013/067956, dated May 5, 2015, 9 pages.

(56) References Cited

OTHER PUBLICATIONS

PCT International Search Report and Written Opinion in International Appln. No. PCT/JP2018/027895, dated Sep. 11, 2018, 9 pages (with English translation).

PCT International Search Report and Written Opinion in International Appln. No. PCT/US2013/067956, dated Feb. 17, 2014, 13 pages.

Powers, "Ibrutinib, Ublituximab, TGR-1202 Triplet Active in Relapsed B-Cell Malignancies," reporting on 13th International Conference on Malignant Lymphoma, held Jun. 17-20, 2015 in Lugano, Switzerland; published Jun. 19, 2015, 3 pages.

Puri et al., "Selective inhibitors of phosphoinositide 3-kinase delta: modulators of B-cell function with potential for treating autoimmune inflammatory diseases and B-cell malignancies," Frontiers in Immunology, Aug. 23, 2012, 3:256.

Sharman et al., "Ublituximab (TG-1101), a novel glycoengineered anti-CD 20 antibody, in combination with ibrutinib is safe and highly active in patients with relapsed and/or refractory chronic lymphocytic leukaemia: results of a phase 2 trial," British Journal of Haematology, Feb. 2017, 176(3):412-20.

Sharman et al., "Ublituximab (TG-1101), a novel glycoengineered anti-CD20 monoclonal antibody, in combination with ibrutinib is highly active in patients with relapsed and/or refractory CLL and MCL; results of a phase II trial (abstract)," Blood, Nov. 14, 2014 (abstract from Dec. 6, 2014), 124(21):4679, 3 pages.

Sharman et al., "Ublituximab and Ibrutinib for Previously Treated Genetically High-Risk Chronic Lymphocytic Leukemia: Results of the Genuine Phase 3 Study," Oral Presentation, Hematological Oncology, Jun. 2017, 35(52), 3 pages.

Sharman et al., "Ublituximab and Ibrutinib for Previously Treated Genetically High-Risk Chronic Lymphocytic Leukemia: Results of the Genuine Phase 3 Study," Poster for Presentation, Jun. 3, 2017, retrieved Nov. 11, 2022 from URL <https://www.tgtherapeutics.com/wp-content/uploads/2019/03/ASCO%202017%20Sharman%20Final.pdf>, 17 pages.

Sharman et al., "xaxaaaac), a Novel Glycoengineered Anti-CD20 Monoclonal Antibody, in Combination with Ibrutinib Achieves 95% ORR in Patients with High-Risk Relapsed/Refractory CLL," Abstract 105, Hematological Oncology, Jun. 19, 2015, vol. 33, 1 page.

Sloka et al., "The mechanism of action of methylprednisolone in the treatment of multiple sclerosis," Multiple Sclerosis Journal, Aug. 2005, 11(4):425, 11 pages.

Smith et al., "Comparison of biosequences," Advances in Applied Mathematics, Dec. 1, 1981, 2(4):482-9.

Smith, "Chiral toxicology: it's the same thing ... only different," Toxicological Sciences, Jul. 1, 2009, 110(1):4-30.

Tam, "The BTK inhibitor, Bgb-3111, is safe, tolerable, and highly active in patients with relapsed/refractory B-cell malignancies: initial report of a phase 1 first-in-human trial," Blood, Abstract #832, American Society of Hematology (ASH) Annual Meeting, Orlando, FL, Dec. 5-8, 2015.

Vanhaesebroeck et al., "Signalling by PI3K isoforms: insights from gene-targeted mice," Trends in Biochemical Sciences, Apr. 1, 2005, 30(4):194-204.

Vivanco et al., "The phosphatidylinositol 3-kinase-AKT pathway in human cancer," Nature Reviews Cancer, Jul. 2002, 2(7):489-501.

Winiarska et al., "Molecular mechanisms of the antitumor effects of anti-CD20 antibodies," Frontiers in Bioscience-Landmark, Jan. 1, 2011, 16(1):277-306.

Won et al., "T-Cell-Targeted Signaling Inhibitors," International Reviews of Immunology, Jan. 1, 2008, 27(1-2):19-41.

Xu, "LC-MS multi-attribute method for characterization of biologics," Journal of Applied Bionalysis, Apr. 12, 2017, 3(2):21.

Yasuhiro et al., "ONO-WG-307, a novel, potent and selective inhibitor of Bruton's tyrosine kinase (Btk), results in sustained inhibition of the ERK, AKT and PKD signaling pathways," Abstract 2021, Cancer Research, Jun. 2012, 72(8 supp).

Zhang, "Ofatumumab," MAbs, Aug. 1, 2009, 326-31.

U.S. Appl. No. 63/145,863, Hossler et al., filed Feb. 4, 2021.

Barr et al., "A Phase 1/2 Study of Umbralisib, Ublituximab, and Venetoclax (U2-Ven) in Patients with Relapsed or Refractory Chronic Lymphocytic Leukemia (CLL)," Abstract 3137, American Society of Hematology (ASH) Annual Meeting (2020): American Society of Hematology (ASH) Annual Meeting, Dec. 7, 2020, 4 pages.

Gribben et al., "Umbralisib Plus Ublituximab (U2) Is Superior to Obinutuzumab Plus Chlorambucil (O+Chl) in Patients with Treatment Naïve (TN) and Relapsed/Refractory (R/R) Chronic Lymphocytic Leukemia (CLL): Results from the Phase 3 UNITY-CLL Study," Publication: 543, American Society of Hematology (ASH) Annual Meeting, Dec. 7, 2020, 5 pages.

Bar-Or et al., "Priuximab in relapsing-remitting multiple sclerosis: a 72-week, open-label, phase I trial," Annals of Neurology, Mar. 2008, 63(3):395-400.

Barr et al., "A Phase 1/2 Study of Umbralisib, Ublituximab, and Venetoclax (U2-Ven) in Patients with Relapsed or Refractory Chronic Lymphocytic Leukemia (CLL)," American Society of Hematology (2020), Blood, 136(supp 1), Nov. 5, 2020, 4 pages.

Cheah et al., "Clinical activity of TG-1701, as monotherapy and in combination with ublituximab and umbralisib (U2), in patients with B-cell malignancies," American Society of Hematology 62nd Congress, Blood, Dec. 2020, 136:1130, 14 pages.

Compston et al., "Multiple sclerosis," The Lancet, Oct. 25, 2008, 372(9648):1502-17.

Dolgin, "BTK blockers make headway in multiple sclerosis," Nature Biotechnology, Jan. 1, 2021, 39(1):3-6.

Fischer et al., "National MS Society Clinical Outcomes Assessment Task Force. The Multiple Sclerosis Functional Composite measure (MSFC): an integrated approach to MS clinical outcome assessment," Multiple Sclerosis Journal, Aug. 1999, 5(4):244-50.

Garff-Tavernier et al., "Antibody-dependent cellular cytotoxicity of the optimized anti-CD20 monoclonal antibody ublituximab on chronic lymphocytic leukemia cells with the 17p deletion," Leukemia, Jan. 2014, 28(1):230-3.

Graf et al., "B cells to modify MS, NMOSD, and MOGAD: part 1," Neurology-Neuroimmunology Neuroinflammation, Jan. 1, 2021, 8(1), 12 pages.

Greenfield et al., "B-cell therapy for multiple sclerosis: entering an era," Annals of Neurology, Jan. 2018, 83(1):13-26.

Gribben et al., "Umbralisib plus ublituximab (U2) is superior to obinutuzumab plus chlorambucil (O+ Chl) in patients with treatment naïve (TN) and relapsed/refractory (R/R) chronic lymphocytic leukemia (CLL): results from the phase 3 Unity-CLL study," American Society of Hematology (ASH) Annual Meeting (2020), Blood, Nov. 5, 2020, 136:37, 8 pages.

Hauser et al., "B-cell depletion with rituximab in relapsing-remitting multiple sclerosis," New England Journal of Medicine, Feb. 14, 2008, 358(7):676-88.

Hauser et al., "Ocrelizumab versus interferon beta-1a in relapsing multiple sclerosis," New England Journal of Medicine, Jan. 19, 2017, 376(3):221-34.

Hauser et al., "Ofatumumab versus teriflunomide in multiple sclerosis," New England Journal of Medicine, Aug. 6, 2020, 383(6):546-57.

Hauser et al., "Treatment of multiple sclerosis: a review," The American Journal of Medicine, Dec. 1, 2020, 133(12): 1380-90.

Ihle et al., "Take your PIK: phosphatidylinositol 3-kinase inhibitors race through the clinic and toward cancer therapy," Molecular Cancer Therapeutics, Jan. 2009, 8(1):1-9.

Kappos et al., "Ocrelizumab in relapsing-remitting multiple sclerosis: a phase 2, randomised, placebo-controlled, multicentre trial," The Lancet, Nov. 19, 2011, 378(9805): 1779-87.

Kaunzner et al., "MRI in the assessment and monitoring of multiple sclerosis: an update on best practice," Therapeutic Advances in Neurological Disorders, Jun. 2017, 10(6):247-61.

Kocsis et al., "Two Classes of T1 Hypointense Lesions in Multiple Sclerosis With Different Clinical Relevance," Frontiers in Neurology, Mar. 3, 2021, 12:619135.

Lublin et al., "Defining the clinical course of multiple sclerosis: results of an international survey," Neurology, Apr. 1, 1996, 46(4):907-11.

Lublin et al., "Defining the clinical course of multiple sclerosis: the 2013 revisions," Neurology, Jul. 15, 2014, 83(3):278-86.

(56) References Cited

OTHER PUBLICATIONS

Lublin et al., "The 2013 clinical course descriptors for multiple sclerosis: A clarification," Neurology, Jun. 16, 2020, 94(24): 1088-92.
Lunning et al., "Ublituximab + TGR-1202 Demonstrates Activity and a Favorable Safety Profile in Relapsed/Refractory B-Cell NHL and High-Risk CLL: Phase I Results," Abstract 1538, American Society of Hematology Annual Meeting and Exposition, Dec. 5-8, 2015, 1 page.
Miller et al., "Primary-progressive multiple sclerosis," The Lancet Neurology, Oct. 1, 2007, 6(10):903-12.
NCBI NP_068769.2, "B-lymphocyte antigen CD20 [*Homo sapiens*]," dated Nov. 8, 2021, 3 pages.
NCBI NP_690605.1, "B-lymphocyte antigen CD20 [*Homo sapiens*]," dated Nov. 8, 2021, 4 pages.
Ontaneda et al., "Progressive multiple sclerosis: prospects for disease therapy, repair, and restoration of function," The Lancet, Apr. 2017, 389(10076): 1357, 33 pages.
Reich et al., "Multiple Sclerosis," New England Journal of Medicine, Jan. 11, 2018, 378(2): 169, 17 pages.
Rovira et al., "MAGNIMS consensus guidelines on the use of MRI in multiple sclerosis—clinical implementation in the diagnostic process," Nature Reviews Neurology, Aug. 2015, 11(8):471-82.
Sharman et al., "Ublituximab (TG-1101), a Novel Glycoengineered Anti-CD20 Monoclonal Antibody, in Combination with Ibrutinib Is Highly Active in Patients with Relapsed and/or Refractory Mantle Cell Lymphoma; Results of a Phase II Trial," Abstract 3980, American Society of Hematology Annual Meeting and Exposition, Dec. 5-8, 2015.
Sormani et al., "Magnetic resonance imaging as a potential surrogate for relapses in multiple sclerosis: a meta-analytic approach," Annals of Neurology: Official Journal of the American Neurological Association and the Child Neurology Society, Mar. 2009, 65(3):268-75.
Sormani et al., "MRI lesions as a surrogate for relapses in multiple sclerosis: a meta-analysis of randomised trials," The Lancet Neurology, Jul. 1, 2013, 12(7):669-76.
Teeling et al., "The biological activity of human CD20 monoclonal antibodies is linked to unique epitopes on CD20," The Journal of Immunology, Jul. 1, 2006, 177(1):362-71.
Thompson et al., "Diagnosis of multiple sclerosis: 2017 revisions of the McDonald criteria," The Lancet Neurology, Feb. 1, 2018, 17(2): 162-73.
Wallin et al., "The prevalence of MS in the United States: a population-based estimate using health claims data, " Neurology, Mar. 5, 2019, 92(10):e1029-40.
[No Author] "Gazyva, Highlights of Prescribing Information," Jan. 2013, 31 pages.
[No Author] "Rituximab, Highlights of Prescribing Information," Jan. 1997, 35 pages.
[No Author] "Riximyo, Product Information," Aug. 2018, 63 pages.
[No Author], "Assessment Report—Blitzima, Procedure No. EMEA/H/C/004723/0000," European Medicines Agency, May 2017, 161 pages.
Carillo et al., "Comparing different domains of analysis for the characterisation of N-glycans on monoclonal antibodies," Journal of Pharmaceutical Analysis, Feb. 1, 2020, 10(1):23-34.
Center for Drug Evaluation and Research (CDER), "Ruxience, Product Quality Review," Apr. 15, 2023, 120 pages.
EP Office Action in European Appln. No. 17803731.3, dated Feb. 15, 2022, 7 pages.
Kelley, "Very large scale monoclonal antibody purification: the case for conventional unit operations," Biotechnology Progress, Sep. 2007, 23(5):995-1008.
Reusch et al., "Fc glycans of therapeutic antibodies as critical quality attributes," Glycobiology, Dec. 1, 2015, 25(12): 1325-34.
U.S. Non-Final Office Action in U.S. Appl. No. 17/892,465, dated Jun. 22, 2023, 46 pages.

Blinding Code: 50K068:70T:2003=Gazyva; 52W243:70T:2003=ARZERRA; 54A167:70T:2003=Rituxan

| Covariate | Percentile | Value | Ratio [95%CI] |
|---|---|---|---|
| ADA | | Positive | 0.837 [0.78, 0.901] |
| Time | | >416 days | 1.18 [1.17, 1.19] |
| Region | | Eastern Europe | 1.03 [1.02, 1.04] |
| Sex | | Female | 0.982 [0.974, 0.989] |
| Weight | 5% | 50 | 1.24 [1.19, 1.29] |
| | 50% | 73 | 1 [1,1] |
| | 95% | 111 | 0.781 [0.739, 0.826] |
| BSV | 90% CI | N/A | 1 [0.484, 1.57] |

| Covariate | Percentile | Value | Ratio [95%CI] |
|---|---|---|---|
| ADA | | Positive | 0.999 [0.999, 0.999] |
| Time | | >416 days | 1 [1, 1] |
| Region | | Eastern Europe | 0.906 [0.875, 0.942] |
| Sex | | Female | 1.07 [1.05, 1.11] |
| Weight | 5% | 50 | 1.18 [1.15, 1.21] |
| | 50% | 73 | 1 [1,1] |
| | 95% | 111 | 0.833 [0.807, 0.859] |
| BSV | 90% CI | N/A | 1 [0.759, 1.26] |

| Covariate | Percentile | Value | Ratio [95%CI] |
|---|---|---|---|
| ADA | | Positive | 0.924 [0.896, 0.954] |
| Time | | >416 days | 1.08 [1.08, 1.08] |
| Region | | Eastern Europe | 0.98 [0.973, 0.988] |
| Sex | | Female | 1.01 [1.01, 1.02] |
| Weight | 5% | 50 | 1.16 [1.13, 1.18] |
| | 50% | 73 | 1 [1,1] |
| | 95% | 111 | 0.846 [0.825, 0.866] |
| BSV | 90% CI | N/A | 1 [0.695, 1.31] |

ANTI-CD20 ANTIBODY COMPOSITIONS

1. CROSS-REFERENCE PARAGRAPH

This application claims the benefit of priority to U.S. Provisional Appl. No. 63/347,852 filed Jun. 1, 2022, which is incorporated by reference in its entirety herein.

SEQUENCE LISTING

This application contains a Sequence Listing that has been submitted electronically as an XML file named "50581-0004001_SL_ST26.XML." The XML file, created on Dec. 16, 2022, is 39,134 bytes in size. The material in the XML file is hereby incorporated by reference in its entirety.

2. FIELD OF THE DISCLOSURE

The present disclosure is in the field of recombinant anti-CD20 antibodies, methods of producing such antibodies, and uses of such antibodies.

3. BACKGROUND OF THE DISCLOSURE

Therapeutic monoclonal antibodies (mAbs) produced in mammalian cells are heterogeneous as a result of post-translational modifications (PTMs). PTMs can occur during mAb production, purification, storage, and post-administration. PTMs are therapeutic mAb product quality attributes (PQAs). Controlling PQAs within predefined acceptance criteria is vital to the biopharmaceutical industry because it ensures consistent product quality and reduces potential impacts on drug safety and efficacy (Xu, X. et al., *Journal of Applied Bioanalysis* 3(2):21-5 (2017)).

The critical importance of sequence variation in antibodies is well recognized. Sequence diversity in antibody variable domains is essential for specific antigen recognition while linkage to different constant domains leads to distinct Fc-mediated effector activities. PTMs of these domains provide an additional immune mechanism by which the binding and activity of antibodies can be modulated. PTMs vary from chain additions, such as N- and O-linked glycosylation, glycation, cysteinylation and sulfation; chain trimming, such as C-terminal lysine clipping; amino acid modifications such as cyclization (into a N-terminal pyroglutamic acid), deamidation, oxidation, isomerization and carbamylation; to disulfide scrambling of hinge region interchain disulfide bonds. Each antibody can therefore give rise to a myriad of distinct antibody molecules with large activity and potency differences. Although post-translational modifications of antibodies have been observed and studied for decades, the full impact of the microheterogeneity is yet to be further studied. PTMs can impact antibody functions, for example, pharmacokinetics and pharmacodynamics properties and clinical efficacy.

Having specified ranges of post-translational modifications can be critical for a population of mAbs to possess consistent product quality, clinical safety, and efficacy.

4. SUMMARY OF THE DISCLOSURE

Provided herein are compositions comprising a population of anti-CD20 antibody proteins, wherein the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans. In some embodiments, the N-glycan profile comprises 23% to 36% fucosylated glycans. In some embodiments, the N-glycan profile comprises about 30% fucosylated glycans. In some embodiments, the N-glycan profile comprises 16 to 18% galactosylated glycans. In some embodiments, the N-glycan profile comprises about 17% galactosylated glycans. In some embodiments, the N-glycan profile comprises 12% to 30% bisecting N-glycans. In some embodiments, the N-glycan profile comprises about 18% bisecting N-glycans. In some embodiments, the bisecting N-glycans comprise one or more of G0B, G0FB, G1FB, G2FBS1, and G2FBS2.

In some aspects, composition comprising the population of anti-CD20 antibody proteins further comprises at least two N-glycans within the following relative abundance ranges:
(a) 0.3% to 2% G0-GN;
(b) 0.1% to 2% G0F-GN;
(c) 30% to 60% G0;
(d) 0.1% to 1% G1-GN;
(e) 5% to 20% G0B;
(f) 5% to 30% G0F;
(g) 0.1% to 1.5% Man5;
(h) 1% to 15% G0FB;
(i) 1% to 13% G1;
(j) 0.5% to 10% G1';
(k) 0.5% to 6% G1B;
(l) 0.5% to 12% G1F;
(m) 0.1% to 3% G1F';
(n) 0.1% to 3% G1FB;
(o) 0.1% to 2% G2; and
(p) 0.1% to 2% G2F.

In some embodiments, the population of anti-CD20 antibody proteins further comprises at least two N-glycans within the following relative abundance range:
(a) 0.8% to 1.1% G0-GN;
(b) 0.5% to 1.1% G0F-GN;
(c) 42.5% to 48.8% G0;
(d) 0.3% to 0.6% G1-GN;
(e) 9.5% to 14.1% G0B;
(f) 12.8% to 19.7% G0F;
(g) 0.4% to 0.7% Man5;
(h) 5.1% to 7.0% G0FB;
(i) 5.7% to 6.4% G1;
(j) 2.7% to 3.3% G1';
(k) 1.4% to 2.0% G1B;
(l) 2.6% to 4.2% G1F;
(m) 1.1% to 1.6% G1F';
(n) 1.1% to 1.8% G1FB;
(o) 0.5% to 0.7% G2; and
(p) 0.3% to 0.5% G2F.

In some embodiments, the population of anti-CD20 antibody proteins further comprises at least two N-glycans in the following relative abundance:
(a) 0.9% G0-GN;
(b) 0.8% G0F-GN;
(c) 46.1% G0;
(d) 0.5% G1-GN;
(e) 10.9% G0B;
(f) 17.0% G0F;
(g) 0.6% Man5;
(h) 6.0% G0FB;
(i) 6.1% G1;
(j) 2.9% G1';
(k) 1.6% G1B;

(l) 3.2% G1F;
(m) 1.3% G1F';
(n) 1.3% G1FB;
(o) 0.5% G2; and
(p) 0.3% G2F.

In some embodiments, the population of anti-CD20 antibody proteins further comprises at least three, four or five N-glycans within the following relative abundance ranges:
(a) 0.3% to 2% G0-GN;
(b) 0.1% to 2% G0F-GN;
(c) 30% to 60% G0;
(d) 0.1% to 1% G1-GN;
(e) 5% to 20% G0B;
(f) 5% to 30% G0F;
(g) 0.1% to 1.5% Man5;
(h) 1% to 15% G0FB;
(i) 1% to 13% G1;
(j) 0.5% to 10% G1';
(k) 0.5% to 6% G1B;
(l) 0.5% to 12% G1F;
(m) 0.1% to 3% G1F';
(n) 0.1% to 3% G1FB;
(o) 0.1% to 2% G2; and
(p) 0.1% to 2% G2F.

In some embodiments, wherein less than 10% of the anti-CD20 antibody proteins in the population is non-glycosylated.

In some embodiments, wherein less than 5% of the anti-CD20 antibody proteins in the population is non-glycosylated.

In some embodiments, wherein less than 1% of the anti-CD20 antibody proteins in the population is non-glycosylated.

In some embodiments, the anti-CD20 antibody proteins in the population induces greater cytotoxicity in a cell-based antibody-dependent cellular cytotoxicity (ADCC) assay compared to obinutuzumab, ofatumumab, rituximab, veltuzumab, ibritumomab tiuxetan and/or ocrelizumab.

In some embodiments, the population has a relative potency of 90 to 163% in a cell-based ADCC assay compared to a commercial reference standard.

In some embodiments, the population has a relative potency of 78% to 116% or 73% to 128% in a cell-based complement dependent cytotoxicity (CDC) assay compared to that of a commercial reference standard.

Provided herein are compositions comprising a population of anti-CD20 antibody protein. In one aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 35% fucosylated glycans.

In certain embodiments, the N-glycan profile comprises 28 to 33% fucosylated glycans. In certain embodiments, the N-glycan profile comprises about 30% fucosylated glycans. In certain embodiments, the N-glycan profile comprises 16 to 18% galactosylated glycans. In certain embodiments, the N-glycan profile comprises about 17% galactosylated glycans.

In certain embodiments, the relative abundance of fucosylated glycans is the percent of fucosylated glycans among all glycans in the N-glycan profile. In certain embodiments, the relative abundance of galactosylated glycans is the percent of galactosylated glycans among all glycans in the N-glycan profile.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising at least about 10% bisecting N-glycans.

In certain embodiments, the N-glycan profile comprises 12% to 30% bisecting N-glycans. In certain embodiments, the N-glycan profile comprises about 18% bisecting N-glycans.

In certain embodiments, the bisection N-glycan comprises one or more of G0B, G0FB, G1FB, G2FBS1, and G2FBS2.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising less than 5% sialylated glycans.

In certain embodiments, the N-glycan profile comprises less than 4%, 3%, 2.5%, 2%, 1%, or 0.5% sialylated glycan. In certain embodiments, the N-glycan profile comprises no detectable amount of sialylated glycan.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 5 to 15% G0B N-glycan.

In certain embodiments, the N-glycan profile comprises 9 to 11% G0B N-glycan. In certain embodiments, the N-glycan profile comprises about 10% G0B N-glycan.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 0.1% to 1.5% Man5 N-glycan.

In certain embodiments, the N-glycan profile comprises 0.4% to 0.7% Man5 N-glycan. In certain embodiments, the N-glycan profile comprises about 0.6% Man5 N-glycan. In certain embodiments, Man5 N-glycan is the only high mannose species in the N-glycan profile.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins comprises 0.20 to 0.40 mol isoaspartate per mol protein.

In certain embodiments, the population of anti-CD20 antibody proteins comprises 0.25 to 0.35 mol isoaspartate per mol protein.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the glutamate at position 1 of the heavy chain is a pyroglutamate and wherein the glutamate at position 1 of the light chain is a pyroglutamate.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising a relative abundance ratio of 0.1 to 0.15 G1 to G0 N-glycans.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising a relative abundance ratio of 0.5 to 0.9 G1F to G1 N-glycans.

In certain embodiments, the population of anti-CD20 antibody proteins further comprises at least two N-glycans within the following relative abundance range:
(a) 0.3% to 2% G0-GN;
(b) 0.1% to 2% G0F-GN;
(c) 0.1% to 1% G1-GN;
(d) 5% to 20% G0B;
(e) 5% to 30% G0F;
(f) 0.1% to 1.5% Man5;
(g) 1% to 15% G0FB;
(h) 1% to 13% G1;
(i) 0.5% to 10% G1';
(j) 0.5% to 6% G1B;
(k) 0.5% to 12% G1F;
(l) 0.1% to 3% G1F';
(m) 0.1% to 3% G1FB;
(n) 0.1% to 2% G2; and
(o) 0.1% to 2% G2F.

In certain embodiments, the population of anti-CD20 antibody proteins further comprises at least two N-glycans within the following relative abundance range:
(a) 0.8% to 1.1% G0-GN;
(b) 0.5% to 1.1% G0F-GN;
(c) 0.3% to 0.6% G1-GN;
(d) 9.5% to 14.1% G0B;
(e) 12.8% to 19.7% G0F;
(f) 0.4% to 0.7% Man5;
(g) 5.1% to 7.0% G0FB;
(h) 5.7% to 6.4% G1;
(i) 2.7% to 3.3% G1';
(j) 1.4% to 2.0% G1B;
(k) 2.6% to 4.2% G1F;
(l) 1.1% to 1.6% G1F';
(m) 1.1% to 1.8% G1FB;
(n) 0.5% to 0.7% G2; and
(o) 0.3% to 0.5% G2F.

In certain embodiments, the population of anti-CD20 antibody proteins further comprises at least two N-glycans in the following relative abundance:
(a) 0.9% G0-GN;
(b) 0.8% G0F-GN;
(c) 0.5% G1-GN;
(d) 10.9% G0B;
(e) 17.0% G0F;
(f) 0.6% Man5;
(g) 6.0% G0FB;
(h) 6.1% G1;
(i) 2.9% G1';
(j) 1.6% G1B;
(k) 3.2% G1F;
(l) 1.3% G1F';
(m) 1.3% G1FB;
(n) 0.5% G2; and
(o) 0.3% G2F.

In certain embodiments, the population of anti-CD20 antibody proteins further comprises at least three, four or five N-glycans within the relative abundance or relative abundance range as described herein.

In certain embodiments, the N-glycan profile of the population of anti-CD20 antibody proteins is determined using a method comprising:
(a) incubate the population of anti-CD20 antibody proteins with an enzyme, wherein the enzyme catalyzes releasing of the N-glycans from the anti-CD20 antibody;
(b) measure the relevant abundance of the released N-gylcans using one or more methods selected from chromatography, mass spectrometry, capillary electrophoresis, and the combination thereof.

In certain embodiments, the enzyme is PNGase F. In certain embodiments, the method further comprises after step (a) and before step (b) the following steps:
(c) purify the N-glycans; and
(d) label the N-glycans with a fluorescent compound.

In certain embodiments, the fluorescent compound is 2-aminobenzamide (2-AB).

In certain embodiments, less than 10% of the anti-CD20 antibody proteins in the population is non-glycosylated. In certain embodiments, less than 5% of the anti-CD20 antibody proteins in the population is non-glycosylated. In certain embodiments, less than 1% of the anti-CD20 antibody proteins in the population is non-glycosylated.

In certain embodiments, the N-glycan profile of the population of anti-CD20 antibody proteins is substantially as shown in FIG. 2.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins comprises two or more secondary structures as determined by circular dichroism at 205 nm to 260 nm as follows:

(a) 8.0% to 10.0% α-helix;
(b) 32.0% to 36.0% Anti-parallel β-sheet;
(c) 5.0% to 6.0% Parallel β-sheet;
(d) 16.0% to 18.0% β-Turn; and
(e) 35.0% to 36.0% random coil.

In certain embodiments, the population of anti-CD20 antibody proteins comprises secondary structures as determined by circular dichroism at 205 nm to 260 nm as follows:
(a) 8.0% to 10.0% α-helix;
(b) 32.0% to 36.0% Anti-parallel β-sheet;
(c) 5.0% to 6.0% Parallel β-sheet;
(d) 16.0% to 18.0% β-Turn; and
(e) 35.0% to 36.0% random coil.

(c) about 5.6% Parallel β-sheet;
(d) about 17.5% β-Turn; and
(e) about 35.2% random coil.

In another aspect, provided herein is a composition comprising a population of anti-CD20 antibody proteins, wherein the anti-CD20 antibody in said population is expressed from one or more nucleic acid sequences encoding a heavy chain ("HC") comprising the amino acid sequence of SEQ ID NO:1 and a light chain ("LC") comprising the amino acid sequence of SEQ ID NO:2, wherein the population of anti-CD20 antibody proteins further comprises one or more of the following post-translational modifications at the specified abundance:

| Site | Position [in bold and underlined] | Modification | Abundance |
|---|---|---|---|
| HC (20-23) | MSCK (SEQ ID NO: 17) | Oxidation | <0.1 |
| HC (24-38) | ASGYTFTSYNMHWVK (SEQ ID NO: 18) | Oxidation<br>Deamidation | 0.8<br>0.3 |
| HC (39-63) | QTPRQGLEWIGGIYPGNGDTSYNQK (SEQ ID NO: 19) | Deamidation | 4.5 |
| HC (66-74) | GKATLTVGK (SEQ ID NO: 20) | Glycation | 0.6 |
| HC (75-122) | SSSTAYMQLSSLTSEDSAVYFCARYDYNYAMDYWGQGTSVTVSSASTK (SEQ ID NO: 21) | Oxidation | 0.3 |
| HC (149-206) | DYFPEPVTVSWNSGALTSGVHTFPAVLQSSGLYSLSSVVTVPSSSLGTQTYICNVNHK (SEQ ID NO: 22) | Deamidation | 1.5 |
| HC (248-275) | PKDTLMISRTPEVTCVVVDVSHEDPEVK (SEQ ID NO: 23) | Glycation | 0.2 |
| HC (250-275) | DTLMISRTPEVTCVVVDVSHEDPEVK (SEQ ID NO: 24) | Oxidation | 2.7 |
| HC (276-289) | FNWYVDGVEVHNAK (SEQ ID NO: 25) | Deamidation | 0.6 |
| HC (324-335) | VSNKALPAPIEK (SEQ ID NO: 26) | Glycation | 0.2 |
| HC (362-371) | NQVSLTCLVK (SEQ ID NO: 27) | Deamidation | 2.0 |
| HC (372-393) | GFYPSDIAVEWESNGQPENNYK (SEQ ID NO: 28) | Deamidation | 14.7 |
| HC (416-440) | SRWQQGNVFSCSVMHEALHNHYTQK (SEQ ID NO: 29) | Oxidation | 0.8 |
| LC (19-38) | VTMTCRASSSVSYMHWYQQK (SEQ ID NO: 30) | Oxidation | 1.3 |
| LC (126-144) | SGTASVVCLLNNFYPREAK (SEQ ID NO: 31) | Deamidation | 1.1 |
| LC (149-168) | VDNALQSGNSQESVTEQDSK (SEQ ID NO: 32) | Deamidation | 0.7 |

In certain embodiments, the population of anti-CD20 antibody proteins comprises two or more secondary structures as determined by circular dichroism at 205 nm to 260 nm as follows:
(a) about 9.0% α-helix;
(b) about 33.0% Anti-parallel β-sheet;

In certain embodiments, the population of anti-CD20 antibody proteins two, three, four, five or more of the post translational modifications.

In certain embodiments, the population of anti-CD20 antibody proteins comprises the following post-translational modification at the specified abundance:

| Site | Position [in bold and underlined] | Modification | Abundance |
|---|---|---|---|
| HC (39-63) | QTPRQGLEWIGGIYPGNGDTSYNQK (SEQ ID NO: 19) | Deamidation | 4.5 |

In certain embodiments, the population of anti-CD20 antibody proteins comprises the following post-translational modification at the specified abundance:

| Site | Position [in bold and underlined] | Modification | Abundance |
|---|---|---|---|
| LC (19-38) | VTMTCRASSSVSYMHWYQQK (SEQ ID NO: 30) | Oxidation | 1.3 |

In certain embodiments, one or more of the post-translational modifications are measured by peptide mapping using liquid chromatography-mass spectrometry (LC-MS).

In certain embodiments, the deamidation is measured by isoaspartate detection or peptide mapping using LC-MS.

In another aspect, provided herein is a composition comprising a population of anti-CD20 antibody proteins provided herein, wherein the anti-CD20 antibody in said population is expressed from one or more nucleic acid sequences encoding a heavy chain ("HC") comprising the amino acid sequence of SEQ ID NO:1 and a light chain ("LC") comprising the amino acid sequence of SEQ ID NO:2, wherein the population of anti-CD20 antibody proteins has the following properties:

| Property | Range |
|---|---|
| Total Protein ($A_{280}$) | 22.5 to 27.5 mg/mL |
| ADCC potency assay | 50 to 180% |
| CDC activity by cell-based bioassay | 55 to 142% |
| CD20 binding activity by cell-based bioassay | 70 to 143% |
| FcγRIIIa-158V binding by surface plasmon resonance | 65 to 145% |
| C1q binding by ELISA | 70 to 125% |
| CD16 Activity | 71 to 150% |

In certain embodiments, the population has an amount of total protein of 25.5-25.8 mg/mL as measured by absorbance at 280 nm. In certain embodiments, the population has an amount of total protein of about 25.6 mg/mL as measured by absorbance at 280 nm.

In certain embodiments, the population induces greater cytotoxicity in a cell-based antibody-dependent cellular cytotoxicity (ADCC) assay compared to obinutuzumab, ofatumumab, rituximab, veltuzumab, ibritumomab tiuxetan and/or ocrelizumab. In certain embodiments, the population has a relative potency of 90 to 163% in a cell-based ADCC assay compared to a commercial reference standard. In certain embodiments, the population has a relative potency of about 117% in a cell-based ADCC assay compared to a commercial reference standard. In certain embodiments, the cell-based ADCC assay uses effector cells selected from CD16 effector cells and primary NK cells. In certain embodiments, the population performs in a cell-based ADCC using CD16 effector cells at more than 100% of that of a commercial reference standard.

In certain embodiments, the population exhibits greater B cell depletion activity in a human whole blood B cell depletion assay compared to obinutuzumab, ofatumumab, rituximab, veltuzumab, ibritumomab tiuxetan and/or ocrelizumab.

In certain embodiments, the population has a relative potency of 78% to 116%, 73% to 128%, or 74% to 127% in a cell-based complement dependent cytotoxicity (CDC) assay compared to that of a commercial reference standard.

In certain embodiments, the population has a relative potency of about 91% in a cell-based CDC assay compared to that of a commercial reference standard.

In certain embodiments, the population has a relative potency of 92 to 118% or 82 to 138% in a cell-based CD20 binding activity bioassay compared to that of a commercial reference standard. In certain embodiments, the population has a relative potency of about 109% in a cell-based CD20 binding activity bioassay compared to that of a commercial reference standard.

In certain embodiments, the population has a KD value 30 to 70 nM in an FcγRIIIa-158V binding assay as measured by surface plasmon resonance. In certain embodiments, the population has a KD value about 59 nM in an FcγRIIIa-158V binding assay as measured by surface plasmon resonance. In certain embodiments, the population has a KD value 500 to 1000 nM in an FcγRIIIa 158F binding assay as measured by surface plasmon resonance. In certain embodiments, the population has a KD value 760 nM in an FcγRIIIa 158F binding assay as measured by surface plasmon resonance. In certain embodiments, the population has significantly higher binding affinity to FcγRIIIa 158V or FcγRIIIa 158F than rituximab.

In certain embodiments, the population has a relative potency of 88 to 113%, 86 to 116%, or 86 to 117% in a C1q binding assay as measured by ELISA compared to a commercial reference standard. In certain embodiments, the population has a relative potency of about 99% in a C1q binding assay as measured by ELISA compared to a commercial reference standard.

In certain embodiments, the population has a relative potency of 106 to 126% in a CD16 activity assay compared to a commercial reference standard. In certain embodiments, the population has a relative potency of about 115% in a CD16 activity assay compared to a commercial reference standard.

In certain embodiments, the population of anti-CD20 antibody proteins has a purification profile as follows:

| Assay | Range |
|---|---|
| Size Exclusion Chromatography (SEC) | Monomer: ≥95.0%, ≥97.6%, ≥97.1%, or ≥96.7%<br>Dimers: ≤4.0%, ≤2.0%, ≤2.7%, or ≤3.1%<br>Aggregates + Fragments: ≤1.6% |
| Capillary Gel Electrophoresis (Non-Reduced) | ≥85.0%, ≥91.0% or ≥95.6% IgG<br>≤3.0%, ≤0.7%, or ≤1.3% HMWS<br>≤3.0% or ≤2.0% Light Chain (LC) |
| Capillary Gel Electrophoresis (Reduced) | ≥94.0%, ≥97.1%, or ≥95.6% HC + LC |

In certain embodiments, the population has 99.2 to 99.9% monomers as detected by size exclusion chromatography (SEC). In certain embodiments, the population has 0.1 to 0.8% dimers as detected by SEC. In certain embodiments, the population has undetectable level of aggregates as detected by SEC. In certain embodiments, the population has undetectable level of fragments as detected by SEC.

In certain embodiments, the population has 93.6 to 95.9% IgG after purification by non-reduced capillary gel electrophoresis (CGE). In certain embodiments, the population has 0.1 to 0.3% high molecular weight species (HMWS) after purification by non-reduced CGE. In certain embodiments, the population has 0.7 to 1.2% free light chain (LC) after purification by non-reduced CGE. In certain embodiments, the population has 97.7 to 98.0% heavy chain plus light chain species (HC+LC) after purification by reduced CGE.

In certain embodiments, the population of anti-CD20 antibody proteins has a distribution of charged isoforms as follows:

| Assay | Range |
|---|---|
| Imaged Capillary Isoelectric Focusing (iCIEF) | Acidic Peaks: ≤32%, ≤26%, ≤30%, or ≤31% <br> Main Peak: ≥40%, ≥49%, or ≥46% <br> Basic Peaks: ≤40% or ≤34% |

In certain embodiments, the population has 20 to 25% acidic isoforms as detected by imaged capillary isoelectric focusing (iCIEF). In certain embodiments, the population has 50 to 60% main isoforms as detected by iCIEF. In certain embodiments, the population has 20 to 30% basic isoforms as detected by iCIEF.

In certain embodiments, the population has an average molar ratio of free thiol to anti-CD20 antibody of about 2.0 to 2.2.

In certain embodiments, the amino acid sequence of the anti-CD20 antibody in said population comprises a deletion of the N-terminal residue. In certain embodiments, the amino acid sequence of the anti-CD20 antibody in said population comprises a deletion of up to 5 N-terminal residues. In certain embodiments, the amino acid sequence of the anti-CD20 antibody in said population comprises a deletion of up to 10 N-terminal residues.

In certain embodiments, the terminal lysine amino acid residue of the heavy chain in the anti-CD20 antibody in said population is truncated.

In certain embodiments, the administration of the anti-CD20 antibody to a human patient results in one or more of the following pharmacokinetic parameters:
(a) an AUC between 2,160 µg/mL and 3,840 µg/mL;
(b) a Cmax between 118,011 ng/mL and 159,989 ng/mL;
(c) a Cmin between 40 ng/mL and 375 ng/mL; and
(d) a Cavg is between 6,437 ng/mL and 11,443 ng/mL, and
wherein the anti-CD20 antibody is administered as i) a first infusion at a dose of about 150 mg, ii) a second infusion two weeks later at a dose of about 450 mg, and iii) subsequent infusions every six months at a dose of about 450 mg.

In certain embodiments, the administration of the anti-CD20 antibody to a human patient results in one or more of the following pharmacokinetic parameters:
(a) an AUC about 3,000 µg/mL;
(b) a Cmax about 139,000 ng/mL;
(c) a Cmin about 139 ng/mL; and
(d) a Cavg about 8,940 ng/mL.

In certain embodiments, the antibody proteins of the population are present in a single dosage form.

Also provided herein are pharmaceutical formulations comprising the composition provide herein. In one aspect, provided herein is a pharmaceutical formulation comprising the composition provide herein, wherein the anti-CD20 antibody is present in the pharmaceutical formulation at a concentration of about 25 mg/mL.

In one aspect, provided herein is a pharmaceutical formulation comprising an anti-CD20 antibody provided herein, wherein the anti-CD20 antibody comprises a heavy chain comprising the amino acid sequence of SEQ ID NO:1 and a light chain comprising the amino acid sequence of SEQ ID NO:2, wherein the pharmaceutical formulation comprises one or more of the following: sodium chloride, trisodium citrate dehydrate, polysorbate 80, and hydrochloric acid.

In certain embodiments, the pharmaceutical formulation comprises about 9.0 mg/mL of sodium chloride. In certain embodiments, the pharmaceutical formulation comprises about 7.4 mg/mL of trisodium citrate dehydrate. In certain embodiments, the pharmaceutical formulation comprises about 0.7 mg/mL of polysorbate 80. In certain embodiments, the pharmaceutical formulation comprises about 0.4 mg/mL of hydrochloric acid.

Also provided herein are single batch preparations of a population of anti-CD20 antibody proteins provided herein. In one aspect, provided herein is a single batch preparation of a population of anti-CD20 antibody proteins provided herein, wherein the anti-CD20 antibody comprises a heavy chain comprising the amino acid sequence of SEQ ID NO:1 and a light chain comprising the amino acid sequence of SEQ ID NO:2, wherein the single batch comprises at least 100 g of the anti-CD20 antibody proteins.

In one aspect, provided herein is a single batch preparation of a population of anti-CD20 antibody proteins provided herein, wherein the anti-CD20 antibody comprises a heavy chain comprising the amino acid sequence of SEQ ID NO:1 and a light chain comprising the amino acid sequence of SEQ ID NO:2, wherein the single batch comprises at least 120 g of the anti-CD20 antibody proteins.

In one aspect, provided herein is a single batch preparation of a population of anti-CD20 antibody proteins provided herein, wherein the anti-CD20 antibody comprises a heavy chain comprising the amino acid sequence of SEQ ID NO:1 and a light chain comprising the amino acid sequence of SEQ ID NO:2, wherein the single batch comprises at least 150 g of the anti-CD20 antibody proteins.

Also provided herein is a population of anti-CD20 antibody proteins as provided herein, wherein the population of anti-CD20 antibody proteins is produced in a 15,000 L or 20,000 L bioreactor.

Also provided herein are methods of treating an autoimmune disease. In one aspect, provided herein is a method of treating an autoimmune disease, wherein the method comprises administering the composition provided herein to a subject in need thereof, and wherein the autoimmune disease is selected from the group consisting of psoriasis, rheumatoid arthritis, vasculitis, inflammatory bowel disease, dermatitis, osteoarthritis, inflammatory muscle disease, allergic rhinitis, vaginitis, interstitial cystitis, scleroderma, osteoporosis, eczema, allogenic or xenogenic transplantation, graft rejection, graft-versus-host disease, lupus erythematosus, inflammatory disease, type 1 diabetes, pulmonary fibrosis, dermatomyositis, Sjogren's syndrome, thyroiditis, myasthenia gravis, autoimmune hemolytic anemia, cystic fibrosis, chronic relapsing hepatitis, primary biliary cirrhosis, allergic conjunctivitis, atopic dermatitis, chronic obstructive pulmonary disease, glomerulonephritis, neuroinflammatory diseases, Addison disease, celiac disease, Graves disease, pernicious anemia, Guillain-Barre, Crohn's disease, vitiligo reactive arthritis, and uveitis.

Also provided herein are methods of treating multiple sclerosis. In one aspect, provided herein is a method of treating multiple sclerosis, wherein the method comprises administering the composition provided herein to a subject in need thereof.

In certain embodiments, the multiple sclerosis (MS) is a relapsing form of MS. In certain embodiments, the relapsing form of MS is selected from clinically isolated syndrome (CIS), relapsing-remitting MS (RRMS) and active secondary progressive MS (SPMS). In certain embodiments, the relapsing form of MS is a clinically isolated syndrome (CIS). In certain embodiments, the relapsing form of MS is relapse-remitting multiple sclerosis (RRMS). In certain embodiments, the relapsing form of MS is active secondary progressive multiple sclerosis (SPMS).

Also provided herein are methods of treating a neoplastic disease. In one aspect, provided herein is a method of treating a neoplastic disease, wherein the method comprises administering the composition provided herein to a subject in need thereof.

In certain embodiments, the neoplastic disease is acute B lymphoblastic leukaemia, B-cell lymphoma, mature B-cell lymphoma, including B-type Chronic Lymphocytic Leukaemia (B-CLL), small B-cell lymphoma, B-cell prolymphocytic leukaemia, lymphoplasmocytic lymphoma, mantle cell lymphoma, follicular lymphoma, marginal zone MALT-type lymphoma, lymph node marginal zone lymphoma with or without monocytoid B cells, splenic marginal zone lymphoma (with or without villous lymphocytes), tricholeucocytic leukaemia, diffuse large B-cell lymphoma, or Burkitt's lymphoma.

In certain embodiments, the subject is a human.

Also provided herein are methods for inactivating a virus or adventitious agents in rat myeloma cells expressing the anti-CD20 antibody proteins provided herein. In one aspect, provided herein is a method for inactivating a virus or adventitious agents in rat myeloma cells expressing the anti-CD20 antibody proteins in the composition provided herein, wherein the method maintains suitability for antibody production in a 15,000 L or 20,000 L bioreactor.

Also provided herein are methods of reducing immunogenicity of the anti-CD20 antibody proteins in the composition provided herein. In one aspect, provided herein is a method of reducing immunogenicity of the anti-CD20 antibody proteins in the composition provided herein, wherein the method maintains suitability for antibody production in a 15,000 L or 20,000 L bioreactor.

Also provided herein are methods of analyzing an TG-1101 (TG Therapeutics, Inc.) preparation. In one aspect, provided herein is a method of analyzing an TG-1101 (TG Therapeutics, Inc.) preparation, comprising:
(i) providing an isolated N-glycan fraction from the TG-1101 (TG Therapeutics, Inc.) preparation;
(ii) analyzing the N-glycan fraction to determine if one or more N-glycans are the following N-glycans within the following relative abundance range:
(a) 0.3% to 2% G0-GN;
(b) 0.1% to 2% G0F-GN;
(c) 0.1% to 1% G1-GN;
(d) 5% to 20% G0B;
(e) 5% to 30% G0F;
(f) 0.1% to 1.5% Man5;
(g) 1% to 15% G0FB;
(h) 1% to 13% G1;
(i) 0.5% to 10% G1';
(j) 0.5% to 6% G1B;
(k) 0.5% to 12% G1F;
(l) 0.1% to 3% G1F';
(m) 0.1% to 3% G1FB;
(n) 0.1% to 2% G2; and
(o) 0.1% to 2% G2F; and In certain embodiments, the method comprises analyzing the N-glycan fraction to determine if one or more N-glycans are the following N-glycans within the following relative abundance range:
(a) 0.8% to 1.1% G0-GN;
(b) 0.5% to 1.1% G0F-GN;
(c) 0.3% to 0.6% G1-GN;
(d) 9.5% to 14.1% G0B;
(e) 12.8% to 19.7% G0F;
(f) 0.4% to 0.7% Man5;
(g) 5.1% to 7.0% G0FB;
(h) 5.7% to 6.4% G1;
(i) 2.7% to 3.3% G1';
(j) 1.4% to 2.0% G1B;
(k) 2.6% to 4.2% G1F;
(l) 1.1% to 1.6% G1F';
(m) 1.1% to 1.8% G1FB;
(n) 0.5% to 0.7% G2; and
(o) 0.3% to 0.5% G2F.

In certain embodiments, the method comprises analyzing the N-glycan fraction to determine if one or more N-glycans are in the following relative abundance:
(a) 0.9% G0-GN;
(b) 0.8% G0F-GN;
(c) 0.5% G1-GN;
(d) 10.9% G0B;
(e) 17.0% G0F;
(f) 0.6% Man5;
(g) 6.0% G0FB;
(h) 6.1% G1;
(i) 2.9% G1';
(j) 1.6% G1B;
(k) 3.2% G1F;
(l) 1.3% G1F';
(m) 1.3% G1FB;
(n) 0.5% G2; and
(o) 0.3% G2F.

In another aspect, provided herein is a composition comprising a population of anti-CD20 antibody proteins, wherein the anti-CD20 antibody in said population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins further comprises at least two N-glycans in the following relative abundance:
(a) 0.9% G0-GN;
(b) 0.8% G0F-GN;
(c) 0.5% G1-GN;
(d) 10.9% G0B;
(e) 17.0% G0F;
(f) 0.6% Man5;
(g) 6.0% G0FB;
(h) 6.1% G1;
(i) 2.9% G1';
(j) 1.6% G1B;
(k) 3.2% G1F;
(l) 1.3% G1F';
(m) 1.3% G1FB;
(n) 0.5% G2; and
(o) 0.3% G2F, and
wherein the population of anti-CD20 antibody proteins is made in a rat hybridoma cell.

In certain embodiments, the rat hybridoma cell is YB2/0 cell.

5. BRIEF DESCRIPTION OF THE DRAWINGS

Figure 11A:
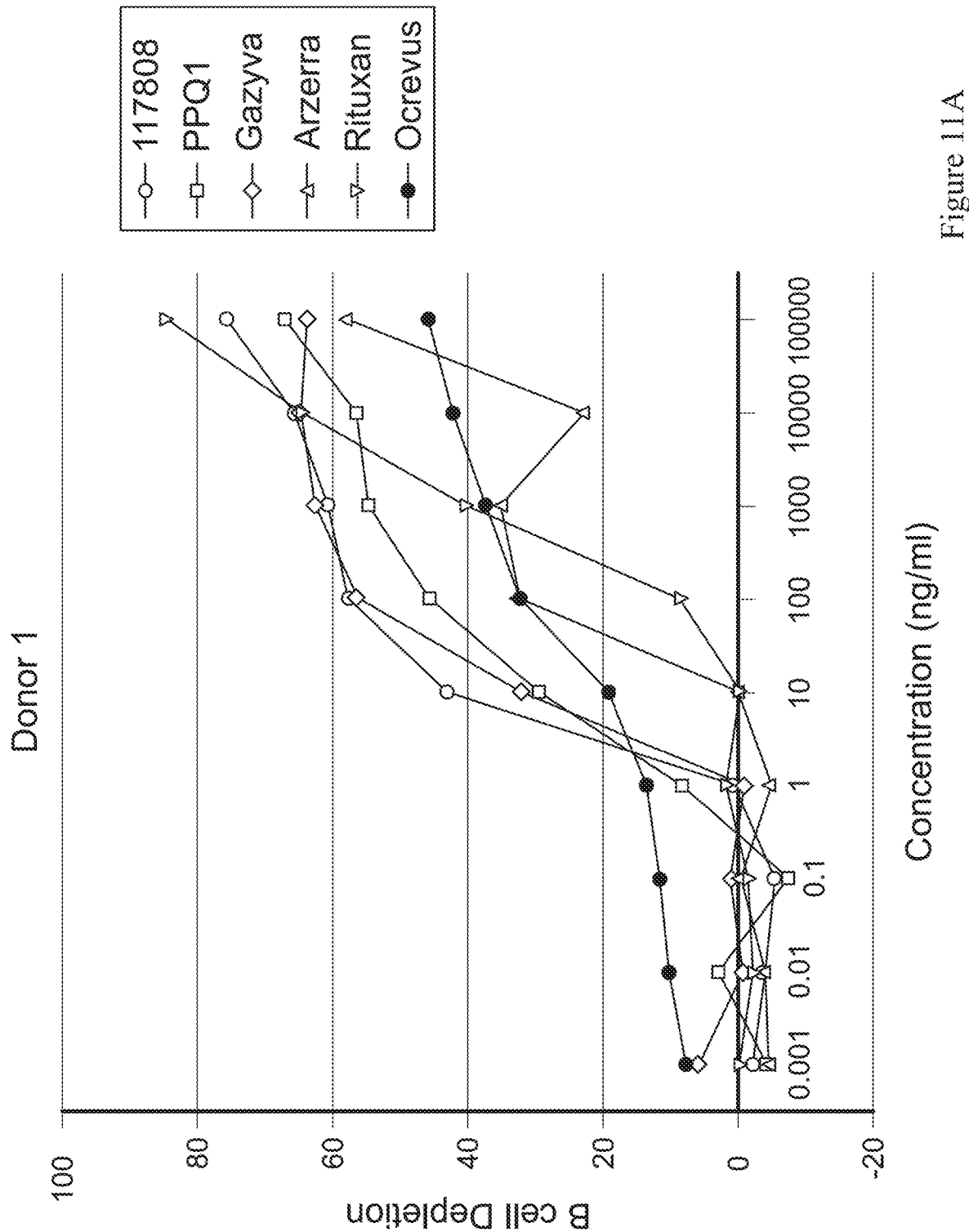
Figure 11B:
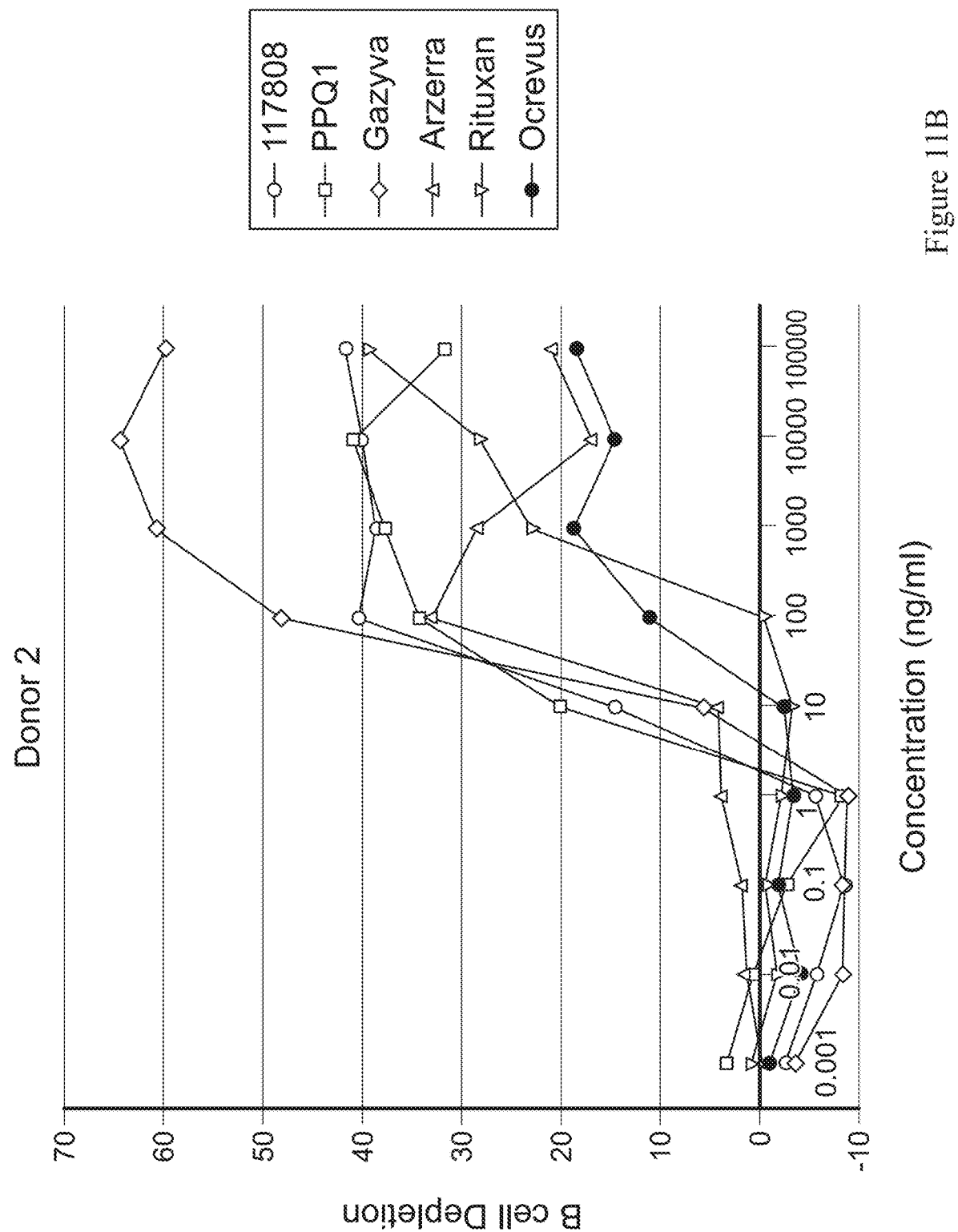
Figure 11C:
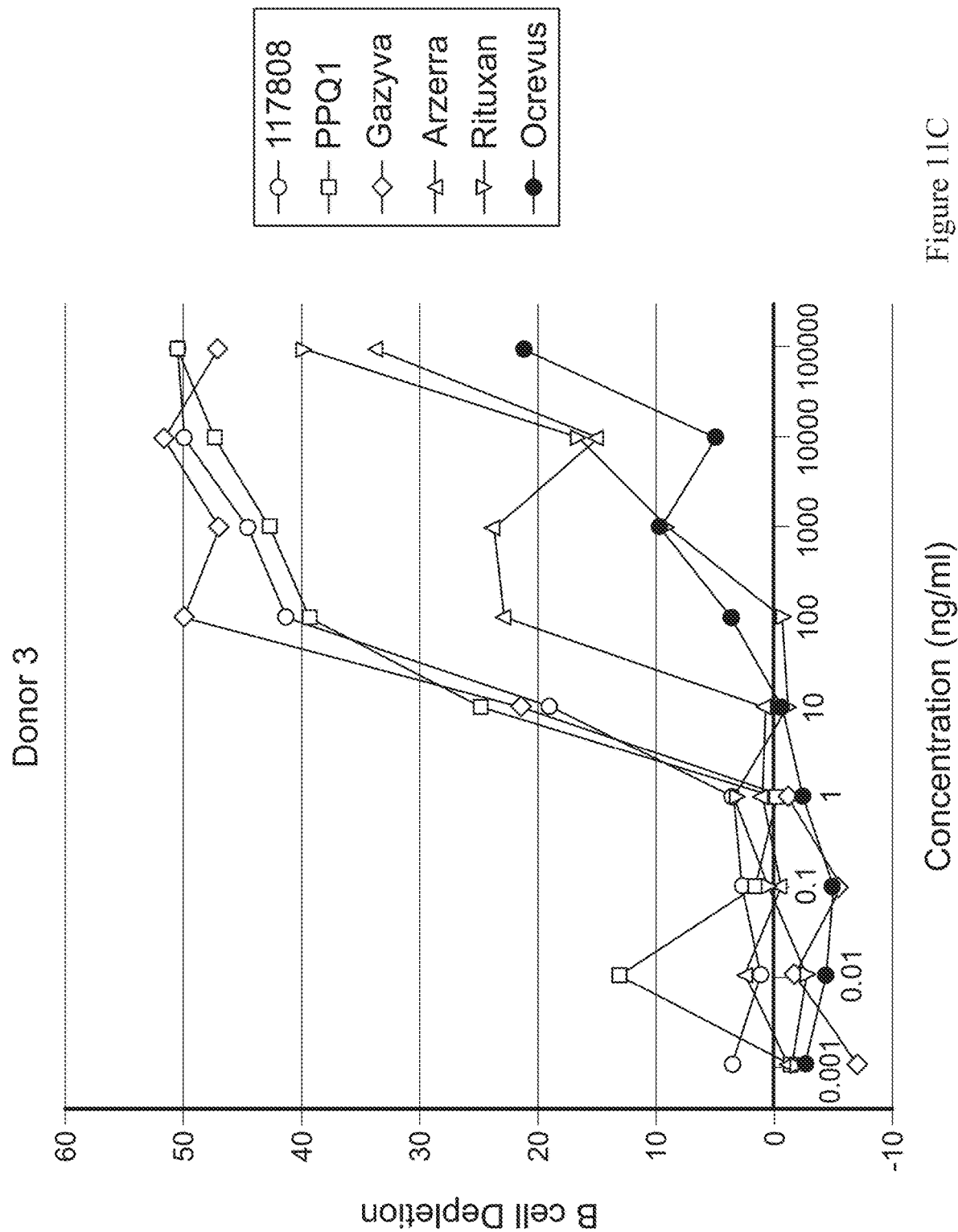

FIGS. 11A-C illustrate human whole blood B cell depletion from three donors. B cell depletion calculated based on data using CD19 as B cell marker.

Figure 12:
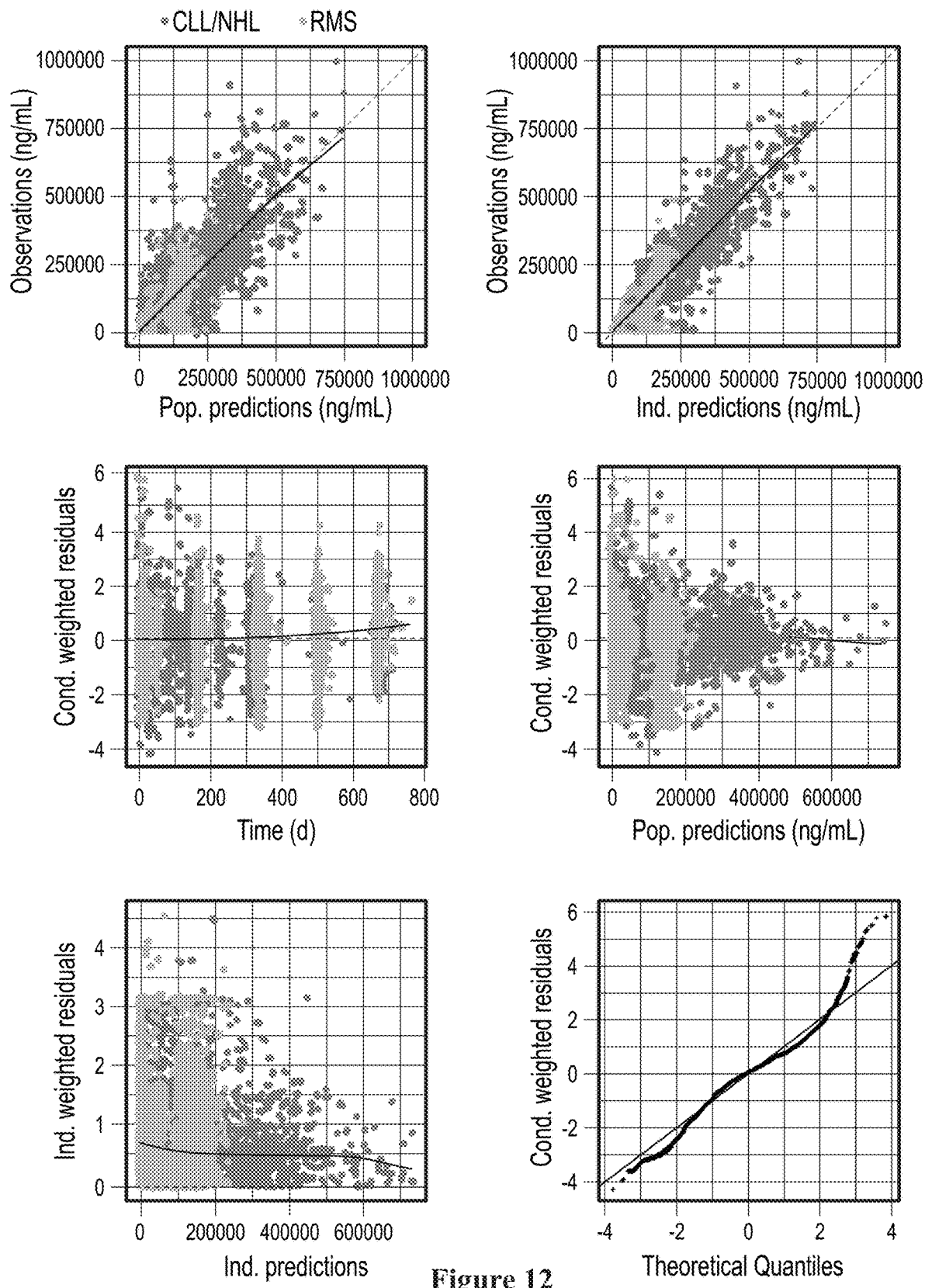

FIG. 12 illustrates the Goodness-of-Fit (G0F) diagnostics of the TG-1101 final model.

Figure 13:
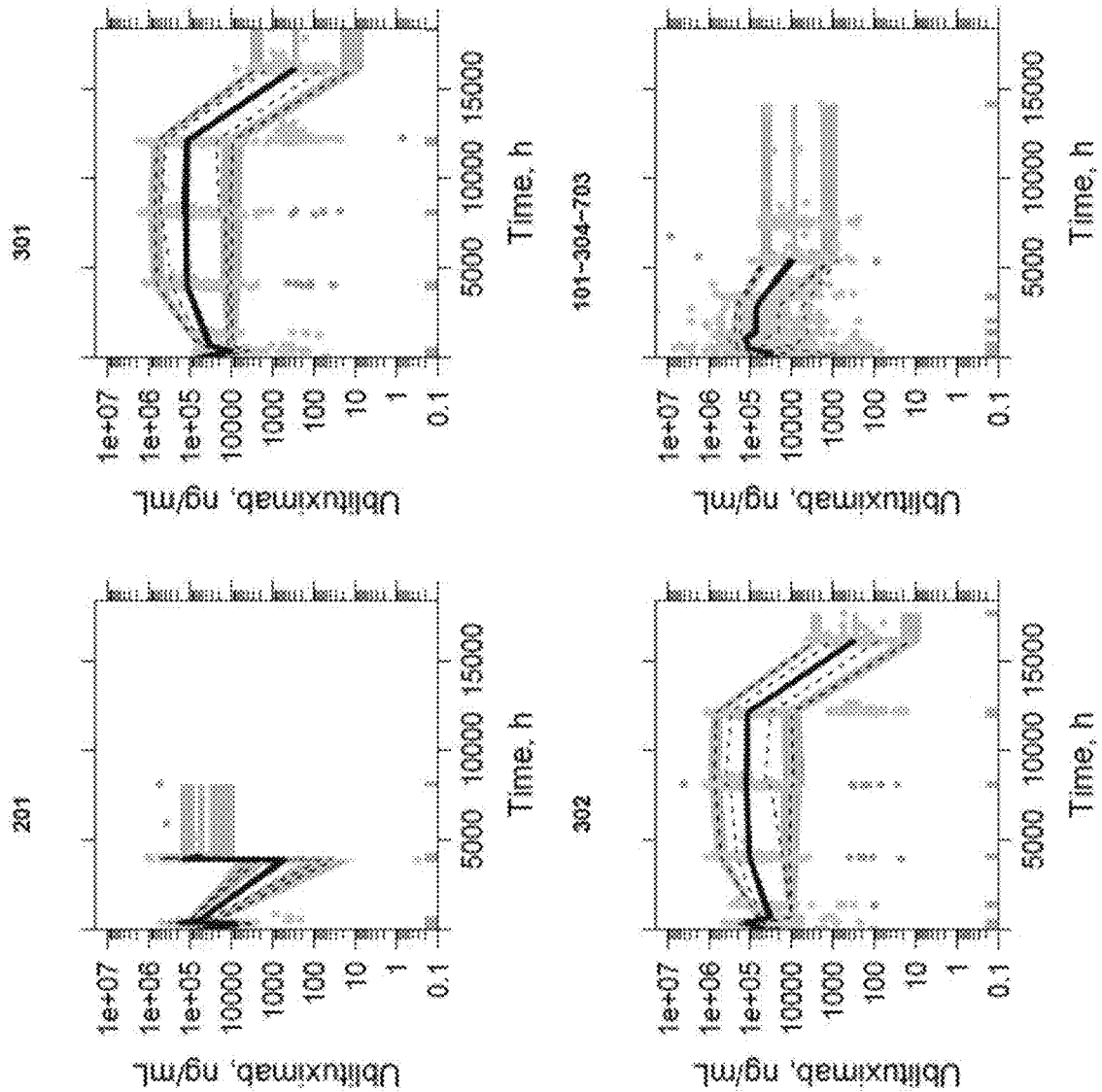

FIG. 13 illustrates the pcVPC for the TG-1101 final PK model by study. The blue dots are prediction-corrected observed concentrations; the blue lines are the 50th (solid), 5th (dashed), and 95th (dashed) percentiles of observed concentrations; and the black lines are the (solid), 5th (dashed), and 95th (dashed) percentiles of simulations. The gray bands are the 95% PIs for the corresponding black lines based on 500 simulations. The short yellow lines indicate bin intervals. The numbers 201,301,302 and 101-304-703 represent the study numbers, TG1101-RMS201, TG1101-RMS301 and TG1101-RMS302 and the studies in the previous analysis set in subjects with hematologic malignancies, respectively. Abbreviations: pcVPC—prediction-corrected visual predictive check; PI—prediction interval; pred-corr—prediction-corrected; popPK—population pharmacokinetic(s).

Figure 14:
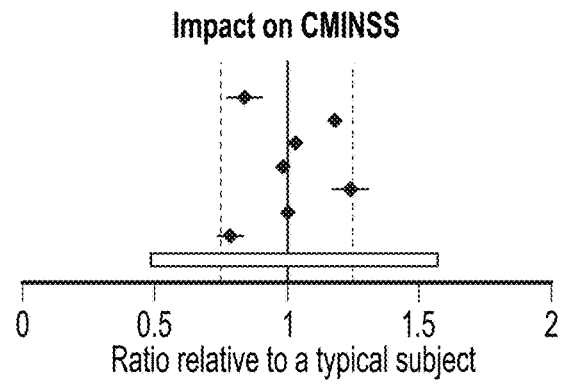
Figure 14:
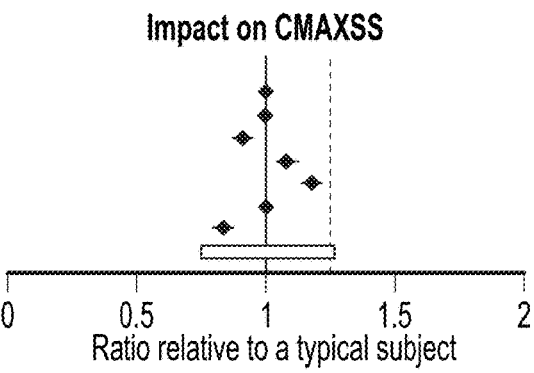
Figure 14:
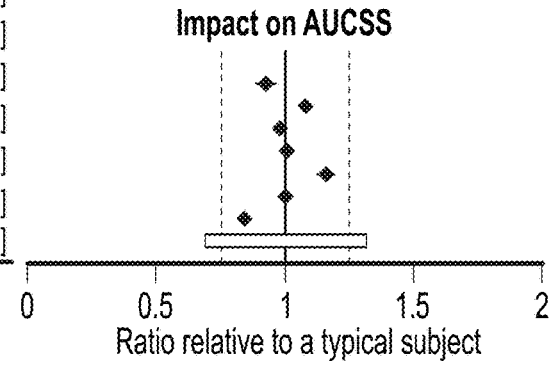

FIG. 14 illustrates the forest plot of covariate effects on TG-1101 drug exposure. The first and second dashed vertical lines correspond to ratios of 0.8 and 1.25, respectively. The solid vertical line corresponds to a ratio of 1 and represents a typical subject. Points and whiskers represent the estimate and 90% confidence interval, respectively. The blue-gray horizontal bar shows the range of exposures due to between-subject variability. A typical subject is defined as a male subject from North America/Western Europe with a body weight of 73 kg, is ADA negative and has been on treatment for <416 days. Abbreviations: ADA—antidrug antibody; AUCss—area under the serum TG-1101 concentration-time curve at steady state; BSV—between-subject or inter-individual variability; CI—confidence interval; CMAXSS—maximum TG-1101 concentration at steady state; CMINSS—minimum TG-1101 concentration at steady state; N/A—not applicable.

Figure 15:
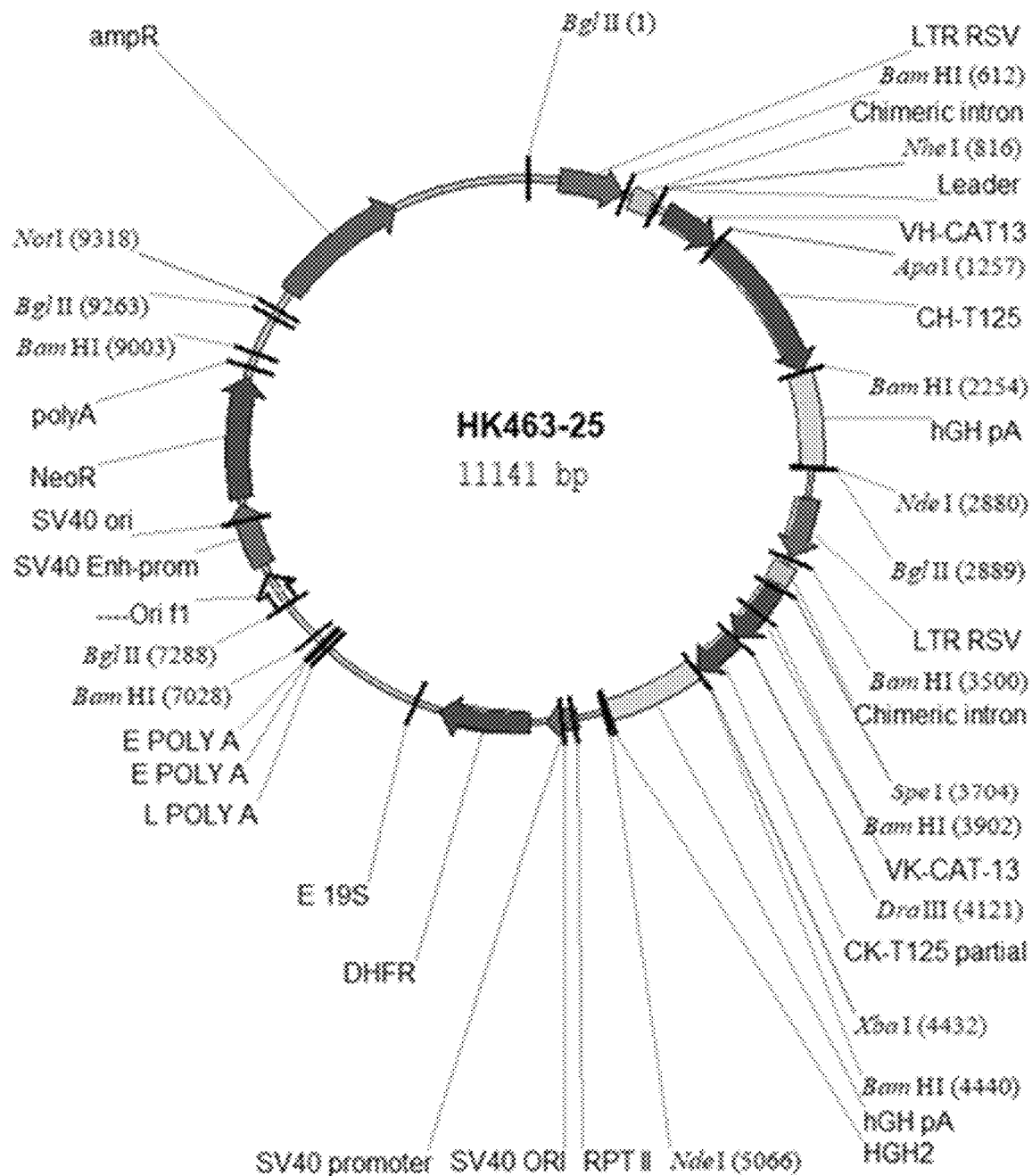

FIG. 15 depicts the map of expression vector, HK463-25, containing the immunoglobulin heavy and light chain cDNA sequences of source anti-CD20 antibody, TG-1101, described herein.

6. DETAILED DESCRIPTION OF THE DISCLOSURE

Provided herein are populations of anti-CD20 antibody proteins with specified ranges of post-translational modifications. The primary amino acid sequences of such antibodies are provided in Section 6.3. Types of such post-translational modifications and their respective abundance in the anti-CD20 antibody populations are described in Section 6.4. Compositions, including single-batch compositions, of such populations of anti-CD20 antibody proteins with specified ranges of post-translational modifications and ranges of purity are described in Section 6.5(e). Assays for quantifying such post-translational modifications in a population of anti-CD20 antibody proteins are described in Section 6.5. Assays for analyzing populations of anti-CD20 antibody proteins are described in Section 6.5. Assays for demonstrating the biological and clinical significance of such post-translational modifications in a population of anti-CD20 antibody proteins are described in Section 6.7(a). Methods of using such populations of anti-CD20 antibody proteins for the treatment and prevention of medical conditions are described in Section 6.8. Pharmacokinetic and pharmacodynamic properties of the compositions provided herein in human patients are described in Section 6.9. Methods of making such populations of anti-CD20 antibody proteins are described in Section 6.10.

As used herein, "TG-1101" (TG Therapeutics, Inc.) (also known as ublituximab, UBX, UTX, TG-1101, TGTX-1101, UTUXIN™, LFB-R603, TG20, EMAB603) is the source antibody for the anti-CD20 antibody described herein having a unique glycosylation profile that is produced by the disclosed methods.

The source antibody, TG-1101, is a monoclonal antibody that targets epitopes on CD20, e.g., IRAHT (SEQ ID NO: 37), and EPAN (SEQ ID NO: 38). See, Fox, E. et al., *Mult. Scler.* 27:420-429 (March 2021); Babiker et al., *Expert Opin Investig Drugs* 27:407-412 (2018); Cotchett, K R et al., *Multiple Sclerosis and Related Disorders* 49:102787 (2021); Miller et al., *Blood* 120:Abstract No. 2756 (2012); Deng, C. et. al., *J. Clin. Oncol.* 31:Abstract No. 8575 (2013). TG-1101 is also described in U.S. Pat. Nos. 9,234,045 and 9,873,745.

6.1 Abbreviations and Conventions

The following abbreviations are used throughout this application.

| Abbreviation/symbol | Meaning |
| --- | --- |
| ADCC | antibody-dependent cellular cytotoxicity |
| ADCP | antibody-dependent cellular phagocytosis |
| ARR | annualized relapse rate |
| AUC | area under the curve |
| CIS | clinically isolated syndrome |
| CDC | complement dependent cytotoxicity |
| CLL | chronic lymphocytic leukemia |
| CIDP | chronic inflammatory demyelinating polyneuropathy |
| DDT | Dithiothreitol |
| EDSS | Expanded Disability Status Scale |
| GlcNAC | N-Acetylglucosamine |
| HbsAg | hepatitis B virus surface antigen |
| HBV | hepatitis B virus |
| Open square | N-Acetylglucosamine |
| Man | Mannose |
| Filled, black circle | Mannose |
| Ga | Galactose |

Figure 1:
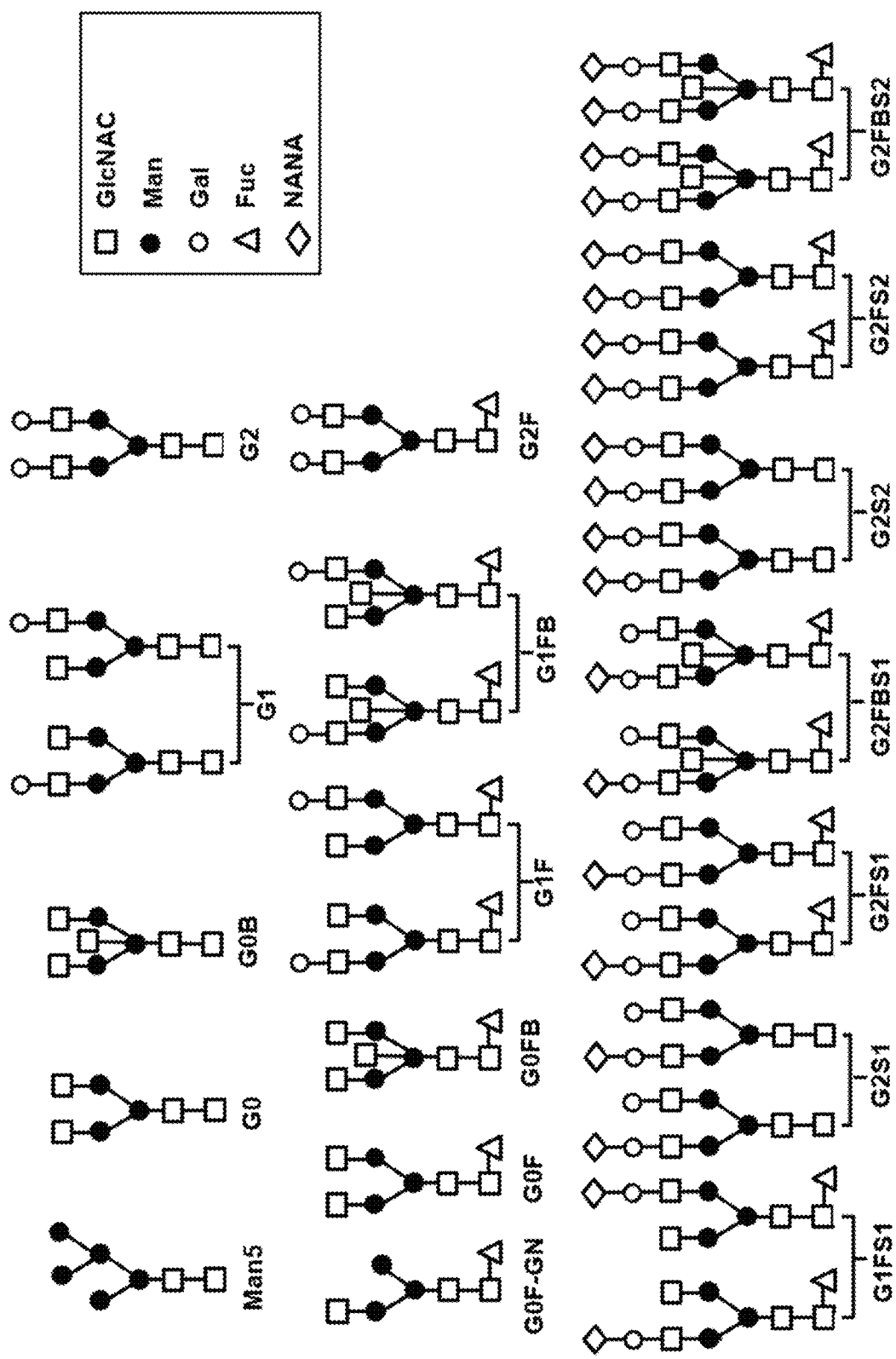
FIG. 1 illustrates the structure and abbreviations for various N-glycans.

| Abbreviation/symbol | Meaning |
|---|---|
| Open circle | Galactose |
| Open triangle | Fucose |
| Fuc | Fucose |
| Open diamond | N-Acetylneuraminic acid |
| NANA or Neu5Ac | N-Acetylneuraminic acid |
| Man5 | See structure in FIG. 1 |
| G0 | See structure in FIG. 1 |
| G0B | See structure in FIG. 1 |
| G1 | See structure in FIG. 1 |
| G2 | See structure in FIG. 1 |
| G0F-GN | See structure in FIG. 1 |
| G0F | See structure in FIG. 1 |
| G0FB | See structure in FIG. 1 |
| G1F | See structure in FIG. 1 |
| G1FB | See structure in FIG. 1 |
| G2F | See structure in FIG. 1 |
| G1FS1 | See structure in FIG. 1 |
| G2S1 | See structure in FIG. 1 |
| G2FS1 | See structure in FIG. 1 |
| G2FBS1 | See structure in FIG. 1 |
| G2S2 | See structure in FIG. 1 |
| G2FS2 | See structure in FIG. 1 |
| G2FBS2 | See structure in FIG. 1 |
| GPA | granulomatosis with Pollyangiitis |
| GVHD | Graft Versus Host Disease |
| HC | heavy chain |
| HILIC | hydrophilic interaction liquid chromatography |
| iCIEF | Imaged Capillary Isoelectric Focusing |
| IRAP | Independent Relapse Adjudication Panel |
| $K_D$ | equilibrium dissociation constants |
| LC | light chain |
| LC-MS | liquid chromatography-coupled mass spectrometer |
| MAG | Myelin Associated Glycoprotein |
| MCNS | Minimal Change Nephrotic Syndrome |
| MG | Myasthenia Gravis |
| MOA | mechanism of action |
| MPA | Microscopic Polyangiitis |
| MS | multiple sclerosis |
| MZL | marginal zone lymphoma |
| NHL | non-Hodgkin's lymphoma |
| PCNSL | primary central nervous system lymphoma |
| PPMS | primary progressive multiple sclerosis |
| RA | Rheumatoid Arthritis |
| RMS | relapsing form of multiple sclerosis |
| RRMS | relapsing-remitting multiple sclerosis |
| SDS | sodium dodecyl sulfate |
| SLL | small lymphocytic lymphoma |
| SPMS | secondary progressive multiple sclerosis |
| TPA | tripropylamine |
| TTP | Thrombotic Thrombocytopeniarpura |
| WM | Waldenstrom's macroglobulinemia |

6.2 Definitions

As used herein, the term "population of anti-CD20 antibody proteins" refers to a composition of anti-CD20 antibody proteins that is being tested for the abundance of post-translational modifications. The individual anti-CD20 antibody proteins in a population can comprise similar or different post-translational modifications. In a specific embodiment, a population of anti-CD20 antibody proteins refers to all anti-CD20 antibody proteins that are present in a single dosage form. In another specific embodiment, a population of anti-CD20 antibody proteins refers to all anti-CD20 antibody proteins that are present in a single batch. In another specific embodiment, a population of anti-CD20 antibody proteins is an amount sufficient to determine whether the batch of anti-CD20 antibody proteins, when compared to a reference standard, meets or fails a predetermined acceptable range of comparison value or values.

As used herein, the term "single batch" in the context of anti-CD20 antibody proteins refers to a composition derived from a single production or run from a single bioreactor of a specified volume. For example, the anti-CD20 antibody proteins obtained from a single run of a bioreactor can be referred to as a single batch. In certain embodiments, the bioreactor has a capacity of at least 100; 200; 300; 400; 500; 750; 1,000; 2,000; 3,000; 4,000; 5,000; 7,500; 15,000; 20,000; or at least 25,000 L.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1 or 2 standard deviations. In certain embodiments, the term "about" or "approximately" means within 10%, 9%, 8%, 7%, 6%, 5%, 4%, 3%, 2%, 1%, 0.5%, or 0.05% of a given value or range.

6.3 Primary Amino Acid Sequence of the Anti-CD20 Antibody

In some aspects, the anti-CD20 antibody proteins provided herein are expressed from one or more nucleic acid sequences encoding a heavy chain comprising the amino acid sequence of SEQ ID NO:1 and a light chain comprising the amino acid sequence of SEQ ID NO:2. Sequences are provided below in the Sequence Table.

In some aspects, the anti-CD20 antibody proteins provided herein are expressed from one or more nucleic acid sequences encoding a heavy chain comprising the amino acid sequence of SEQ ID NO:1 or an amino acid that is at least 90%, 91%, 92%, 93%, 94%, 95%, 96%, 97%, 98%, or at least 99% identical to SEQ ID NO:1; and a light chain comprising the amino acid sequence of SEQ ID NO:2 or an amino acid that is at least 90%, 91%, 92%, 93%, 94%, 95%, 96%, 97%, 98%, or at least 99% identical to SEQ ID NO:2.

In some aspects, the anti-CD20 antibody proteins provided herein comprises the VH CDR1, CDR2, and CDR3 region of sequences SEQ ID NOs: 3, 4, and 5, and the VL CDR1, CDR2, and CDR3 region of sequences SEQ ID NOs: 8, 9, and 10.

In some aspects, the anti-CD20 antibody proteins provided herein comprises the VH of SEQ ID NO:6 and the VL of SEQ ID NO:11.

In some aspect, the nucleic acid sequence encoding the heavy chain of the anti-CD20 antibody proteins provided herein comprises the nucleic acid sequence of SEQ ID NO:35. In some aspect, the nucleic acid sequence encoding the light chain of the anti-CD20 antibody proteins provided herein comprises the nucleic acid sequence of SEQ ID NO:36.

In some aspects, the anti-CD20 antibody proteins provided herein bind to the same epitope as TG-1101 (TG Therapeutics, Inc.).

In some aspects, the anti-CD20 antibody proteins provided herein are chimeric immunoglobulin G1 (IgG1) anti-CD20 monoclonal antibody proteins, each comprised of a tetrameric assembly from two light chains (213 amino acids) and two heavy chains (448 amino acids).

In some aspects, the anti-CD20 antibody proteins provided herein are expressed from one or more nucleic acid sequences encoding a heavy chain comprising the amino acid sequence of SEQ ID NO:1 and a light chain comprising the amino acid sequence of SEQ ID NO:2 and comprise a pyroglutamate at position 1 of light chain and/or heavy chain instead of glutamine, thus resulting in an amino sequence of SEQ ID NO:13 for the heavy chain and/or an amino acid sequence of SEQ ID NO:14 for the light chain.

In some aspects, the anti-CD20 antibody proteins provided herein are expressed from one or more nucleic acid sequences encoding a heavy chain comprising the amino acid sequence of SEQ ID NO:1 and a light chain comprising the amino acid sequence of SEQ ID NO:2 and comprise a deletion of the C-terminal lysine at the heavy chain thus resulting in the amino acid sequence of SEQ ID NO:15.

In certain embodiments, provided herein is a composition or population of anti-CD20 antibody proteins wherein at least 50%, 60%, 70%, 80%, 90%, 95%, or 98% comprises (i) a pyroglutamate at position 1 (instead of glutamine) of the heavy chain, (ii) a pyroglutamate at position 1 (instead of glutamine) of the light chain, and/or (iii) a deletion of the C-terminal lysine of the heavy chain.

In some aspects, an anti-CD20 antibody is expressed from one or more nucleic acid sequences encoding a light chain comprising the amino acid sequence of SEQ ID NO:16.

6.4 Anti-CD20 Antibody Compositions

The anti-CD20 antibody compositions provided herein can be described by various post-translational modifications and/or by their three-dimensional conformation (see Section 6.5(e)). The respective levels of the various post-translational modifications can be quantified as described in Section 6.5. Without being bound by theory, these structural properties of the anti-CD20 antibody compositions provided herein result in the biological and clinical properties described below in Sections 6.7 and 6.9.

The anti-CD20 antibody compositions produced in vitro have various post-translational modifications. It is understood that each individual anti-CD20 antibody protein may have its own specific pattern of post-translational modifications. To describe the properties of a population of multiple anti-CD20 antibody proteins, the overall presence of a specific post-translational modification can be quantified. Without being bound by theory, the levels of a specific post-translational modification in a population of anti-CD20 proteins can determine the biological and clinical properties of the composition (such as a dose of a pharmaceutical formulation). Without being bound by theory, the post-translational modifications are rendered by the expression in a rat hybridoma cell (e.g., YB2/0 cell) in cell culture.

In certain embodiments, a type of post-translational modification that can be used to describe the anti-CD20 antibody compositions provided herein is glycosylation. Various glycosylations are known. In one aspect, the glycosylation is N-glycosylation. N-glycans that can be present can be any one of the N-glycans shown in FIG. 1. Levels of N-glycosylation are discussed in the Section 6.4(a) below and can be quantified using the assays in Section 6.5.

In certain embodiments, a type of post-translational modification that can be used to describe the anti-CD20 antibody compositions provided herein is deamidation. Deamidation is a chemical reaction in which an amide functional group in the side chain of the amino acid asparagine or glutamine is removed or converted to another functional group. Typically, asparagine is converted to aspartic acid or isoaspartic acid. Levels of deamidation at a specific amino acid position in the anti-CD20 antibody compositions provided herein are described in Section 6.4(b) below and can be determined as described in Section 6.5 herein.

(a) N-glycosylation

Various forms of N-glycosylation can be present in the anti-CD20 antibody compositions provided herein. Without being bound by theory, the relative distribution of the various N-glycans, or individual sugar residues present in those N-glycans, among the individual anti-CD20 antibody proteins in a population of anti-CD20 antibody proteins can determine the biological and clinical properties (such as the biological and clinical properties discussed in Sections 6.7 and 6.9) of the anti-CD20 antibody composition provided herein. The anti-CD20 antibody composition provided herein can be described by any one, two, three, four, five, six, seven, eight, nine, ten, eleven, twelve, thirteen, fourteen, fifteen, sixteen, seventeen, eighteen, nineteen, twenty or all of the N-glycans or individual sugar residues described in the following subsections.

In a specific embodiment, an anti-CD20 antibody composition provided herein comprises at least two, three, four, five, six, seven, eight, nine, ten, 11, 12, 13, 14, or 15 N-glycans within the following relative abundance range:
  (a) 0.3% to 2% G0-GN;
  (b) 0.1% to 2% G0F-GN;
  (c) 30% to 60% G0;
  (d) 0.1% to 1% G1-GN;
  (e) 5% to 20% G0B;
  (f) 5% to 30% G0F;
  (g) 0.1% to 1.5% Man5;
  (h) 1% to 15% G0FB;
  (i) 1% to 13% G1;
  (j) 0.5% to 10% G1';
  (k) 0.5% to 6% G1B;
  (l) 0.5% to 12% G1F;
  (m) 0.1% to 3% G1F';
  (n) 0.1% to 3% G1FB;
  (o) 0.1% to 2% G2; and
  (p) 0.1% to 2% G2F.

In a more specific embodiment, an anti-CD20 antibody composition provided herein comprises at least two, three, four, five, six, seven, eight, nine, ten, 11, 12, 13, 14, or 15 N-glycans within the following relative abundance range:
  (a) 0.8% to 1.1% G0-GN;
  (b) 0.5% to 1.1% G0F-GN;
  (c) 42.5% to 48.8% G0;
  (d) 0.3% to 0.6% G1-GN;
  (e) 9.5% to 14.1% G0B;
  (f) 12.8% to 19.7% G0F;
  (g) 0.4% to 0.7% Man5;
  (h) 5.1% to 7.0% G0FB;
  (i) 5.7% to 6.4% G1;
  (j) 2.7% to 3.3% G1';
  (k) 1.4% to 2.0% G1B;
  (l) 2.6% to 4.2% G1F;
  (m) 1.1% to 1.6% G1F';
  (n) 1.1% to 1.8% G1FB;
  (o) 0.5% to 0.7% G2; and
  (p) 0.3% to 0.5% G2F.

In an even more specific embodiment, an anti-CD20 antibody composition provided herein comprises at least two, three, four, five, six, seven, eight, nine, ten, 11, 12, 13, 14, or 15 N-glycans within the following relative abundance range:
  (a) 0.9% G0-GN;
  (b) 0.8% G0F-GN;
  (c) 46.1% G0;
  (d) 0.5% G1-GN;
  (e) 10.9% G0B;
  (f) 17.0% G0F;
  (g) 0.6% Man5;
  (h) 6.0% G0FB;
  (i) 6.1% G1;

(j) 2.9% G1';
(k) 1.6% G1B;
(l) 3.2% G1F;
(m) 1.3% G1F';
(n) 1.3% G1FB;
(o) 0.5% G2; and
(p) 0.3% G2F.

In certain embodiments, the population of anti-CD20 antibody proteins comprises an N-glycan profile comprising a relative abundance of from about 0.3% to about 2% G0-GN, from about 0.8% to about 1.1% G0-GN, or about 0.9% G0-GN. In certain embodiments, the population of anti-CD20 antibody proteins comprises an N-glycan profile comprising a relative abundance of from about 0.1% to about 2% G0F-GN, from about 0.5% to about 1.1% G0F-GN, or about 0.8% G0F-GN. In certain embodiments, the population of anti-CD20 antibody proteins comprises an N-glycan profile comprising a relative abundance of from about 30% to 60% G0, from about 42.5% to 48.8% G0, or about 46.1% G0. In certain embodiments, the population of anti-CD20 antibody proteins comprises an N-glycan profile comprising a relative abundance of from about 0.1% to about 1% G1-GN, from about 0.3% to about 0.6% G1-GN, or about 0.5% G1-GN. In certain embodiments, the population of anti-CD20 antibody proteins comprises an N-glycan profile comprising a relative abundance of from about 5% to about 20% G0B, from about 5% to about 15% G0B, from about 9.5% to about 14.1% G0B, about 10.9% G0B, or about 10% G0B. In certain embodiments, the population of anti-CD20 antibody proteins comprises an N-glycan profile comprising a relative abundance of from about 5% to about 30% G0F, from about 12.8% to about 19.7% G0F, or about 17.0% G0F. In certain embodiments, the population of anti-CD20 antibody proteins comprises an N-glycan profile comprising a relative abundance of from about 0.1% to about 1.5% Man5, from about 0.4% to about 0.7% Man5, or about 0.6% Man5. In some embodiments, Man5 is the only high mannose N-glycan in the N-glycan profile. In certain embodiments, the population of anti-CD20 antibody proteins comprises an N-glycan profile comprising a relative abundance of from about 1% to about 15% G0FB, from about 5.1% to about 7.0% G0FB, or about 6.0% G0FB. In certain embodiments, the population of anti-CD20 antibody proteins comprises an N-glycan profile comprising a relative abundance of from about 1% to about 13% G1, from about 5.7% to about 6.4% G1, or about 6.1% G1. In certain embodiments, the population of anti-CD20 antibody proteins comprises an N-glycan profile comprising a relative abundance of from about 0.5% to about 10% G1', from about 2.7% to about 3.3% G1', or about 2.9% G1'. In certain embodiments, the population of anti-CD20 antibody proteins comprises an N-glycan profile comprising a relative abundance of from about to about 6% G1B, from about 1.4% to about 2.0% G1B, or about 1.6% G1B. In certain embodiments, the population of anti-CD20 antibody proteins comprises an N-glycan profile comprising a relative abundance of from about 0.5% to about 12% G1F, from about 2.6% to about 4.2% G1F, or about 3.2% G1F. In certain embodiments, the population of anti-CD20 antibody proteins comprises an N-glycan profile comprising a relative abundance of from about to about 3% G1F', from about 1.1% to about 1.6% G1F', or about 1.3% G1F'. In certain embodiments, the population of anti-CD20 antibody proteins comprises an N-glycan profile comprising a relative abundance of from about 0.1% to about 3% G1FB, from about 1.1% to about 1.8% G1FB, or about 1.3 G1FB. In certain embodiments, the population of anti-CD20 antibody proteins comprises an N-glycan profile comprising a relative abundance of from about to about 2% G2, from about 0.5% to about 0.7% G2, or about 0.5% G2. In certain embodiments, the population of anti-CD20 antibody proteins comprises a relative abundance of from an N-glycan profile comprising about 0.1% to about 2% G2F, from about 0.3% to about G2F, or about 0.3% G2F.

In certain embodiments, the population of anti-CD20 antibody proteins comprises an N-glycan profile comprising a relative abundance of from about 0.3% to about 2% G0-GN, from about 0.1% to about 2% G0F-GN, from about 30% to 60% G0, from about 0.1% to about 1% G1-GN, from about 5% to about 20% G0B, from about 5% to about 30% G0F, from about 0.1% to about 1.5% Man5, from about 1% to about 15% G0FB, from about 1% to about 13% G1, from about 0.5% to about 10% G1', from about 0.5% to about 6% G1B, from about 0.5% to about 12% G1F, from about 0.1% to about 3% G1F', from about 0.1% to about 3% G1FB, from about to about 2% G2, and from about 0.1% to about 2% G2F. In some embodiments, Man5 is the only high mannose N-glycan in the N-glycan profile.

In certain embodiments, the population of anti-CD20 antibody proteins comprises an N-glycan profile comprising a relative abundance of from about 0.8% to about 1.1% G0-GN, from about 0.5% to about 1.1% G0F-GN, from about 42.5% to 48.8% G0, from about 0.3% to about 0.6% G1-GN, from about 9.5% to about 14.1% G0B, from about 12.8% to about 19.7% G0F, from about 0.4% to about 0.7% Man5, from about 5.1% to about 7.0% G0FB, from about to about 6.4% G1, from about 2.7% to about 3.3% G1', from about 1.4% to about 2.0% G1B, from about 2.6% to about 4.2% G1F, from about 1.1% to about 1.6% G1F', from about 1.1% to about 1.8% G1FB, from about 0.5% to about 0.7% G2, and from about 0.3% to about 0.5% G2F. In some embodiments, Man5 is the only high mannose N-glycan in the N-glycan profile.

In certain embodiments, the population of anti-CD20 antibody proteins comprises an N-glycan profile comprising a relative abundance of about 0.9% G0-GN, about 0.8% G0F-GN, about 46.1% G0, about 0.5% G1-GN, about 10.9% G0B, about 17.0% G0F, about 0.6% Man5, about 6.0% G0FB, about 6.1% G1, about 2.9% G1', about 1.6% G1B, about 3.2% G1F, about 1.3% G1F', about 1.3 G1FB, about 0.5% G2, and about 0.3% G2F. In some embodiments, Man5 is the only high mannose N-glycan in the N-glycan profile.

In certain embodiments, the population of anti-CD20 antibody proteins comprises an N-glycan profile comprising a relative abundance ratio of about 0.1 to about 0.15 G1 to G0 N-glycans. In certain embodiments, the population of anti-CD20 antibody proteins comprises an N-glycan profile comprising a relative abundance ratio of about 0.5 to about 0.9 G1F to G1 N-glycans.

Figure 2:
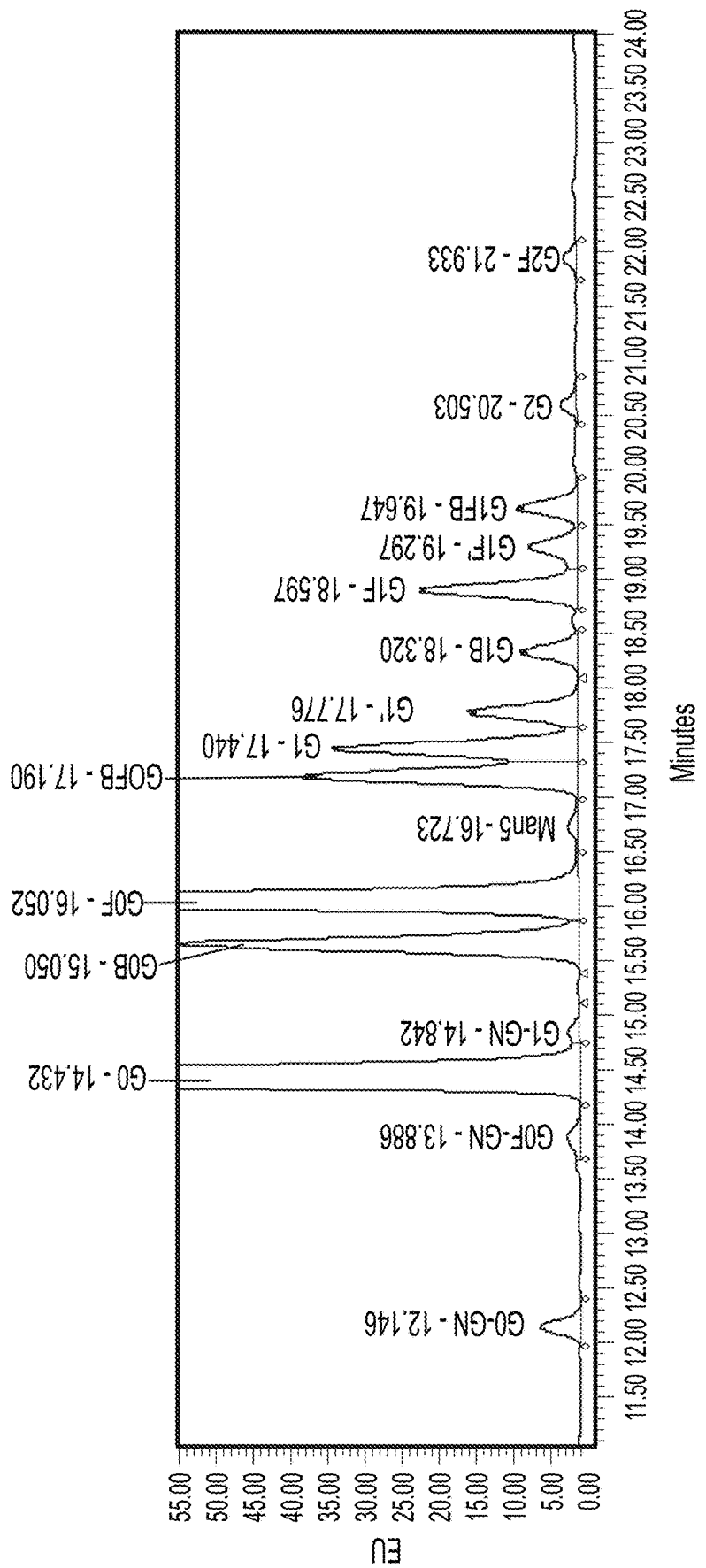
FIG. 2 illustrates the glycosylation profile of a sample of anti-CD20 antibody proteins provided herein.

In one embodiment, an anti-CD20 antibody composition has an N-glycan profile as shown in FIG. 2.

Specific ranges and values for various N-glycans are provided below. The compositions or populations of anti-CD20 antibody proteins provided herein can be described by any one of the prevalence of any of these N-glycans or by any group or by all of these N-glycans.

(i) Galactosylation

In certain embodiments, an anti-CD20 antibody composition provided herein comprises between 10-20% galactosylated glycans. Galactosylated glycans are those N-glycans shown in FIG. 1 that carry a galactose residue (shown as open circle in FIG. 1). Assays for determining the percentage of galactosylation (or galactosylated N-glycans) are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of galactosylated N-glycans is the percent of galactosylated N-glycans among N-glycans that were cleaved using the enzymatic digest.

In certain embodiments, an anti-CD20 antibody composition provided herein comprises between at least 10%, 11%, 12%, 13%, 14%, 15%, 16%, 17%, or at least 18% and at most 12%, 13%, 14%, 15%, 16%, 17%, 18%, 19%, or at most 20% galactosylated glycans. In more specific embodiments, an anti-CD20 antibody composition provided herein comprises between 11% and 19%, 12% and 18%, 13% and 17%, or 14% and 16% of galactosylated glycans. In a specific embodiment, an anti-CD20 antibody composition provided herein comprises about 17% galactosylated glycans (wherein "about" means+/−1, 2, 3, 4, 5, 6, 7, 8, 9, or 10%).

(ii) Fucosylation

In certain embodiments, an anti-CD20 antibody composition provided herein comprises between 20% to 40% fucosylated glycans; between 23% to 36% fucosylated glycans; between 20% and 35% fucosylated glycans; between 28% and 33% fucosylated glycans; or about 33% fucosylated glycans (wherein "about" means+/−1, 2, 3, 4, 5, 6, 7, 8, 9, or 10%). Fucosylated glycans are those N-glycans shown in FIG. 1 that carry a fucose residue (shown as open triangle in FIG. 1). Assays for determining the percentage of fucosylation (or fucosylated N-glycans) are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of fucosylated N-glycans is the percent of fucosylated N-glycans among N-glycans that were cleaved using the enzymatic digest.

In certain embodiments, an anti-CD20 antibody composition provided herein comprises between at least 20%, 21%, 22%, 23%, 24%, 25%, 26%, 27%, 28%, 29%, 30%, 31%, 32%, or at least 33% and at most 22%, 23%, 24%, 25%, 26%, 27%, 28%, 29%, 30%, 31%, 32%, 33%, 34%, 35%, 36%, 37%, 39%, 40%, 41%, or at most 42% fucosylated glycans.

(iii) Galactosylation to Fucosylation Ratio

In certain embodiments, an anti-CD20 antibody composition provided is characterized by a specified ratio of total fucosylated glycans to total galactosylated glycans (or "Fucose/Galactose ratio"). Specifically, this Fucose/Galactose ratio can be between 1.5 and 2.1; between 1.5 and 2; between 1.5 and 1.9; between 1.5 and 1.8; between 1.6 and 2.1; between 1.7 and 2.1; between 1.8 and 2.8; between 1.6 and 2.0; between 1.7 and 1.9; between 1.6 and 1.8; or the Fucose/Galactose ratio can be about 1.75 (wherein "about" means+/−1, 2, 3, 4, 5, 6, 7, 8, 9, or 10%). Fucosylated glycans are those N-glycans shown in FIG. 1 that carry a fucose residue (shown as open triangle in FIG. 1). Galactosylated glycans are those N-glycans shown in FIG. 1 that carry a galactose residue (shown as open circle in FIG. 1). Assays for determining the percentage of fucosylation (or fucosylated N-glycans) are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of fucosylated N-glycans is the percent of fucosylated N-glycans among N-glycans that were cleaved using the enzymatic digest.

(iv) Bisecting N-glycans

In certain embodiments, an anti-CD20 antibody composition provided herein comprises at least 10%, 15%, 20%, 25%, or at least 30% bisecting N-glycans; between 10% and 30%, between 12% and 30%, between 12% and 25%, between 12% and 20%, between 15% and 30%, between 15% and 25%, between 15% and 20%, between 18% and 30%, or between 18% and 25% bisecting N-glycans. Bisecting N-glycans are those N-glycans shown in FIG. 1 that have a third GlcNAc attached to the mannose residue closest to the protein backbone (shown as open triangle in FIG. 1). Assays for determining the percentage of bisecting N-glycans) are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of fucosylated N-glycans is the percent of bisecting N-glycans among N-glycans that were cleaved using the enzymatic digest.

(v) Sialylation

In certain embodiments, an anti-CD20 antibody composition provided herein comprises less than 10%, 8%, 5%, 4%, 3%, 2.5%, 2%, 1%, or 0.5% sialylated glycans. In certain embodiments, an anti-CD20 antibody composition provided herein comprises between 10% and sialylated glycans; between 10% and 5% sialylated glycans; between 5% and 0.5% sialylated glycans; between 4% and 0.5% sialylated glycans; between 2% and 0.5% sialylated glycans; or no detectable amount of sialylated glycans. Assays for determining the percentage of sialylation (or sialylated N-glycans) are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of sialylated N-glycans is the percent of sialylated N-glycans among N-glycans that were cleaved using the enzymatic digest.

In certain embodiments, an anti-CD20 antibody composition provided herein comprises between at least no detectable amount, 0.5%, 1%, 2%, 3%, 4%, or at least 5% and at most 0.5%, 1%, 2%, 3%, 4%, 5% or at most 10% sialylated glycans. In certain embodiments, an anti-CD20 antibody composition provided herein comprises no detectable amount of sialylated glycans.

(vi) G0B N-glycan

In certain embodiments, an anti-CD20 antibody composition provided herein comprises between 5% and 15% G0B N-glycans; between 9% and 11% G0B N-glycan; or about 10% G0B N-glycans (wherein "about" means+/−1, 2, 3, 4, 5, 6, 7, 8, 9, or 10%). G0B N-glycans are shown in FIG. 1. Assays for determining the percentage of G0B N-glycans are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of G0B N-glycans is the percent of G0B N-glycans among N-glycans that were cleaved using the enzymatic digest.

In certain embodiments, an anti-CD20 antibody composition provided herein comprises between at least 5%, 6%, 7%, 8%, 9%, 10%, or at least 11% and at most 7%, 8%, 9%, 10%, 11%, 12% or at most 13% G0B N-glycans.

(vii) Man5 N-glycan

In certain embodiments, an anti-CD20 antibody composition provided herein comprises between 0.1% and 1.5%

Man5 N-glycans; between 0.4% and 0.7% G0B N-glycan; or about 0.6% Man5 N-glycans (wherein "about" means+/−1, 2, 3, 4, 5, 6, 7, 8, 9, or 10%). Man5 N-glycans are shown in FIG. 1. Assays for determining the percentage of Man5 N-glycans are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of Man5 N-glycans is the percent of Man5 N-glycans among N-glycans that were cleaved using the enzymatic digest.

In certain embodiments, an anti-CD20 antibody composition provided herein comprises between at least 0.05%, 0.1%, 0.2%, 0.3%, 0.4%, 0.5%, 0.6%, or at least 0.7% and at most 0.2%, 0.3%, 0.4%, 0.5%, 0.6%, 0.7%, 0.8%, or at most 0.9% Man5 N-glycans.

In certain embodiments, Man5 N-glycan is the only high mannose species in the N-glycan profile.

(viii) G0 N-glycan

In certain embodiments, an anti-CD20 antibody composition provided herein comprises between about 42% and about 52.8% G0 N-glycans (wherein "about" means+/−1, 2, 3, 4, 5, 6, 7, 8, 9, or 10%). G0 N-glycans are shown in FIG. 1. Assays for determining the percentage of G0 N-glycans are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of G0 N-glycans is the percent of G0 N-glycans among N-glycans that were cleaved using the enzymatic digest.

In certain embodiments, an anti-CD20 antibody composition provided herein comprises between at least 35%, 36%, 37%, 38%, 39%, 40%, 41%, 42%, 43%, 44%, 45%, 46%, 47% or at least 48% and at most 45%, 46%, 47%, 48%, 49%, 50%, 51%, 52%, 52.8%, 53%, 54%, 55%, 56%, 57% or at most 58% G0 N-glycans.

(ix) G1 to G0 N-glycans Ratio

In certain embodiments, an anti-CD20 antibody composition provided is characterized by a specified abundance ratio of G1 to G0 N-glycans. Specifically, the abundance ratio of G1 to G0 N-glycans can be between 0.02 and 0.3; between 0.05 and 0.25; between 0.08 and 0.22; between 0.09 and 0.2; between 0.1 and 0.19; between 0.1 and 0.18; between 0.1 and between 0.1 and 0.16; or the abundance ratio of G1 to G0 N-glycans can be between 0.1 and 0.15. G1 and G1 N-glycans are shown in FIG. 1. Assays for determining the percentage of G1 or G0 glycans are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of G1 or G0 glycans is the percent of G1 or G0 glycans, respectively, among N-glycans that were cleaved using the enzymatic digest.

(x) G1F to G1 N-glycans Ratio

In certain embodiments, an anti-CD20 antibody composition provided is characterized by a specified abundance ratio of G1F to G1 N-glycans. Specifically, the abundance ratio of G1F to G1 N-glycans can be between 0.1 and 1.2; between 0.2 and 1.1; between 0.3 and 1; between 0.4 and 1; between 0.5 and 1; or the abundance ratio of G1 to G0 N-glycans can be between 0.5 and 0.9. G1F and G1 N-glycans are shown in FIG. 1. Assays for determining the percentage of G1F or G1 glycans are described in Section 6.5. In short, a sample or a population of anti-CD20 antibody proteins is subjected to enzymatic deglycosylation so that all N-glycans are cleaved from the core. The resulting N-glycans can subsequently be analyzed, e.g., by mass spectrometry. The percent of G1F or G1 glycans is the percent of G1F or G1 glycans, respectively, among N-glycans that were cleaved using the enzymatic digest.

(b) Deamidation

In certain embodiments, the population of anti-CD20 antibody proteins as described herein comprises asparagine deamidation at one or more asparagine residues present in a heavy chain. In some embodiments, the one or more deamidated asparagine residues present in the heavy chain are selected from Asn-33 (as shown in SEQ ID NO:18), Asn-55 (as shown in SEQ ID NO:19), Asn-61 (as shown in SEQ ID NO:19), Asn-160 (as shown in SEQ ID NO:22), Asn-202 (as shown in SEQ ID NO:22), Asn-204 (as shown in SEQ ID NO:22), Asn-277 (as shown in SEQ ID NO:25), Asn-287 (as shown in SEQ ID NO:25), Asn-362 (as shown in SEQ ID NO:27), or Asn-385 (as shown in SEQ ID NO:28). In certain embodiments, the population of anti-CD20 antibody proteins as described herein comprises asparagine deamidation at one or more asparagine residues present in a light chain. In some embodiments, the one or more deamidated asparagine residues present in the light chain are selected from Asn-136 (as shown in SEQ ID NO:31), Asn-137 (as shown in SEQ ID NO:31), Asn-151 (as shown in SEQ ID NO:32), or Asn-157 (as shown in SEQ ID NO:32).

(c) Oxidation

In certain embodiments, the population of anti-CD20 antibody proteins comprises methionine oxidation at one or more methionine residues present in a heavy chain. In some embodiments, the one or more methionine residues present in the heavy chain are selected from Met-20, Met-34, Met-81, Met-253 or Met-428 as shown in SEQ ID NO:17, 18, 21, 24, or 29, respectively. In certain embodiments, the population of anti-CD20 antibody proteins comprises methionine oxidation at one or more methionine residues present in a light chain. In some embodiments, the one or more methionine residues present in the light chain are selected from Met-21 or Met-32 as shown in SEQ ID NO:30.

(d) Pyroglutamation

In certain embodiments, the population of anti-CD20 antibody proteins comprises pyroglutamation at the N-terminal glutamine residue present in a heavy chain or a light chain. In some embodiments, the pyroglutamation at the N-terminal glutamine residue is present in the heavy chain, for example, pGlu-1 as shown in SEQ ID NO:13. In some embodiments, the pyroglutamation at the N-terminal glutamine residue is present in the light chain, for example, pGlu-1 as shown in SEQ ID NO:14. In certain embodiments, the glutamate at position 1 of the heavy chain is a pyroglutamate and the glutamate at position 1 of the light chain is a pyroglutamate.

(e) Lysine truncation

In certain embodiments, the population of anti-CD20 antibody proteins comprises a deletion of the C-terminal lysine amino acid residue present in a heavy chain or a light chain. In certain embodiments, the C-terminal lysine amino acid residue of the heavy chain in the anti-CD20 antibody in said population is truncated. In certain embodiments, the population of anti-CD20 antibody proteins comprises a deletion of the C-terminal lysine at the heavy chain. In certain embodiments, the heavy chain of the anti-CD20 antibody proteins comprises the amino acid sequence of SEQ ID NO:15.

(f) Conformation

Three-dimensional conformation or protein folding can be determined using the assay described in Section 6.5(e).

In some aspects, a composition or population of anti-CD20 antibody proteins provided herein (e.g., such that are expressed from one or more nucleic acid sequences encoding a heavy chain comprising the amino acid sequence of SEQ ID NO:1 and a light chain comprising the amino acid sequence of SEQ ID NO:2) have a specified three-dimensional folding pattern or confirmation. In certain embodiments, the population of anti-CD20 antibody proteins comprises two or more of the following secondary structures as determined by circular dichroism (CD) spectroscopy at 205 nm to 260 nm: α-helix at a range of 3.0% to 15.0%; Anti-parallel β-sheet at a range of 25.0% to 40.0%; Parallel β-sheet at a range of 0.5% to 12.0%; β-Turn at a range of 10.0% to 25.0%; and random coil at a range of 30.0% to 42.0%.

In a preferred aspect, the population of anti-CD20 antibody proteins comprises two or more of the following secondary structures as determined by circular dichroism (CD) spectroscopy at 205 nm to 260 nm: α-helix at a range of 8.0% to 10.0%; Anti-parallel β-sheet at a range of 32.0% to 36.0%; Parallel β-sheet at a range of 5.0% to 6.0%; β-Turn at a range of 16.0% to 18.0%; and random coil at a range of 35.0% to 36.0%.

In another preferred aspect, the population of anti-CD20 antibody proteins comprises two or more of the following secondary structures as determined by circular dichroism (CD) spectroscopy at 205 nm to 260 nm: α-helix at about 9.0%; Anti-parallel β-sheet at about 33.0%; Parallel β-sheet at about 5.6%; β-Turn at about 17.5%; and random coil at about 35.2%, wherein the term "about" means±5%.

6.5 Assays for Quantifying Post-Translational Modifications

In some aspects, provided herein is a method of determining the amount of post-translational modifications in a population of anti-CD20 antibody proteins. In certain embodiments, the post-translational modification is selected from asparagine deamidation, methionine oxidation, glycosylation, pyroglutamate formation, and lysine truncation.

(a) General Digestion

In certain embodiments, the method of determining the amount of post-translational modifications in a population of anti-CD20 antibody proteins comprises a step of digesting the population of anti-CD20 antibody proteins with an endoproteinase. In certain embodiments, the population of anti-CD20 antibody proteins is reduced prior to digestion. In certain embodiments, the population of anti-CD20 antibody proteins is alkylated prior to digestion. In some embodiments, the endoproteinase is selected from Asp-N, Lys-C, or trypsin. In some embodiments, the step of digestion occurs at 37° C. for at least 8 hours, at least 12 hours, at least 16 hours, at least 20 hours, overnight, and/or less than 24 hours. In specific embodiments, the population of anti-CD20 antibody proteins is digested using Asp-N or Lys-C at 37° C. overnight. In specific embodiments, the population of anti-CD20 antibody proteins is digested using trypsin at ratio of 50:1 (w:w) at 37° C. overnight. In some embodiments, the digested population of anti-CD20 antibody proteins is purified from digestion reaction components and/or undigested anti-CD20 antibody proteins.

(b) Methods of Determining N-Glycosylation

Exemplary assays and their results are discussed in the Examples in Sections 7.1 and 7.2 below.

In certain embodiments, the method comprises a step for deglycosylating a population of anti-CD20 antibody proteins, thereby producing released N-glycans for labeling. In some embodiments, deglycosylating comprises breaking the glycosidic bond between one or more or all N-glycans from a population of anti-CD20 antibody proteins. In some embodiments, deglycosylating comprises releasing some or most or substantially all of the N-glycans from a population of anti-CD20 antibody proteins. In some embodiments, deglycosylating releases greater than 50 percent, greater than 60 percent, greater than 70 percent, greater than 80 percent, greater than 90 percent, greater than 95 percent, greater than 97 percent, greater than 98 percent, greater than 99 percent, or 100 percent of N-glycans present on a population of anti-CD20 antibody proteins.

In certain embodiments, deglycosylating comprises contacting the population of anti-CD20 antibody proteins with one or more deglycosylating reagent, which cleaves N-glycans or N-linked oligosaccharides. In certain embodiments, the deglycosylating reagent is a deglycosylating enzyme or chemical agent. In specific embodiments, the deglycosylating enzyme is PNGase F.

In certain embodiments, deglycosylating comprises contacting the population of anti-CD20 antibody proteins with one or more deglycosylating enzyme or chemical agent at a deglycosylation temperature of from about 25° C. to about 50° C., from about 37° C. to about 50° C., about 25 C, about 37° C., about 42° C., or about 50° C. In specific embodiments, the deglycosylation temperature is 37° C. The rate of deglycosylation may be increased by increasing the deglycosylation temperature. In certain embodiments, deglycosylation comprises contacting a population of anti-CD20 antibody proteins with one or more deglycosylating enzyme or chemical agent for a period of time sufficient to release some or most or substantially all of the N-glycans from the population of anti-CD20 antibody proteins. In some embodiments, deglycosylating comprises contacting a population of anti-CD20 antibody proteins with said one or more deglycosylating enzyme or chemical agent for at least 30 minutes, at least 1 hour, at least 2 hours, at least 4 hours, at least 8 hours, at least 12 hours, at least 16 hours, at least 20 hours, at least 24 hours, at least 30 hours, and/or less than 48 hours. In some embodiments, deglycosylating comprises contacting a population of anti-CD20 antibody proteins with said one or more deglycosylating enzyme or chemical agent for a period of time of from about 30 minutes to about 2 hours, about 2 hours to about 4 hours, about 4 hours to about 8 hours, about 8 hours to about 12 hours, about 12 hours to about 20 hours, about 20 to about 30 hours, greater than about hours, and/or less than 48 hours. In specific embodiments, deglycosylating comprises contacting a population of anti-CD20 antibody proteins with one or more deglycosylating enzyme or chemical agent for about 12 to about 20 hours. In specific embodiments, deglycosylation comprises contacting a population of anti-CD20 antibody proteins with PNGase F at about 37° C. for about 12 to about 20 hours. In specific embodiments, deglycosylation comprises contacting an anti-CD20 antibody with PNGase F at 37° C. for a time period of from 12-20 hours. In specific embodiments, deglycosylation with PNGase F occurs in the presence of a non-ionic detergent (i.e., NP-40).

In certain embodiments, deglycosylation comprises denaturing the population of anti-CD20 antibody proteins prior to contacting the population with said one or more deglycosylating enzyme or chemical agent. In certain embodiments, denaturing comprises thermal denaturation, chemical denaturation, or a combination of both. In certain embodiments, thermal denaturation comprises incubating a population of anti-CD20 antibody proteins at a denaturation temperature and denaturation time sufficient to unfold some or most or all of the immunoglobulin fold domains of anti-CD20 antibody proteins of said population. In certain embodiments, the denaturation temperature is at least 50° C., at least 60° C., at least 65° C., at least 70° C., at least ° C., at least 80° C., at least 85° C., at least 90° C., and/or less than about 100° C. In some embodiments, the denaturation temperature is from about 50° C. to about 60° C., from about 60° C. to about 70° C., from about 70° C. to about 80° C., from about 80° C. to about 90° C., or from 90° C. to about 100° C. In some embodiments, the denaturation temperature is about 50° C., about 60° C., about 65° C., about 70° C., about 75° C., about 80° C., about 85° C., about 90° C., or about 100° C. In specific embodiments, the denaturation temperature is 70° C. In certain embodiments, chemical denaturation comprises incubating a population of anti-CD20 antibody proteins at a denaturation temperature of at least 25° C., at least 30° C., at least 37° C., or an elevated temperature (i.e., a thermal denaturation temperature). In some embodiments, the denaturation time is at least 5 minutes, at least 10 minutes, at least 15 minutes, at least 30 minutes, at least 1 hour, at least 2 hours, at least 4 hours, at least 10 hours, or at least 24 hours. In some embodiments, the denaturation time is about 5 minutes, about 10 minutes, about 15 minutes, about 30 minutes, about 1 hour, about 2 hours, about 4 hours, about 10 hours, or about 24 hours. In specific embodiments, the denaturation time is 10 minutes. In certain embodiments, chemical denaturation comprises contacting the population of anti-CD20 antibody proteins with one or more chemical denaturant. In some embodiments, the one or more chemical denaturant is selected from an ionic detergent, non-ionic detergent, zwitterionic detergent, chaotropic detergent, or reducing agent. In some embodiments, the chemical denaturant is selected from sodium dodecyl sulfate (SDS), urea, or dithiothreitol (DDT). The effects of certain chemical denaturants may interfere with deglycosylation (i.e., enzymatic deglycosylation) and can be countered in solution. In certain embodiments, the chemical denaturant is countered by addition of a non-ionic detergent to the solution. In specific embodiments, the chemical denaturant is SDS and the additional non-ionic detergent is NP-40. In specific embodiments, denaturing a population of anti-CD20 antibody proteins comprises thermal denaturation at 70° C. for 10 minutes.

In certain embodiments, the method comprises purifying released N-glycans of a population of anti-CD20 antibody proteins from a deglycosylation reaction mixture. In certain embodiments, the released N-glycans are substantially pure of deglycosylating reagent and deglycosylated or unreacted anti-CD20 antibodies. In certain embodiments, the released N-glycans are substantially pure of salts and/or detergents. In certain embodiments, the released N-glycans are purified by hydrophilic interaction. In certain embodiments, the released N-glycans are purified by chromatography comprising a hydrophilic stationary phase and reversed-phase eluent. In certain embodiments, the released N-glycans are purified by hydrophilic interaction liquid chromatography (HILIC). In specific embodiments, the released N-glycans are purified via a Waters HILIC MassPrep μElution plate, in accordance to manufacturer's protocol. In specific embodiments, the released N-glycans are purified to a purity level equivalent to the purity level obtained when purifying via a Waters HILIC MassPrep μElution plate, in accordance to manufacturer's protocol.

In certain aspects, the method comprises a step for labeling released N-glycans of a population of anti-CD20 antibody proteins, thereby producing labeled N-glycans for detection. In certain embodiments, labeling released N-glycans comprises chemical derivatization, for example to provide a detectable charge, ultraviolet activity, or fluorescent characteristic to the released N-glycans. In certain embodiments, labeling released N-glycans comprises reductive amination, hydrazide labeling, methylation, Michael addition, or permethylation. In some embodiments, labeling released N-glycans comprises contacting the released N-glycans with a label selected from 2-aminobenzamide (2-AB), 2-aminobenzoic acid (2-AA), 2-aminopyridine (PA), 2-aminonaphthalene trisulfonic acid (ANTS), or 1-aminopyrene-3,6,8-trisulfonic acid (APTS). In specific embodiments, the label is 2-AB. In certain embodiments, labeling of released N-glycans by reductive amination comprises the use of a reducing agent. In some embodiments, the reducing agent is selected from sodium cyanoborohydride or 2-picoline borane. In specific embodiments, the reducing agent is cyanoborohydride. In certain embodiments, labeling released N-glycans by reductive amination comprises contacting the released N-glycans with a label suitable for reductive amination and a reducing agent, at a reaction temperature and reaction time sufficient for labeling to occur. In certain embodiments, the reaction temperature is of from about 25° C. to about 40° C., from about 40° C. to about 50° C., from about 50° C. to about 60° C., from about 60° C. to about 70° C., or from about 70° C. to about ° C. In certain embodiments, the reaction temperature is about 25° C., about 30° C., about ° C., about 40° C., about 45° C., about 50° C., about 55° C., about 60° C., about 65° C., about ° C., or about 75° C. In specific embodiments, the reaction temperature is 65° C. In certain embodiments, the reaction time is at least 30 minutes, at least 1 hour, at least 2 hours, at least 3 hours, at least 4 hours, or at least 6 hours. In certain embodiments, the reaction time is of from about 30 minutes to about 1 hour, from about 1 hours to about 2 hours, from about 2 hours to about 3 hours, from about 3 hours to about 4 hours, or from about 4 hours to about 6 hours. In certain embodiments, the reaction time is about 30 minutes, about 1 hours, about 2 hours, about 3 hours, about 4 hours, or about 6 hours. In specific embodiments, the reaction time is 3 hours. In specific embodiments, labeling released N-glycans from a population of anti-CD20 antibody proteins comprises reductive amination using 2-AB and cyanoborohydride at 65° C. for 3 hours, thereby producing labeled N-glycans.

In certain aspects, the method comprises purifying labeled N-glycans of a population of anti-CD20 antibody proteins from a labeling reaction mixture. In certain embodiments, the labeled N-glycans are substantially pure of unreacted label. In certain embodiments, the labeled N-glycans are substantially pure of unreacted released N-glycans. In certain embodiments, the labeled N-glycans are substantially pure of reducing agent (i.e., cyanoborohydride). In certain embodiments, the labeled N-glycans are purified by hydrophilic interaction. In certain embodiments, the labeled N-glycans are purified by chromatography comprising a hydrophilic stationary phase and reversed-phase eluent. In certain embodiments, the labeled N-glycans are purified by hydrophilic interaction liquid chromatography (HILIC). In specific embodiments, the labeled N-glycans are purified via a Waters HILIC MassPrep 11Elution plate, in accordance to manufacturer's protocol. In specific embodiments, the labeled N-glycans are purified to a purity level equivalent to the purity level obtained when purifying via a Waters HILIC MassPrep 11Elution plate, in accordance to manufacturer's protocol.

In certain aspects, the method comprises a step for separating labeled N-glycans of a population of anti-CD20 antibody proteins and determining an N-glycan profile of the population. In certain embodiments, separating labeled N-glycans comprises separation by hydrophilicity. In certain embodiments, separating labeled N-glycans comprises chromatography, which comprises a hydrophilic stationary phase and a reversed-phase eluent. In specific embodiments, the chromatography is hydrophilic interaction liquid chromatography (HILIC). In certain embodiments of the method, separating labeled N-glycans comprises chromatography comprising an amide stationary phase. In specific embodiments, the amide stationary phase is a glycan BEH amide column. In certain embodiments, the reversed-phase eluent comprises one or more mobile phase, wherein the mobile phase comprises an acidic ammonium buffer and/or acetonitrile.

In certain embodiments, chromatography is performed using parameters for flow rate, stationary phase (i.e., column) temperature, mobile phase gradient, and period of time, wherein the parameters in combination are sufficient to separate labeled N-glycans. In certain embodiments, chromatography is performed using a chromatography system that controls these parameters (i.e., an HPLC or UPLC system). In certain embodiments, the chromatography system is coupled to a detector, for detecting labeled N-glycans of a population of anti-CD20 antibody proteins. In some embodiments, the detector is a fluorescence detector that detects fluorescence from the label (e.g., the label that is contacted with the released N-glycans of a population of anti-CD20 antibody proteins in a labeling step). In specific embodiments, the label is 2-AB. In specific embodiments, detecting fluorescence comprises exciting with 360 nm wavelength light and observing fluorescent emission at 428 nm wavelength light. In certain embodiments, the chromatography system is a HILIC-UPLC system. In specific embodiments, separation and detection of labeled N-glycans is performed using a hydrophilic interaction stationary phase, a reversed-phase eluent, and a Waters UPLC equipped with fluorescence detector. In specific embodiments, the hydrophilic interaction stationary phase comprises a glycan BEH amide column (130 Å, 1.7 µm, 2.1 mm×150 mm). In specific embodiments, the stationary phase (i.e., column) temperature is 50° C. In specific embodiments, the flow rate is 0.50 mL/min. In specific embodiments, the reversed-phase eluent comprises one or more mobile phases comprising a first mobile phase comprising about 250 mM ammonium formate, at a pH of about 4.4, and a second mobile phase comprising acetonitrile. In specific embodiments, the mobile phase gradient comprises an increase of said first mobile phase of from 22.0% to 44.1% over 38.5 minutes.

In certain embodiments, detecting fluorescence comprises generating a chromatogram, wherein the dependent variable is selected from mobile phase volume, eluent volume passed through the chromatographic column, or time, and the observable is fluorescence. In certain embodiments, determining an N-glycan profile of a population of anti-CD20 antibody proteins comprises quantifying the relative amounts of labeled G0-GN, G0F-GN, G0, G1-GN, G0B, G0F, Man5, G0FB, G1, G1', G1B, G1F, G1F', G1FB, G2, and G2F N-glycans of said population. In certain embodiments, chromatography (i.e., HILIC-UPLC) is performed using a flow rate, column temperature, mobile phase gradient, and period of time parameters sufficient to separate the N-glycans of G0-GN, G0F-GN, G0, G1-GN, G0B, G0F, Man5, G0FB, G1, G1', G1B, G1F, G1F', G1FB, G2, and G2F for quantification. In certain embodiments, the amount of an N-glycan is quantified by calculating its area under a curve comprising labeled G0-GN, G0F-GN, G0, G1-GN, G0B, G0F, Man5, G0FB, G1, G1', G1B, G1F, G1F', G1FB, G2, and G2F N-glycans in a chromatograph separating said N-glycans. In certain embodiments, the relative abundance of an N-glycan selected from G0-GN, G0F-GN, G0, G1-GN, G0B, G0F, Man5, G0FB, G1, G1', G1B, G1F, G1F', G1FB, G2, or G2F is quantified by calculating the percent peak area of said N-glycan relative to total peak area of G0-GN, G0F-GN, G0, G1-GN, G0B, G0F, Man5, G0FB, G1, G1', G1B, G1F, G1F', G1FB, G2, and G2F N-glycans in a chromatograph separating said N-glycans. In certain embodiments, the peak area of an N-glycan in the chromatograph is greater than or equal to 0.25%. In certain embodiments, the peak area of an N-glycan in the chromatograph has a signal-to-noise ratio of greater than or equal to 3.0.

An N-glycan profile of a population of anti-CD20 antibody proteins may be determining the relative amounts of glycosylation of the population via a liquid chromatography-coupled mass spectrometer (LC-MS) peptide mapping method, for example, by summing site specific glycosylation results of a digested population of anti-CD20 antibody proteins.

In certain embodiments, the LC-MS peptide mapping comprises determining the molecular weight of peptides derived from a Lys-C digested population of anti-CD20 antibody proteins to determine the presence and amount of glycosylated residues (i.e., G0, G0F, G0B, G0FB, G1, or G1F). In specific embodiments, the population of anti-CD20 antibody proteins is reduced and alkylated prior to digestion. In certain embodiments, the LC is performed using parameters for flow rate, stationary phase (i.e., column) temperature, mobile phase gradient, and period of time, wherein the parameters in combination are sufficient to separate the peptides of the Lys-C digest. In certain embodiments, the relative abundance of a peptide of a Lys-C digest is calculated by integrating its area under the curve compared to total area.

In certain embodiments, the observed molecular weights are compared to theoretical masses for glycosylated peptides selected from Table 1, column 2. In certain embodiments, the observed molecular weights are compared to theoretical masses selected from Table 1, column 4.

TABLE 1

Peptides for determining glycosylation following Lys-C digestion

| Site | Peptide Sequence | Glycan | Theoretical MW (Da) |
|---|---|---|---|
| HC (290-318) | TKPREEQYNSTYRVVSVLTVLHQDW LNGK (SEQ ID NO: 33) | G0<br>G0F | 4529.1232<br>4675.1812 |

TABLE 1-continued

Peptides for determining glycosylation following Lys-C digestion

| Site | Peptide Sequence | Glycan | Theoretical MW (Da) |
|---|---|---|---|
| | | G0B | 4732.2026 |
| | | G0FB | 4878.2605 |
| | | G1 | 4691.1761 |
| | | G1F | 4837.2340 |

In certain embodiments, the population of anti-CD20 antibody proteins comprises glycosylation at residue Asn-298 of SEQ ID NO:33 present in a heavy chain.

(c) Method of Determining Deamidation (i) Deamidation in General

In some aspects, provided herein is a method of determining the amount of asparagine deamidation in a population of anti-CD20 antibody proteins. In certain embodiments, the amount of asparagine deamidation in a population of anti-CD20 antibody proteins is the amount of isoaspartate residues in the population. In specific embodiments, the method comprises detecting the amount of isoaspartate residues in a digested population of anti-CD20 antibody proteins.

(ii) Deamidation By Isoquant

The amount of asparagine deamidation or isoaspartate in a population or digested population of anti-CD20 antibody proteins may determined via enzymatic method, for example, by the addition of a methyltransferase (i.e., protein isoaspartyl methyltransferase (PIN/IT)), which catalyzes the transfer of a methyl group from S-adenosyl methionine (SAM) to isoaspartic acid. This PIMT-catalyzed reaction produces S-adenosyl homocysteine (SAH) in an amount that is directly proportional (~1:1 stoichiometry) to the level of isoaspartate present in a sample. SAH can be directly measured by separating SAH (i.e., via ultra performance liquid chromatography (UPLC) or reversed-phase high performance liquid chromatography (RP-HPLC)), detecting at 260 nm, and quantifying the amount of SAH by comparing to a SAH standard curve (i.e., Trp-Ala-Gly-Gly-isoAsp-Ala-Ser-Gly-Glu peptide).

In certain embodiments, the method comprises a step of derivatization comprising contacting the population of anti-CD20 antibody proteins with PIMT and SAM. In some embodiments, the population of anti-CD20 antibody proteins is contacted with PIMT and SAM at a temperature and for a period of time sufficient for derivatization (i.e., methylation) of substantially all of the aspartate residues present in the population. In certain embodiments, the method optionally comprises a step of quenching the derivatization reaction. In certain embodiments, the method comprises a step of separating SAH by hydrophobicity for quantification of isoaspartate. In some embodiments, separating SAH comprises chromatography, which comprises a hydrophobic interaction stationary phase and a reversed-phase eluent. In some embodiments, separating SAH comprises chromatography using a C18 stationary phase. In specific embodiments, the C18 stationary phase is a Hydro-RP column. In certain embodiments, the reversed-phase eluent comprises one or more mobile phase (i.e., a weakly acidic phosphate buffer and/or methanol). In certain embodiments, chromatography is performed using parameters for flow rate, stationary phase (i.e., column) temperature, mobile phase gradient, and period of time, wherein the parameters in combination are sufficient to separate SAH from the derivatization reaction components. In certain embodiments, chromatography is performed using a chromatography system that controls these parameters (i.e., an HPLC or UPLC system). In certain embodiments, the chromatography system is coupled to a detector, for detecting SAH after derivatization (i.e., absorbance at 260 nm). In specific embodiments, separation and detection of SAM is performed using a hydrophilic interaction stationary phase, a reversed-phase eluent, and a RP-HPLC or UPLC system equipped with detector for absorbance of SAH at about 260 nm. In specific embodiments, the hydrophobic interaction stationary phase comprises a Synergi Hydro-RP (4.6 mm×150 mm). In specific embodiments, the stationary phase (i.e., column) temperature is about 25° C. or room temperature. In specific embodiments, the flow rate is 1 mL/min. In specific embodiments, the reversed-phase eluent comprises one or more mobile phases comprising a first mobile phase comprising about 50 mM potassium phosphate, at a pH of about 6.2, and a second mobile phase comprising methanol. In specific embodiments, the mobile phase gradient comprises said second mobile phase at 10.0% at 0 minutes, 40% at 7.5 minutes, 80% at 10.5 minutes, 80% at 12.5 minutes, 10% at 13.5 minutes, 10% at 20 minutes, and 10% at 25 minutes. In certain embodiments, the amount of SAH is quantified by comparing its integrated curve area to a SAH standard curve. In specific embodiments, the SAH standard curve is prepared using Trp-Ala-Gly-Gly-isoAsp-Ala-Ser-Gly-Glu. In specific embodiments, the amount of asparagine deamidation or isoaspartate in a population of anti-CD20 antibody proteins is determined using the Promega Isoquant kit along with Isoasp-DSIP standard, in accordance to manufacturer's protocol.

(iii) Deamidation by LC-MS

The amount of asparagine deamidation or isoaspartate in a population or digested population of anti-CD20 antibody proteins may determined via a liquid chromatography-coupled mass spectrometer (LC-MS) peptide mapping method, for example, by summing site specific deamidation results of a digested population of anti-CD20 antibody proteins.

In certain embodiments, the LC-MS peptide mapping comprises determining the molecular weight and/or relative abundance of peptides derived from a Lys-C digested population of anti-CD20 antibody proteins to determine the presence and amount of deamidation or isoaspartate residues. In specific embodiments, the population of anti-CD20 antibody proteins is reduced and alkylated prior to digestion. In certain embodiments, the LC is performed using parameters for flow rate, stationary phase (i.e., column) temperature, mobile phase gradient, and period of time, wherein the parameters in combination are sufficient to separate the peptides of the Lys-C digest. In certain embodiments, the relative abundance of a peptide of a Lys-C digest is calculated by integrating its area under the curve compared to total area.

In certain embodiments, the observed molecular weights are compared to theoretical masses for deamidated peptides selected from Table 2, column 2. In certain embodiments, the observed molecular weights are compared to theoretical masses selected from Table 2, column 3.

TABLE 2

Peptides for determining deamidation following Lys-C digestion

| Site | Peptide Sequence | Theoretical Deamidated MW (Da) |
|---|---|---|
| HC (24-38) | ASGYTFTSYNMHWVK (SEQ ID NO: 18) | 1791.7927 |
| HC (39-63) | QTPRQGLEWIGGIYPGNGDTSYNQK (SEQ ID NO: 19) | 2779.3202 |
| HC (149-206) | DYFPEPVTVSWNSGALTSGVHTFPAVLQSSGLYSLSSVVTVPSSSLGTQTYICNVNHK (SEQ ID NO: 22) | 6186.0209 |
| HC (276-289) | FNWYVDGVEVHNAK (SEQ ID NO: 25) | 1677.7787 |
| HC (362-371) | NQVSLTCLVK (SEQ ID NO: 27) | 1161.6064 |
| HC (372-393) | GFYPSDIA VEWESNGQPENNYK (SEQ ID NO: 28) | 2543.1241; 2544.1081 |
| HC (416-440) | SRWQQGNVFSCSVMHEALHNHYTQK (SEQ ID NO: 29) | 3044.377 |
| LC (126-144) | SGTASVVCLLNNFYPREAK (SEQ ID NO: 31) | 2126.0466 |
| LC (149-168) | VDNALQSGNSQESVTEQDSK (SEQ ID NO: 32) | 2135.9455 |

In certain embodiments, the LC-MS peptide mapping comprises determining the molecular weight and/or relative abundance of peptides derived from an Asp-N digested population of anti-CD20 antibody proteins to determine the presence and amount of deamidation or isoaspartate residues. In specific embodiments, the population of anti-CD20 antibody proteins is reduced and alkylated prior to digestion. In certain embodiments, the LC is performed using parameters for flow rate, stationary phase (i.e., column) temperature, mobile phase gradient, and period of time, wherein the parameters in combination are sufficient to separate the peptides of the Asp-N digest. In certain embodiments, the relative abundance of a peptide of an Asp-N digest is calculated by integrating its area under the curve compared to total area.

In certain embodiments, the observed molecular weights are compared to theoretical masses for deamidated peptides selected from Table 3, column 2. In certain embodiments, the observed molecular weights are compared to theoretical masses selected from Table 3, column 3.

TABLE 3

Peptides for determining deamidation following Asn-N digestion

| Site | Peptide Sequence | Theoretical Deamidated MW (Da) |
|---|---|---|
| HC (377-399) | DIAVEWESNGQPENNYKTTPPVL (SEQ ID NO: 34) | 2601.2235 |

(d) Method of Determining Oxidation (i) Oxidation in General

In some aspects, provided herein is a method of determining the level of methionine oxidation in a population of anti-CD20 antibody proteins as described herein. In certain embodiments, the amount of methionine oxidation in a population of anti-CD20 antibody proteins is the amount of Met sulfoxide (MetO) residues in the population. In specific embodiments, the method comprises detecting the amount of Met sulfoxide (MetO) residues in the population.

(ii) Oxidation by LC-MS

The amount of methionine oxidation or Met sulfoxide (MetO) residues in a population or digested population of anti-CD20 antibody proteins may be determined via a liquid chromatography-coupled mass spectrometer (LC-MS) peptide mapping method, for example, by summing site specific oxidation results of a digested population of anti-CD20 antibody proteins.

In certain embodiments, the LC-MS peptide mapping comprises determining the molecular weight of peptides derived from a Lys-C digested population of anti-CD20 antibody proteins to determine the presence and amount of oxidation or MetO residues. In specific embodiments, the population of anti-CD20 antibody proteins is reduced and alkylated prior to digestion. In certain embodiments, the LC is performed using parameters for flow rate, stationary phase (i.e., column) temperature, mobile phase gradient, and period of time, wherein the parameters in combination are sufficient to separate the peptides of the Lys-C digest. In certain embodiments, the relative abundance of a peptide of a Lys-C digest is calculated by integrating its area under the curve compared to total area.

In certain embodiments, the observed molecular weights are compared to theoretical masses for oxidized peptides selected from Table 4, column 2. In certain embodiments, the observed molecular weights are compared to theoretical masses selected from Table 4, column 3.

TABLE 4

Peptides for determining oxidation following Lys-C digestion

| Site | Peptide Sequence | Theoretical Oxidated MW (Da) |
|---|---|---|
| HC (20-23) | MSCK (SEQ ID NO: 17) | 540.2036 |
| HC (24-38) | ASGYTFTSYNMHWVK (SEQ ID NO: 18) | 1806.8036 |
| HC (75-122) | SSSTAYMQLSSLTSEDSAVYFCARYDYNYAMDYWGQGTSVTVSSASTK (SEQ ID NO: 21) | 5351.317 |
| HC (250-275) | DTLMISRTPEVTCVVVDVSHEDPEVK (SEQ ID NO: 24) | 2970.4314 |
| HC (416-440) | SRWQQGNVFSCSVMHEALHNHYTQK (SEQ ID NO: 29) | 3059.3879 |
| LC (19-38) | VTMTCRASSSVSYMHWYQQK (SEQ ID NO: 30) | 2465.0926 |

In certain embodiments, the population of anti-CD20 antibody proteins comprises methionine oxidation at one or more methionine residues present in a heavy chain. In some embodiments, the one or more methionine residues present in the heavy chain are selected from Met-20, Met-34, Met-81, Met-253 or Met-428 as shown in SEQ ID NO:17, 18, 21, 24, or 29, respectively. In certain embodiments, the population of anti-CD20 antibody proteins comprises methionine oxidation at one or more methionine residues present in a light chain. In some embodiments, the one or more methionine residues present in the light chain are selected from Met-21 or Met-32 as shown in SEQ ID NO:30.

(e) Assay for Determining Protein Conformation—Circular Dichroism

In some embodiments, the secondary structures of anti-CD20 antibody proteins are analyzed using Circular Dichroism (CD) spectroscopy by measuring the difference in absorption between left and right circularly polarized light due to structural asymmetry. The CD spectroscopy using far-ultraviolet spectra with a wavelength between approximately 170 and 260 nm. At these wavelengths, the different secondary structures commonly found in protein can be analyzed, since α-helix, parallel and anti-parallel β-sheet, β-Turn, and random coil conformations each give rise to a characteristic spectra, the spectrum of a given protein can be used to estimate its percentage content on the secondary structures.

6.6 Single Batch Compositions

Provided herein are compositions or populations of anti-CD20 antibody proteins described in Section 6.4 at scaled up quantities. In certain embodiments, these scaled up quantities are present in a single batch, ie, a composition derived from a single run from a single bioreactor of a specified volume. For example, the anti-CD20 antibody proteins obtained from a single run of a 15,000 L bioreactor can be referred to as a single batch. In certain embodiments, the bioreactor has a capacity of at least 100; 200; 300; 400; 500; 750; 1,000; 2,000; 3,000; 4,000; 7,500; 10,000; 15,000; 20,000; or at least 25,000 L. In certain embodiments, anti-CD20 antibody proteins are present in such a single batch at a concentration of at least 10 mg/ml; 20 mg/ml; 25 mg/ml; or at least 30 mg/ml as determined using an assay described in Section 6.6(a). In certain embodiments, anti-CD20 antibody proteins are present in such a single batch at a concentration of at between 10 to 35 mg/ml; 10 to 30 mg/ml; 10 to 25 mg/ml; 10 to 20 mg/ml; 10 to 15 mg/ml; 15 to 35 mg/ml; 15 to 30 mg/ml; 15 to 25 mg/ml; 15 to 20 mg/ml; 20 to 25 mg/ml; 20 to 30 mg/ml; 20 to 25 mg/ml; 25 to 35 mg/ml; or 25 to 30 mg/ml as determined using an assay described in Section 6.6(a). In certain embodiments, anti-CD20 antibody proteins are present in such a single batch at a concentration of about 15 mg/ml; about 20 mg/ml; about about 25 mg/ml; about 30 mg/ml; or about 35 mg/ml as determined using an assay described in Section 6.6(a) (wherein "about" means+/−1, 2, 3, 4, 5, 6, 7, 8, 9, or 10%).

In some aspects, the anti-CD20 antibody proteins disclosed herein are produced at a commercial scale. In certain embodiments, the commercial scale is 10,000 to 25,000 L.

(a) Total Protein

In certain embodiments, the amount of total protein is measured using spectrophotometry. In certain embodiments, the amount of total protein is measured by absorbance at 280 nm.

In certain embodiments, the amount of total protein can be measured using the following assay procedures. This method determines the concentration of the anti-CD20 antibody proteins using an ultraviolet absorbance measurement at 280 nm with a light scattering correction at 320 nm. The calculation of concentration is based on the Beer-Lambert law. The extinction coefficient of the anti-CD20 antibody protein at 280 nm is 1.61 mL/mg/cm as determined by the amino acid composition. The extinction coefficient can be used. The method is suitable for use for post Protein A purification in-process sample testing, release testing, and stability testing. Test samples are diluted gravimetrically in triplicate with 0.9% sodium chloride to a target protein concentration of 0.4 mg/mL. Saline is used as a blank for the instrument. Bovine serum albumin is used as a system suitability control and is tested before and after sample measurements. Test samples are loaded into a quartz cuvette with a 1 cm pathlength and the absorbances at 280 and 320 nm are measured. The test samples are tested in triplicate. In certain embodiments, the amount of total protein can be measured using the critical material and equipment listed in Table 5. In certain embodiments, the amount of total protein can be measured using the protein concentration system suitability criteria listed in Table 6.

TABLE 5

Critical Material and Equipment Used in the Protein Concentration Assay

| Item | Use |
| --- | --- |
| Bovine Serum Albumin | Ensure spectrophotometer performance |
| UV/Vis spectrophotometer | Readout of protein concentration |

UV—ultraviolet; Vis—visible light

TABLE 6

Protein Concentration System Suitability Criteria

| System Suitability Type | Suitability Criteria |
| --- | --- |
| Blank absorbance | 0.000 ± 0.004 AU |
| Bovine Serum Albumin Concentration | BSA concentration must be within 0.08 mg/mL of the COA value |
| Sample absorbance | 0.2-0.9 AU |
| CV for triplicate protein concentration measurement | CV ≤ 2.0% |

AU—absorbance unit; CV—coefficient of variation

In certain embodiments, the population of anti-CD20 antibody proteins provided herein has an amount of total protein of 25.5-25.8 mg/mL. In certain embodiments, the population has an amount of total protein of about 25.6 mg/mL.

6.7 Biological Properties

In some aspects, the populations of anti-CD20 antibody proteins provided herein possess biological properties detailed in this section. In certain embodiments, the biological properties can be measured using the assays described in Section 6.7(a). The biological properties of the anti-CD20 antibody protein compositions provided herein are described in Section 6.7(b).

(a) Assays (i) Cell-Based Antibody-Dependent Cellular Cytotoxicity (ADCC)

In certain embodiments, the cell-based ADCC assay uses Raji cells as target cells. In certain embodiments, the Raji cells express CD20. In certain embodiments, the cell-based ADCC assay uses effector cells selected from CD16 effector cells and primary NK cells. In certain embodiments, the cell-based ADCC assay uses Raji cells as target cells and KILR CD16a effector cells effector cells. In certain embodiments, the cell-based ADCC assay uses Raji cells as target cells and primary NK cells as effector cells. In certain embodiments, the KILR CD16a effector cells are single donor-derived human CD8+T-lymphocytes engineered to express CD16/FcγRIII on their plasma membrane surface.

In certain embodiments, the cell-based ADCC assay uses target cell lysis as the read out. In certain embodiments, the target cell lysis is quantified using CYTOTOX GLO™ luminescent cytotoxicity assay (Promega). In certain embodiments, the cell-based ADCC assay shows relative potency of the population against a commercial reference standard. In certain embodiments, the cell-based ADCC assay produces a dose-response curve and an EC50 value. In certain embodiments, a composition or population of anti-CD20 antibody proteins provided herein performs in a cell-based ADCC using CD16 effector cells at more than 100% of that of commercial reference standard RS-117808.

In certain embodiments, the ADCC activity can be measured using a CD16 activity assay. In certain embodiments, the CD16 activity assay assesses ADCC activity using a surrogate read-out. In certain embodiments, the CD16 activity assay uses WIL2-S as target cells. In certain embodiments, the effector cells used are a stably transformed Jurkat cell line expressing a chimeric molecule comprising of the extracellular domain of FcγRIIIa joined to the transmembrane and intracellular domains of the gamma chain of the mast cell/basophil Fc receptor for IgE. In certain embodiments, cells are combined and treated with a serial dilution of the anti-CD20 antibody in the presence of PMA (Phorbol 12-Myristate 13-Acetate). In certain embodiments, the activation of the effector cells induces the release of IL-2, which is measured by a commercial ELISA kit. In certain embodiments, the potency is reported as a percentage relative to a reference standard.

In certain embodiments, the population has a relative potency of 106 to 126% in a CD16 activity assay compared to a commercial reference standard. In certain embodiments, the population has a relative potency of about 115% in a CD16 activity assay compared to a commercial reference standard. In certain embodiments, the commercial reference standard is RS-117808.

In certain embodiments, the cell-based ADCC assay uses the following assay procedures. Eight-point dilution series of the Reference Standard, QC Reference Control, and Test Materials are used in the concentration range of 250.00 pg/mL to 0.04 pg/mL (250, 50, 16.7, 1.9, 0.6, 0.2, 0.04 pg/mL). Two independent preparations of the materials are prepared and assayed across duplicate plates. Assay controls are prepared in triplicates and include: Target Cells Alone Control, Target Cells Death Control, Effector Cells Alone Control, and Effector & Target Cells Control. KILR cells are obtained from Eurofins. They come from a master cell bank made from a unique human donor. A Master and Working cell bank system and qualification protocol allows the vendor to create many thousands of vials in a reproducible manner and TG maintains a secure supply of this critical reagent. Procedures, such as incoming material qualification process, provide assurance that highly reproducible cells are used in every assay. KILR cells are thawed and cultured at $1\times10^6$ cells/mL in media supplemented with IL-2, and are rested for a minimum of 6 days before use and are not be used beyond 14 days post thaw. To perform the KILR ADCC assay, Raji cells, also managed through a master and working cell banking system, are seeded at $1\times10^5$ cells/mL, and reference standard, internal assay control, and testing samples dilutions are added to the Raji cells. KILR Effector cells are seeded at $5\times10^5$ cells/mL to a final effector: target (E:T) ratio of 5:1. Cells are cultured at 36±1° C., 5±1% $CO_2$ for 18 to 22 hours. At the end of the incubation, a CYTO-TOX GLO' preparation is added, and plates are incubated for 30±10 minutes. The plates are read using the SPECTRA-MAX® plate reader. SOFTMAX® PRO is used to analyze the data with weighted nonlinear regression using a 4-parameter logistic fit. The resulting data is evaluated using the SOFTMAX® PRO software for potency against the reference standard. Representative reference standard and sample dose response curves are shown. Results are reported as percentage potency relative to the primary reference standard or its derivative.

In certain embodiments, the cell-based ADCC assay is used as a potency assay for batch release. In certain embodiments, the cell-based ADCC assay is used as a potency assay for stability testing. In certain embodiments, the cell-based ADCC assay is used as a potency assay in the manufacturing quality controls and processes. In certain embodiments, the cell-based ADCC assay is used in comparison studies (for example, in research and development or clinical studies).

In certain embodiments, the higher potency of the population in a cell-based ADCC assay is related to the lower level of fucose content in the N-glycan profile of the population. In certain embodiments, the higher potency of the population in a cell-based ADCC assay is due to the lower level of fucose content in the N-glycan profile of the population.

(ii) Antibody-Dependent Cellular Phagocytosis (ADCP)

In certain embodiments, the antibody-dependent cellular phagocytosis (ADCP) activity can be measured using CD20 expressing Daudi cells as target cells (labeled by PKH26). In certain embodiments, human monocytes are isolated from PBMC and differentiated in vitro using GM-CSF to yield macrophages. In certain embodiments, macrophages are co-cultured with PKH26-labeled target cells previously incubated with serial diluted anti-CD20 antibody samples. In certain embodiments, target cell phagocytosis was assessed by flow cytometry. In certain embodiments, the dose response curves, as well as calculated IC50s of the samples tested can be shown.

(iii) Complement Dependent Cytotoxicity (CDC)

In certain embodiments, the cell-based CDC assay uses Jeko-1 cells as target cells and rabbit compliment system. In certain embodiments, the cell-based CDC assay uses Raji cells as target cells and human complement system. In certain embodiments, the cell-based CDC assay uses target cell lysis as the read out.

In certain embodiments, the cell-based CDC assay uses the following assay procedures. Nine-point dilution series of the Reference Standard, QC Reference Control, and Test Materials are used in the concentration range of 10,000 ng/mL to 10.42 ng/mL (10,000.00, 3333.33, 1666.67, 833.33, 416.67, 208.33, 104.17, 52.08, 10.42 ng/mL). Two independent preparations of the materials are prepared and assayed across duplicate plates. Assay negative controls are prepared in triplicates and include target cells and complement control and target cells alone control. In this assay, Jeko-1 cells, obtained from the ATCC and maintained through a master banking system, are seeded at $3\times10^5$ cells/mL and incubated for 60-90 minutes. Reference standard, internal assay control, and test samples diluted in duplicate in cell culture medium are added. Complement is then added to the wells and the plates are incubated for approximately 2 hours at 36° C.±1° C. followed by 25±5 minutes at room temperature. Controls include a target cells with complement only control and a target cell only control to provide a basal level of target cell viability over the course of the assay. The CELL TITER-GLO™ luminescent cell viability reagent is then added and incubated an additional 30±10 minutes at room temperature. At the end of the assay, the plates are read using a SPECTRAMAX® M5 plate reader. SOFTMAX® PRO data analysis software is used to analyze the data with weighted nonlinear regression using a 4-parameter logistic fit. The resulting data are evaluated using the SOFTMAX® PRO software for potency against the reference standard. Results are reported as % potency relative to the reference standard. Representative reference standard and sample dose response curves are shown.

(iv) CD20 Binding Activity

In certain embodiments, the cell-based CD20 binding assay uses Jeko-1 cells and an MSD assays. In certain embodiments, the cell-based CD20 binding assay produces a dose dependent binding curve and a EC50 value.

In certain embodiments, the cell-based CD20 binding assay uses the following assay procedures. Eight-point dilution series of the Reference Standard, QC Reference Control, and Test Materials are prepared in the concentration range of 40,000.00 µg/mL to 0.23 ng/mL (40,000.00, 4,000.00, 1,000.00, 333.30, 111.10, 37.00, 4.60, 0.23 ng/mL). Two independent preparations of the Test Material are prepared for each 2-plate Test Material assessment. Assay controls include No cell control (Reference Standard/Test Material dilution+detection reagent, omitting cells) and Cell only control (Cells+detection reagent, omitting Reference Standard/Test Material). Jeko-1 cells are seeded onto MSD high bind plate in PBS at $3\times10^5$ cells per mL, in a final volume of 100 µL per well, and incubated at 35 to 37° C. for 2 hours±10 minutes. Unbound cells are removed by a PBS wash, the plates are blocked with 45% FBS. Fifty µL of Reference Standard, QC Reference Control, or Test Materials dilutions are added, and the plate is incubated at room temperature for 1 hour±10 min while shaking. Following incubation and three PBS washes, 50 µL anti-human Fc detection antibody conjugated with STREP-SULFOTAG is added and incubated for 1 hour±5 minutes at room temperature while shaking. The plates are washed again with PBS and 150 µL of the MesoScale read buffer, containing tripropylamine (TPA), is added as a co-reactant for light generation for an electrochemiluminescence read out. Plates are read immediately on a MSD Reader using Workbench 4.0. The resulting data are evaluated using the PLA software and analyzed using a constrained 4 parameter logistic model to generate a relative binding, 95% confidence intervals and results relative to the reference standard. Binding activity results are reported as percentage potency relative to the reference standard. Representative reference standard and testing sample dose response curves, from which relative potency test result is calculated.

(v) FcγRIIIa 158V and FcγRIIIa 158F Binding Activity

In certain embodiments, the FcγRIIIa binding assay uses Surface Plasmon Resonance (SPR). In certain embodiments, the FcγRIIIa binding assay produces sensorgrams showing a dose dependent binding, saturation, and dissociation. In certain embodiments, the FcγRIIIa binding assay calculates dissociation constant by the on and off rate and steady state kinetics. In certain embodiments, the binding affinity to FcγRIIIa 158V of the population is approximately one order of magnitude higher than binding affinity to FcγRIIIa 158F of the population. In certain embodiments, the binding affinity to FcγRIIIa 158V of the population is significantly higher than RITUXAN® (rituximab). In certain embodiments, the binding affinity to FcγRIIIa 158F of the population is significantly higher than RITUXAN®. In certain embodiments, the binding affinities of the population to both FcγRIIIa 158V and FcγRIIIa 158F are significantly higher than RITUXAN®.

In certain embodiments, the FcγRIIIa binding assay uses the following assay procedure. FcγRIIIa 158V receptor (1.2 µg/ml) is immobilized on the chip surface using covalent amine coupling chemistry. Eight-point dilution series of the Reference Standard, QC Reference Control, and Test Materials are prepared in the concentration range of 2000 nM to nM with a dilution factor of 2. Independent duplicates of sample dilutions are injected over the chip, followed by surface regeneration between each cycle. The binding is measured in response units (RU). The kinetics of the binding reaction is determined by measuring changes in SPR due to the increase in mass in the close proximity to the biosensor chip surface. Change in the mass of the complex as a function of time is visualized as a sensorgram. The equilibrium dissociation constants (KD) and the relative affinities of each sample relative to the Reference Standard are determined for each receptor. The rates of change of the SPR signal are analyzed using a 1:1 Langmuir model for FcγRIIIa 158V variant to yield apparent rate constants for the association and dissociation phases of the reaction, and equilibrium dissociation constants. KD is determined using steady state affinity for the FcγRIIIa 158F variant. The binding signals are exported into PLA to determine the relative binding response. Results are reported as % potency relative to the reference standard for each FcγRIIIa variant, 158V and 158F.

(vi) C1q Binding Activity

In certain embodiments, the C1q binding activity can be as measured using ELISA. In certain embodiments, the C1q binding activity can be as measured using the following assay procedure. A 7-point dilution series of the reference standard, QC reference control, and test materials are prepared in the concentration range of 15.00 pg/mL to 0.12 pg/mL. Reference standard, QC reference control, and test materials dilutions are coated onto an ELISA plates, and the plates incubated for 1 hour±30 minutes at room temperature (shaking 150 to 200 rpm). After coating, the plates are washed (3× with PBS/0.05% Tween), blocked (with 1% BSA and incubated for 1 hour±10 minutes at room temperature and shaking 150 to 200 rpm), and washed (3× with PBS/0.05% Tween). C1q that has been conjugated with peroxidase is then added, and the plates incubated for 1.5 hours±30 minutes at room temperature (shaking 150 to 200 rpm). After incubation and washing, a tetramethylbenzidine (TMB) substrate solution is added and plates incubated at room temperature for 7 minutes (−1 minute/+30 seconds). This produces a colorimetric reaction which is proportional to the level of C1q bound. The reaction is stopped with the addition of 1M sulfuric acid and the color is measured at 450 nm using a Molecular Devices SPECTRAMAX® microplate reader. SOFTMAX® PRO is used to analyze the data with weighted nonlinear regression using a 4-parameter logistic fit. The resulting data are evaluated using the SOFTMAX® PRO software for potency against the reference standard. C1q binding activity results are reported as percentage potency relative to the reference standard. Representative dose response curves from one assay can be shown.

(vii) B-Cell Depletion Activity

In certain embodiments, the B-cell depletion activity can be measured in a human whole blood B-cell depletion assay. In certain embodiments, the B-cell depletion activity can be measured in an autologous normal human whole blood B-cell depletion assay. In certain embodiments, the B-cell depletion can be measured by displaying cells in the CD45-positive lymphocyte gate, and enumerating CD3-positive T cells, CD19-positive B-cells, and CD20-positive B-cells. In certain embodiments, percent of B-cell depletion (100−([100/B-/T-cell ratio in sample without antibody]×[B-/T-cell ratio in sample containing antibody])) can be calculated and plotted against sample concentration.

In certain embodiments, the B-cell depletion activity can be measured using blood from three healthy donor(s). In certain embodiments, the B-cell depletion can be measured by displaying cells in the CD45-positive lymphocyte gate, and enumerating CD3-positive T cells, CD19-positive B-cells, and CD20-positive B-cells.

(b) Biological Properties

In certain embodiments, the biological properties of a composition or population of anti-CD20 antibody proteins provided herein can be measured and described in an assay described in Section 6.7(a) and with the use of a comparison with a reference standard. In certain embodiments, the reference standard is a commercial reference standard.

In certain embodiments, the reference standard is an anti-CD20 antibody. In certain embodiments, the reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab).

In certain embodiments, the commercial reference standard is RS-117808. In certain embodiments, the populations of anti-CD20 antibody proteins provided herein possess the biological properties as shown in Table 7. RS-117808 ("antibody Ublituximab (TG-1101)") was deposited according to the terms of the Budapest Treaty at the American Type Culture Collection (ATCC), located at 10801 University Boulevard, Manassas, VA 20110, received by the ATCC on Apr. 15, 2022, and assigned unofficial patent deposit number PTA-127294.

TABLE 7

Biological Properties in Comparison to Reference Standard

| Property | Percentage Against Reference Standard |
| --- | --- |
| ADCC potency assay | 50 to 180% |
| CDC activity by cell-based bioassay | 55 to 142% |
| CD20 binding activity by cell-based bioassay | 70 to 143% |
| FcγRIIIa-158V binding by surface plasmon resonance | 65 to 145% |
| C1q binding by ELISA | 70 to 125% |
| CD16 Activity | 71 to 150% |

(i) Cell-Based Antibody-Dependent Cellular Cytotoxicity (ADCC)

In certain embodiments, a composition or population of anti-CD20 antibody proteins provided herein performs in a cell-based ADCC using CD16 effector cells assay (see Section 6.7(a)(i)) with are relevant potency that is at least 110%, 120%, 130%, 140%, 150%, 160%, 170%, 180%, 190%, or at least 200% of that of the commercial reference standard RS-117808. In certain embodiments, a composition or population of anti-CD20 antibody proteins provided herein performs in a cell-based ADCC using CD16 effector cells assay (see Section 6.7(a)(i)) with are relevant potency that is at least 110%, 120%, 130%, 140%, 150%, 160%, 170%, 180%, 190%, 200%, 5-fold, 10-fold, 15-fold, 20-fold, 30-fold, 50-fold, 75-fold, 100-fold, 125-fold, 150-fold, or at least 200-fold of that of the commercially available RITUXAN® (Genentech/Biogen).

In certain embodiments, the population induces cytotoxicity in a cell-based antibody-dependent cellular cytotoxicity (ADCC) assay. In certain embodiments, the population induces greater cytotoxicity in an ADCC assay compared to a commercial reference standard.

In certain embodiments, the population induces greater cytotoxicity in an ADCC assay compared to an anti-CD20 antibody. In certain embodiments, the population induces greater cytotoxicity in an ADCC assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population induces greater cytotoxicity in an ADCC assay compared to GAZYVA (obinutuzumab). In certain embodiments, the population induces greater cytotoxicity in an ADCC assay compared to ARZERRA (ofatumumab). In certain embodiments, the population induces greater cytotoxicity in an ADCC assay compared to RITUXAN (rituximab). In certain embodiments, the population induces greater cytotoxicity in an ADCC assay compared to veltuzumab (IMMU-106). In certain embodiments, the population induces greater cytotoxicity in an ADCC assay compared to ZEVALIN (ibritumomab tiuxetan). In certain embodiments, the population induces greater cytotoxicity in an ADCC assay compared to OCREVUS (ocrelizumab).

In certain embodiments, the population has a relative potency of at least 1000%, 750%, 500%, 250%, 100%, 75%, 50%, or at least 25% in a cell-based ADCC assay compared to a commercial reference standard. In certain embodiments, the population has a relative potency of at least 110%, 120%, 130%, 140%, 150%, 160%, 170%, 180%, 190%, 200%, 5-fold, 10-fold, 20-fold, 30-fold, 50-fold, 75-fold, 100-fold, 125-fold, 150-fold, or at least 200-fold in a cell-based ADCC assay compared to a commercial reference standard. In certain embodiments, the population has a relative potency of at least more than 100% in a cell-based ADCC assay compared to a commercial reference standard. In certain embodiments, the population has a relative potency of more than 100% in a cell-based ADCC assay compared to a commercial reference standard.

In certain embodiments, the population has a relative potency of between at least 20%, 30%, 40%, 50%, 60%, 70%, 80%, 90%, 100%, 200%, 500%, 750% 1000%, 15-fold, 20-fold, 30-fold, 50-fold, 75-fold, 100-fold, 125-fold, 150-fold, or at least 200-fold and at most 30%, 40%, 50%, 60%, 70%, 80%, 90%, 100%, 200%, 500%, 750%, 1000%, 15-fold, 20-fold, 50-fold, 75-fold, 100-fold, 125-fold, 150-fold, 200-fold or at most 300-fold in a cell-based ADCC assay compared to a commercial reference standard. In certain embodiments, the population has a relative potency of between 5% and 50%, 50% and 100%, 100% and 500%, 500% and 1000%, 10-fold and 50-fold, 50-fold and 100-fold, 100-fold and 150-fold, or between 150-fold and 300-fold in a cell-based ADCC assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative potency of about 38% to about 3-fold in a cell-based ADCC assay compared to GAZYVA (obinutuzumab). In certain embodiments, the population has a relative potency of about 10-fold to about 31-fold in a cell-based ADCC assay compared to ARZERRA (ofatumumab). In certain embodiments, the population has a relative potency of about 28-fold to about 2250-fold in a cell-based ADCC assay compared to RITUXAN (rituximab). In certain embodiments, the population has a relative potency of about 25-fold in a cell-based ADCC assay compared to OCREVUS (ocrelizumab).

In certain embodiments, the population has a relative potency of 60 to 200%, 70 to 190%, 80% to 180%, 85 to 170%, or 90 to 163% in a cell-based ADCC assay compared to a commercial reference standard. In certain embodiments, the population has a relative potency of to 163% in a cell-based ADCC assay compared to a commercial reference standard. In certain embodiments, the population has a relative potency of about 117% in a cell-based ADCC assay compared to a commercial reference standard. In certain embodiments, the commercial reference standard is RS-117808.

In certain embodiments, the EC50 value for the ADCC potency as measured in a cell-based ADCC assay of the population is between 2 and 6 pg/mL. In certain embodiments, the EC50 value for the ADCC potency as measured in a cell-based ADCC assay of the population is between 0.2 and 20 pg/mL, 0.3 and 18 pg/mL, 0.4 and 15 pg/mL, 0.5 and 12 pg/mL, 0.6 and 10 pg/mL, 0.7 and 9 pg/mL, 0.8 and 8 pg/mL, 0.9 and 7 pg/mL, or 1 and 6 pg/mL. In certain embodiments, the EC50 value for the ADCC potency is the average EC50 value calculated from the EC50 values obtained in two, three, four, five, six, seven, eight, nine, ten, fifteen, twenty, thirty, forty, fifty, sixty or more repeated cell-based ADCC assays. In certain embodiments, the EC50 value for the ADCC potency as measured in a cell-based ADCC assay (e.g., using the Eurofins/DiscoverX KILR CD16a effector cells) of the population is about 5.45 pg/mL. In certain embodiments, the EC50 value for the ADCC potency as measured in a cell-based ADCC assay (e.g., using the Eurofins/DiscoverX KILR CD16a effector cells) of the population is about 2.42 pg/mL.

(ii) Antibody-Dependent Cellular Phagocytosis (ADCP)

In certain embodiments, the population induces antibody-dependent cellular phagocytosis (ADCP). In certain embodiments, the population induces greater phagocytosis in an ADCP assay compared to a commercial reference standard. In certain embodiments, the population induces greater phagocytosis in an ADCP assay compared to an anti-CD20 antibody.

In certain embodiments, the population induces greater phagocytosis in an ADCP assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population induces phagocytosis in an ADCP assay compared to GAZYVA (obinutuzumab). In certain embodiments, the population induces greater cytotoxicity in a CDC assay compared to ARZERRA (ofatumumab). In certain embodiments, the population induces greater phagocytosis in an ADCP assay compared to RITUXAN (rituximab). In certain embodiments, the population induces greater cytotoxicity in a CDC assay compared to veltuzumab (IMMU-106). In certain embodiments, the population induces greater phagocytosis in an ADCP assay compared to ZEVALIN (ibritumomab tiuxetan). In certain embodiments, the population induces greater phagocytosis in an ADCP assay compared to OCREVUS (ocrelizumab).

In certain embodiments, the population has a relative potency of at least 1000%, 750%, 500%, 250%, 100%, 75%, 50%, or at least 25% in an ADCP assay compared to a commercial reference standard. In certain embodiments, the population has a relative potency of at least 150%, 160%, 170%, 180%, 190%, 200%, 5-fold, 10-fold, 15-fold, 20-fold, 30-fold, 50-fold, 75-fold, 100-fold, 125-fold, 150-fold, or at least 200-fold in an ADCP assay compared to a commercial reference standard. In certain embodiments, the population has a relative potency of at least more than 100% in an ADCP assay compared to a commercial reference standard. In certain embodiments, the population has a relative potency of more than 100% in an ADCP assay compared to a commercial reference standard.

In certain embodiments, the population has a relative potency of between at least 50%, 60%, 70%, 80%, 90%, 100%, 200%, 500%, 750% 1000%, 15-fold, 20-fold, 30-fold, 50-fold, 75-fold, 100-fold, 125-fold, 150-fold, or at least 200-fold and at most 60%, 70%, 80%, 90%, 100%, 200%, 500%, 750%, 1000%, 15-fold, 20-fold, 30-fold, 50-fold, 75-fold, 100-fold, 125-fold, 150-fold, 200-fold or at most 300-fold in an ADCP assay compared to a commercial reference standard. In certain embodiments, the population has a relative potency of between 5% and 50%, 50% and 100%, 100% and 500%, 500% and 1000%, 10-fold and 50-fold, 50-fold and 100-fold, 100-fold and 150-fold, or between 150-fold and 300-fold in an ADCP assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative potency of about 7-fold in an ADCP assay compared to ARZERRA (ofatumumab). In certain embodiments, the population has a relative potency of about 15-fold in an ADCP assay compared to RITUXAN (rituximab). In certain embodiments, the population has a relative potency of about 23-fold in an ADCP assay compared to GAZYVA (obinutuzumab).

In certain embodiments, the EC50 value for the ADCP potency as measured in an ADCP assay of the population is between 0.1 and 1 ng/mL. In certain embodiments, the EC50 value for the ADCP potency as measured in an ADCP assay of the population is between 1 and 2 and 9, 3 and 8, 4 and 7, or 5 and 6 ng/mL. In certain embodiments, the EC50 value for the ADCP potency as measured in an ADCP assay of the population is between 0.05 and 20 ng/mL, and 19 ng/mL, 0.15 and 18 ng/mL, 0.2 and 18 ng/mL, 0.25 and 15 ng/mL, 0.3 and 12 ng/mL, and 10 ng/mL, 0.3 and 9 ng/mL, 0.3 and 8 ng/mL, 0.3 and 7 ng/mL, or 0.3 and 6 ng/mL. In certain embodiments, the EC50 value for the ADCP potency is the average EC50 value calculated from the EC50 values obtained in two, three, four, five, six, seven, eight, nine, ten, or more repeated ADCP assays. In certain embodiments, the EC50 value for the ADCP potency as measured in an ADCP assay of the population is about 5.50 ng/mL.

(iii) Complement Dependent Cytotoxicity (CDC)

In certain embodiments, the population induces complement dependent cytotoxicity (CDC). In certain embodiments, the population induces greater cytotoxicity in a CDC assay compared to a commercial reference standard. In certain embodiments, the population induces greater cytotoxicity in a CDC assay compared to an anti-CD20 antibody.

In certain embodiments, the population induces greater cytotoxicity in a CDC assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population induces greater cytotoxicity in a CDC assay compared to GAZYVA (obinutuzumab). In certain embodiments, the population induces greater cytotoxicity in a CDC assay compared to ARZERRA (ofatumumab). In certain embodiments, the population induces greater cytotoxicity in a CDC assay compared to RITUXAN (rituximab). In certain embodiments, the population induces greater cytotoxicity in a CDC assay compared to veltuzumab (IMMU-106). In certain embodiments, the population induces greater cytotoxicity in a CDC assay compared to ZEVALIN (ibritumomab tiuxetan). In certain embodiments, the population induces greater cytotoxicity in a CDC assay assay compared to OCREVUS (ocrelizumab).

In certain embodiments, the population has a relative potency of at least 1000%, 750%, 500%, 250%, 100%, 75%, 50%, 25%, 12%, or at least 5% in a cell-based CDC assay compared to a commercial reference standard. In certain embodiments, the population has a relative potency of at least 110%, 120%, 130%, 140%, 150%, 160%, 170%, 180%, 190%, 200%, 10-fold, 15-fold, 20-fold, 30-fold, 50-fold, 75-fold, 100-fold, 125-fold, 150-fold, or at least 200-fold in a cell-based CDC assay compared to a commercial reference standard. In certain embodiments, the population has a relative potency of at least more than 100% in a cell-based CDC assay compared to a commercial reference standard. In certain embodiments, the population has a relative potency of more than 100% in a cell-based CDC assay compared to a commercial reference standard.

In certain embodiments, the population has a relative potency of between at least 5%, 10%, 20%, 30%, 40%, 50%, 60%, 70%, 80%, 90%, 100%, 200%, 500%, 750% 1000%, 15-fold, 30-fold, 50-fold, 75-fold, 100-fold, 125-fold, 150-fold, or at least 200-fold and at most 10%, 20%, 30%, 40%, 50%, 60%, 70%, 80%, 90%, 100%, 200%, 500%, 750%, 1000%, 15-fold, 30-fold, 50-fold, 75-fold, 100-fold, 125-fold, 150-fold, 200-fold or at most 300-fold in a cell-based CDC assay compared to a commercial reference standard. In certain embodiments, the population has a relative potency of between 5% and 50%, 50% and 100%, 100% and 500%, 500% and 1000%, 10-fold and 50-fold, 50-fold and 100-fold, 100-fold and 150-fold, or between 150-fold and 300-fold in a cell-based CDC assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative potency of about 50% in a cell-based CDC assay compared to ARZERRA (ofatumumab). In certain embodiments, the population has a relative potency of about 37% in a cell-based CDC assay compared to RITUXAN (rituximab). In certain embodiments, the population has a relative potency of about 1.8-fold in a cell-based CDC assay compared to OCREVUS (ocrelizumab).

In certain embodiments, the population has a relative potency of 50 to 150%, 60 to 140%, 70 to 130%, 75 to 120%, or 78 to 116% in a cell-based CDC assay compared to that of a commercial reference standard. In certain embodiments, the population has a relative potency of 78 to 116% in a cell-based CDC assay compared to that of a commercial reference standard. In certain embodiments, the population has a relative potency of 73 to 128% or 74 to 127% in a cell-based CDC assay compared to that of a commercial reference standard. In certain embodiments, the population has a relative potency of about 91% in a cell-based CDC assay compared to that of a commercial reference standard. In certain embodiments, the commercial reference standard is RS-117808.

In certain embodiments, the EC50 value for the CDC potency as measured in a cell-based CDC assay of the population is between 0.4 and 0.7 µg/mL or between 0.4 and 0.6 µg/mL.

In certain embodiments, the EC50 value for the CDC potency as measured in a cell-based CDC assay of the population is between 0.05 and 5 µg/mL, 0.1 and 4 µg/mL, 0.15 and 3 µg/mL, 0.2 and 2 µg/mL, 0.25 and 1 µg/mL, 0.3 and 0.9 µg/mL, 0.3 and 0.8 µg/mL, or 0.3 and 0.7 µg/mL. In certain embodiments, the EC50 value for the CDC potency is the average EC50 value calculated from the EC50 values obtained in two, three, four, five, six, seven, eight, nine, ten, or more repeated cell-based CDC assays. In certain embodiments, the EC50 value for the CDC potency as measured in a cell-based CDC assay of the population is about 0.5 µg/mL.

(iv) CD20 Binding Activity

In certain embodiments, the population possesses CD20 binding activity in a cell-based CD20 binding assay. In certain embodiments, the population possesses greater CD20 binding activity in a cell-based CD20 binding assay compared to a commercial reference standard.

In certain embodiments, the population possesses greater CD20 binding activity in a cell-based CD20 binding assay compared to an anti-CD20 antibody. In certain embodiments, the population possesses greater CD20 binding activity in a cell-based CD20 binding assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population possesses greater CD20 binding activity compared to GAZYVA (obinutuzumab). In certain embodiments, the population possesses greater CD20 binding activity compared to ARZERRA (ofatumumab). In certain embodiments, the population possesses greater CD20 binding activity compared to RITUXAN (rituximab). In certain embodiments, the population possesses greater CD20 binding activity compared to veltuzumab (IMMU-106). In certain embodiments, the population possesses greater CD20 binding activity compared to ZEVALIN (ibritumomab tiuxetan). In certain embodiments, the population induces possesses greater CD20 binding activity compared to OCREVUS (ocrelizumab).

In certain embodiments, the population has a relative potency of at least 1000%, 750%, 500%, 250%, 100%, 75%, 50%, 25%, 12%, or at least 5% in a CD20 binding assay compared to a commercial reference standard. In certain embodiments, the population has a relative potency of at least 110%, 120%, 130%, 140%, 150%, 160%, 170%, 180%, 190%, 200%, 10-fold, 15-fold, 20-fold, 30-fold, 50-fold, 75-fold, 100-fold, 125-fold, 150-fold, or at least 200-fold in a CD20 binding assay compared to a commercial reference standard. In certain embodiments, the population has a relative potency of at least more than 100% in a CD20 binding compared to a commercial reference standard. In certain embodiments, the population has a relative potency of more than 100% in a CD20 binding compared to a commercial reference standard.

In certain embodiments, the population has a relative potency of between at least 5%, 10%, 20%, 30%, 40%, 50%, 60%, 70%, 80%, 90%, 100%, 200%, 500%, 750% 1000%, 15-fold, 30-fold, 50-fold, 75-fold, 100-fold, 125-fold, 150-fold, or at least 200-fold and at most 10%, 20%, 30%, 40%, 50%, 60%, 70%, 80%, 90%, 100%, 200%, 500%, 750%, 1000%, 15-fold, 30-fold, 50-fold, 75-fold, 100-fold, 125-fold, 150-fold, 200-fold or at most 300-fold in a CD20 binding assay compared to a commercial reference standard. In certain embodiments, the population has a relative potency of between 5% and 50%, 50% and 100%, 100% and 500%, 500% and 1000%, 10-fold and 50-fold, 50-fold and 100-fold, 100-fold and 150-fold, or between 150-fold and 300-fold in a CD20 binding assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative potency of about 1.6-fold to about 5.8-fold in a CD20 binding assay compared to GAZYVA (obinutuzumab). In certain embodiments, the population has a relative potency of about 81% to about 4.3-fold in a CD20 binding assay compared to ARZERRA (ofatumumab). In certain embodiments, the population has a relative potency of about 1.6-fold to about 4.1-fold in a CD20 binding assay compared to RITUXAN (rituximab).

In certain embodiments, the population has a relative potency of 50 to 150%, 60 to 140%, 70 to 130%, 80 to 120%, 90 to 120%, or 92 to 118% in a cell-based CD20 binding activity bioassay compared to that of a commercial reference standard. In certain embodiments, the population has a relative potency of 92 to 118% in a cell-based CD20 binding activity bioassay compared to that of a commercial reference standard. In certain embodiments, the population has a relative potency of 82 to 138% in a cell-based CD20 binding activity bioassay compared to that of a commercial reference standard. In certain embodiments, the population has a relative potency of about 109% in a cell-based CD20 binding activity bioassay compared to that of a commercial reference standard. In certain embodiments, the commercial reference standard is RS-117808.

In certain embodiments, the EC50 value for the CD20 binding potency as measured in a cell-based CD20 binding activity bioassay of the population is between 0.05 and 0.1 pg/mL. In certain embodiments, the EC50 value for the CD20 binding potency as measured in a cell-based CD20 binding activity bioassay of the population is between 0.01 and 0.5 pg/mL, 0.02 and pg/mL, 0.03 and 0.3 pg/mL, 0.04 and 0.2 pg/mL, or 0.05 and 0.1 pg/mL. In certain embodiments, the EC50 value for the CD20 binding potency is the average EC50 value calculated from the EC50 values obtained in two, three, four, five, six, seven, eight, nine, ten, or more repeated cell-based CD20 binding activity bioassays. In certain embodiments, the EC50 value for the CD20 binding potency as measured in a cell-based CD20 binding activity bioassay of the population is about 0.093 pg/mL. In certain embodiments, the EC50 value for the CD20 binding potency as measured in a cell-based CD20 binding activity bioassay of the population is about 0.063 µg/mL.

(v) FcγRIIIa 158V and FcγRIIIa 158F Binding Activity

In certain embodiments, the population possesses FcγRIIIa 158V binding activity in an FcγRIIIa binding assay. In certain embodiments, the population possesses greater FcγRIIIa 158V binding activity in an FcγRIIIa binding assay compared to a commercial reference standard.

In certain embodiments, the population possesses greater FcγRIIIa 158V binding activity in an FcγRIIIa binding assay compared to an anti-CD20 antibody. In certain embodiments, the population possesses greater CD20 binding activity in a cell-based CD20 binding assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population possesses greater FcγRIIIa 158V binding activity in an FcγRIIIa binding assay compared to GAZYVA (obinutuzumab). In certain embodiments, the population possesses greater FcγRIIIa 158V binding activity in an FcγRIIIa binding assay compared to ARZERRA (ofatumumab). In certain embodiments, the population possesses greater FcγRIIIa 158V binding activity in an FcγRIIIa binding assay compared to RITUXAN (rituximab). In certain embodiments, the population possesses greater FcγRIIIa 158V binding activity in an FcγRIIIa binding assay compared to veltuzumab (IMMU-106). In certain embodiments, the population possesses greater FcγRIIIa 158V binding activity in an FcγRIIIa binding assay compared to ZEVALIN (ibritumomab tiuxetan). In certain embodiments, the population possesses greater FcγRIIIa 158V binding activity in an FcγRIIIa binding assay compared to OCREVUS (ocrelizumab).

In certain embodiments, the population has a relative FcγRIIIa 158V binding activity of at least 1000%, 750%, 500%, 250%, 100%, 75%, or at least 50% in an FcγRIIIa binding assay compared to a commercial reference standard. In certain embodiments, the population has a relative FcγRIIIa 158V binding activity of at least 110%, 120%, 130%, 140%, 150%, 160%, 170%, 180%, 190%, 200%, 5-fold, 10-fold, 15-fold, 20-fold, 30-fold, 50-fold, 75-fold, 100-fold, 125-fold, 150-fold, or at least 200-fold in an FcγRIIIa binding assay compared to a commercial reference standard. In certain embodiments, the population has a relative FcγRIIIa 158V binding activity of at least more than 100% in a cell-based ADCC assay compared to a commercial reference standard. In certain embodiments, the population has a relative relative FcγRIIIa 158V binding activity of more than 100% in an FcγRIIIa binding assay compared to a commercial reference standard.

In certain embodiments, the population has a relative FcγRIIIa 158V binding activity of at least 50%, 60%, 70%, 80%, 90%, 100%, 200%, 500%, 750% 1000%, 15-fold, 20-fold, 30-fold, 50-fold, 75-fold, 100-fold, 125-fold, 150-fold, or at least 200-fold and at most 60%, 70%, 80%, 90%, 100%, 200%, 500%, 750%, 1000%, 15-fold, 20-fold, 30-fold, 50-fold, 75-fold, 100-fold, 125-fold, 150-fold, 200-fold or at most 300-fold in an FcγRIIIa binding assay compared to a commercial reference standard. In certain embodiments, the population has a relative FcγRIIIa 158V binding activity of at least between 50% and 100%, 100% and 500%, 500% and 1000%, and 50-fold, 50-fold and 100-fold, 100-fold and 150-fold, or between 150-fold and 300-fold in an FcγRIIIa binding assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative FcγRIIIa 158V binding activity of about 3.8-fold in an FcγRIIIa binding assay compared to GAZYVA (obinutuzumab). In certain embodiments, the population has a relative FcγRIIIa 158V binding activity of about 25.6-fold in an FcγRIIIa binding assay compared to ARZERRA (ofatumumab). In certain embodiments, the population has a relative FcγRIIIa 158V binding activity of about 18.7-fold in an FcγRIIIa binding assay compared to RITUXAN (rituximab). In certain embodiments, the population has a relative FcγRIIIa 158V binding activity of about 16-fold in an FcγRIIIa binding assay compared to OCREVUS (ocrelizumab).

In certain embodiments, the population possesses FcγRIIIa 158F binding activity in a FcγRIIIa binding assay. In certain embodiments, the population possesses greater FcγRIIIa 158F binding activity in an FcγRIIIa binding assay compared to a commercial reference standard. In certain embodiments, the population possesses greater FcγRIIIa 158F binding activity in an FcγRIIIa binding assay compared to an anti-CD20 antibody. In certain embodiments, the population possesses greater CD20 binding activity in a cell-based CD20 binding assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population possesses greater FcγRIIIa 158F binding activity in an FcγRIIIa binding assay compared to GAZYVA (obinutuzumab). In certain embodiments, the population possesses greater FcγRIIIa 158F binding activity in an FcγRIIIa binding assay compared to ARZERRA (ofatumumab). In certain embodiments, the population possesses greater FcγRIIIa 158F binding activity in an FcγRIIIa binding assay compared to RITUXAN (rituximab). In certain embodiments, the population possesses greater FcγRIIIa 158F binding activity in an FcγRIIIa binding assay compared to veltuzumab (IMMU-106). In certain embodiments, the population possesses greater FcγRIIIa 158F binding activity in an FcγRIIIa binding assay compared to ZEVALIN (ibritumomab tiuxetan). In certain embodiments, the population possesses greater FcγRIIIa 158F binding activity in an FcγRIIIa binding assay compared to OCREVUS (ocrelizumab).

In certain embodiments, the population has a relative FcγRIIIa 158F binding activity of at least 1000%, 750%, 500%, 250%, 100%, 75%, or at least 50% in an FcγRIIIa binding assay compared to a commercial reference standard. In certain embodiments, the population has a relative FcγRIIIa 158F binding activity of at least 110%, 120%, 130%, 140%, 150%, 160%, 170%, 180%, 190%, 200%, 5-fold, 10-fold, 15-fold, 20-fold, 30-fold, 50-fold, 75-fold, 100-fold, 125-fold, 150-fold, or at least 200-fold in an FcγRIIIa binding assay compared to a commercial reference standard. In certain embodiments, the population has a relative FcγRIIIa 158F binding activity of at least more than 100% in a cell-FcγRIIIa binding assay compared to a commercial reference standard. In certain embodiments, the population has a relative relative FcγRIIIa 158F binding activity of more than 100% in an FcγRIIIa binding assay compared to a commercial reference standard.

In certain embodiments, the population has a relative FcγRIIIa 158F binding activity of at least 50%, 60%, 70%, 80%, 90%, 100%, 200%, 500%, 750% 1000%, 15-fold, 20-fold, 30-fold, 50-fold, 75-fold, 100-fold, 125-fold, 150-fold, or at least 200-fold and at most 60%, 70%, 80%, 90%, 100%, 200%, 500%, 750%, 1000%, 15-fold, 20-fold, 30-fold, 50-fold, 75-fold, 100-fold, 125-fold, 150-fold, 200-fold or at most 300-fold in an FcγRIIIa binding assay compared to a commercial reference standard. In certain embodiments, the population has a relative FcγRIIIa 158F binding activity of at least between 5% and 50%, 50% and 100%, 100% and 500%, 500% and 1000%, 10-fold and 50-fold, 50-fold and 100-fold, 100-fold and 150-fold, or between 150-fold and 300-fold in an FcγRIIIa binding assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative FcγRIIIa 158F binding activity of about 2.6-fold in an FcγRIIIa binding assay compared to GAZYVA (obinutuzumab). In certain embodiments, the population has a relative FcγRIIIa 158F binding activity of about 21.8-fold in an FcγRIIIa binding assay compared to ARZERRA (ofatumumab). In certain embodiments, the population has a relative FcγRIIIa 158F binding activity of about 10.2-fold in an FcγRIIIa binding assay compared to RITUXAN (rituximab). In certain embodiments, the population has a relative FcγRIIIa 158F binding activity of about 9.9-fold in an FcγRIIIa binding assay compared to OCREVUS (ocrelizumab). In certain embodiments, the population has significantly higher binding affinity to FcγRIIIa 158V or FcγRIIIa 158F than rituximab.

In certain embodiments, the population has a relative potency of 20 to 300%, 30 to 250%, 40% to 220%, or 50 to 200% in a cell-based FcγRIIIa binding assay compared to a commercial reference standard. In certain embodiments, the population has a relative potency of to 200% in a cell-based FcγRIIIa binding assay compared to a commercial reference standard. In certain embodiments, the population has a relative potency of 76 to 130% or 82 to 130% in a cell-based FcγRIIIa 158V binding assay compared to a commercial reference standard. In certain embodiments, the commercial reference standard is RS-117808.

In certain embodiments, the population has a KD value 55 to 70 nM in an FcγRIIIa-158V binding assay as measured by surface plasmon resonance. In certain embodiments, the population has a KD value 10 to 100 nM, 15 to 90 nM, 10 to 80 nM, or 30 to 70 nM in an FcγRIIIa-158V binding assay as measured by surface plasmon resonance. In certain embodiments, the population has a KD value 30 to 70 nM in an FcγRIIIa-158V binding assay as measured by surface plasmon resonance. In certain embodiments, the KD value is the average KD value calculated from the KD values obtained in two, three, four, five, six, seven, eight, nine, ten, or more repeated FcγRIIIa-158V binding assays. In certain embodiments, the population has a KD value about 59 nM in an FcγRIIIa-158V binding assay as measured by surface plasmon resonance. In certain embodiments, the population has a KD value about 64.1 nM in an FcγRIIIa-158V binding assay as measured by surface plasmon resonance.

In certain embodiments, the population has a KD value 600 to 800 nM in an FcγRIIIa 158F binding assay as measured by surface plasmon resonance. In certain embodiments, the population has a K D value 100 to 2000 nM, 200 to 1800 nM, 300 to 1700 nM, 400 to 1600 nM, 500 to 1500 nM, 500 to 1200 nM, 600 to 1000 nM, or 600 to 800 nM in an FcγRIIIa 158F binding assay as measured by surface plasmon resonance. In certain embodiments, the population has a KD value 500 to 1000 nM in an FcγRIIIa 158F binding assay as measured by surface plasmon resonance. In certain embodiments, the KD value is the average KD value calculated from the KD values obtained in two, three, four, five, six, seven, eight, nine, ten, or more repeated FcγRIIIa-158V binding assays. In certain embodiments, the population has a KD value 760 nM in an FcγRIIIa 158F binding assay as measured by surface plasmon resonance. In certain embodiments, the population has a KD value 680.3 nM in an FcγRIIIa 158F binding assay as measured by surface plasmon resonance.

(vi) C1q Binding Activity

In certain embodiments, the population possesses C1q binding activity as measured by ELISA. In certain embodiments, the population possesses greater C1q binding activity as measured by ELISA compared to a commercial reference standard.

In certain embodiments, the population possesses greater C1q binding activity as measured by ELISA compared to an anti-CD20 antibody. In certain embodiments, the population possesses greater C1q binding activity as measured by ELISA compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, possesses greater C1q binding activity as measured by ELISA compared to GAZYVA (obinutuzumab). In certain embodiments, possesses greater C1q binding activity as measured by ELISA compared to ARZERRA (ofatumumab). In certain embodiments, possesses greater C1q binding activity as measured by ELISA compared to RITUXAN (rituximab). In certain embodiments, the population possesses greater C1q binding activity as measured by ELISA compared to veltuzumab (IMMU-106). In certain embodiments, the population possesses greater C1q binding activity as measured by ELISA compared to compared to ZEVALIN (ibritumomab tiuxetan). In certain embodiments, the population induces possesses possesses greater C1q binding activity as measured by ELISA compared to compared to OCREVUS (ocrelizumab).

In certain embodiments, the population has a relative potency of at least 1000%, 750%, 500%, 250%, 100%, 75%, 50%, or at least 25% in a C1q binding assay as measured by ELISA compared to a commercial reference standard. In certain embodiments, the population has a relative potency of at least 110%, 120%, 130%, 140%, 150%, 160%, 170%, 180%, 190%, 200%, 5-fold, 10-fold, 15-fold, 20-fold, 30-fold, 50-fold, 75-fold, 100-fold, 125-fold, 150-fold, or at least 200-fold in a C1q binding assay as measured by ELISA compared to a commercial reference standard. In certain embodiments, the population has a relative potency of at least more than 100% in a C1q binding assay as measured by ELISA compared to a commercial reference standard. In certain embodiments, the population has a relative potency of more than 100% in a C1q binding assay as measured by ELISA compared to a commercial reference standard.

In certain embodiments, the population has a relative potency of between at least 50%, 60%, 70%, 80%, 90%, 100%, 200%, 500%, 750% 1000%, 15-fold, 20-fold, 30-fold, 50-fold, 75-fold, 100-fold, 125-fold, 150-fold, or at least 200-fold and at most 60%, 70%, 80%, 90%, 100%, 200%, 500%, 750%, 1000%, 15-fold, 20-fold, 30-fold, 50-fold, 75-fold, 100-fold, 125-fold, 150-fold, 200-fold or at most 300-fold in a C1q binding assay as measured by ELISA compared to a commercial reference standard. In certain embodiments, the population has a relative potency of between 5% and 50%, 50% and 100%, 100% and 500%, 500% and 1000%, 10-fold and 50-fold, 50-fold and 100-fold, 100-fold and 150-fold, or between 150-fold and 300-fold in a C1q binding assay as measured by ELISA compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab). In certain embodiments, the population has a relative potency of about 142% in a C1q binding assay as measured by ELISA compared to ARZERRA (ofatumumab). In certain embodiments, the population has a relative potency of about 123% in a C1q binding assay as measured by ELISA compared to RITUXAN (rituximab). In certain embodiments, the population has a relative potency of about 112% in a C1q binding assay as measured by ELISA compared to OCREVUS (ocrelizumab).

In certain embodiments, the population has a relative potency of 30 to 180%, 40 to 170%, 50 to 160%, 60 to 150%, 70 to 140%, 80 to 130%, 85% to 120%, or 88 to 113% in a C1q binding assay as measured by ELISA compared to a commercial reference standard. In certain embodiments, the population has a relative potency of 88 to 113% or 86 to 117% in a C1q binding assay as measured by ELISA compared to a commercial reference standard. In certain embodiments, the population has a relative potency of 86 to 116% in a C1q binding assay as measured by ELISA compared to a commercial reference standard. In certain embodiments, the population has a relative potency of about 99% in a C1q binding assay as measured by ELISA compared to a commercial reference standard. In certain embodiments, the commercial reference standard is RS-117808.

In certain embodiments, the EC50 value for the C1q binding activity as measured by ELISA of the population is between 1.5 and 3 µg/mL. In certain embodiments, the EC50 value for the C1q binding activity as measured by ELISA of the population is between 0.2 and 9 µg/mL, 0.3 and 8 µg/mL, 0.4 and 7 µg/mL, 0.5 and 6 µg/mL, 0.6 and 5 µg/mL, 0.7 and 4 µg/mL, 0.8 and 3 µg/mL, 0.9 and 2.9 µg/mL, or 1 and 2.8 µg/mL. In certain embodiments, the EC50 value for the C1q binding activity is the average EC50 value calculated from the EC50 values obtained in two, three, four, five, six, seven, eight, nine, ten, or more repeated ELISA experiments. In certain embodiments, the EC50 value for the C1q binding activity as measured by ELISA of the population is about 1.92 µg/mL. In certain embodiments, the EC50 value for the C1q binding activity as measured by ELISA of the population is about 2.6 µg/mL.

(vii) B Cell Depletion Activity

In certain embodiments, the population possesses B cell depletion activity as measured in a human whole blood B cell depletion assay. In certain embodiments, the population possesses greater B cell depletion activity as measured in a human whole blood B cell depletion assay compared to a commercial reference standard.

In certain embodiments, the population possesses greater B cell depletion activity as measured in a human whole blood B cell depletion assay compared to an anti-CD20 antibody. In certain embodiments, the population possesses greater B cell depletion activity as measured in a human whole blood B cell depletion assay compared to GAZYVA (obinutuzumab), ARZERRA (ofatumumab), RITUXAN (rituximab), veltuzumab (IMMU-106), ZEVALIN (ibritumomab tiuxetan) and/or OCREVUS (ocrelizumab). In certain embodiments, the population possesses greater B cell depletion activity as measured in a human whole blood B cell depletion assay compared to GAZYVA (obinutuzumab). In certain embodiments, the population possesses greater B cell depletion activity as measured in a human whole blood B cell depletion assay compared to ARZERRA (ofatumumab). In certain embodiments, the population possesses greater B cell depletion activity as measured in a human whole blood B cell depletion assay compared to RITUXAN (rituximab). In certain embodiments, the population possesses greater B cell depletion activity as measured in a human whole blood B cell depletion assay compared to veltuzumab (IMMU-106). In certain embodiments, the population possesses greater B cell depletion activity as measured in a human whole blood B cell depletion assay compared to ZEVALIN (ibritumomab tiuxetan). In certain embodiments, the population possesses greater B cell depletion activity as measured in a human whole blood B cell depletion assay compared to OCREVUS (ocrelizumab).

In certain embodiments, the population has a relative potency of at least 1000%, 750%, 500%, 250%, 100%, 75%, 50%, 25%, 12%, or at least 5% in a human whole blood B cell depletion assay compared to a commercial reference standard. In certain embodiments, the population has a relative potency of at least 110%, 120%, 130%, 140%, 150%, 160%, 170%, 180%, 190%, 200%, 5-fold, 10-fold, 15-fold, 20-fold, 30-fold, 50-fold, 75-fold, 100-fold, 125-fold, 150-fold, or at least 200-fold in a human whole blood B cell depletion assay compared to a commercial reference standard. In certain embodiments, the population has a relative potency of at least more than 100% in a human whole blood B cell depletion assay compared to a commercial reference standard. In certain embodiments, the population has a relative potency of more than 100% in a human whole blood B cell depletion assay compared to a commercial reference standard.

In certain embodiments, the population has a relative potency of between at least 5%, 10%, 20%, 30%, 40%, 50%, 60%, 70%, 80%, 90%, 100%, 200%, 500%, 750% 1000%, 15-fold, 30-fold, 50-fold, 75-fold, 100-fold, 125-fold, 150-fold, or at least 200-fold and at most 10%, 20%, 30%, 40%, 50%, 60%, 70%, 80%, 90%, 100%, 200%, 500%, 750%, 1000%, 15-fold, 30-fold, 50-fold, 75-fold, 100-fold, 125-fold, 150-fold, 200-fold or at most 300-fold in a human whole blood B cell depletion assay compared to a commercial reference standard. In certain embodiments, the population has a relative potency of between 5% and 50%, 50% and 100%, 100% and 500%, 500% and 1000%, 10-fold and 50-fold, 50-fold and 100-fold, 100-fold and 150-fold, or between 150-fold and 300-fold in a human whole blood B cell depletion assay compared to a commercial reference standard.

In certain embodiments, the commercial reference standard is an anti-CD20 antibody. In certain embodiments, the commercial reference standard is GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab).

6.8 Methods of Treating and Preventing Medical Conditions

In some aspects, provided herein is a method of treating a relapsing form of multiple sclerosis (RMS) in a subject in need thereof, comprising administering to the subject an effective amount of an anti-CD20 antibody composition as described herein. In some embodiments, the relapsing form of multiple sclerosis (RMS) is selected from a clinically isolated syndrome ("CIS"), relapsing-remitting ("RRMS"), or active secondary progressive disease ("SPMS"). In some embodiments, the RMS is a CIS. In some embodiments, the RMS is RRMS. In some embodiments, the RMS is SPMS. In some embodiments, the subject is diagnosed with RMS in accordance to McDonald Criteria (2010).

In certain embodiments, the method comprises administering to the subject the anti-CD20 antibody composition as described herein by intravenous infusion. In some embodiments, the intravenous infusion comprises a multi-infusion dosage regimen, comprising: a) a first infusion comprising about 100 to about 200 mg of the anti-CD20 antibody composition as described herein at day 1; b) a second infusion comprising about 400 to about 500 mg of the anti-CD20 antibody composition at about 2 weeks after the first infusion; c) a first subsequent infusion comprising about 400 to about 500 mg of the anti-CD20 antibody composition at about six months after the first infusion; and d) one or more subsequent infusions comprising about 400 to about 500 mg of the anti-CD20 antibody composition at about six months after the prior infusion.

In some embodiments, the intravenous infusion comprises a multi-infusion dosage regimen, comprising: a) a first infusion comprising 150 mg of the anti-CD20 antibody composition as described herein at day 1; b) a second infusion comprising 450 mg of the anti-CD20 antibody composition at about 2 weeks after the first infusion; c) a first subsequent infusion comprising 450 mg of the anti-CD20 antibody composition at about six months after the first infusion; and d) one or more subsequent infusions comprising 450 mg of the anti-CD20 antibody composition at about six months after the prior infusion. In some embodiments, the first infusion is administered over 4 hours; the second infusion is administered over 1 hour; and subsequent infusions are administered over 1 hour.

In certain embodiments, the method comprises a first administration of an anti-CD20 antibody composition (e.g., GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab)) by intravenous infusion to the subject and then a second administration of the anti-CD20 antibody as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) to the subject. Specifically, in some embodiments, the intravenous infusion comprises a multi-infusion dosage regimen, comprising: a) a first infusion comprising a prescribed dosage of an anti-CD20 antibody composition (e.g., GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab)) herein at day 1; b) a second infusion comprising about 400 to about 500 mg of the anti-CD20 antibody composition as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) at about 2 weeks after the first infusion; c) a first subsequent infusion comprising about 400 to about 500 mg of the anti-CD20 antibody composition as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) at about six months after the first infusion; and d) one or more subsequent infusions comprising about 400 to about 500 mg of the anti-CD20 antibody composition as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) at about six months after the prior infusion.

In some embodiments, the intravenous infusion comprises a multi-infusion dosage regimen, comprising: a) a first infusion comprising a prescribed dosage of an anti-CD20 antibody composition (e.g., GAZYVA (obinutuzumab), ARZERRA (ofatumumab), RITUXAN (rituximab), veltuzumab (IMMU-106), ZEVALIN (ibritumomab tiuxetan) or OCREVUS (ocrelizumab)) herein at day 1; b) a second infusion comprising 450 mg of the anti-CD20 antibody composition as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) at about 2 weeks after the first infusion; c) a first subsequent infusion comprising 450 mg of the anti-CD20 antibody composition as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) at about six months after the first infusion; and d) one or more subsequent infusions comprising 450 mg of the anti-CD20 antibody composition as described herein (i.e., the anti-CD20 antibody in the population is expressed from one or more nucleic acid sequences encoding a heavy chain comprising the amino acid sequence of SEQ ID NO:1 and a light chain comprising the amino acid sequence of SEQ ID NO:2, wherein the population of anti-CD20 antibody proteins has an N-glycan profile comprising 10 to 20% galactosylated glycans and about 20 to 40% fucosylated glycans) at about six months after the prior infusion. In some embodiments, the first infusion is administered over 4 hours; the second infusion is administered over 1 hour; and subsequent infusions are administered over 1 hour.

In certain embodiments, the method comprises a treatment period of at least 48 weeks. In some embodiments, the method comprises a treatment period of at least 96 weeks.

In certain embodiments, the subject is a human. In some embodiments, the human subject is an adult. In some embodiments, the subject has experienced at least one relapse in the previous year prior to treatment or two relapses in the previous two years prior to treatment. In some embodiments, the subject has or had the presence of a Ti gadolinium (Gd)-enhancing lesion in the previous year prior to treatment with the anti-CD20 antibody composition as described herein. In some embodiments, the subject has an Expanded Disability Status Scale (EDSS) score of from 0 to 5.5 prior to treatment with the anti-CD20 antibody composition as described herein.

In certain embodiments of the method, the subject has not been treated with a non-steroid therapy for MS in the previous five years prior to treatment with the anti-CD20 antibody composition as described herein. In some embodiments, the subject is naïve to treatment for MS. In certain embodiments, the subject is negative for hepatitis B virus (HBV). In some embodiments, the subject is negative for hepatitis B virus surface antigen (HBsAg). In some embodiments, the subject is negative for anti-hepatitis B virus core antibodies. In certain embodiments, the subject has not been immunized with a vaccine for at least 2 weeks or at least 4 weeks prior to treatment with the anti-CD20 antibody composition as described herein.

In certain embodiments of the method, the subject is pre-medicated with an amount of a corticosteroid about 30 to about 60 minutes prior to administration of the anti-CD20 antibody composition as described herein. In some embodiments, the corticosteroid is methylprednisone or a corticosteroid bioequivalent thereto. In some embodiments, the amount of a corticosteroid is 100 mg methylprednisone. In some embodiments, the corticosteroid is dexamethasone or a corticosteroid bioequivalent thereto. In some embodiments, the amount of a corticosteroid is of from 10 to 20 mg dexamethasone. In certain embodiments, the subject is pre-medicated with an amount of an antipyretic about 30 to about 60 minutes prior to administration of the anti-CD20 antibody composition as described herein. In some embodiments, the antipyretic is acetaminophen or an antipyretic bioequivalent thereto. In some embodiments, the subject is pre-medicated with an amount of a antihistamine about 30 to about 60 minutes prior to administration of the anti-CD20 antibody composition as described herein. In some embodiments, the antihistamine is diphenhydramine HCl or an antihistamine bioequivalent thereof. In some embodiments, the amount of an antihistamine is from about 25 to 50 mg diphenhydramine HCl. In some embodiments, the subject is pre-medicated with an amount of a corticosteroid (as described above) and an amount of an antihistamine (as described above) about 30 to about 60 minutes prior to administration of the anti-CD20 antibody composition as described herein.

In certain embodiments, the method alleviates or delays progression of one or more symptoms of MS in the subject. In certain embodiments, the method reduces the annualized relapse rate (ARR) in the subject following administration of the anti-CD20 antibody composition as described herein. In some embodiments, ARR is the total number of relapse for a subject divided by the sum of treatment duration. In some embodiments, ARR is number of Independent Relapse Adjudication Panel (TRAP)-confirmed relapses for a subject per year. In some embodiments, reduction of ARR is assessed at about 96 weeks after the first infusion. In certain embodiments, the method reduces the total number of T1 gadolinium (Gd)-enhancing lesions in the subject following administration of the anti-CD20 antibody composition as described herein. In some embodiments, reduction of Gd-enhancing Ti lesions is assessed by MRI scan. In some embodiments, reduction of Gd-enhancing T1 lesions is assessed at about 96 weeks after the first infusion. In certain embodiments, the method reduces the number of new or enlarging T2 hyperintense lesions in the subject following administration of the anti-CD20 antibody composition as described herein. In some embodiments, reduction of the number of new or enlarging T2 hyperintense lesions is assessed by Mill scan. In some embodiments, reduction of the number of new or enlarging T2 hyperintense lesions is assessed at about 96 weeks after the first infusion. In certain embodiments, the method achieves confirmed disability progression in the subject following administration of the anti-CD20 antibody composition as described herein. In some embodiments, confirmation of disability progression comprises an increase of greater than or equal to 1.0 point from a baseline EDSS score of the subject attributable to MS, wherein said baseline EDSS score is 5.5 or less. In some embodiments, confirmation of disability progression comprises an increase of greater than or equal to 0.5 point from a baseline EDSS score of the subject attributable to MS, wherein said baseline EDSS score is greater than 5.5.

In some aspects, provided herein is a method of treating a cancer in a subject in need thereof, comprising administering to the subject an effective amount of an anti-CD20 antibody composition as described herein. In some embodiments, the cancer is a bladder cancer, a breast cancer, a cervical cancer, a colorectal cancer, a gynecologic cancer (i.e., cervical, ovarian, uterine, vaginal, or vulvar cancer), head and neck cancer, kidney cancer, liver cancer, lung cancer, lymphoma, mesothelioma, myeloma, prostate cancer, skin cancer, or thyroid cancer.

In some aspects, provided herein is a method of treating a disease or disorder associated with excessive B-cell proliferation in a subject in need thereof, comprising administering to the subject an effective amount of an anti-CD20 antibody composition as described herein. In some embodiments, the disease or disorder associated with excessive B-cell proliferation is a hematological cancer. In some embodiments, the hematological cancer is lymphoma, leukemia, or myeloma. In some embodiments, the hematological cancer is selected from B-cell lymphoma, acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), Richter's transformation, or primary central nervous system lymphoma (PCNSL). In various aspects of the method, the anti-CD20 antibody composition as described herein comprises anti-CD20 antibodies, which are IgG1 antibodies comprising heavy chains each comprising the amino acid sequence of SEQ ID NO:1, and light chains each comprising the amino acid sequence of SEQ ID NO:2.

In certain embodiments, the hematological cancer is B-cell lymphoma. In some embodiments, the B-cell lymphoma is relapsed or refractory. In certain embodiments, the hematological cancer is non-Hodgkin's lymphoma (NHL). In some embodiments, the NHL is relapsed or refractory. In certain embodiments, the hematological cancer is Waldenstrom's macroglobulinemia (WM). In some embodiments, the WM is relapsed or refractory. In certain embodiments, the hematological cancer is marginal zone lymphoma (MZL). In some embodiments, the MZL is relapsed or refractory. In certain embodiments, the hematological cancer is chronic lymphocytic leukemia (CLL). In some embodiments, the CLL is relapsed or refractory. In certain embodiments, the hematological cancer is small lymphocytic lymphoma (SLL). In some embodiments, the SLL is relapsed or refractory. In certain embodiments, the hematological cancer is primary central nervous system lymphoma (PCNSL). In some embodiments, the PCNSL is relapsed or refractory.

In certain embodiments, the method of treating a hematological cancer comprises administering to the subject the anti-CD20 antibody composition as described herein by intravenous infusion. In some embodiments, the intravenous infusion comprises: a) an infusion comprising about 900 mg of the anti-CD20 antibody composition as described herein on days 1 and 2 (split into a 150 mg dose on day 1 and a 750 mg dose on day 2), day 8, and day 15 of Cycle 1 (each Cycle being 28 days); day 1 of Cycles 2-6; and day 1 of every 3 cycles after Cycle 6. In some embodiments, the hematological cancer is CLL.

In some embodiments, the intravenous infusion comprises a multi-infusion dosage regimen, comprising: a) a first infusion comprising about 400 to about 500 mg of the anti-CD20 antibody composition as described herein at day 1; b) a second infusion comprising about 500 to about 700 mg, about 800 to about 1000 mg, or about 1100 to about 1300 mg of the anti-CD20 antibody composition at about 1 week after the first infusion; c) a third infusion comprising about 500 to about 700 mg, about 800 to about 1000 mg, or about 1100 to about 1300 mg of the anti-CD20 antibody composition at about 2 weeks after the first infusion; d) a fourth infusion comprising about 500 to about 700 mg, about 800 to about 1000 mg, or about 1100 to about 1300 mg of the anti-CD20 antibody composition at about 3 weeks after the first infusion; and e) one or more subsequent infusions comprising about 400 to about 500 mg, about 500 to about 700 mg, about 800 to about 1000 mg, or about 1100 to about 1300 mg of the anti-CD20 antibody composition at about one month after the prior infusion.

In some embodiments, the intravenous infusion comprises a multi-infusion dosage regimen, comprising: a) a first infusion comprising 450 mg of the anti-CD20 antibody composition as described herein at day 1; b) a second infusion comprising 600, 900, or 1200 mg of the anti-CD20 antibody composition at about 1 week after the first infusion; c) a third infusion comprising 600, 900, or 1200 mg of the anti-CD20 antibody composition at about 2 weeks after the first infusion; d) a fourth infusion comprising 600, 900, or 1200 mg of the anti-CD20 antibody composition at about 3 weeks after the first infusion; and e) one or more subsequent infusions comprising 450, 600, 900, or 1200 mg of the anti-CD20 antibody composition at about one month after the prior infusion.

In some embodiments, the intravenous infusion comprises a multi-infusion dosage regimen, comprising: a) a first infusion comprising about 400 to about 500 mg of the anti-CD20 antibody composition as described herein at day 1; b) a second infusion comprising about 500 to about 700 mg of the anti-CD20 antibody composition at about 1 week after the first infusion; c) a third infusion comprising about 800 to about 1000 mg of the anti-CD20 antibody composition at about 2 weeks after the first infusion; and d) one or more subsequent infusions comprising about 400 to about 1000 mg of the anti-CD20 antibody composition at about one month after the prior infusion. In some embodiments, the intravenous infusion comprises a multi-infusion dosage regimen, comprising: a) a first infusion comprising 450 mg of the anti-CD20 antibody composition as described herein at day 1; b) a second infusion comprising 600 mg of the anti-CD20 antibody composition at about 1 week after the first infusion; c) a third infusion comprising 900 mg of the anti-CD20 antibody composition at about 2 weeks after the first infusion; and d) one or more subsequent infusions comprising 450, 600, or 900 mg of the anti-CD20 antibody composition at about one month after the prior infusion.

In some embodiments, the intravenous infusion comprises a multi-infusion dosage regimen, comprising: a) a first infusion comprising about 5 mg of the anti-CD20 antibody composition as described herein at day 1; and b) one or more subsequent infusions comprising about 5 to about 450 mg of the anti-CD20 antibody composition at about one week after the prior infusion, wherein each subsequent infusion is at higher dose than the prior infusion.

In some embodiments, the intravenous infusion comprises a multi-infusion dosage regimen, comprising: a) a first infusion comprising about 100 to about 200 mg of the anti-CD20 antibody composition as described herein at day 1; and b) one or more subsequent infusions comprising about 400 to about 500 mg of the anti-CD20 antibody composition at about one week after the prior infusion. In some embodiments, the intravenous infusion comprises a multi-infusion dosage regimen, comprising: a) a first infusion comprising 150 mg of the anti-CD20 antibody composition at day 1; and d) one or more subsequent infusions comprising 450 mg of the anti-CD20 antibody composition at about one week after the prior infusion. In some embodiments, the method comprises seven or more subsequent infusions. In some embodiments, the method comprises seven subsequent infusions.

In some embodiments, the intravenous infusion comprises a multi-infusion dosage regimen, comprising: a) a first infusion comprising about 500 to about 1000 mg of the anti-CD20 antibody composition as described herein at day 1; b) a second infusion comprising about 500 to about 1000 mg of the anti-CD20 antibody at about 1 week after the first infusion; c) a third infusion comprising about 500 to about 1000 mg of the anti-CD20 antibody composition at about 2 weeks after the first infusion; and d) one or more subsequent infusions comprising about 500 to about 1000 mg of the anti-CD20 antibody composition at about one month after the prior infusion. In certain embodiments, the one or more subsequent infusions each comprise 600 mg of the anti-CD20 antibody composition as described herein. In certain embodiments, the first infusion, second infusion, third infusion, and one or more subsequent infusions each comprise 600 mg of the anti-CD20 antibody composition as described herein. In some embodiments, the first infusion, second infusion, third infusion, and one or more subsequent infusions each comprise 900 mg of the anti-CD20 antibody composition as described herein.

In some embodiments, the intravenous infusion comprises a multi-infusion dosage regimen, comprising: a) a first infusion comprising about 100 to about 200 mg of the anti-CD20 antibody composition as described herein at day 1; b) a second infusion comprising about 700 to about 800 mg of the anti-CD20 antibody composition at about 1 week after the first infusion; c) a third infusion comprising about 850 to about 950 mg of the anti-CD20 antibody composition at about 2 weeks after the first infusion; and d) one or more subsequent infusions comprising about 850 to about 950 mg of the anti-CD20 antibody composition at about one month after the prior infusion. In some embodiments, the first infusion comprises 150 mg of the anti-CD20 antibody composition, the second infusion comprises 750 mg of the anti-CD20 antibody composition, the third and one or more subsequent infusions comprise 900 mg of the anti-CD20 antibody composition.

In certain embodiments, the subject is a human. In some embodiments, the human subject is an adult. In some embodiments, the subject has relapsed or refractory B-cell lymphoma. In some embodiments, the subject has been previously treated with at least one prior course of rituximab or a rituximab-based therapy. In some embodiments, the subject has been previously treated with at least one prior course of fludarabine or a fludarabine-based therapy. In some embodiments, the subject is naïve to treatment for a B-cell lymphoma. In some embodiments, the subject is eligible for high dose or combination chemotherapy and/or stem cell transplant. In some embodiments, the subject has an Eastern Cooperative Oncology Group (ECOG) score of from 0 to 2 prior to treatment with the anti-CD20 antibody composition as described herein. In some embodiments, the subject has a peripheral blood lymphocyte count of greater than 5,000/4, prior to treatment with the anti-CD20 antibody composition as described herein.

In other embodiments, the anti-CD20 antibody compositions provided herein can be used to treat and/or prevent Chronic inflammatory demyelinating polyneuropathy (CIDP); Myositis; Lupus Nephritis; other forms of MS-PPMS, SPMS; Myasthenia Gravis (MG); Antiphospholipid Syndrome; Thrombotic Thrombocytopenic Purpura (TTP); Ulcerative Colitis; Minimal Change Nephrotic Syndrome (MCNS); Aplastic Anemia; Autoimmune Glomerulopathies; Rheumatoid Arthritis (RA); Interstitial Lung Disease; Myasthenia Gravis (MG); Subepidermal Autoimmune Blistering Disease; Pulmonary Infectious Diseases; Acquired Hemophilia; Refractory Mixed Cryoglobulinemia; Primary Immune Thrombocytopenia; Graft Versus Host Disease (GVHD); Autoimmune Blistering Disease; Anti-Myelin Associated Glycoprotein (MAG) Polyneuropathy; Granulomatosis with Pollyangiitis (GPA); Neuromyelitis Optica; Systemic Lupus Erythematosus; Pemphigus; Post-Transplant Lymphoproliferative Disorders; Autoimmune Hemolytic Anemia; Cerebral Vasculitis; Microscopic Polyangiitis (MPA); or Idiopathic Nephritic Syndrome.

6.9 Pharmacokinetic Properties

In some aspects, provided herein is a method of treating a human patient afflicted with a disease (e.g., an autoimmune disease) comprising administering to the patient the anti-CD20 antibody provided herein.

In certain embodiments, the anti-CD20 antibody are administered as i) a first infusion at a dose of about 150 mg, ii) a second infusion two week later at a dose of about 450 mg, and iii) subsequent infusions every six months at a dose of about 450 mg.

In certain embodiments, the administration of the anti-CD20 antibody produces an area under the curve (AUC) of between about 2,160 µg/mL and about 3,840 µg/mL. In certain embodiments, the AUC is about 3,000 µg/mL. In certain embodiments, the AUC is the steady state AUC.

In certain embodiments, the administration of the anti-CD20 antibody produces an Cmax of between about 118,011 ng/mL and about 159,989 ng/mL. In certain embodiments, the Cmax is about 139,000 ng/mL. In certain embodiments, the Cmax is the steady state Cmax.

In certain embodiments, the administration of the anti-CD20 antibody produces a Cmin of about 0 ng/mL and about 375 ng/mL. In certain embodiments, the Cmin is about 139 ng/mL. In certain embodiments, the Cmin is the steady state Cmin.

In certain embodiments, the administration of the anti-CD20 antibody produces a Cavg of between about 6,437 ng/mL and about 11,443 ng/mL. In certain embodiments, the Cavg is about 8,940 ng/mL. In certain embodiments, the Cavg is the steady state Cavg.

In certain embodiments, the autoimmune disease is selected from the group consisting of multiple sclerosis, psoriasis, rheumatoid arthritis, vasculitis, inflammatory bowel disease, dermatitis, osteoarthritis, inflammatory muscle disease, allergic rhinitis, vaginitis, interstitial cystitis, scleroderma, osteoporosis, eczema, allogenic or xenogenic transplantation (organ, bone marrow, stem cells and other cells and tissues), graft rejection, graft-versus-host disease, lupus erythematosus, inflammatory disease, type 1 diabetes, pulmonary fibrosis, dermatomyositis, Sjogren's syndrome, thyroiditis (e.g., Hasimoto's and autoimmune thyroiditis), myasthenia gravis, autoimmune hemolytic anemia, cystic fibrosis, chronic relapsing hepatitis, primary biliary cirrhosis, allergic conjunctivitis, atopic dermatitis, chronic obstructive pulmonary disease, glomerulonephritis, neuroinflammatory diseases, and uveitis.

In certain embodiments, the autoimmune disease is multiple sclerosis. In certain embodiments, the multiple sclerosis is a relapsing form of multiple sclerosis. In certain embodiments, the relapsing form of multiple sclerosis is a clinically isolated syndrome (CIS); relapsing-remitting MS (RRMS); active secondary progressive MS (SPMS); or primary progressive MS (PPMS). In certain embodiments, the relapsing form of MS is a clinically isolated syndrome (CIS). In certain embodiments, the relapsing form of MS is relapse-remitting multiple sclerosis (RRMS). In certain embodiments, the relapsing form of MS is active secondary progressive multiple sclerosis (SPMS). In certain embodiments, the relapsing form of MS is primary progressive MS (PPMS).

In certain embodiments, the anti-CD20 antibody is administered intravenously.

6.10 Methods of Making

In some aspects, provided herein are methods of making the populations of anti-CD20 antibody proteins with specified ranges of post-translational modifications provided herein. Example 15 provides exemplary methods of making the populations of anti-CD20 antibody proteins provided herein.

In certain embodiments, the methods of making the populations of anti-CD20 antibody proteins with specified ranges of post-translational modifications as described above comprises: i) culturing the rat hybridoma cells at a first culture pH of about 7.0 to about 7.55 for 0 to 3 days, ii) culturing the rat hybridoma cells at a second culture pH of about 6.5 to about 6.99 on day 3, iii) maintaining the culture pH at the second culture pH of about 6.5 to about 6.99 from culture day 3 until day 14 of the cell culture, and iv) controlling culture $pCO_2$ levels to less than about 200 mmHg throughout the culture period. In some embodiments, the second culture pH is about 6.60 to about 6.96 (e.g., the second culture pH is 6.8).

In some embodiments, the second culture pH results in higher integrated viable cell density (IVCD) and higher titer at harvest.

In some embodiments, the second culture pH results in lower percent fucosylation.

In some embodiments, the rat hybridoma cells expressing the recombinant protein are cultured in a basal media that is chemically defined and animal-derived component free (ADCF) culture medium In some embodiments, the basal medium is supplemented with a feed medium.

In some aspects, the method further comprises an initial temperature set point of about 37° C., wherein said initial temperature set point is set on culture day 0 to culture day 1.

In some aspects, the method further comprises a second temperature set point of about 35° C., wherein said second temperature set point is set at the end of culture day 1 to culture day 3.

In some aspects, the method further comprises comprising a third temperature set point of about 32° C. to about 33° C., wherein said third temperature set point is set on culture day 3 and is maintained though harvest. The term "harvest" refers to the point of time in the mammalian cell culture process when cells containing the recombinant protein are separated and removed from the cell culture media and subject to additional processing, such as, e.g., centrifugation, filtration, or purification.

In some aspects, harvest of the cells will occur on process day 12, 13, or 14 of the cell culture, or when cell viability drops below 20%, whichever comes first.

In some aspects, the method further comprises harvesting the recombinant protein produced by the rat hybridoma cell.

In some aspects, the method further comprises purifying the recombinant protein by affinity chromatography and/or ion exchange chromatography. In some embodiments, the affinity chromatography comprises protein A purification.

In some aspects, the methods result in an increased yield of recombinant protein. For example, the recombinant protein is increased by at least about 30%, at least about 40%, at least about 50%, at least about 60%, at least about 70%, at least about 80%, at least about 90%, at least about 100%, at least about 110%, at least about 120%, at least about 130%, at least about 140%, or at least about 150%, relative to a recombinant protein produced by a culturing process that does not employ the culture conditions as recited above.

```
                              Sequence Table
SEQ
ID
NO:  Description      Sequence 1   Heavy chain      QAYLQQSGAE LVRPGASVKM SCKASGYTFT SYNMHWVKQT PRQGLEWIGG
                      IYPGNGDTSY NQKFKGKATL TVGKSSSTAY MQLSSLTSED SAVYFCARYD
                      YNYAMDYWGQ GTSVTVSSAS TKGPSVFPLA PSSKSTSGGT AALGCLVKDY
                      FPEPVTVSWN SGALTSGVHT FPAVLQSSGL YSLSSVVTVP SSSLGTQTYI
                      CNVNHKPSNT KVDKKVEPKS CDKTHTCPPC PAPELLGGPS VFLFPPKPKD
                      TLMISRTPEV TCVVVDVSHE DPEVKFNWYV DGVEVHNAKT KPREEQYNST
                      YRVVSVLTVL HQDWLNGKEY KCKVSNKALP APIEKTISKA KGQPREPQVY
                      TLPPSRDELT KNQVSLTCLV KGFYPSDIAV EWESNGQPEN NYKTTPPVLD
                      SDGSFFLYSK LTVDKSRWQQ GNVFSCSVMH EALHNHYTQK SLSLSPGK 2   Light chain      QIVLSQSPAI LSASPGEKVT MTCRASSSVS YMHWYQQKPG SSPKPWIYAT
                      SNLASGVPAR FSGSGSGTSY SFTISRVEAE DAATYYCQQW TENPPTFGGG
                      TRLEIKRTVA APSVFIFPPS DEQLKSGTAS VVCLLNNFYP REAKVQWKVD
                      NALQSGNSQE SVTEQDSKDS TYSLSSTLTL SKADYEKHKV YACEVTHQGL
                      SSPVTKSENR GEC 3   Variable         GYTFTSY
     heavy chain
     (VH) CDR1

4   Variable         YPGNGD
     heavy chain
     (VH) CDR2

5   Variable         YDYNYAMDY
     heavy chain
     (VH) CDR3

6   Variable         QAYLQQSGAE LVRPGASVKM SCKASGYTFT SYNMHWVKQT PRQGLEWIGG
     heavy chain      IYPGNGDTSY NQKFKGKATL TVGKSSSTAY MQLSSLTSED SAVYFCARYD
     (VH)             YNYAMDYWGQ GTSVTVSS 7   Constant         ASTKGPSVFP LAPSSKSTSG GTAALGCLVK DYFPEPVTVS WNSGALTSGV
     heavy chain      HTFPAVLQSS GLYSLSSVVT VPSSSLGTQT YICNVNHKPS NTKVDKKVEP
                      KSCDKTHTCP PCPAPELLGG PSVFLFPPKP KDTLMISRTP EVTCVVVDVS
                      HEDPEVKFNW YVDGVEVHNA KTKPREEQYN STYRVVSVLT VLHQDWLNGK
                      EYKCKVSNKA LPAPIEKTIS KAKGQPREPQ VYTLPPSRDE LTKNQVSLTC
                      LVKGFYPSDI AVEWESNGQP ENNYKTTPPV LDSDGSFFLY SKLTVDKSRW
                      QQGNVFSCSV MHEALHNHYT QKSLSLSPGK 8   Variable         RASSSVSYMH
     light chain
     (VL) CDR1

9   Variable         ATSNLAS
     light chain
     (VL) CDR2

10   Variable         QQWTENPPT
     light chain
     (VL) CDR3

11   Variable         QIVLSQSPAI LSASPGEKVT MTCRASSSVS YMHWYQQKPG SSPKPWIYAT
     light chain      SNLASGVPAR FSGSGSGTSY SFTISRVEAE DAATYYCQQW TENPPTFGGG
     (VL)             TRLEIKR 12   Constant         TVAAPSVFIF PPSDEQLKSG TASVVCLLNN FYPREAKVQW KVDNALQSGN
     light chain      SQESVTEQDS KDSTYSLSST LTLSKADYEK HKVYACEVTH QGLSSPVTKS
                      FNRGEC 13   Modified         pGlu Ala Tyr Leu Gln Gln Ser Gly Ala Glu Leu Val Arg Pro
     heavy chain      Gly Ala Ser Val Lys Met Ser Cys Lys Ala Ser Gly Tyr Thr
     (substitution    Phe Thr Ser Tyr Asn Met His Trp Val Lys Gln Thr Pro Arg
     of               Gln Gly Leu Glu Trp Ile Gly Ile Tyr Pro Gly Asn Gly
     glutamine        Asp Thr Ser Tyr Asn Gln Thr Val Gly Lys Ser Ser Ser Leu
     at position      Thr Val Gly Lys Ser Ser Ser Thr Ala Tyr Met Gln Leu Ser
     1 with           Ser Leu thr Ser Glu Asp Ser Ala Val Tyr Phe Cys Ala Arg
     pyroglutamate)   Tyr Asp Tyr Asn Tyr Ala Met Asp Tyr Trp Gly Gln gly Thr
                      Ser Val Thr Val Ser Ser Ala Ser Thr Lys Gly Pro Ser Val
```

Sequence Table

| SEQ ID NO: | Description | Sequence |
|---|---|---|
| | | Phe Pro Leu Ala Pro Ser Ser Lys Ser Thr Ser Gly Gly Thr<br>Ala Ala Leu Gly Cys Leu Val Lys Asp Tyr Phe Pro Glu Pro<br>Val Thr Val Ser Trp Asn Ser Gly Ala Leu Thr Ser Gly Val<br>His Thr Phe Pro Ala Val Leu Gln Ser Ser Gly Leu Tyr Ser<br>Leu Ser Ser Val Val Thr Val Pro Ser Ser Ser Leu Gly Thr<br>Gln Thr Tyr Ile Cys Asn Val Asn His Lys Pro Ser Asn Thr<br>Lys Val Asp Lys Lys Val Glu Pro Lys Ser Cys Asp Lys Thr<br>His Thr Cys Pro Pro Cys Pro Ala Pro Glu Leu Leu Gly Gly<br>Pro Ser Val Phe Leu Phe Pro Pro Lys Pro Lys Asp Thr Leu<br>Met Ile Ser Arg Thr Pro Glu Val Thr Cys Val Val Val Asp<br>Val Ser His Glu Asp Pro Glu Val Lys Phe Asn Trp Tyr Val<br>Asp Gly Val Glu Val His Asn Ala Lys Thr Lys Pro Arg Glu<br>Glu Gln Tyr Asn Ser Thr Tyr Arg Val Val Ser Val Leu Thr<br>Val Leu His Gln Asp Trp Leu Asn Gly Lys Glu Tyr Lys Cys<br>Lys Val Ser Asn Lys Ala Leu Pro Ala Pro Ile Glu Lys Thr<br>Ile Ser Lys Ala Lys Gly Gln Pro Arg Glu Pro Gln Val Tyr<br>Thr Leu Pro Pro Ser Arg Asp Glu Leu Thr Lys Asn Gln Val<br>Ser Leu Thr Cys Leu Val Lys Gly Phe Tyr Pro Ser Asp Ile<br>Ala Val Glu Trp Glu Ser Asn Gly Gln Pro Glu Asn Asn Tyr<br>Lys Thr Thr Pro Pro Val Leu Asp Ser Asp Gly Ser Phe Phe<br>Leu Tyr Ser Lys Leu Thr Val Asp Lys Ser Arg Trp Gln Gln<br>Gly Asn Val Phe Ser Cys Ser Val Met His Glu Ala Leu His<br>Asn His Tyr Thr Gln Lys Ser Leu Ser Leu Ser Pro Gly Lys |
| 14 | Modified light chain (substitution of glutamine at position 1 with pyroglutamate) | pGlu Ile Val Leu Ser Gln Ser Pro Ala Ile Leu Ser Ala Ser<br>Pro Gly Glu Lys Val Thr Met Thr Cys Arg Ala Ser Ser Ser<br>Val Ser Tyr Met His Trp Tyr Gln Gln Lys Pro Gly Ser Ser<br>Pro Lys Pro Trp Ile Tyr Ala Thr Ser Asn Leu Ala Ser Gly<br>Val Pro Ala Arg Phe Ser Gly Ser Gly Ser Gly Thr Ser Tyr<br>Ser Phe Thr Ile Ser Arg Val Glu Ala Glu Asp Ala Ala Thr<br>Tyr Tyr Cys Gln Gln Trp Thr Phe Asn Pro Pro Thr Phe Gly<br>Gly Gly Thr Arg Leu Glu Ile Lys Arg Thr Val Ala Ala Pro<br>Ser Val Phe Ile Phe Pro Pro Ser Asp Glu Gln Leu Lys Ser<br>Gly Thr Ala Ser Val Val Cys Leu Leu Asn Asn Phe Tyr Pro<br>Arg Glu Ala Lys Val Gln Trp Lys Val Asp Asn Ala Leu Gln<br>Ser Gly Asn Ser Gln Glu Ser Val Thr Glu Gln Asp Ser Lys<br>Asp Ser Thr Tyr Ser Leu Ser Ser Thr Leu Thr Leu Ser Lys<br>Ala Asp Tyr Glu Lys His Lys Val Tyr Ala Cys Glu Val Thr<br>His Gln Gly Leu Ser Ser Pro Val Thr Lys Ser Phe Asn Arg<br>Gly Glu Cys |
| 15 | Modified heavy chain (deletion of the C-terminal lysine) | QAYLQQSGAE LVRPGASVKM SCKASGYTFT SYNMHWVKQT PRQGLEWIGG<br>IYPGNGDTSY NQKFKGKATL TVGKSSSTAY MQLSSLTSED SAVYFCARYD<br>YNYAMDYWGQ GTSVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKKVEPKS CDKTHTCPPC PAPELLGGPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSRDELT KNQVSLTCLV KGFYPSDIAV EWESNGQPEN NYKTTPPVLD<br>SDGSFFLYSK LTVDKSRWQQ GNVFSCSVMH EALHNHYTQK SLSLSPG |
| 16 | Light chain with one amino acid mismatch at position 106 | QIVLSQSPAI LSASPGEKVT MTCRASSSVS YMHWYQQKPG SSPKPWIYAT<br>SNLASGVPAR FSGSGSGTSY SFTISRVEAE DAATYYCQQW TENPPTFGGG<br>TRLEINRTVA APSVFIFPPS DEQLKSGTAS VVCLLNNFYP REAKVQWKVD<br>NALQSGNSQE SVTEQDSKDS TYSLSSTLTL SKADYEKHKV YACEVTHQGL<br>SSPVTKSENR GEC |
| 17 | Post-translational modification site HC (20-23) | MSCK |
| 18 | Post-translational modification site HC (24-38) | ASGYTFTSYNMHWVK |

-continued

Sequence Table

| SEQ ID NO: | Description | Sequence |
|---|---|---|
| 19 | Post-translational modification site HC (39-63) | QTPRQGLEWIGGIYPGNGDTSYNQK |
| 20 | Post-translational modification site HC (66-74) | GKATLTVGK |
| 21 | Post-translational modification site HC (75-122) | SSSTAYMQLSSLTSEDSAVYFCARYDYNYAMDYWGQGTSVTVSSASTK |
| 22 | Post-translational modification site HC (149-206) | DYFPEPVTVSWNSGALTSGVHTFPAVLQSSGLYSLSSVVTVPSSSLGTQTYICNVN**HK |
| 23 | Post-translational modification site HC (248-275) | PKDTLMISRTPEVTCVVVDVSHEDPEVK |
| 24 | Post-translational modification site HC (250-275) | DTLMISRTPEVTCVVVDVSHEDPEVK |
| 25 | Post-translational modification site HC (276-289) | FNWYVDGVEVHNAK |
| 26 | Post-translational modification site HC (324-335) | VSNKALPAPIEK |
| 27 | Post-translational modification site HC (362-371) | NQVSLTCLVK |
| 28 | Post-translational modification site HC (372-393) | GFYPSDIAVEWESNGQPENNYK |
| 29 | Post-translational modification site HC (416-440) | SRWQQGNVFSCSVMHEALHNHYTQK |
| 30 | Post-translational modification site LC (19-38) | VTMTCRASSSVSYMHWYQQK |

-continued

Sequence Table

| SEQ ID NO: | Description | Sequence |
|---|---|---|
| 31 | Post-translational modification site LC (126-144) | SGTASVVCLLNNFYPREAK |
| 32 | Post-translational modification site LC (149-168) | VDNALQSGNSQESVTEQDSK |
| 33 | Peptide for determining glycosylation following Lys-C digestion HC (290-318) | TKPREEQYNSTYRVVSVLTVLHQDWLNGK |
| 34 | Peptide for determining deamidation following Asn-N digestion HC (377-399) | DIAVEWESNGQPENNYKTTPPVL |
| 35 | Nucleic acid sequence of the heavy chain | caggcttatctacagcagtctgggctgagctggtgaggcctggggcctcagtgaagatgtcc tgcaaggcttctggctacacatttaccagttacaatatgcactgggtaaagcagacacctaga cagggcctggaatggattggaggtatttatccaggaaatggtgatacttcctacaatcagaag ttcaagggcaaggccacactgactgtaggcaaatcctccagcacagcctacatgcagctcagc agcctgacatctgaagactctgcggtctatttctgtgcaagatatgactacaactatgctatg gactactggggtcaaggaacctcagtcaccgtctcctcagcctccaccaagggcccatcggtc ttccccctggcaccctcctccaagagcacctctgggggcacagcggccctgggctgcctggtc aaggactacttccccgaaccggtgacggtgtcgtggaactcaggcgccctgaccagcggcgtg cacaccttcccggctgtcctacagtcctcaggactctactccctcagcagcgtggtgaccgtg ccctccagcagcttgggcacccagacctacatctgcaacgtgaatcacaagcccagcaacacc aaggtggacaagaaagttgagcccaaatcttgtgacaaaactcacacatgcccaccgtgccca gcacctgaactcctggggggaccgtcagtcttcctcttccccccaaaacccaaggacaccctc atgatctcccggacccctgaggtcacatgcgtggtggtggacgtgagccacgaagaccctgag gtcaagttcaactggtacgtggacggcgtggaggtgcataatgccaagacaaagccgcgggag gagcagtacaacagcacgtaccgtgtggtcagcgtcctcaccgtcctgcaccaggactggctg aatggcaaggagtacaagtgcaaggtctccaacaaagccctcccagcccccatcgagaaaacc atctccaaagccaaagggcagccccgagaaccacaggtgtacaccctgcccccatcccgggat gagctgaccaagaaccaggtcagcctgacctgcctggtcaaaggcttctatcccagcgacatc gccgtggagtgggagagcaatgggcagccggagaacaactacaagaccacgcctcccgtgctg gactccgacggctccttcttcctctacagcaagctcaccgtggacaagagcaggtggcagcag gggaacgtcttctcatgctccgtgatgcatgaggctctgcacaaccactacacgcagaagagc ctctccctgtctccgggtaaa |
| 36 | Nucleic acid sequence of the light chain | caaattgttctctcccagtctccagcaatcctgtctgcatctccaggggagaaggtcacaatg acttgcagggccagctcaagtgtaagttacatgcactggtaccagcagaagccaggatcctcc cccaaaccctggatttatgccacatccaacctggcttctggagtccctgctcgcttcagtggc agtgggtctgggacctcttattctttcacaatcagcagtggaggctgaagatgctgccact tattactgccagcagtggactttaacccaccacgttcggaggggggaccaggctggaaata aaacggactgtggctgcaccaagtgtcttcatcttcccgccatctgatgagcagttgaaatct ggaactgcctctgttgtgtgcctgctgaataacttctatcccagagaggccaaagtacagtgg aaggtggataacgccctccaatcgggtaactcccaggagagtgtcacagagcaggacagcaag gacagcacctacagcctcagcagcaccctgacgctgagcaaagcagactacgagaaacacaaa gtctacgcctgcgaagtcacccatcagggcctgagctcgcccgtcacaaagagcttcaacagg ggagagtgt |
| 37 | Epitope on CD20 | IRAHT |
| 38 | Epitope on CD20 | EPAN |

The following examples are offered by way of illustration, and not by way of limitation.

7.1 Example 1—Glycosylation Profile

The glycosylation profile of a sample of anti-CD20 antibody proteins provided herein was determined by measuring fluorescently labeled N-glycans (fluorescent label is 2-aminobenzamide) that were enzymatically cleaved from the anti-CD20 antibody proteins using PNGase F. The labeled glycans are resolved using a hydrophilic interaction column equipped. The glycans flow through a fluorescence detector after separation. Peak identification from the test sample chromatograms is identified based on retention time and relative to peaks in the glycan standard which have been confirmed by mass spectrometry. The relative percentage of each N-glycan is calculated based on the N-glycan peak area divided by the total peak area of all N-glycans. The glycosylation profile is shown in FIG. 2.

7.2 Example 2—Intact Mass Method

Figure 3:
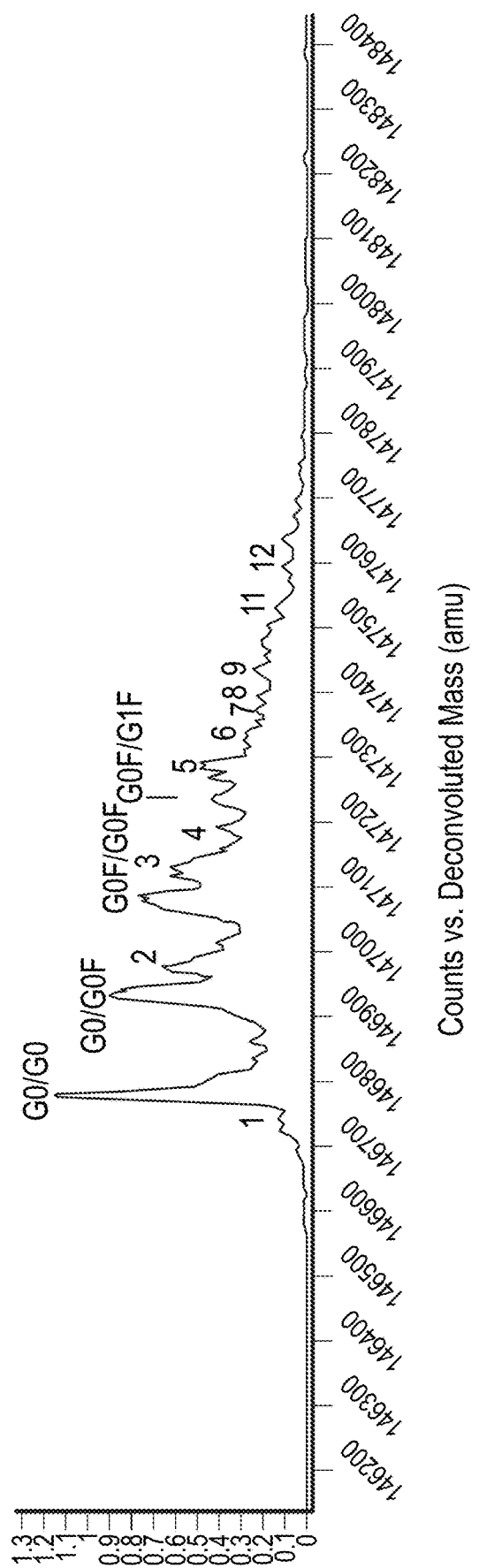
FIG. 3 illustrates the intact MS Spectra of a sample of anti-CD20 antibody proteins provided herein.

The glycosylation profile of anti-CD20 antibody proteins provided herein was assessed by intact mass analysis (LC-MS) under non-reducing conditions. The sample of anti-CD20 antibody proteins provided herein is first exchanged into MS appropriate buffers during the chromatography step using SEC and a mobile phase containing TFA, acetonitrile, and water. The sample is then introduced into an ESI-QTOF for intact mass analysis. The mass spectra are deconvoluted and the peaks are assigned based on mass. The relative abundance of each anti-CD20 antibody proteins provided herein containing N-glycan was calculated by taking the abundance of an N-glycan and dividing by the total abundance of all identified peaks. Results are provided in the table below and in FIG. 3.

TABLE 8

Intact Molecular Weights for Sample of anti-CD20 antibody proteins by LC-MS

| Mass Species | Batch Process | GMP1/RM-105238 B2 | GMP16/RS-117808 C1 | CR C2 |
|---|---|---|---|---|
| G0/G0 (Theoretical MW, 146779.3) | Observed MW Relative Abundance (%) | 146779.6 14.1 | 146781.3 16.9 | 146780.1 18.9 |
| G0/GF (Theoretical MW, 146925.4) | Observed MW Relative Abundance (%) | 146927.5 16.0 | 146931.3 14.9 | 146929.8 16.7 |
| G0F/G0F (Theoretical MW, 147071.6) | Observed MW Relative Abundance (%) | 147071.9 18.3 | 147073.5 12.3 | 147073.6 13.8 |
| G0F/G1F (Theoretical MW, 147233.7) | Observed MW Relative Abundance (%) | 147235.7 10.8 | 147229.7 7.4 | 147233.7 6.9 |
| 1-G0/G1-GlcNAc (Theoretical MW, 146738.2) | Observed MW Relative Abundance (%) | 146730.1 2.1 | 146736.4 2.7 | 146739.4 3.1 |
| 2-G0/G0B (Theoretical MW, 146982.3) | Observed MW Relative Abundance (%) | 146980.6 5.6 | 146982.2 10.8 | 146981.3 11.7 |
| 3-G0F/G0B (Theoretical MW, 147128.5) | Observed MW Relative Abundance (%) | ND | 147130.3 10.5 | 147128.3 9.7 |
| 4-G0F/G0F+K (Theoretical MW, 147199.7) | Observed MW Relative Abundance (%) | 147199.3 7.1 | ND | ND |
| 5-G0F/G0FB (Theoretical MW, 147274.6) | Observed MW Relative Abundance (%) | ND | 147271.7 8.3 | 147273.6 7.1 |
| 6-G0F/G0F+2K (Theoretical MW, 147327.9) | Observed MW Relative Abundance (%) | 147330.9 4.0 | ND | ND |
| 7-G0F/G1F+1K (Theoretical MW, 147361.9) | Observed MW Relative Abundance (%) | 147360.2 5.1 | ND | ND |
| 8-G1F/G1F+1K (Theoretical MW, 147395.8) | Observed MW Relative Abundance (%) | 147396.4 5.8 | 147396.3 4.0 | 147396.5 4.2 |
| 9-G0F/G1FB (Theoretical MW, 147436.7) | Observed MW Relative Abundance (%) | 147432.0 2.6 | 147436.6 4.4 | 147436.2 4.3 |
| 10-G0F/G1F+2K (Theoretical MW, 147490.1) | Observed MW Relative Abundance (%) | 147488.0 2.2 | 147488.2 3.8 | ND |
| 11-G1F/G1F+K (Theoretical MW, 147524.0) | Observed MW Relative Abundance (%) | 147528.6 2.4 | 147524.9 2.2 | 147529.2 1.9 |
| 12-G1F/G1FB (Theoretical MW, 147598.7) | Observed MW Relative Abundance (%) | 147596.2 1.2 | 147597.6 1.7 | 147600.3 1.7 |
| 13-G1F/G1F+2K (Theoretical MW, 147652.2) | Observed MW Relative Abundance (%) | 147653.3 1.1 | ND | ND |

Abbreviation: ND—not detected.

7.3 Example 3—Cell-Based ADCC Assay (a) Materials and Method

Antibody dependent cytotoxicity (ADCC) is mediated through binding of the Fc portion of TG-1101 (TG Therapeutics, Inc.) to the FcγIIIA Receptor on the effector cells. The assay used for this analysis employs Eurofins-DiscoverX's "KILR CD16a effector cells", which are single donor-derived human CD8+T-lymphocytes engineered to express CD16 (FcγRIII) on their plasma membrane surface. These cytotoxic T cells provide reduced background killing, increased accuracy and reproducibility compared to PMBC preparations isolated from fresh blood. Raji cells are used as target cells, and ADCC activity is determined from the lysis of the target cells.

KILR cells are obtained from Eurofins, and Raji cells from ATCC. Master and Working cell bank system was used to ensure quality of the reagents. Raji cells were seeded at $1 \times 10^5$ cells/mL, KILR Effector cells were seeded at $5 \times 10^5$ cells/mL, and final effector: target (E:T) ratio was 5:1. An eight-point dilution series of the samples were used in the concentration range of 250.00 pg/ml-0.04 pg/ml (250, 50, 16.7, 5.6, 1.9, 0.6, 0.2, 0.04 pg/ml). Cell mixtures and testing samples were cultured at 36±1° C., 5±1% $CO_2$ for 18-22 hours. At the end of the incubation, a CYTOTOX GLO™ preparation is added, and plates are incubated for 30±10 minutes. The plates are read using the SPECTRAMAX® plate reader. Two independent preparations of the materials are prepared and assayed across duplicate plates. Assay controls are prepared in triplicates and include: Target Cells Alone Control, Target Cells Death Control, Effector Cells Alone Control, and Effector & Target Cells Control. SOFTMAX® PRO was used to analyze the data with weighted nonlinear regression using a 4-parameter logistic fit. Results are reported as percentage ADCC activity compared to Ublituximan reference standard. EC50 of each testing sample, based on the 4-parameter logistic fitted curve, were generated for additional information. This test method is a validated assay, CTSOP482, used for TG-1101 (TG Therapeutics, Inc.) drug substance and drug product release and stability testing.

(b) Results

Figure 4:
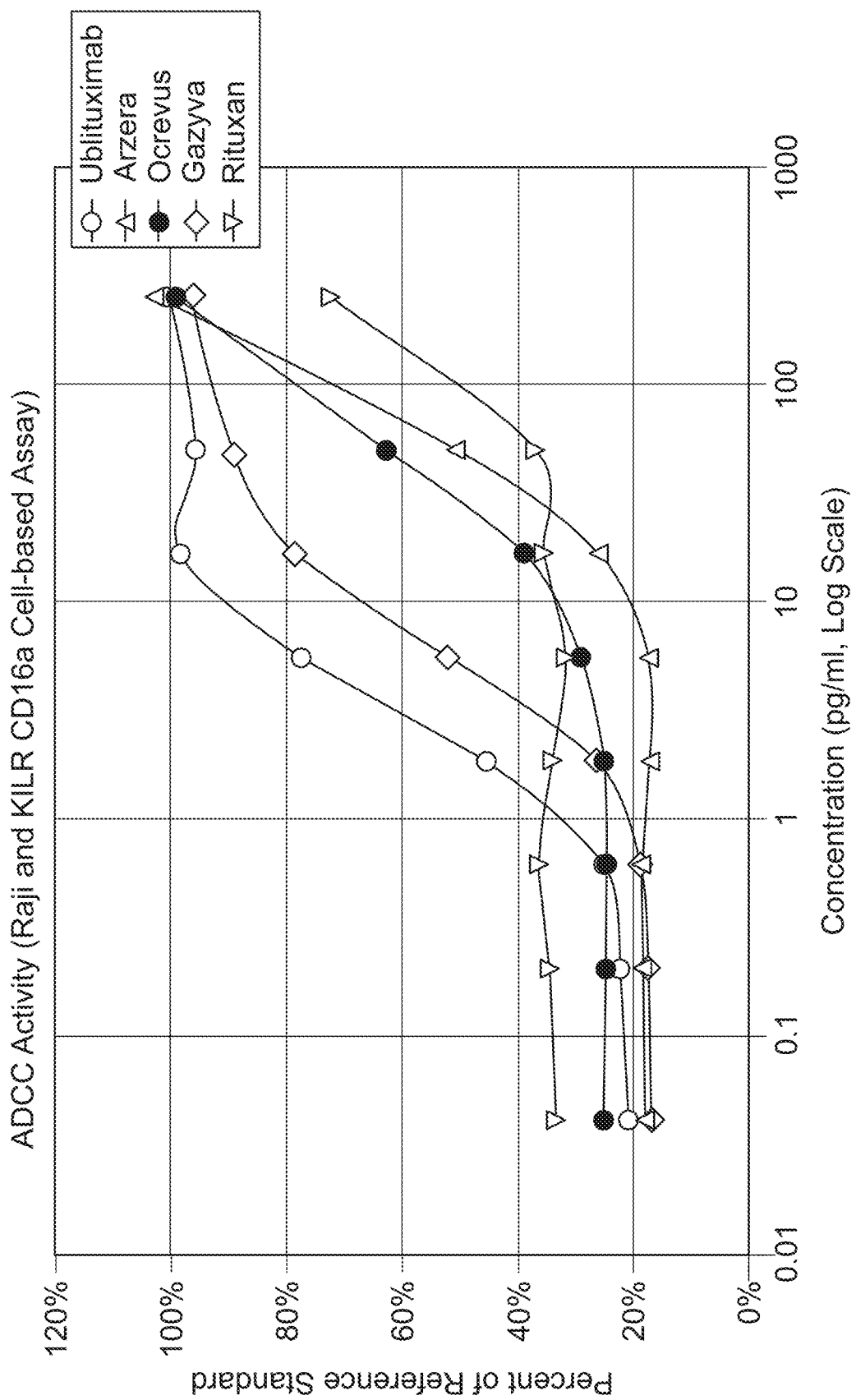
FIG. 4 illustrates antibody-dependent cellular cytotoxicity (ADCC) activity dose response curves using Raji cells and KILR CD16a cells.

Samples tested include TG-1101 (TG Therapeutics, Inc.), GAZYVA® (obinutuzumab), RITUXAN®, OCREVUS® (ocrelizumab), and ARZERRA® (ofatumumab). TG-1101 (TG Therapeutics, Inc.) commercial reference standard RS-117808 (117808) was used as control, As shown in FIG. 4, all anti-CD20 samples exhibited dose-dependent ADCC activity, TG-1101 (TG Therapeutics, Inc.) has highest ADCC activity compared to other anti-CD20. The ADCC activity expressed as percentage of the TG-1101 (TG Therapeutics, Inc.) reference standard is shown in Table 9, compared to TG-1101 (TG Therapeutics, Inc.), GAZYVA® has ADCC activity that is relative similar to TG-1101 (TG Therapeutics, Inc.), while the ADCC activities of RITUXAN®, OCREVUS, and ARZERRA® are significantly lower. The ED50s of each anti-CD20 are also shown in Table 9, overall TG-1101 (TG Therapeutics, Inc.) and GAZYVA® have lower EC50 than ARZERRA®, RITUXAN®, and OCREVUS®. EC50 of TG-1101 (TG Therapeutics, Inc.) is approximately 25 fold lower than OCREVUS®.

TABLE 9

ADCC Activity and EC50

| TG-1101 | Percentage Activity Against Ref. Std. | EC50 (pg/ml) |
|---|---|---|
| (TG Therapeutics, Inc.) | 110.9 % | 2.42 |
| GAZYVA ® | 59.3% | 6.58 |
| ARZERRA ® | 8.3% | 74.1 |
| RITUXAN ® | 0.8% | 5457.0 |
| OCREVUS ® | 5.6% | 60.8 |

7.4 Example 4—Cell-Based ADCC Assay Using Primary NK Cells (a) Materials and Method This ADCC assay was performed using CD20 expressing Raji cells as target cells, primary NK cells as effector cells, and LDH as target cell lysis read-out. Raji cells (ATCC, Cat #CCL-86TM) were seeded at $1 \times 10^5$ cells/well on plates. Primary NK cells isolated from human donor PBMC using Miltenyibiotec kit (Cat #130-092-657). E/T ratio of 5:1 for NK92/CD16a cells and primary NK cells was used in the assay. An eight-point dilution series of the samples, in triplicates, were used in the concentration range of 0.01 µg/ml-0 µg/ml with a dilution factor of 10. The target cells were incubated with test sample dilutions for 30 min in 37° C. incubator. Effector cells were added to the target cell cultures followed by 6 hours incubation after which supernatants were collected. The background (OD650 nm) subtracted OD492 nm data were used to calculate the LDH release. The percentages of cell lysis was calculated according the formula below: Cell lysis %=100*(ODSample data−ODtumor cells plus effector cells)/(ODMaximum release−OD Minimum release).

(b) Results

Figure 5:
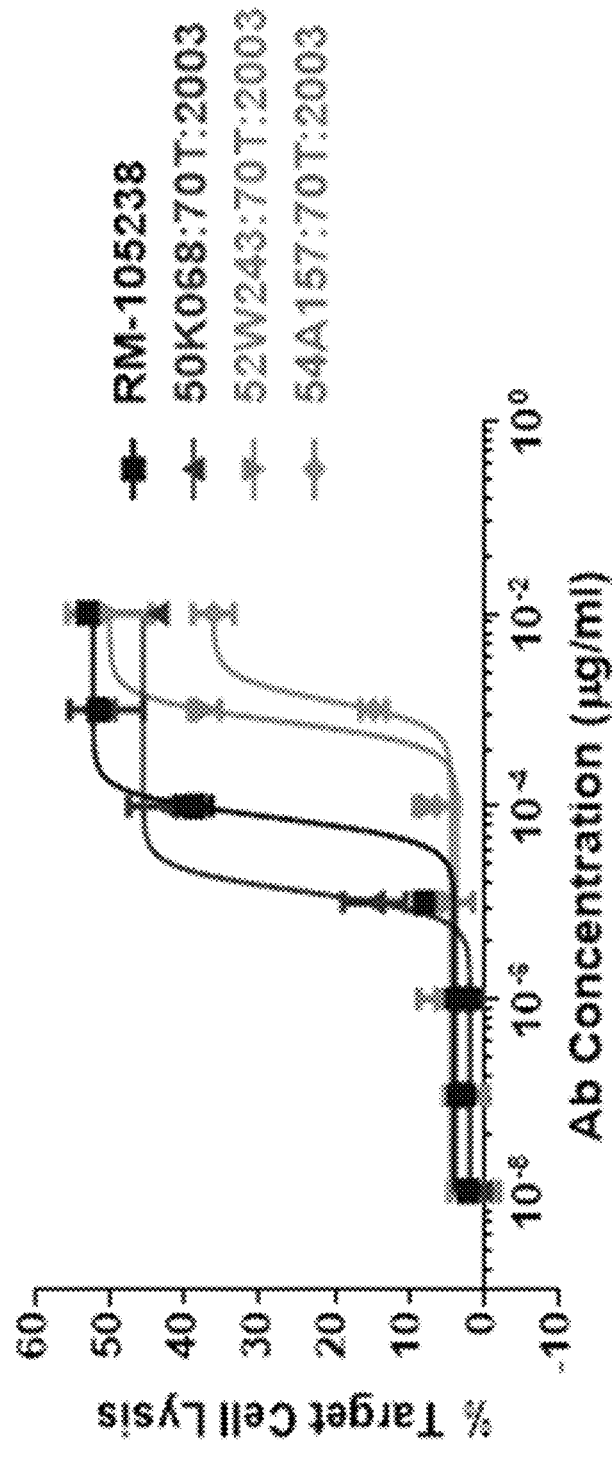
FIG. 5 illustrates ADCC activity dose response curves using Raji cells and primary NK cells.

Samples tested include TG-1101 (TG Therapeutics, Inc.), GAZYVA®, RITUXAN®, and ARZERRA®. As shown in FIG. 5, all anti-CD20 samples exhibited dose-dependent ADCC activity. The calculated EC50 values are summarized in Table 10. TG-1101 (TG Therapeutics, Inc.) and GAZYVA® displayed higher ADCC activities and lower EC50 than RITUXAN® and ARZERRA®.

TABLE 10

EC50 of ADCC assay Using Primary NK Cells

| | TG-1101 (TG Therapeutics, Inc.) (RM-105238) | ARZERRA ® | RITUXAN ® | GAZYVA ® |
|---|---|---|---|---|
| EC50 (ug/ml) | 49 | 500 | 1392 | 19 |

7.5 Example 5—Cell-Based ADCP Assay (a) Materials and Method

Antibody dependent cellular phagocytosis (ADCP) is another potential mechanisms of action (MOAs) for anti-CD20s. ADCP activity was assessed using an assay in which CD20 expressing Daudi cells were used as target cells (ATCC, Cat #CCL-213, labeled by PKH26). Human monocytes were isolated from PBMC from 20 human donors (using human Pan Monocyte Isolation Kit, MiltenyiBiotec, Cat #130-096-537) and differentiated in vitro using GM-CSF to yield macrophages. An E/T ratio of 5:1 was used; and the ADCP was assessed by flow cytometry in this assay. An eight-point dilution series of the samples, in duplicates and in the concentration range of 100 µg/ml-0 µg/ml with a dilution factor of 10, were incubated with PKH26-labeled target cells. Macrophages were then co-cultured with PKH26-labeled target cells for 22 hours. Target cell phagocytosis was assessed by flow cytometry. Controls in the assay included Target cell control of PKH26 stained Daudi cells only; Effector cell control of PKH67 stained MDM only.

Effector and target cells control with a non-specific IgG1 antibody; Effector and target cells control (background control). ADCP was determined by FACS as a percentage of PKH26/PKH67 double positive cell counts/PKH26.

(b) Results

Figure 6:
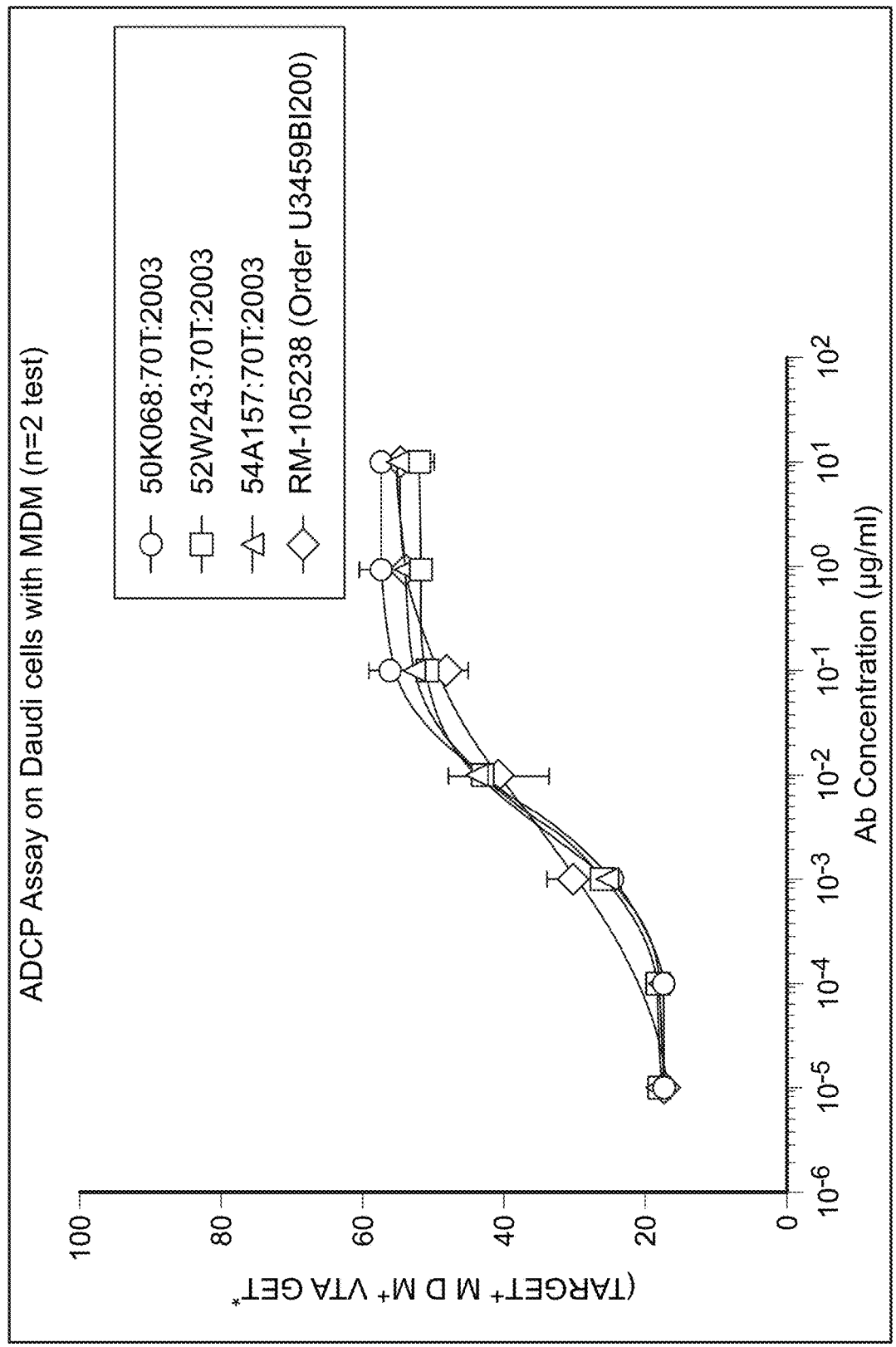
FIG. 6 illustrates antibody-dependent cellular phagocytosis (ADCP) activity dose response curves.

Samples tested include TG-1101 (TG Therapeutics, Inc.), GAZYVA®, RITUXAN®, and ARZERRA®. As shown in FIG. 6, all anti-CD20 samples exhibited dose-dependent ADCP activity. The calculated EC50 values are summarized in Table 11. The EC50s are in the ng/ml range, and given the nature of the test method, the ADCP activities of all samples are considered similar.

TABLE 11

EC50 of ADCP Assay

| | TG-1101 (TG Therapeutics, Inc.) (RM-105238) | ARZERRA ® | RITUXAN ® | GAZYVA ® |
|---|---|---|---|---|
| EC50 (ng/ml) | 0.3306 | 2.354 | 5.059 | 7.639 |

Blinding Code: 50K068:70T:2003 = GAZYVA ®; 52W243:70T:2003 = ARZERRA ®; 54A157:70T:2003 = RITUXAN ®

7.6 Example 6—Cell Based CDC Assay (a) Materials and Method

The Complement Dependent Cytotoxicity (CDC) is mediated through binding of the Fc portion of TG-1101 (TG Therapeutics, Inc.) to C1q Receptor in the complement system. The CDC activity assay used in this analysis is a cell-based assay using the CD20 expressing human mantle cell lymphoma cell line, Jeko-1 and rabbit serum as the source of complement. CDC mediated cell lysis is measured by the CELL TITER-GLO™ reagent (Promega). A nine-point dilution series of the samples are used in the concentration range of 10,000 ng/ml-10.42 ng/ml (10,000.00, 3333.33, 1666.67, 833.33, 416.67, 208.33, 104.17, 52.08, 10.42 ng/ml). Two independent preparations of each sample are prepared and assayed across duplicate plates. Assay negative controls are prepared in triplicates and include target cells & complement control and target cells alone control.

Jeko-1 cells, obtained from the ATCC and maintained through a master banking system, were seeded at $3\times10^5$ cells/mL and incubated for 60-90 minutes. Samples dilutions, and then complement were added, and the plates were incubated for approximately 2 hours at 37° C. and 25 minutes at room temperature. Target cells with complement only control and target cell only control provided a basal level of target cell viability over the course of the assay. The CELL TITER-GLO™ reagent is then added and incubated an additional 30 minutes at room temperature. At the end of the assay the plates are read using a SPECTRAMAX® M5 plate reader. SOFTMAX® PRO is used to analyze the data with weighted nonlinear regression using a 4-parameter logistic fit. The resulting data is evaluated using the PLA software for parallelism and potency against the reference standard. Results are reported as % potency relative to the reference standard. EC50 of each testing sample, based on the 4-parameter logistic fitted curve, were generated for additional information. This test method is a validated assay, CTSOP463, used for TG-1101 (TG Therapeutics, Inc.) drug substance and drug product release and stability testing.

(b) Results

Figure 7:
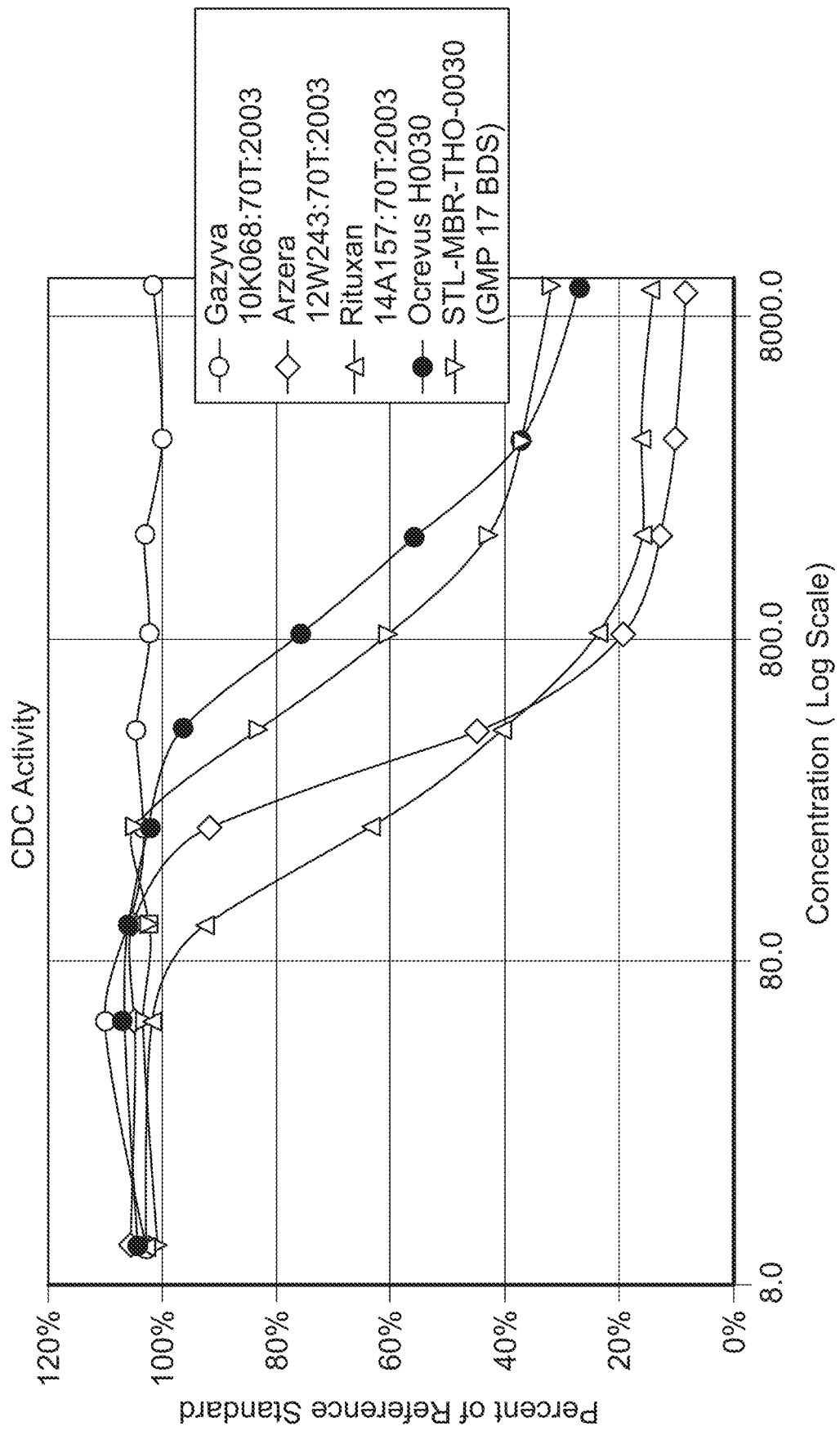
FIG. 7 illustrates complement dependent cytotoxicity (CDC) activity dose response curves.

Samples tested include TG-1101 (TG Therapeutics, Inc.), GAZYVA®, RITUXAN®, OCREVUS®, and ARZERRA®. TG-1101 (TG Therapeutics, Inc.) commercial reference standard RS-117808 (117808) was used as control, As shown in FIG. 7, all samples exhibited dose-dependent CDC activity, except for GAZYVA®, which is known to have reduced CDC activity. RITUXAN® and ARZERRA® have comparable CDC activity; Ubli and OCREVUS® have comparable CDC activity. The CDC activity expressed as percentage of the TG-1101 (TG Therapeutics, Inc.) reference standard is shown in Table 12, compared to TG-1101 (TG Therapeutics, Inc.), GAZYVA® has ADCC activity that is relative similar to TG-1101 (TG Therapeutics, Inc.), while the ADCC activities of RITUXAN®, OCREVUS®, and ARZERRA® are significantly lower. The ED50s of each anti-CD20 are also shown in Table 12, which shows similar comparisons as the level of CDC activities.

TABLE 12

| CDC Activity and EC50 | | |
|---|---|---|
| | Percentage Activity Against TG-1101 (TG Therapeutics, Inc.) Ref. Std. | EC50 (ng/ml) |
| TG-1101 (TG Therapeutics, Inc.) | 88.0% | 670 |
| GAZYVA® | 0.9% | N/A |
| ARZERRA® | 229.1% | 353 |
| RITUXAN® | 333.5% | 245 |
| OCREVUS® | 69.4% | 1206 |

7.7 Example 7—Cell Based CD20 Binding Assay (a) Materials and Method

The CD20 binding used for this analysis is a cell based binding assay that uses a CD20 expressing human mantle cell lymphoma cell line, Jeko-1, and an MSD (MesoScale Discovery) assay format. Jeko-1 target cells are seeded onto MSD plates, test samples are incubated and allowed to bind to Jeko-1 cells, anti-human Fc detection antibody conjugated with streptavidin-SULFOTAG™ is used to emit electrochemiluminescence signal. An eight-point dilution series of test samples were used in the concentration range of 40,000.00 µg/ml-0.23 ng/ml (40,000.00, 4,000.00, 1,000.00, 333.30, 111.10, 37.00, 4.60, 0.23 ng/ml). Two independent preparations of the Test Material are prepared for each 2-plate assessment. Assay controls include No cell control (Reference Standard/Test Material dilution+detection reagent, omitting cells) and Cell only control (Cells+detection reagent, omitting Reference Standard/Test Material).

Jeko-1 cells, obtained from the ATCC and managed through a master banking system, are seeded onto MSD high bind plate in PBS at $3\times10^5$ cells per mL, in a final volume of 100 µL per well, and incubated at 35-37° C. for 2 hours±10 min. Unbound cells are removed by a PBS wash, the plates are blocked then washed. Fifty µL of sample dilutions were added, and the plate is incubated at room temperature for 1 hour±10 min while shaking. Following incubation and three washes, 50 µL anti-human Fc detection antibody conjugated with STREP-SULFOTAG is added and incubated for 1 hour±10 min at room temperature while shaking. The plates are washed again, and 150 µL of the MesoScale read buffer, containing tripropylamine (TPA), is added as a co-reactant for light generation for an electrochemiluminescence read out. Plates are read immediately on a MSD Reader using Workbench 4.0. The resulting data is evaluated using the PLA software and analyzed using a constrained 4 parameter logistic model. Binding activity results are reported as percentage potency relative to the reference standard. EC50 of each testing sample, based on the 4-parameter logistic fitted curve, were generated for additional information. This test method is a validated assay, CTSOP466, used for TG-1101 (TG Therapeutics, Inc.) drug substance and drug product release and stability testing.

(b) Results

Figure 8:
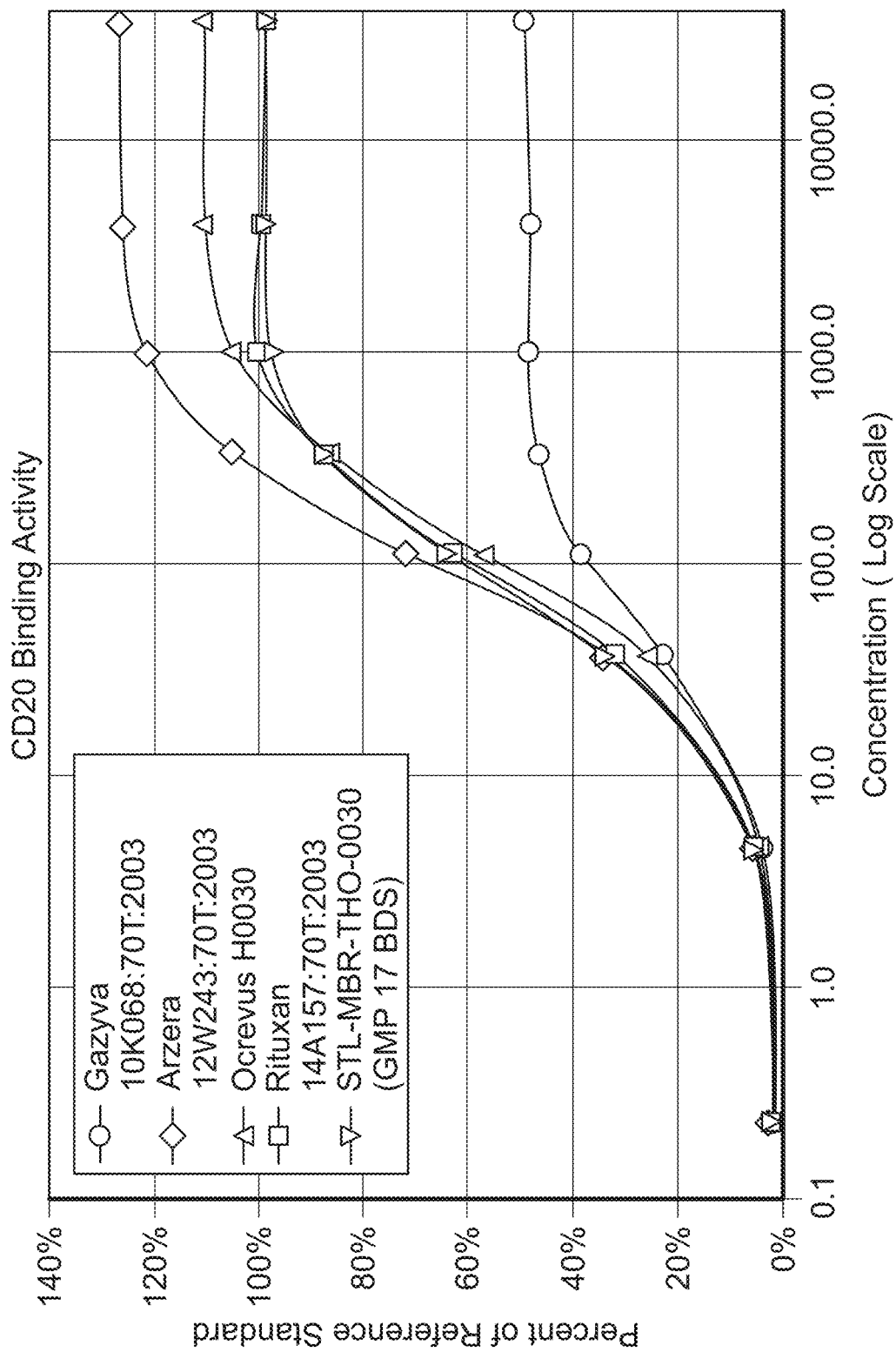
FIG. 8 illustrates CD20 binding dose response curves.

Samples tested include TG-1101 (TG Therapeutics, Inc.), GAZYVA®, RITUXAN®, OCREVUS®, and ARZERRA®. TG-1101 (TG Therapeutics, Inc.) commercial reference standard RS-117808 (117808) was used as control. As shown in FIG. 8, all samples exhibited dose-dependent CD20 binding. With the exception of GAZYVA®, which is a Type II anti-CD20 and is known to have approximately 50% of target occupancy, Ubituximab, RITUXAN®, OCREVUS®, and ARZERRA® have similar maximum binding. The CD20 binding activity expressed as percentage of the TG-1101 (TG Therapeutics, Inc.) reference standard and binding EC50s are shown in Table 13. The CD20 binding affinity of the 4 anti-CD20s are similar.

TABLE 13

CD20 Binding Activity and EC50

| | Percentage Binding Activity Against TG-1101 (TG Therapeutics, Inc.) Ref. Std. | EC50 (ug/ml) |
|---|---|---|
| TG-1101 (TG Therapeutics, Inc.) | 104% | 0.063 |
| GAZYVA ® | N/A | 0.053 |
| ARZERRA ® | 132% | 0.092 |
| RITUXAN ® | 118% | 0.133 |
| OCREVUS ® | 91% | 0.111 |

EC50s values listed are negative, rising from the PLA software log transforms the concentrations to base 2. The actual ED50 (in µg/ml) is $2^n$, where n=the number listed.

7.8 Example 8—Cell Surface CD20 Binding by FACS (a) Materials and Method

The binding of TG-1101 (TG Therapeutics, Inc.) to cell surface CD20 on Raji and Daudi cells was characterized by FACS analysis at LakePharma. A six-point dilution series of the samples, in duplicates and in the concentration range of 40 µg/ml-0 µg/ml with a dilution factor of 5 were used. Cells were incubated with sample dilutions; binding was detected using a PE conjugated anti-human secondary antibody.

(b) Results

Figure 9:
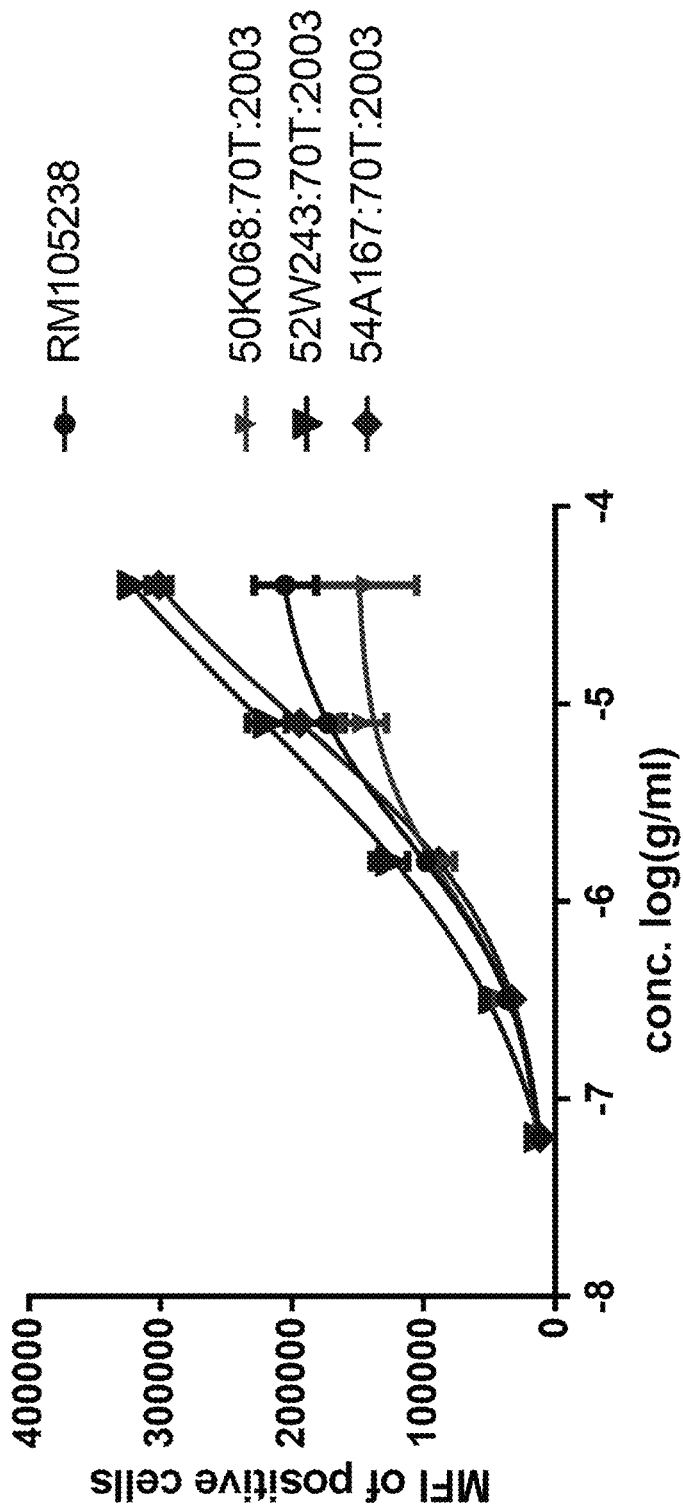
FIG. 9 illustrates CD20 binding dose response curves using FACS.

Samples tested include TG-1101 (TG Therapeutics, Inc.), GAZYVA®, ARZERRA®, and RITUXAN®. As shown in FIG. 9, all anti-CD20 samples exhibited dose-dependent CD20 binding to both Daudi and Raji cells. The binding characteristics as evaluated by the FACS assay are similar to that evaluated by the MSD assay. With the exception of GAZYVA®, which is a Type II anti-CD20 and is known to have approximately 50% of target occupancy, Ubituximab, RITUXAN®, and ARZERRA® have similar maximum binding. The calculated EC50 values are summarized in Table 14. The CD20 binding affinity of the four anti-CD20 antibodies are similar.

TABLE 14

EC50 of Cell Surface CD20 Binding by FACS

| EC50 (ug/ml) | TG-1101 (TG Therapeutics, Inc.) (RM-105238) | GAZYVA ® (50K068) | ARZERRA ® (52W243) | RITUXAN ® (54A157) |
|---|---|---|---|---|
| Daudi Cells | 9.832e-007 | 1.594e-006 | 7.926e-007 | 1.565e-006 |
| Raji Cells | 2.018e-006 | 1.165e-006 | 8.727e-006 | 8.364e-006 |

7.9 Example 9—FcγRIIIA Binding Assay (a) Materials and Method

The assay used in this analysis is a surface plasmon resonance (SPR)-based method that measures the binding to both FcγRIIIa 158V and FcγRIIIa 158F receptors. The method follows a direct binding assay methodology where the FcγRIIIa receptor is directly immobilized onto the flow cell on a sensor chip surface and samples are injected over the chip to assess binding. FcγRIIIa 158V receptor (3 µg/ml) or FcγRIIIa 158F receptor (6 µg/ml) is immobilized on the chip surface using covalent amine coupling chemistry. Eight-point dilution series of the testing samples are prepared in the concentration range of 1000 nM-15.6 nM with a dilution factor of 2. Independent duplicates of sample dilutions are injected over the chip, followed by surface regeneration between each cycle. The binding is measured in response units (RU). The kinetics of the binding reaction is determined by measuring changes in SPR due to the increase in mass in the close proximity to the biosensor chip surface. Change in the mass of the complex as a function of time is visualized as a sensorgram.

The equilibrium dissociation constants ($K_D$) of each sample is determined for each receptor. The rates of change of the SPR signal is analyzed using a 1:1 Langmuir model for FcγRIIIa 158V variant to yield apparent rate constants for the association and dissociation phases of the reaction, and equilibrium dissociation constants. $K_D$ is determined using steady state affinity for the FcγRIIIa 158F variant. The binding signals are exported into PLA to determine the relative binding response, elative affinity and relative binding for samples are also reported relative to the TG-1101 (TG Therapeutics, Inc.) reference standard. This test method is a validated assay, CTSOP477, used for TG-1101 (TG Therapeutics, Inc.) drug substance release testing.

(b) Results

Samples tested include TG-1101 (TG Therapeutics, Inc.), GAZYVA®, RITUXAN®, OCREVUS®, and ARZERRA®. As shown in Table 15, among the anti-CD20 antibodies tested, TG-1101 (TG Therapeutics, Inc.) has the highest binding affinities to both FcγRIIIa 158V and FcγRIIIa 158F receptors. GAZYVA® ranks the 2nd in binding affinities. For the high affinity receptor FcγRIIIa158V, TG-1101 (TG Therapeutics, Inc.) has ~15 folder higher affinity than OCREVUS®; for the low affinity receptor FcγRIIIa158F TG-1101 (TG Therapeutics, Inc.) has ~10 folder higher affinity than OCREVUS®. Shown in Table 16 are relative affinity and relative binding values using TG-1101 (TG Therapeutics, Inc.) ref std. as reference. Results show that TG-1101 (TG Therapeutics, Inc.) has higher relative binding and relative affinity than all the other anti-CD20s.

TABLE 15

KD for FcγRIIIa 158V and FcγRIIIa 158V Binding by SPR

| | Binding KD (nM) | |
|---|---|---|
| Sample | FcγRIIIa 158V Binding (1:1 Kinetics) | FcγRIIIa 158F Binding (Steady State Affinity) |
| TG-1101 (TG Therapeutics, Inc.) | 64.1* | 680.3* |
| GAZYVA ® | 242.0 | 1,793.3 |
| ARZERRA ® | 1,641.4 | 14,815.2 |
| RITUXAN ® | 1199.8 | 6960.9 |
| OCREVUS ® | 1025.8 | 6762.9 |

*Average of 4 values

TABLE 16

Summary of Relative Affinity and Relative Binding Results

| Sample | FcγRIIIa 158V Binding | | FcγRIIIa 158F Binding | |
|---|---|---|---|---|
| | Relative Affinity (%) | Relative Binding (%) | Relative Affinity (%) | Relative Binding (%) |
| TG-1101 (TG Therapeutics, Inc.) | 100.0 | 100.0 | 100.0 | 100.0 |
| GAZYVA® | 27.6 | 19.6 | 37.6 | 33.0 |
| ARZERRA® | 4.1 | 3.9 | 4.6 | 4.1 |
| RITUXAN® | 5.9 | 6.8 | 9.1 | 5.7 |
| OCREVUS® | 6.9 | 10.8 | 9.4 | 7.8 |

7.10 Example 10—Fc Receptor Binding by Octet (a) Materials and Method

This analysis was performed by LakePharma. Binding characterization were carried out on Octet HTX instrument at 25° C. Human Fc receptor panel were loaded onto Anti-Penta His (H1 S1K) biosensors. Loaded sensors were dipped into a serial dilutions of the testing samples (300 nM start, 1:3 dilution, 7 points). Kinetic constants were calculated using a monovalent (1:1) binding model.

(b) Results

Samples tested include TG-1101 (TG Therapeutics, Inc.), GAZYVA®, RITUXAN®, OCREVUS®, and ARZERRA®. As shown in Table 17, among the anti-CD20 antibodies tested, TG-1101 (TG Therapeutics, Inc.) has the highest binding affinities to both FcγRIIIa 158V and FcγRIIIa 158F receptors, corroborating the SPR data. Binding affinities to FCRN, which can affect PK, are similar among all the anti-CD20s. Compared to OCREVUS®, TG-1101 (TG Therapeutics, Inc.) also has higher affinities for FcγRIIA and FcγRIIIB

TABLE 17

Summary of $K_D$ results against Fc Receptors

| KD (nM) | TG-1101 (TG Therapeutics, Inc.) (RS0117808) | GAZYVA® | ARZERRA® | RITUXAN® | OCREVUS® |
|---|---|---|---|---|---|
| FcγRI | 20 | 26 | 21 | 15 | 19 |
| FcγRIIA | 92 | 281 | 232 | 253 | 624 |
| FcγRIIB/C | 158 | 225 | 156 | 211 | 362 |
| FcγRIIIA F158 | 56 | 98 | 482 | 239 | 592 |
| FcγRIIIA V158 | 23 | 40 | 207 | 146 | 138 |
| FcγRIIIB | 169 | 277 | 307 | 309 | 2090 |
| FcRn | 42 | 39 | 64 | 43 | 62 |

7.11 Example 11—C1q Binding Assay (a) Materials and Method

The C1q binding assay used for this analysis is an ELISA assay. Samples were coated on ELISA plates, HRP conjugated human C1q is incubated with samples on the plate. The bound HRP, in the presence of substrate TMB, generates a colorimetric signal. A 7-point dilution series of Test Materials were prepared in the concentration range of 15.00 µg/ml-0.12 µg/ml with a dilution factor of 2. Sample dilutions are coated onto ELISA plates, and the plates incubated for 1 hour±30 min at room temperature. After coating, the plates are washed, blocked, and washed again. Peroxidase conjugated C1q was added, and the plates incubated for 1.5 hours±30 minutes at room temperature. After incubation and washing, a tetramethylbenzidine (TMB) substrate solution was added and plates incubated at room temperature for 7 minutes (−1 min/+30 seconds). This produces a colorimetric reaction which is proportional to the level of C1q bound. The reaction is stopped with the addition of 1M sulfuric acid and the color is measured at 450 nm using a Molecular Devices SPECTRAMAX® microplate reader. SOFTMAX® PRO is used to analyze the data with weighted nonlinear regression using a 4-parameter logistic fit. Binding activity results are reported as percentage potency relative to the TG-1101 (TG Therapeutics, Inc.) reference standard. EC50 of each test sample, based on the 4-parameter logistic fitted curve, were generated for additional information. This test method is a validated assay, CTSOP455, used for TG-1101 (TG Therapeutics, Inc.) drug substance and drug product release and stability testing.

(b) Results

Figure 10:
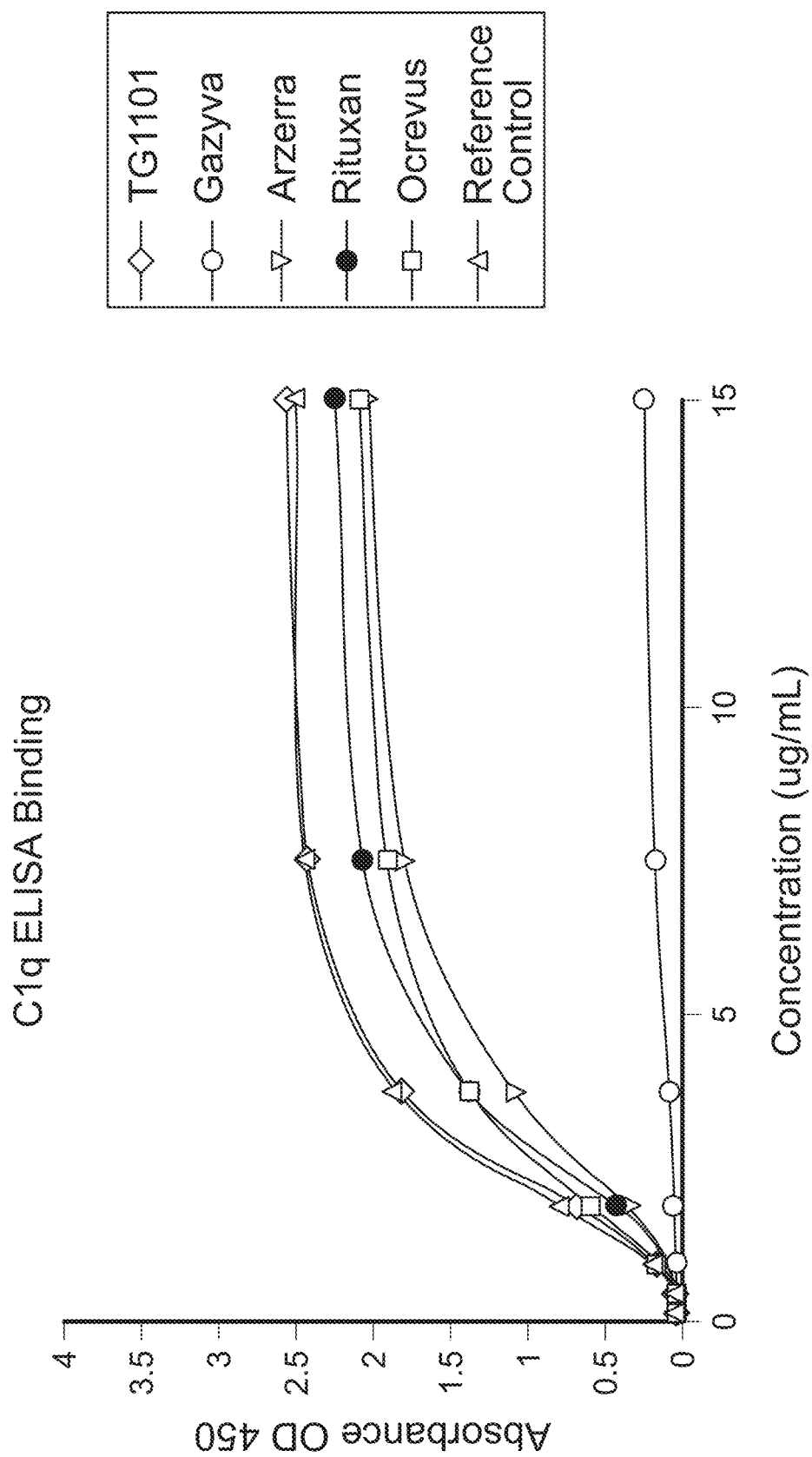
FIG. 10 illustrates C1q binding dose response curves.

Samples tested include TG-1101 (TG Therapeutics, Inc.), GAZYVA®, RITUXAN®, OCREVUS®, and ARZERRA®. TG-1101 (TG Therapeutics, Inc.) commercial reference standard RS-117808 (117808) was used as control, As shown in FIG. 10, GAZYVA® has minimal C1q binding (as expected), and the other 4 anti-CD20s exhibit dose dependent C1q binding. TG-1101 (TG Therapeutics, Inc.) has slightly higher maximum binding. The C1q binding activity expressed as percentage of the TG-1101 (TG Therapeutics, Inc.) reference standard is shown in Table 18. The ED50s of each anti-CD20 are also shown in Table 18, EC50 of TG-1101 (TG Therapeutics, Inc.) is slightly lower than the all anti-CD20s, suggesting TG-1101 (TG Therapeutics, Inc.) has higher affinity for C1q.

TABLE 18

C1q Binding Activity and EC50

| | Percentage C1qBinding Activity Against TG-1101 (TG Therapeutics, Inc.) Ref. Std. | EC50 (ug/ml) |
|---|---|---|
| TG-1101 (TG Therapeutics, Inc.) | 106 | 2.6 |
| GAZYVA® | 9.6 | N/A |
| ARZERRA® | 76 | 3.7 |
| RITUXAN® | 96 | 3.2 |
| OCREVUS® | 57 | 2.9 |

7.12 Example 12—Human Whole Blood B-Cell Depletion Assay (a) Material and Method TG-1101 (TG Therapeutics, Inc.) was characterized in an autologous normal human whole blood B-cell depletion assay in comparison to GAZYVA®, RITUXAN®, OCREVUS®, and ARZERRA®. Whole blood from three human donors was used, and donors were selected to have the 158V/158V genotype for FCGR3A_SNP target (r5396991). Sample dilutions, in the concentration range of 0.000001-100 µg/ml, was added to the whole blood and incubated at 37° C. for 24 hours in a humidified cell incubator. Aliquots of the blood were stained for markers including CD45 (lymphocyte population), CD3 (T cells), CD19 (B cells), and CD20 (B cells). B-cell depletion was evaluated by displaying cells in the CD45-positive lymphocyte gate, and enumerating CD3-positive T cells, CD19-positive B-cells, and CD20-positive B-cells. Percent of B-cell depletion (100–([100/B-/T-cell ratio in sample without antibody]×[B-/T-cell ratio in sample containing antibody])) was calculated and plotted against sample concentration.

(b) Results

Samples tested include TG-1101 (TG Therapeutics, Inc.) commercial reference standard RS-117808 (117808), A drug substance batch manufactured by the commercial process (C2) at Samsung Biologics (PPQ1), GAZYVA®, RITUXAN®, OCREVUS®, and ARZERRA®. As shown in FIGS. 11A-C, all samples exhibited dose-dependent B-cell depletion activity, even though there are some minor donor to donor differences. Overall, TG-1101 (TG Therapeutics, Inc.) and GAZYVA® have higher B cell depletion activities than ARZERRA®, RITUXAN®, and OCREVUS®. Three anti-CD20 antibodies and one anti-CD19 antibody were used in this experiment. The B-cell depletion ED50s calculated using each of the antibodies for B cell labeling are summarized in Table 19. Overall, TG-1101 (TG Therapeutics, Inc.) and GAZYVA® also have lower EC50 than ARZERRA®, RITUXAN®, and OCREVUS®. On average, EC50 of TG-1101 (TG Therapeutics, Inc.) is more than tenfold lower than OCREVUS®.

7.13 Example 13—Calculation of Pharmacokinetic (PK) Values

Relevant steady state PK parameters were calculated according to methods known in the art. A steady-state is reached when the quantity of drug eliminated in the unit of time equals the quantity of the drug that reaches the systemic circulation in the unit of time. Consequently, the half-life represents the time required to reduce the plasma concentration of the drug reached in steady-state by 50%. Wherein; t=Time, Vd=volume of distribution, and Cl=clearance. The half-life was calculated with the following formula:

$$t\left(\frac{1}{2}\right) = .0693 \times \left(\frac{Vd}{CL}\right)$$

The AUC is representative of the total dosage of the drug exposure over time. AUC is utilized as a metric when determining the formulations of an equivalent dosage, and their resulting tissue or plasma exposure. AUC is equivalent to the average concentration over a time interval. Wherein t=Time, and Cpt=the last measured drug concentration with respect to time. The AUC was calculated with the following formula:

$$AUC = \int_{t=0}^{t=\infty} Cp^t \cdot dt$$

The Cmax was obtained by the measurement of the highest point during the time of observation of drug concentration following the end of the absorption phase and the beginning of the elimination phase. The Cmin was obtained by the measurement of the highest point during the time of observation of drug concentration following the end of the absorption phase and the beginning of the elimination phase.

TABLE 19

Summary of ED50 of B Cell Depletion from Multiple B Cell Markers

| | B Cell Marker | TG-1101 (TG Therapeutics, Inc.) | PPQ1 | GAZYVA ® | ARZERRA ® | RITUXAN ® | OCREVUS ® |
|---|---|---|---|---|---|---|---|
| Donor 1 EC50 (µg/ml) | CD20 H147 | 0.021 | 0.018 | 0.065 | 0.048 | 0.678 | 0.131 |
| | CD20 2H7 | 0.080 | 0.151 | 0.045 | 0.135 | 2.466 | 2.843 |
| | CD20 L27 | 0.023 | 0.023 | 0.056 | 0.068 | 0.941 | 0.226 |
| | CD19 | 0.006 | 0.012 | 0.011 | 0.040 | 1.389 | 0.054 |
| Donor 2 EC50 (µg/ml) | CD20 H147 | 0.035 | 0.043 | 0.032 | 0.076 | 0.531 | 0.262 |
| | CD20 2H7 | 0.329 | 0.125 | 0.027 | 0.150 | 2.730 | 3.955 |
| | CD20 L27 | 0.042 | 0.048 | 0.026 | 0.080 | 0.641 | 0.317 |
| | CD19 | 0.012 | 0.010 | 0.015 | 0.013 | 0.294 | 0.124 |
| Donor 3 EC50 (µg/ml) | CD20 H147 | 0.081 | 0.100 | 0.072 | 0.098 | 0.599 | 0.516 |
| | CD20 2H7 | 0.568 | 0.477 | 0.016 | 0.233 | 5.369 | 12.890 |
| | CD20 L27 | 0.144 | 0.168 | 0.206 | 0.141 | 1.123 | 0.962 |
| | CD19 | 0.020 | 0.011 | 0.011 | 0.038 | 8.176 | 2.135 |

7.14 Example 14—Methods for Determining Population Pharmacokinetic (PPK) Values for TG-1101 for Treatment of Autoimmune Disorders TG-1101 serum concentration-time, dose, demographic, and covariate data from one Phase 2 study (TG1101-RMS201) and two Phase 3 studies (TG1101-RMS301 and TG1101-RMS302) in subjects with RMS were pooled for the Pop PK analysis of TG-1101. The dataset was combined with a previous dataset of TG-1101 in subjects with hematologic malignancies.

All subjects in Studies TG1101-RMS201, TG1101-RMS301 and TG1101-RMS302 with at least one TG-1101 dose administration were included in the dataset for the PK analysis. Subjects that did not have at least one quantifiable post-dose TG-1101 concentration were included in the dataset and flagged. Exposures for these subjects were determined based on typical population PK parameters.

In the Phase 2a clinical trial, TG1101-RMS201, TG-1101 was administered as a single agent and compared with placebo to examine the level of B cell depletion by TG-1101 as well as determine the optimal dose and infusion time for TG-1101 in subjects with RMS. Based on the results of this study, a dose of 150 mg (infused over 4 hours) on Week 1 Day 1 followed by a dose of 450 mg (infused over one hour) on Week 3 Day 15 resulted in a median of >99% B cell depletion that was achieved on Week 4 and sustained until Week 24. The dosing regimen was well tolerated by the subjects with infusion-related reactions (Grade 1 and 2) being the commonly reported adverse event. Two Phase 3 studies in subjects with RMS have been completed. Two phase 3 studies, TG1101-RMS301 (aka ULTIMATE I) and TG1101-RMS302 (ULTIMATE II), were randomized, double-blind, double-dummy, active-controlled studies of TG-1101 compared with oral teriflunomide to assess ARR, safety and tolerability in subjects with RMS.

Overall, the dataset for PopPK analysis included a total of 8672 PK samples collected from 931 subjects. Pre-dose samples accounted for 10.02% of PK samples and records with missing information or outliers (>10 standard deviations from the mean TG-1101 concentration at the nominal dosing time) accounted for 0.20% and were excluded. Post-dose samples that were BLQ accounted for 3.47% of the data. Exclusions resulted in no quantifiable post-dose PK samples for 36 subjects. Consequently, the PK analysis dataset included 7485 PK samples from 895 subjects, of which 5624 PK samples were from 591 subjects with RMS.

The final PopPK parameter estimates are presented in Table 20. PK parameter estimates for a typical subject (defined as a male subject that is ADA negative with a body weight of 73 kg from North America or Western Europe) were as follows: CL was estimated to be 11.6 mL/h, with IIV of 38.1%; Vc was estimated to be 3.18 L(IIV=15.0%); Vp was estimated to be 3.60 L (IIV=21.3%); and Q was estimated to be 11.6 mL/h.

Body weight and ADA were found to be statistically significant predictors of TG-1101 CL. TG-1101 CL was modestly increased by 14% in subjects that were ADA positive compared to those had no quantifiable ADA. For the wide range of body weight in the RMS subpopulation (45.1 to 154 kg), CL ranged from 22% lower to 48% higher compared to that for a typical subject with a body weight of 73 kg. In addition at late times (417 d after the start of treatment), CL was reduced by a median of 12.5%.

Body weight, sex and region were found to be a statistically significant predictor of Vc-Subjects from Eastern Europe were found to have slightly higher (10%) Vc than Western Europeans and North Americans and females had slightly lower (7%) Vc than males. For the wide range of body weight in the RMS subpopulation (45.1 to 154 kg), Vc ranged from 19% lower to 38% higher than that for a typical subject with a body weight of 73 kg.

After inclusion of body weight in the model, there was no effect of age, hemoglobin concentration, platelet count, white blood cell count, renal impairment or hepatic impairment on TG-1101 PK.

TABLE 20

Parameter Estimates of the Final TG-1101 PK Model

| Parameter | Estimate | RSE[a] (%) | IIV[b] (CV %) | RSE (%) | Shrinkage[c] (%) |
|---|---|---|---|---|---|
| Clearance (CL, mL/h) | 11.6 | 2.91 | 38.1 | 11.6 | 5.32 |
| Volume of central compartment (Vc, L) | 3.18 | 2.40 | 15.0 | 18.5 | 32.6 |
| Inter-compartmental clearance (Q, mL/h) | 11.6 | 10.5 | | | |
| Volume of peripheral compartment (Vp, L) | 3.60 | 3.55 | 21.3 | 27.1 | 40.0 |
| Fractional change in CL for Study CD20-0703 | 3.07 | 17.5 | | | |
| Fractional change in Vc for Study CD20-0703 | 1.68 | 6.25 | | | |
| Fractional change in CL for doses <300 mg due to TMDD | 4.89 | 17.4 | | | |
| Fractional change in CL at Time >10000 h (or 417 days) | 0.875 | 0.41 | | | |
| Effect of ADA on CL | 1.14 | 3.12 | | | |
| Effect of body weight on CL | 0.524 | 10.8 | | | |
| Effect of body weight on Vc | 0.434 | 10.9 | | | |
| Effect of Eastern Europe region on Vc | 1.10 | 2.26 | | | |
| Effect of female sex on Vc | 0.931 | 1.75 | | | |
| Covariance of CL and Vc[d] | 0.0248 | 25.4 | | | |
| Residual error | | | | | 8.35 |
| Proportional residual error (all studies except CD20-0703 (%)) | 31.7 | 2.35 | | | |
| Proportional residual error-Study CD20-0703 (%) | 60.3 | 6.57 | | | |

Abbreviations: CL—clearance; CV %—percent coefficient of variation; ETA—individual-specific random effect; IIV—inter-individual variability; Q—inter-compartmental clearance; RSE—relative standard error; SD—standard deviation; SE—standard error; U2—TG-1101 + umbralisib; Vc—volume of the central compartment; Vp—volume of the peripheral compartment.
[a]The RSE of the parameter estimate is calculated as 100 × (SE/typical value); the RSE of the IIV magnitude is calculated as 100 × (SE/variance estimate).
[b]Estimates for random effects and IIV are presented in CV % and based on the estimated values, calculated as √variance × 100.
[c]Shrinkage (%) as calculated as 100 × (1-SD[ETA]/√[variance]).
[d]The correlation coefficient between CL and Vc was estimated as 0.434.

In the evaluation of the final TG-1101 PopPK model, standard errors were obtained and presented together with the parameter estimates in Table 20. Model parameters were precisely estimated with RSE<20% for structural and covariate model parameters and RSE<30% for random effects estimates. Shrinkage was acceptable for CL and Vc (5.32% and 32.6%, respectively) with large shrinkage on Vp (40%).

Key Goodness-of-fit (GOF) diagnostics for the TG-1101 final PopPK model suggested satisfactory fit with minimal bias in residuals over time and across predicted concentration values and showed good agreement between predicted and observed concentrations. Relative to the base model, ETA—covariate relationships were resolved and no further trends between ETAs (on CL and Vc) and covariates were evident in the RMS subpopulation, suggesting that the model adequately captured significant covariate relationships. Overall, the prediction-corrected visual predictive check (pcVPC) plots suggests that the model well predicts the central tendency of the observed TG-1101 concentrations and adequately captures the range of the data.

The relative importance of covariate effects included in the final PoPK model was evaluated with a forest plot of relative changes in exposure ($C_{max,ss}$, $C_{min,ss}$, and $AUC_{ss}$) when covariates were varied one at a time (i.e., univariate analysis). The effects of these covariates, including body weight, sex, region ADA and the fractional change in CL at late times, on TG-1101 exposures fell within the range of 0.8 to 1.25 compared to the reference exposure (defined as the exposure for a male subject from North America/Western Europe with a body weight of 73 kg, who is ADA negative and has been on treatment for <416 days. Consequently, none of the covariates were deemed clinically relevant. Furthermore, the covariates did not have a significant impact on the magnitude of IIV on CL or Vc. The combined effects of body weight and ADA reduced IIV by only 2.8%, from 39.2% in the base model to 38.1% (Table 20) in the final model. Similarly, body weight, sex and region reduced IIV by 18.5% in Vc from 18.4% in the base model to 15.0% in the final model.

FIG. 12 shows the Goodness-of-Fit (GOF) diagnostics of the TG-1101 final model. FIG. 13 shows the pcVPC for the TG-1101 final PK model by study. FIG. 14 shows the forest plot of covariate effects on TG-1101 drug exposure.

The final PopPK model was re-estimated with the dataset including excluded outliers. All structural parameters were precisely estimated with no relevant change in those estimates, while the IIV terms were inflated with the inclusion of the outliers. It can therefore be expected that exclusion of outliers during the model development eliminated the influence of these outliers and minimized spurious findings in the covariate analysis. The final PopPK model was also re-estimated including the RMS subpopulation only. The fit of the model to the RMS data resulted in similar structural parameters and random effects, with the exception of marginally lower IIV on CL; precision of parameter estimation was also similar.

Conclusions: TG-1101 PPK Analysis

The final model of TG-1101 was utilized to obtain individual post hoc estimates of PK parameters. For each subject enrolled in studies TG1101-RMS201, TG1101-RMS301, TG1101-RMS302, PK parameters ($AUC_{ss}$, $C_{avg,ss}$, $C_{max,ss}$, and $C_{min,ss}$) at Week 48 were estimated based on post hoc PK parameters.

The geometric mean 1½ (90% confidence interval [CI]) was calculated to be 21.8 days (21.4, 22.1 days). Median time to reach steady state was determined to be 15.5 weeks. Accordingly, there was no accumulation for subjects that received the per-protocol regimen of 150 mg TG-1101 on Day 1 followed by 450 mg on Day 15, Week 24 and Week 48. The median Cmax ratio at Week 24 to Cmax on Day 1 was 3.04 (range 3.00 to 3.42) consistent with the 3-fold increase in the amount of the dose and indicative of no accumulation. Similarly, the Cmax ratio at Week 48 to Week 24 was 1, indicative of no accumulation.

The model-predicted geometric mean $AUC_{ss}$, $C_{avg,ss}$, $C_{max,ss}$, and $C_{min,ss}$ was 3000 μg·d/mL (±28%), 8940 ng/mL (±28%), 139000 (±15.1%), and 139 (±170%), respectively.

7.15 Example 15—Commercial-Scale Manufacturing Process of Making TG-1101 in YB2/0 Rat Hybridoma Cells In this Example, the manufacturing process for TG-1101 expressed in YB2/0 rat hybridoma cells at 15,000 L is described. An overview of the manufacturing process for TG-1101 is illustrated in the flow diagram of Table 21.

TABLE 21

TG-1101 Manufacturing Process Flow Diagram

Vial of TG-1101 Working Cell Bank

↓

Inoculum Expansion
(Shake flasks, 50 L cellbag)

↓

Seed Bioreactors
(120 L, 600 L, 3000 L)

↓

Production Bioreactor
(Fed-batch 15,000 L)

↓

Harvest
(Disc centrifuge)
(A1HC Pod depth filter, 1.2/0.5 μm filter, 0.45/0.2 μm filter)

↓

Capture Column Chromatography
(MabSelect SuRe Protein A)

↓

Solvent/Detergent Viral Inactivation (SDVI)
(TnBP/Polysorbate 80)

↓

Cation Exchange Chromatorgraphy (CEX)
(SP Sepharose)

↓

TABLE 21-continued

TG-1101 Manufacturing Process Flow Diagram

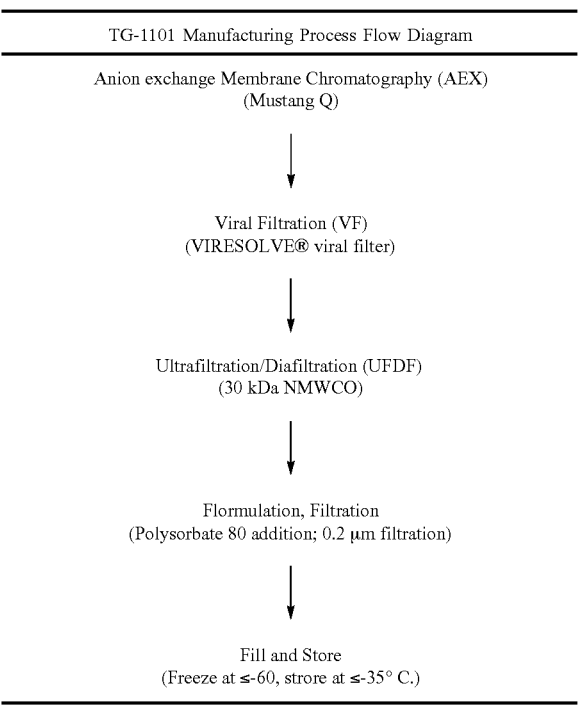

In summary, the production of each batch of TG-1101 began with the thaw of a working cell back (WCB) vial, described further below. The culture was expanded through a series of shake flasks and seed bioreactors to meet the inoculum requirements of the 15,000 L production bioreactor, which was operated in fed-batch mode. The bioreactor was harvested and clarified by centrifugation followed by depth filtration. The clarified harvest was purified by three chromatography steps including Protein A, cation exchange, and anion exchange, designed to purify the TG-1101 and to reduce process impurities such as host cell protein and residual DNA. The purification process (as illustrated in Example 4) contained steps to ensure viral safety including viral inactivation (solvent/detergent) and a viral filtration step. Final UFDF and formulation steps are used to concentrate and buffer exchange TG-1101 into the formulation buffer and to the desired product concentration. The ready to fill drug substance was formulated to obtain TG-1101 at a concentration of 25.0 mg/mL in 25 mM sodium citrate, 154 mM sodium chloride, 0.07% polysorbate 80, pH 6.5. After filling, the TG-1101 drug substance was frozen at <−60° C. and then stored frozen at <−35° C.

Additional descriptions of the upstream and downstream process operations are provided below.

(a) Expression Vector, Production Cell Line, and Cell Banks

The host cell line used for generation of the TG-1101 producing cell line was the rat cell line YB2/0. The production cell line, R603-12D11, was developed after transfecting the expression vector 11K463-25 (containing the immunoglobulin heavy and light chain cDNA sequences of TG-1101) into the YB2/0 host cell line. FIG. 15 depicts the expression vector map of HK463-25 to produce TG-1101, in a 15,000 L bioreactor.

Expression Vector

The expression vector HK463-25 included various elements that were optimized for stable expression in the YB2/0 host cell line. The Rous Sarcoma Virus Long Terminal Repeat (RSV LTR) promoter was used for the constitutive expression of both heavy and light chain cDNAs. This promoter corresponds to the Long Terminal Repeat of the RSV genome which contains enhancer elements in its 5' region and has strong transcriptional activity in the YB2/0 cell line. Transcriptional termination and polyadenylation of both heavy and light chain cDNAs were provided by the human growth hormone polyadenylation sequence (hGH polyA). A chimeric intron was introduced 5' to the cDNA sequence of each antibody chain to improve expression. This intron was optimized for splicing and is composed of a 5' donor sequence from human beta-globin and a 3' acceptor sequence from an Ig heavy chain variable gene. The beta lactamase gene conferred ampicillin resistance (AmpR) and was provided to enable production of the plasmid in E. coli. The enzyme neomycin-phosphotransferase II (NeoR) was under the control of the SV40 promoter and confers resistance to the transfected cell line to the antibiotic G418, thus acting as a selectable marker. Dihydrofolate reductase (Dhfr) was under the control of the SV40 promoter and conferred resistance to methotrexate (MTX) and can also act as a selectable and amplifiable marker in the transfected cell line.

The HK463-25 expression vector (FIG. 15) was 11.1 kb in size and contained five open reading frames for the antibody heavy chain, light chain, Dhfr, NeoR and AmpR genes in the same orientation. The restriction sites shown in the figure were used for Southern blot analysis of the integration of the construct. A unique NotI restriction site located 3' to the NeoR gene was used for linearization of the vector prior to transfection.

The Production Cell Line, R603-12D11

The production cell line, R603-12D11, was generated after transfection of the host cell line, selection and screening of transfectants, and then limiting dilution cloning. The clones were screened, production cell line R603-12D11 was selected, and adapted to serum free medium. A pre-seed stock (PSS) cell bank was prepared. An overview of the steps involved in the generation of production cell line R603-12D11 is shown in Table 22.

TABLE 22

Production Cell Line R603-12D11 Generation

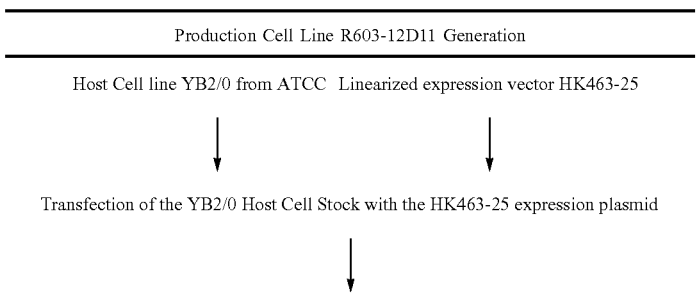

TABLE 22-continued

Production Cell Line R603-12D11 Generation

Selection of transfectants with G418
↓
Screening of transfectants to identify candidate cell lines
↓
Cloning by limiting dilution at 0.4 cell/well
↓
Screening of clones leading to the selection of cell line R603-12D11
↓
Expansion and adaptation of R603-12D11 to serum free media
↓
Expansion and preparation of a pre-seed stock (PSS)/cell bank for R603-12D11 (serum free)

A cryovial of the YB2/0 cell bank (YB2/0-301 04/147) was thawed and the cells were grown by dilution to a cell density of $1\times10^5$ cells/mL every 3 to 4 days with fresh culture medium (EMS medium with 5% FCS). The cells were seeded at a density of $2\times10^5$ cells/mL on the day before transfection in order to reach exponential phase prior to transfection. 44.5 µg of the NotI-linearized expression vector HK463-25 (FIG. 15) was transfected into $5\times10^6$ cells by electroporation using the animal component free Optimix reagent (Equibio). The cells were diluted in culture medium and seeded at 100 cells/well in 96-well plates. Selection with 1 g/L G418 in the culture medium was initiated three days after electroporation.

The transformants were initially screened for titer by ELISA after selection in the G418 medium. Over 3000 transformants were screened and over 200 of the best producing wells were selected for further testing and for continued passaging. A second titer screen was performed to further reduce the number of clones. This screen was followed by additional screening for antibody fucose level by ELISA. Fucose levels less than 40% were considered desirable in order to provide the expected level of activation of CD16 by the antibody; CD16 activation is inversely related to the fucose levels. Further screening using a cell-based CD16 activation test with assessment of IL-2 secretion in addition to assessment of the free Kappa/IgG ratio (<0.2 for purification ease) resulted in narrowing to a total of 5 cell lines for further development.

The 5 candidate cell lines were cloned by limiting dilution at 0.4 cells/well in EMS medium with 5% FCS. Clones were screened for IgG productivity, fucose levels, CD16 activation, and free Kappa/IgG ratio to identify production cell line R603-12D11. As the selected cell line was expanded from the cloning step, it also underwent a transition into serum free media and was re-screened to ensure the desired phenotype before the preparation of a small cell bank. This small cell bank was then thawed and expanded to generate the R603-12D11 pre-seed stock cell bank (PSS). The R603-12D11 PSS cell bank was demonstrated to be free from mycoplasmal, adventitious virus and microbial contamination prior to the generation of the MCB.

Characterization of the master and working cell banks derived from the R603-12D11 production cell line, included testing for identity, genotypic and phenotypic features, as well as for the presence of adventitious agents.

Master Cell Bank (MCP) Preparation and Testing

The MCB was manufactured at Henogen (later acquired by NovaSep). The MCB lot G071/MCB/070208 was prepared by thawing and expanding one vial of the production cell line R603-12D11 pre-seed stock in serum-free medium EM-SF2 P500 H4 (EMS basal medium supplemented with 2-mercaptoethanol, ethanolamine, $NaHCO_3$, ferric citrate, pluronic acid, HEPES and recombinant human insulin). The cells were expanded in T-flasks and roller bottles for eleven days. The cell suspension was concentrated by centrifugation and aliquoted into 13 separate fractions. Each fraction was centrifuged and resuspended to a target cell density of $10\times10^6$ cell/mL in freezing medium (90% EM-SF2 P500 H4+10% DMSO). The suspended fractions were then each aliquoted into 18 cryovials per fraction resulting in a total of 234 cryovials of the MCB. The cryovials were placed on dry ice and then into cryoboxes which were placed in a −80° C. freezer for 21 hr. The cryovials were transferred into liquid nitrogen tanks on 19 Feb. 2007 for long-term storage and are currently stored in multiple locations. The number of cell generations from the PSS of the production cell line to the MCB is 10.4.

Following the generation of MCB lot G071/MCB/070208, direct testing of the MCB, as well as further characterization by testing a WCB derived from it, were performed. Identity testing of the MCB was performed; testing results confirm the identity of the MCB as rat derived. Performance qualification was confirmed by thawing a vial of the MCB and monitoring for cell viability. Assessments of copy number, restriction endonuclease profile, number of integration sites, integrity of RNA coding sequence, and RNA quantitation were conducted. The number of heavy and light chain copies integrated into the genome was estimated at 1.13 and 2.14, respectively, by quantitative polymerase chain reaction (Q-PCR). Southern blot assessment of the plasmid integration site demonstrated comparable hybridization patterns for the MCB and PSS. The number of integration sites for both the MCB and WCB was similarly measured to be 1 in both cell banks via Southern blot. In addition, intra-chromosomic integration of the HK463-25 expression plasmid with insertion at a single locus of a metacentric chromosome was demonstrated by fluorescence in situ hybridization (FISH) analysis. For the MCB, integrity of the RNA coding sequence was consistent with the reference sequence, and RNA quantitation was consistent with the PSS cell bank for both heavy and light chains.

Next generation nucleic acid sequencing (NGS) using targeted locus amplification (TLA) was performed (Cergentis, Utrecht, Netherlands) on the MCB to confirm that the expressed TG-1101 antibody has the correct amino acid sequence, and to also interrogate for low levels of sequence variants. Adventitious viral, mycoplasmal and microbial agent testing of the MCB was carried out and acceptance criteria established for release of the MCB including those for adventitious viral, mycoplasmal and microbial agents were met. The collective MCB testing results confirmed the suitability for the establishment of the MCB.

Working Cell Bank Lot G140/R603/WCB001

The first WCB was manufactured at NovaSep (after acquiring Henogen). To prepare the WCB, one vial of MCB G071/MCB/070208 was thawed and expanded in serum-free medium EM-SF2 P500 H4 in flasks and roller bottles over eleven days. The expanded cell suspension was concentrated by centrifugation and aliquoted into 22 identical fractions. Each fraction was centrifuged and resuspended to a target cell density of $12.1 \times 10^6$ cell/mL in freezing medium (90% EM-SF2 P500 H4+10% DMSO). The suspended fractions were then each aliquoted into 18 cryovials resulting in a total of 396 cryovials of the WCB. The lot was designated as G140/R603/WCB001. The cryovials were placed on dry ice and then into cryoboxes which were placed in a $-80°$ C. freezer for 24 hr. The cryovials were transferred into liquid nitrogen tanks for long-term storage on 22 Sep. 2009. The WCB is stored in at least two different storage sites including smaller numbers of vials stored for shorter duration at the manufacturer. The number of cell generations from the PSS of the production cell line to the WCB is 21.4.

Testing of WCB lot G140/R603/WCB001 was performed including identity testing. Testing results confirmed the identity of the WCB as rat derived. Performance qualification was confirmed by thawing a vial of the WCB and monitoring for cell viability, doubling time, and IgG productivity. Assessments of copy number, restriction endonuclease profile, and number of integration sites, were conducted. The number of heavy and light chain copies integrated into the genome was estimated at 1.2 and 2.5, respectively, by quantitative polymerase chain reaction (Q-PCR). These results are consistent with that of the MCB. Southern blot assessment of the plasmid integration site demonstrated comparable hybridization patterns for the WCB and MCB. The number of integration sites for the WCB was measured to be 1 via Southern blot.

Next generation nucleic acid sequencing (NGS) using targeted locus amplification (TLA) was performed (Cergentis, Utrecht, Netherlands) on the WCB to confirm that the expressed TG-1101 antibody has the correct amino acid sequence, and to also interrogate for low levels of sequence variants. Adventitious viral, mycoplasmal, and microbial agent testing was conducted and all acceptance criteria established for release of the WCB including those for adventitious viral, mycoplasmal and microbial agents were met. The collective WCB testing results confirmed the suitability for the establishment of the WCB.

Phenotypic Characterization of Cell Banks

Cell line phenotypic stability studies were performed for the MCB and two WCBs generated for manufacturing of TG-1101. One vial each of the MCB, WCB lot G140/R603/WCB001, and a new WCB lot 127646-001. were thawed and passaged for approximately 60 generations. VCD, cell viability, and titer samples were taken at every passage. At intervals of approximately 15 cell generations, cells were cryopreserved as research cell banks (RCBs). After approximately 60 generations, vials from each RCB were thawed and expanded for 7 days. On day 7, shake flasks were inoculated, cultured under fed-batch conditions, and cultivated for 12 days. Daily sampling for VCD, cell viability, titer, specific productivity, and quality attributes of the harvested fed batch culture were used to assess the stability of each cell bank at its corresponding generation number. Comparability in cell growth, titer, and product quality was used as a general basis for determining phenotypic stability of the cell banks. In addition, specific productivity results that exceed 70% of the results from control cultures with low number of generations were used as a specific basis for determining phenotypic stability of the cell banks. The results for the three cell bank phenotypic stability studies are shown in Table 23 for MCB lot G071/MCB/070208, Table 24 for WCB lot G140/R603/WCB001, and Table 25 for WCB lot 127646.

TABLE 23

Phenotypic Stability Results of MCB Lot G071/MCB/070208

| | Number of Generations[a] | | | | |
|---|---|---|---|---|---|
| Parameter | 9 | 28 | 40 | 54 | 71 |
| Peak viable cell density ($\times 10^6$ cells/mL) | 12.6 | 11.7 | 12.4 | 11.9 | 11.9 |
| Harvest titer (mg/L) | 681 | 703 | 718 | 704 | 679 |
| Average specific productivity (pg/cell/day) | 6.6 | 6.7 | 6.8 | 6.8 | 6.6 |
| Glycosylation: % fucosylation | 32.8 | 34.1 | 37.4 | 36.1 | 37.1 |
| iCIEF: | | | | | |
| % acidic species | 26.0 | 27.2 | 27.8 | 27.7 | 28.9 |
| % main species | 38.1 | 47.5 | 46.4 | 46.4 | 48.4 |
| % basic species | 35.9 | 25.3 | 25.8 | 25.9 | 22.7 |
| SEC: | | | | | |
| % monomer | 97.7 | 97.6 | 97.5 | 97.5 | 97.3 |
| % dimer | 1.6 | 1.7 | 1.8 | 1.8 | 2.0 |
| % aggregates | 2.3 | 2.4 | 2.4 | 2.5 | 2.7 |
| % fragments | 0.1 | 0.1 | 0.1 | 0.1 | 0.1 |

[a]After MCB vial thaw to the start of production fedbatch culture

TABLE 24

Phenotypic Stability Results of WCB Lot G140/R603/WCB001

| | Number of Generations[a] | | | | |
|---|---|---|---|---|---|
| Parameter | 9 | 26 | 40 | 54 | 71 |
| Peak viable cell density ($\times 10^6$ cells/mL) | 15.6 | 17.0 | 14.7 | 15.6 | 16.1 |
| Harvest titer (mg/L) | 730 | 775 | 631 | 584 | 646 |
| Average specific productivity (pg/cell/day) | 5.2 | 5.6 | 5.5 | 5.1 | 4.8 |
| Glycosylation: % fucosylation | 37.4 | 39.7 | 39.2 | 38.7 | 39.7 |
| iCIEF: | | | | | |
| % acidic species | 22.7 | 25.6 | 30.0 | 27.4 | 29.7 |
| % main species | 52.6 | 44.2 | 42.9 | 45.8 | 44.9 |
| % basic species | 24.7 | 30.2 | 27.2 | 26.8 | 25.5 |
| SEC: | | | | | |
| % monomer | 98.1 | 97.7 | 97.4 | 97.7 | 97.6 |
| % dimer | 1.3 | 1.7 | 1.8 | 1.8 | 1.8 |
| % aggregates | 1.8 | 2.2 | 2.5 | 2.2 | 2.4 |
| % fragments | 0.1 | 0.1 | 0.1 | 0.1 | 0.1 |

[a]After WCB vial thaw to the start of production fedbatch culture

TABLE 25

Phenotypic Stability Results of WCB Lot 127646

| Parameter | Number of Generations[a] | | | | |
|---|---|---|---|---|---|
| | 9 | 27 | 42 | 55 | 69 |
| Peak viable cell density ($\times 10^6$ cells/mL) | 14.6 | 15.3 | 15.3 | 14.0 | 14.6 |
| Harvest titer (mg/L) | 770.5 | 865.5 | 801.3 | 886.2 | 849.7 |
| Average specific productivity (pg/cell/day) | 6.2 | 6.2 | 6.1 | 6.4 | 6.0 |
| Glycosylation: % fucosylation | 30.9 | 30.2 | 33.2 | 36.6 | 37.6 |
| iCIEF: | | | | | |
| % acidic species | 23.8 | 25.8 | 25.8 | 28.2 | 28.5 |
| % main species | 40.1 | 50.7 | 42.8 | 34.0 | 36.7 |
| % basic species | 36.1 | 23.5 | 31.4 | 37.8 | 34.8 |
| SEC: | | | | | |
| % monomer | 98.2 | 98.2 | 98.4 | 98.0 | 97.6 |
| % dimer | 1.3 | 1.3 | 1.2 | 1.4 | 1.8 |
| % aggregates | 1.8 | 1.7 | 1.6 | 1.9 | 2.4 |
| % fragments | 0.1 | 0.1 | 0.1 | 0.1 | 0.1 |

[a]After WCB vial thaw to the start of production fedbatch culture

Thawed MCB and WCB that were use during production of TG-1101 at 15,000 L were tested for viable cell density and cell viability results to assess and confirm cell bank storage stability.

(b) Upstream Process and Process Controls

A process flow diagram of the upstream unit operations including operational controls and in-process controls are provided in Table 26. Among other controls, bioburden and endotoxin were measured in the batched media of the seed and production bioreactor stages.

TABLE 26

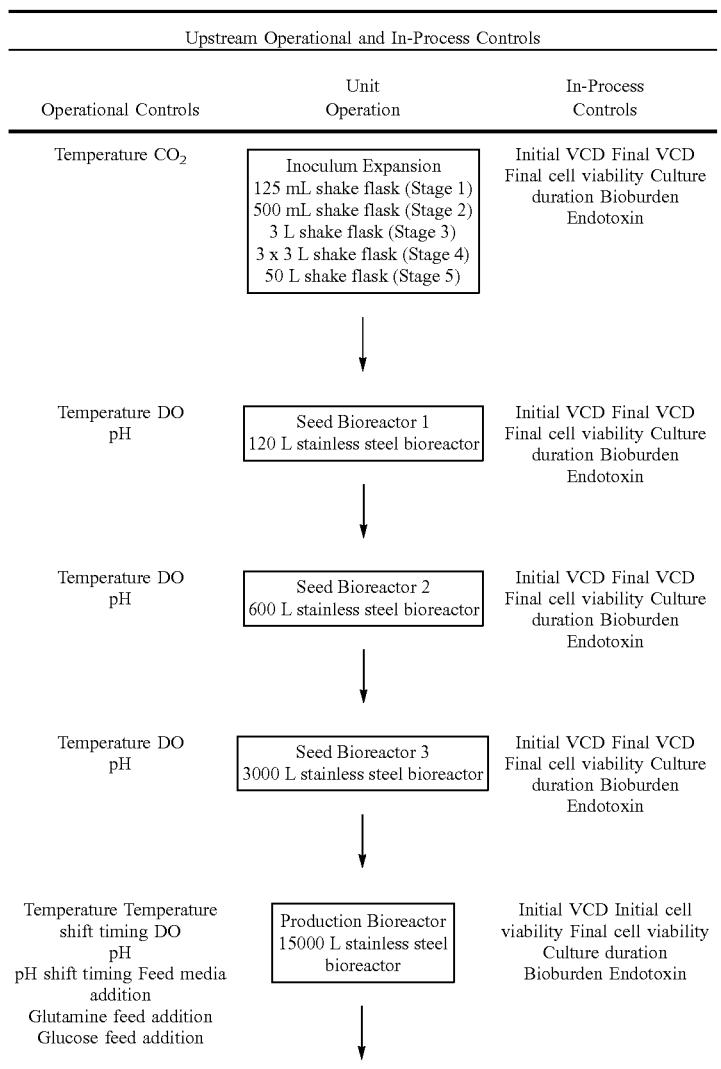

Upstream Operational and In-Process Controls

Cell Culture Media and Feeds Preparation

Cell culture growth medium (CDM4Mab) and feeds (BalanCD CHO Feed4, glucose feed, and glutamine feed) were prepared with Water for Injection (WFI). Media and feeds were filtered (≤0.2 µm) into sterile vessels and stored prior to use as needed. A cholesterol lipid concentrate was supplemented into the CDM4Mab growth medium during preparation to support cell growth from the inoculum expansion stages through the production bioreactor. In addition, the cholesterol lipid concentrate was added to the production bioreactor as fixed bolus feed additions on process days 0 and 4. Operational and in-process controls for cell culture media and feeds are described in Table 27.

TABLE 27

Cell Culture Media and Feeds Preparation and Storage Controls

| Cell Culture Media and Feeds | Operational/ In-Process Controls | Target | AR |
|---|---|---|---|
| CDM4Mab (liquid growth medium) | pH | 7.00 | 6.95-7.40 |
| | Osmolality (mOsm/kg) | N/A | 280-320 |
| | Turbidity (NTU) | ≤4.1 | N/A |
| | Post-filtration storage at 2-8° C. (days) | N/A | ≤30 |
| | Post-filtration storage at room temperature (hrs)[a] | N/A | ≤ 36 |
| | Hold time at operating temperature (hrs)[b] | N/A | ≤36 |
| BalanCD CHO Feed 4 (liquid feed medium) | pH | 7.00 | 7.00-7.40 |
| | Osmolality (mOsm/kg) | 1385 | 1360-1410 |
| | Post-filtration storage at room temperature (days)[a] | N/A | ≤21 |
| | Post-filtration storage at 2-8° C. (days) | N/A | ≤18 |
| Glucose Feed | Post-filtration storage at room temperature (days)[a] | N/A | ≤69 |
| Glutamine Feed | Osmolality (mOsm/kg) | N/A | 180-220 |
| | Post-filtration storage at 2-8° C. (days) | N/A | ≤14 |
| Sodium Hydroxide | Conductivity (mS/cm) | N/A | 140-190 |
| | Post-filtration storage at room temperature (days)[a] | N/A | ≤31 |
| Cholesterol Lipid Concentrate 1000X | pH | Report only (vendor CoA) | |
| | Osmolality (mOsm/kg) | Report only (vendor CoA) | |
| | Storage at 2-8° C. (days) | N/A | ≤526 |

[a]Room temperature at SBL: 17-25° C.
[b]Operating temperature: 37.0° C. (36.5-37.5° C.)

Inoculum Expansion

Inoculum expansion steps included thaw of the WCB vial and growth in shake flasks and/or cellbags of increasing size and volume to provide sufficient cell mass to inoculate the seed bioreactor stages. The steps are performed by growth in inoculum expansion growth medium (CDM4Mab). To initiate the process, a vial of WCB G140/R603/WCB001 was thawed in pre-warmed water in a 37.0° C. water bath. The thawed vial contents were transferred into pre-warmed medium and diluted to achieve a target seed density of $0.55 \times 10^6$ viable cells/mL.

The culture was placed in an initial 125 mL shake flask and grown in a shaking incubator at 37.0° C./5.0% $CO_2$ for 1 day. Every 2 to 3 days, the culture was expanded into shake flasks of larger volume and/or to multiple shake flasks. At each stage, a seeding density of $0.30 \times 10^6$ viable cells/mL was targeted. The final inoculum preparation stage consisted of a 50 L cellbag. After 2 to 3 days of growth, the viable cell density was checked and culture was further processed to the seed bioreactor stages. Operational and in-process controls for inoculum expansion are described in Table 28.

TABLE 28

Inoculum Expansion Controls

| Process Step | Process Parameter | Target | NOR | AR |
|---|---|---|---|---|
| Stage 1: | Operational Parameters | | | |
| 125 mL shake flask | Vial thaw duration (min) | N/A | ≤3 | ≤3 |
| | Incubator temperature (° C.) | 37.0 | 36.5-37.5 | 36.5-37.5 |
| | Incubator $CO_2$ level (%) | 5.0 | 4.0-6.0 | 4.0-6.0 |
| | Agitation rate (rpm)[a] | 96 | 91-101 | 91-101 |
| | Culture duration (hrs) | 24 | 18-30 | 18-35 |
| | Performance parameters | | | |
| | Initial viable cell density ($\times 10^6$ cells/mL) | 0.55 | 0.40-0.70 | 0.40-0.90 |
| | Final viable cell density ($\times 10^6$ cells/mL) | ≥1.80 | ≥1.60 | ≥1.60 |
| | Final cell viability (%) | ≥90.0 | ≥86.0 | ≥86.0 |
| Stage 2: | Operational Parameters | | | |
| 500 mL shake flask | Incubator temperature (° C.) | 37.0 | 36.5-37.5 | 36.5-37.5 |
| | Incubator $CO_2$ level (%) | 5.0 | 4.0-6.0 | 4.0-6.0 |
| | Agitation rate (rpm)[a] | 96 | 91-101 | 91-101 |
| | Culture duration (hrs) | 72 | 48-78 | 48-91 |
| | Performance parameters | | | |
| | Initial viable cell density ($\times 10^6$ cells/mL) | 0.30 | 0.20-0.40 | 0.10-0.40 |
| | Final viable cell density ($\times 10^6$ cells/mL) | N/A | ≥3.00 | ≥2.40 |
| | Final cell viability (%) | ≥90.0 | ≥86.0 | ≥86.0 |
| Stage 3: | Operational Parameters | | | |
| 3 L shake flask | Incubator temperature (° C.) | 37.0 | 36.5-37.5 | 36.5-37.5 |
| | Incubator $CO_2$ level (%) | 5.0 | 4.0-6.0 | 4.0-6.0 |
| | Agitation rate (rpm)[a] | 96 | 91-101 | 91-101 |
| | Culture duration (hrs) | 72 | 48-78 | 48-94 |
| | Performance Parameters | | | |
| | Initial viable cell density ($\times 10^6$ cells/mL) | 0.30 | 0.20-0.40 | 0.18-0.40 |
| | Final viable cell density ($\times 10^6$ cells/mL) | N/A | ≥3.00 | ≥2.98 |
| | Final cell viability (%) | ≥90.0 | ≥86.0 | ≥86.0 |
| Stage 4: | Operational Parameters | | | |
| 3 × 3 L shake flasks | Incubator temperature (° C.) | 37.0 | 36.5-37.5 | 36.5-37.5 |
| | Incubator $CO_2$ level (%) | 5.0 | 4.0-6.0 | 4.0-6.0 |
| | Agitation rate (rpm)[a] | 96 | 91-101 | 91-101 |
| | Culture duration (hrs) | 72 | 48-78 | 48-78 |
| | Performance Parameters | | | |
| | Initial viable cell density ($\times 10^6$ cells/mL) | 0.30 | 0.20-0.40 | 0.16-0.40 |
| | Final viable cell density ($\times 10^6$ cells/mL) | N/A | ≥3.00 | ≥3.00 |
| | Final cell viability (%) | ≥90.0 | ≥86.0 | ≥86.0 |
| Stage 5: | Operational Parameters | | | |
| 50 L cellbag | Temperature (° C.) | 37.0 | 36.0-38.0 | 36.0-38.0 |
| | $CO_2$ level (%) | 5.0 | 4.0-6.0 | 4.0-6.0 |
| | Agitation rate (rpm) | 25 | 23-27 | 23-27 |
| | Culture duration (hrs) | 72 | 48-78 | 48-78 |
| | Performance Parameters | | | |
| | Initial viable cell density ($\times 10^6$ cells/mL) | 0.30 | 0.20-0.60 | 0.20-0.60 |
| | Final viable cell density ($\times 10^6$ cells/mL) | N/A | ≥3.00 | ≥3.00 |
| | Final cell viability (%) | ≥90.0 | ≥86.0 | ≥86.0 |

[a]Shaker platform throw radius dependent parameter. Shaker platform throw radius: 22 mm Seed Bioreactors The seed bioreactor stages further increase the volume and cell culture biomass prior to inoculation of the production bioreactor. The medium used in these stages was inoculum expansion growth medium (CDM4Mab). The seed bioreactor stages were 120 L, 600 L, and 3000 L stainless steel bioreactors. The bioreactors were equilibrated after media addition. Dissolved oxygen and pH probes were calibrated prior to use. Initial bioreactor set points included temperature, pH, dissolved oxygen, and agitation rate. Each bioreactor was inoculated with cell culture from the preceding stage and the culture was grown for 2 to 3 days. Seed bioreactor operational and in-process controls are summarized in Table 29.

TABLE 29

Seed Bioreactor Controls

| Process Step | Process Parameter | Target | NOR | AR |
|---|---|---|---|---|
| Seed | Operational Parameters | | | |
| Bioreactor 1: 120 L | Temperature (° C.) | 37.0 | 36.5-37.5 | 36.5-37.5 |
| | Agitation (rpm)[a] | 100 | 95-105 | 95-105 |
| | pH | 7.10 | 6.75-7.45 | 6.75-7.47 |
| | Dissolved oxygen (%) | 40.0 | 20.0-100.0 | 20.0-100.0 |
| | Culture duration (hrs) | 72 | 48-78 | 48-112 |
| | Performance Parameters | | | |
| | Initial viable cell density ($\times 10^6$ cells/mL) | 0.50 | 0.40-0.70 | 0.16-0.90 |
| | Final viable cell density ($\times 10^6$ cells/mL) | N/A | ≥3.00 | ≥1.50 |
| | Final cell viability (%) | ≥90.0 | ≥89.0 | ≥89.0 |
| Seed | Operational Parameters | | | |
| Bioreactor 2: 600 L | Temperature (° C.) | 37.0 | 36.5-37.5 | 36.5-37.5 |
| | Agitation (rpm)[a] | 74 | 70-78 | 70-78 |
| | pH | 7.10 | 6.75-7.45 | 6.75-7.50 |
| | Dissolved oxygen (%) | 40.0 | 20.0-100.0 | 20.0-100.0 |
| | Culture duration (hrs) | 72 | 48-78 | 47-87 |
| | Performance Parameters | | | |
| | Initial viable cell density ($\times 10^6$ cells/mL) | 0.50 | 0.40-0.70 | 0.17-0.90 |
| | Final viable cell density ($\times 10^6$ cells/mL) | N/A | ≥3.00 | ≥3.00 |
| | Final cell viability (%) | ≥90.0 | ≥89.0 | ≥89.0 |
| Seed | Operational Parameters | | | |
| Bioreactor 3: 3000 L | Temperature (° C.) | 37.0 | 36.5-37.5 | 36.5-37.5 |
| | Agitation (rpm)[a] | 50 | 47-53 | 47-53 |
| | pH | 7.10 | 6.75-7.45 | 6.75-7.45 |
| | Dissolved oxygen (%) | 40.0 | 20.0-100.0 | 20.0-100.0 |
| | Culture duration (hrs) | 72 | 48-78 | 46-78 |
| | Performance Parameters | | | |
| | Initial viable cell density ($\times 10^6$ cells/mL) | 0.50 | 0.40-0.70 | 0.40-0.90 |
| | Final viable cell density ($\times 10^6$ cells/mL) | N/A | ≥3.00 | ≥3.00 |
| | Final cell viability (%) | ≥90.0 | ≥89.0 | ≥89.0 |

[a] Agitation is dependent on volumetric scale and bioreactor impeller. Target (NOR/AR) are equivalent to power/volume 20 (17-23) W/m³ at SBL.

Production Bioreactor

The production bioreactor stage is the final cell culture process stage which further increases the volume and mass of the cell culture for expression of the TG-1101 antibody with acceptable product quality. The basal medium used in this stage was growth medium (CDM4Mab) and feed additions were performed at specified days or criteria during the process. The production bioreactor was a 15,000 L stainless steel bioreactor.

The production bioreactor was equilibrated after media addition. Inoculum expansion medium was added to an initial volume target. Dissolved oxygen and pH probes were calibrated prior to use. Initial bioreactor set points included temperature, pH, dissolved oxygen, and agitation rate. The bioreactor was inoculated with cell culture from the N-1 seed bioreactor at a viable cell density target of $0.5 \times 10^6$ viable cells/mL. During the production bioreactor process, pH was controlled with base addition and $CO_2$ sparging on demand. Dissolved oxygen was controlled with oxygen and air sparging on demand. Antifoam was added as needed to mitigate foaming concerns. Offline pH, $pCO_2$, $pO_2$, osmolality, and metabolites were monitored daily as were viable cell density (VCD) and viability. The BalanCD CHO Feed4 was added on Days 3, 5, 7, 9 at specified volumes (4.0% of initial bioreactor working volume). A calculated volume of glucose solution was fed (to 4.00 g/L) when daily bioreactor sample measured values were <3.00 g/L on specified process days. A fixed volume of glutamine solution was bolus fed on Day 3 (3.0% of initial bioreactor working volume), and a calculated volume was fed (to 4.00 mM) when daily bioreactor sample measured values were <3.00 mM on specified process days. The production bioreactor was harvested based on either culture duration or cell viability criteria, whichever occurred first.

Unprocessed bulk samples were removed prior to the clarification unit operation for adventitious agent testing as described in Example 4. Production bioreactor operational and in-process controls are described below in Table 30.

TABLE 30

Production Bioreactor Controls

| Process Step | Process Parameter | Target | NOR | AR |
|---|---|---|---|---|
| Production Bioreactor: 15000 L | Operational Parameters | | | |
| | Initial temperature (° C.)[a] | 37.0 | 36.5-37.5 | 36.5-37.5 |
| | Temperature after 1st shift (° C.)[a] | 35.0 | 34.5-35.5 | 34.5-35.5 |
| | 1st temperature shift timing (hrs) | 24 | 18-30 | 17-33 |
| | Temperature after 2nd shift (° C.)[a] | 32.5 | 32.0-33.0 | 32.0-33.0 |
| | $2^{nd}$ temperature shift timing (hrs) | 72 | 66-77 | 62-77 |
| | pH at pre-inoculation | 7.40 | 7.30-7.45 | 7.30-7.45 |
| | pH at post-inoculation | 7.10 | 6.77-7.43 | 6.77-7.51 |
| | pH shift timing (hrs) | 72 | 66-77 | 62-77 |
| | pH after shift 1 | 6.70 | 6.57-6.83 | 6.54-6.96 |
| | Agitation (rpm)[b] | 54 | 51-57 | 51-65 |
| | Dissolved oxygen (%) | 40.0 | 20.0-100.0 | 20.0-100.0 |
| | BalanCD CHO Feed 4 addition amount (% of initial working volume)[c] | 4.0 | 1.8-4.1 | 1.8-4.1 |
| | Glutamine feed amount on Day 3 (% of initial working volume) | 3.0 | N/A | 3.0 |

TABLE 30-continued

Production Bioreactor Controls

| Process Step | Process Parameter | Target | NOR | AR |
|---|---|---|---|---|
| | Glutamine concentration for initiating feeding (mM)[d] | <3.00 | N/A | <3.00 |
| | Glutamine concentration after feeding (mM)[e] | 4.00 | N/A | 4.00 |
| | Glucose concentration for initiating feeding (g/L)[f] | <3.00 | N/A | <3.00 |
| | Glucose concentration after feeding (g/L)[e] | 4.00 | N/A | 4.00 |
| | Antifoam addition amount (g)[g] | 400 | 380-420 | 380-420 |
| | Culture duration (hrs)[h] | 312 | 304-320 | 275-329 |
| Performance Parameters | | | | |
| | Initial viable cell density (×10⁶ cells/mL) | 0.50 | 0.40-0.70 | 0.40-0.95 |
| | Initial cell viability (%) | ≥95.0 | ≥89.0 | ≥89.0 |
| | Final cell viability (%)[h] | N/A | ≥20 | ≥20 |
| | $pCO_2$ (mmHg) | N/A | ≤ 300.0 | ≤ 300.0 |
| | Total cell age (cell doublings from MCB thaw) | N/A | N/A | ≤57 |

[a] Temporary excursions are allowed.
[b] Agitation is dependent on volumetric scale and bioreactor impeller. Target (NOR) are equivalent to power/volume 50 (42-59) W/m3 at SBL. AR is equivalent to power/volume 42-70 W/m³.
[c] Fed on Days 3, 5, 7, 9.
[d] Fed on Days 4-7 as needed.
[e] Glucose/glutamine are not measured after glucose/glutamine feed addition; values refer to target concentrations used in the calculation for determining the glucose/glutamine feed amount required.
[f] Fed on Days 3-12 as needed.
[g] Antifoam amount is calculated based on initial working volume of production bioreactor. Target is addition amount at one time.
[h] Harvest occurs when either culture duration reaches its target/NOR, or when final cell viability drops lower than its NOR, whichever occurs first. As a result, it is possible for harvest to occur when final cell viability is below its NOR, or culture duration is below its NOR.

(c) Downstream Process and Process Controls

A process flow diagram of the downstream steps including operational controls and in-process controls are provided in Table 31. As shown in Table 31, in-process controls were incorporated into the process. Among other controls, bioburden and endotoxin were measured during multiple stages of the downstream process.

TABLE 31

Downstream Operational and In-Process Controls

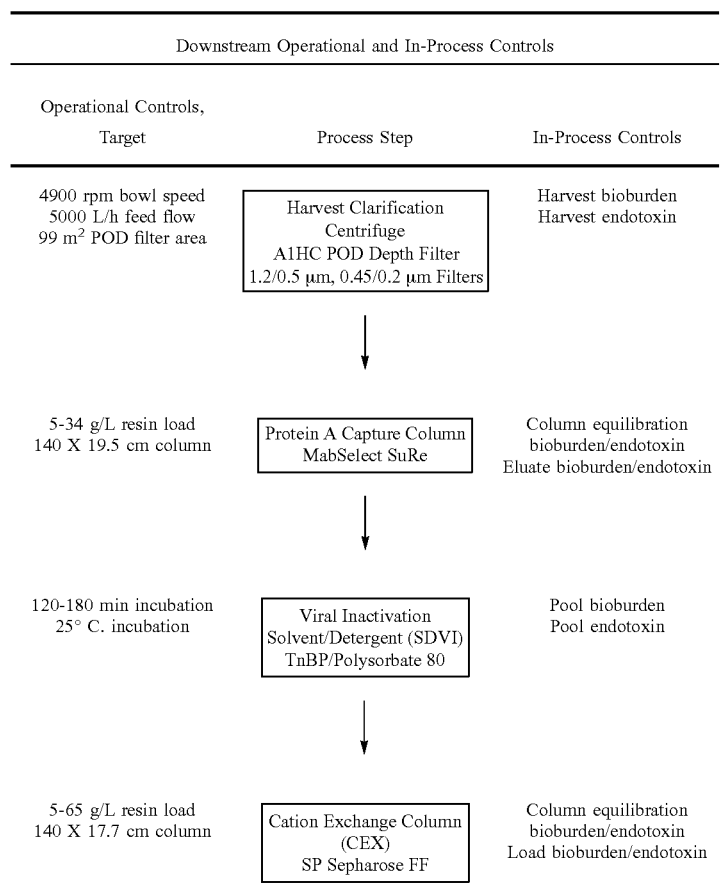

| Operational Controls, Target | Process Step | In-Process Controls |
|---|---|---|
| 4900 rpm bowl speed<br>5000 L/h feed flow<br>99 m² POD filter area | Harvest Clarification Centrifuge<br>A1HC POD Depth Filter<br>1.2/0.5 µm, 0.45/0.2 µm Filters | Harvest bioburden<br>Harvest endotoxin |
| 5-34 g/L resin load<br>140 X 19.5 cm column | Protein A Capture Column<br>MabSelect SuRe | Column equilibration bioburden/endotoxin<br>Eluate bioburden/endotoxin |
| 120-180 min incubation<br>25° C. incubation | Viral Inactivation<br>Solvent/Detergent (SDVI)<br>TnBP/Polysorbate 80 | Pool bioburden<br>Pool endotoxin |
| 5-65 g/L resin load<br>140 X 17.7 cm column | Cation Exchange Column (CEX)<br>SP Sepharose FF | Column equilibration bioburden/endotoxin<br>Load bioburden/endotoxin |

TABLE 31-continued

Downstream Operational and In-Process Controls

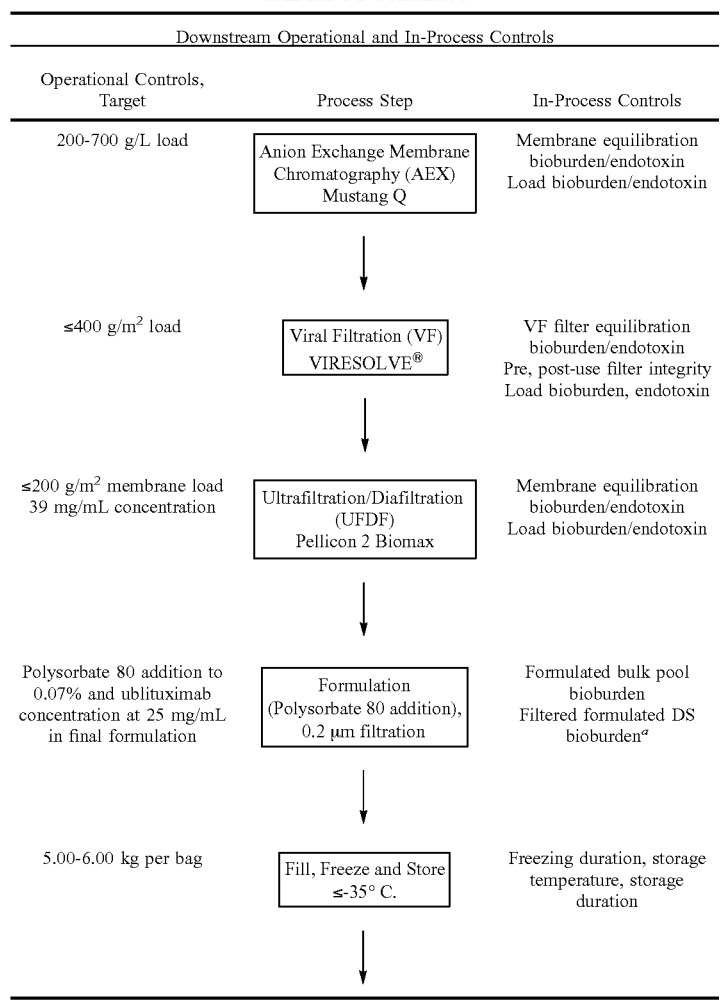

| Operational Controls, Target | Process Step | In-Process Controls |
|---|---|---|
| 200-700 g/L load | Anion Exchange Membrane Chromatography (AEX) Mustang Q | Membrane equilibration bioburden/endotoxin Load bioburden/endotoxin |
| ≤400 g/m² load | Viral Filtration (VF) VIRESOLVE® | VF filter equilibration bioburden/endotoxin Pre, post-use filter integrity Load bioburden, endotoxin |
| ≤200 g/m² membrane load 39 mg/mL concentration | Ultrafiltration/Diafiltration (UFDF) Pellicon 2 Biomax | Membrane equilibration bioburden/endotoxin Load bioburden/endotoxin |
| Polysorbate 80 addition to 0.07% and ublituximab concentration at 25 mg/mL in final formulation | Formulation (Polysorbate 80 addition), 0.2 μm filtration | Formulated bulk pool bioburden Filtered formulated DS bioburden[a] |
| 5.00-6.00 kg per bag | Fill, Freeze and Store ≤-35° C. | Freezing duration, storage temperature, storage duration |

[a]Beginning, middle and end of filling operation

Harvest Clarification

The cell culture supernatant was harvested and clarified from the 15,000 L bioreactor to remove cells and cell debris. The clarification was performed using a continuous centrifugation followed by depth filtration.

The harvest clarification step was operated in a room in which the controlled temperature range was 17-25° C.; the harvest pool vessel was a jacketed tank, which maintains the pool at 2-8° C. The centrifuge shot interval was set based on the packed cell volume percentage (PCV) and adjusted to allow for 80% bowl fill. The flow rate to the centrifuge was actively controlled; the filtration feed flow was the same as the centrifuge feed flow. Process parameters included centrate back pressure, the depth filtration operating pressure, inlet pressure, harvest weight, bioburden and endotoxin.

The centrate was clarified by use of a three-stage filtration process as required to pass through a 0.2 μm filter (Millistak A1HC POD depth filters, 1.2/0.5 μm filters and 0.45/0.22 μm sterilizing grade filters). Before use, the filters were flushed with WFI followed by equilibration. The centrate was pumped through the filters, which are monitored to ensure acceptable back pressure. Air was used to expel the contents in the filters followed by a buffer flush. The clarified harvest was stored at 2 to 8° C. for <11 days.

Protein A Column Chromatography (ProA)

Protein A column chromatography was performed using MabSuRe Select resin (Cytiva) in bind/elute mode. This step provided capture and purification of TG-1101 with reduction of process impurities such as cell culture components, HCP, and residual DNA, as well as for the provision of viral safety.

The packed column was assessed for HETP performance using sodium acetate/benzyl alcohol buffer. During manufacturing, all column operations were performed at 13 to 25° C. Before loading, the column was sanitized with 0.5 M sodium hydroxide and flushed with WFI. The column was equilibrated with Equilibration Buffer (25 mM Tris, 25 mM NaCl, 5 mM EDTA, pH 7.1). The clarified harvest was mixed briefly and then loaded onto the column using a maximum of 36 g TG-1101/L resin load and the column was washed with Wash 1 Buffer (equilibration buffer) followed by a second wash with a high salt, Wash 2 Buffer (25 mM Tris, 1.2 M NaCl, 5 mM EDTA, pH 7.1), followed by an additional wash using Wash 3 Buffer (equilibration buffer). Bound TG-1101 was eluted 200-220 cm/h with elution buffer (25 mM sodium citrate, pH 3.6) using elution peak collection by A280, not to exceed 2.4 column volumes. The eluate was collected in a tank containing neutralization buffer (2.0M Tris, pH 7.5) and filtered via a 0.2 μm filter before transfer to a different tank. The Protein A column was sanitized with 0.5M sodium hydroxide. Up to three cycles per batch may be run; if multiple cycles were required for the Protein A process, the column was re-equilibrated for the next cycle with equilibration buffer. After sanitization, the Protein A column was neutralized with equilibration buffer and stored at 13 to 25° C. in 200 mM sodium acetate, 2% benzyl alcohol, pH 5.0. The pooled (if more than one cycle), neutralized eluate was diluted with 5 mM Sodium Phosphate, pH 7.2 to a concentration of <10 g/L and stored at 13-25° C. for <24 hours or at 2 to 8° C. for <11 days.

Solvent Detergent Viral Inactivation (SDVI)

The Protein A capture chromatography step was followed by a solvent detergent viral inactivation (SDVI) step to inactivate potential viral agents. In the currently validated manufacturing process, the Protein A elution pool was diluted and treated with 3.5% (v/v) TnBP, 12% (w/v) polysorbate 80 and held at 24.0-26.0° C. for at least 120 minutes while mixing. The SDVI pool was filtered with a 0.2 µm filter before transfer to a different tank, where it was diluted with 5 mM sodium phosphate, pH 7.2 to 50 mOsm/kg, and the pH adjusted to 7.2 as needed. After pH adjustment, the pool was held at 13 to 25° C. for <30 hours before proceeding to the CEX column.

Cation Exchange Chromatography (CEX)

Cation exchange column chromatography was performed using SP Sepharose Fast Flow (Cytiva) in bind/elute mode. This step provided further purification of TG-1101, removing residual process impurities (HCPs, DNA, residual polysorbate 80, and TnBP).

The packed column was assessed for HETP performance using a sodium acetate/benzyl alcohol-containing buffer. During manufacturing, all column operations were performed at 13 to 25° C. In the currently validated manufacturing process, before loading, the column was sanitized with 0.5 M sodium hydroxide and rinsed with WFI. The column was equilibrated using equilibration buffer (20 mM sodium phosphate, pH 7.2). The viral inactivated/diluted solution was loaded onto the column at a maximum of 65 g/L resin load. The column was washed with Wash 1 Buffer (equilibration buffer) followed by a second wash with Wash 2 Buffer (equilibration buffer in the reverse direction). Bound TG-1101 was eluted using 20 mM sodium phosphate, 150 mM NaCl, pH 7.2 and elution peak collection by A280 monitoring. The eluate was filtered (0.2 µm) and stored at 13 to 25° C. for <72 hours or at 2 to 8° C. for <11 days. After elution, the column was stripped with 2 M NaCl followed by sanitization with 0.5 M sodium hydroxide. One cycle per batch was allowed. After completion, the column was sanitized (0.5 M sodium hydroxide) and stored in storage buffer (200 mM sodium acetate, 2% benzyl alcohol, pH 5.0).

Anion Exchange Membrane Chromatography (AEX)

Anion exchange membrane chromatography was performed using a Mustang Q (Pall Corporation) membrane absorber (MA) filter in flow-through mode. This step provided further purification of the TG-1101; the product flowed through the membrane and remaining impurities (DNA, HCP and viruses) were retained on the membrane. The membrane was single use (i.e., each individual membrane cannot be reused) and several membrane capsules may be used per batch at the appropriate loading level.

To perform the step, in the currently validated manufacturing process, eluate from the cation exchange column chromatography step was diluted with 20 mM sodium phosphate, pH 8.0, followed by the adjustment of the pH to 8.0. The concentration was determined and the number of cycles calculated based on protein concentration such that the loading was 200 to 700 g TG-1101/L membrane load. The membrane was sanitized with 0.5 M sodium hydroxide, flushed with 2 M NaCl then with WFI, before being equilibrated with Equilibration Buffer (20 mM sodium phosphate, 75 mM NaCl, pH 8.0) in preparation for the load. After loading, the membrane was chased with 20 mM sodium phosphate, 75 mM NaCl, pH 8.0, to maximize recovery. The collected flow-through containing product from all cycles was filtered (0.5/0.2 µm), diluted to <6 g/L with 75 mM sodium citrate, 312 mM NaCl, pH 6.0, and the pH is adjusted to 6.8. The adjusted AEX pool was stored at 13 to 25° C. for <72 hours or at 2 to 8° C. for <11 days.

Viral Filtration (VF)

Viral filtration was performed by filtering through a VIRESOLVE® prefilter in series with a VIRESOLVE® PRO viral filter (Millipore Sigma), at an operating temperature Target Range of 13-25° C. The process used sufficient filters to meet the loading limit. The step was designed to remove potential viruses, including small viruses such as parvovirus.

To perform the filtration, the filters were set up in series and flushed with WFI, integrity tested, then sanitized with 0.5 M sodium hydroxide. This was followed by flushing with equilibration buffer (25 mM sodium citrate, 154 mM NaCl, pH 6.5). The filtered Mustang Q membrane flow-through was processed through the viral reduction filters.

Protein concentration was determined and used to confirm the membrane load ratio was ≤600 g/m². After loading, the membrane was chased with equilibration buffer and post-use integrity testing was performed. Viral filtrate was stored at 13 to 25° C. for <72 hours or at 2 to 8° C. for <11 days.

Ultrafiltration/Diafiltration (UFDF) Controls

The UFDF step was used to concentrate the viral filtrate and buffer exchange into diafiltration buffer at an operating temperature Target Range of 13-25° C. The process used a tangential flow filter with a 30 kDa molecular weight cut-off. The setup included up to sufficient filters to meet the loading limit of <250 g/m². To perform the operation, the membranes were sanitized with 0.5M NaOH, flushed with WFI, and flushed/equilibrated with diafiltration buffer before the start of the unit operation.

The unit operation included an initial ultrafiltration (UF1) step in which the TG-1101 was first concentrated to a target of 39 mg/mL. This was followed by diafiltration (DF) into diafiltration buffer (25 mM sodium citrate 154 mM NaCl, pH 6.5) with 8 diavolumes with an upper limit of <9.2 diavolumes. The ultrafiltration system was flushed with diafiltration buffer to maximize recovery; the flush was transferred to the formulation vessel and combined with the UF/DF Pool. The membranes were flushed with WFI, cleaned with 0.5M NaOH, 250 ppm sodium hypoclorite, flushed with WFI, and stored in 0.1 M sodium hydroxide. The diluted UFDF pool was stored at 15 to 25° C. for <18 hours.

Formulation, Filtration, and Filling

The formulation step included the addition of concentrated polysorbate 80 in formulation buffer to achieve the final drug substance formulation, at an operating temperature Target Range of 17-25° C. The step was performed by adding the stabilization buffer (25 mM sodium citrate 154 mM NaCl, 10 g/L polysorbate 80, pH 6.5). After the addition of the stabilization buffer, the pool was diluted to a target of 23.5 to 26.5 mg/mL with 25 mM sodium citrate 154 mM NaCl, 700 mg/L polysorbate 80, pH 6.5, resulting in a ready-to-fill drug substance in the formulation buffer of 25 mM sodium citrate, 154 mM NaCl, 0.07% polysorbate 80, pH 6.5.

The formulated bulk drug substance was transferred and 0.2 μm filtered into 6 L CELSIUS® FFT bags in a closed, single use system to a target fill volume of 5.50 L. After filling, the formulated bulk drug substance was frozen at ≤−60 for >17 hours and stored at ≤−35° C.

Other aspects, advantages, and modifications are within the scope of the following claims.

```
                             SEQUENCE LISTING

Sequence total quantity: 38
SEQ ID NO: 1            moltype = AA   length = 448
FEATURE                 Location/Qualifiers
source                  1..448
                        mol_type = protein
                        organism = synthetic construct
SEQUENCE: 1
QAYLQQSGAE LVRPGASVKM SCKASGYTFT SYNMHWVKQT PRQGLEWIGG IYPGNGDTSY   60
NQKFKGKATL TVGKSSSTAY MQLSSLTSED SAVYFCARYD YNYAMDYWGQ GTSVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 2            moltype = AA   length = 213
FEATURE                 Location/Qualifiers
source                  1..213
                        mol_type = protein
                        organism = synthetic construct
SEQUENCE: 2
QIVLSQSPAI LSASPGEKVT MTCRASSSVS YMHWYQQKPG SSPKPWIYAT SNLASGVPAR   60
FSGSGSGTSY SFTISRVEAE DAATYYCQQW TFNPPTFGGG TRLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 3            moltype = AA   length = 7
FEATURE                 Location/Qualifiers
source                  1..7
                        mol_type = protein
                        organism = synthetic construct
SEQUENCE: 3
GYTFTSY                                                              7

SEQ ID NO: 4            moltype = AA   length = 6
FEATURE                 Location/Qualifiers
source                  1..6
                        mol_type = protein
                        organism = synthetic construct
SEQUENCE: 4
YPGNGD                                                               6

SEQ ID NO: 5            moltype = AA   length = 9
FEATURE                 Location/Qualifiers
source                  1..9
                        mol_type = protein
                        organism = synthetic construct
SEQUENCE: 5
YDYNYAMDY                                                            9

SEQ ID NO: 6            moltype = AA   length = 118
FEATURE                 Location/Qualifiers
source                  1..118
                        mol_type = protein
                        organism = synthetic construct
SEQUENCE: 6
QAYLQQSGAE LVRPGASVKM SCKASGYTFT SYNMHWVKQT PRQGLEWIGG IYPGNGDTSY   60
NQKFKGKATL TVGKSSSTAY MQLSSLTSED SAVYFCARYD YNYAMDYWGQ GTSVTVSS    118

SEQ ID NO: 7            moltype = AA   length = 330
FEATURE                 Location/Qualifiers
source                  1..330
                        mol_type = protein
                        organism = synthetic construct
SEQUENCE: 7
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
```

-continued

```
QQGNVFSCSV MHEALHNHYT QKSLSLSPGK                                         330

SEQ ID NO: 8            moltype = AA  length = 10
FEATURE                 Location/Qualifiers
source                  1..10
                        mol_type = protein
                        organism = synthetic construct
SEQUENCE: 8
RASSSVSYMH                                                                10

SEQ ID NO: 9            moltype = AA  length = 7
FEATURE                 Location/Qualifiers
source                  1..7
                        mol_type = protein
                        organism = synthetic construct
SEQUENCE: 9
ATSNLAS                                                                    7

SEQ ID NO: 10           moltype = AA  length = 9
FEATURE                 Location/Qualifiers
source                  1..9
                        mol_type = protein
                        organism = synthetic construct
SEQUENCE: 10
QQWTFNPPT                                                                  9

SEQ ID NO: 11           moltype = AA  length = 107
FEATURE                 Location/Qualifiers
source                  1..107
                        mol_type = protein
                        organism = synthetic construct
SEQUENCE: 11
QIVLSQSPAI LSASPGEKVT MTCRASSSVS YMHWYQQKPG SSPKPWIYAT SNLASGVPAR          60
FSGSGSGTSY SFTISRVEAE DAATYYCQQW TFNPPTFGGG TRLEIKR                       107

SEQ ID NO: 12           moltype = AA  length = 106
FEATURE                 Location/Qualifiers
source                  1..106
                        mol_type = protein
                        organism = synthetic construct
SEQUENCE: 12
TVAAPSVFIF PPSDEQLKSG TASVVCLLNN FYPREAKVQW KVDNALQSGN SQESVTEQDS          60
KDSTYSLSST LTLSKADYEK HKVYACEVTH QGLSSPVTKS FNRGEC                       106

SEQ ID NO: 13           moltype = AA  length = 448
FEATURE                 Location/Qualifiers
source                  1..448
                        mol_type = protein
                        note = Modified heavy chain (substitution of glutamine at
                         position 1 with pyroglutamate)
                        organism = synthetic construct
SEQUENCE: 13
EAYLQQSGAE LVRPGASVKM SCKASGYTFT SYNMHWVKQT PRQGLEWIGG IYPGNGDTSY          60
NQKFKGKATL TVGKSSSTAY MQLSSLTSED SAVYFCARYD YNYAMDYWGQ GTSVTVSSAS         120
TKGPSVFPLA PSSKSTSGGT AALGCLVKDY FPEPVTVSWN SGALTSGVHT FPAVLQSSGL         180
YSLSSVVTVP SSSLGTQTYI CNVNHKPSNT KVDKKVEPKS CDKTHTCPPC PAPELLGGPS         240
VFLFPPKPKD TLMISRTPEV TCVVVDVSHE DPEVKFNWYV DGVEVHNAKT KPREEQYNST         300
YRVVSVLTVL HQDWLNGKEY KCKVSNKALP APIEKTISKA KGQPREPQVY TLPPSRDELT         360
KNQVSLTCLV KGFYPSDIAV EWESNGQPEN NYKTTPPVLD SDGSFFLYSK LTVDKSRWQQ         420
GNVFSCSVMH EALHNHYTQK SLSLSPGK                                           448

SEQ ID NO: 14           moltype = AA  length = 213
FEATURE                 Location/Qualifiers
source                  1..213
                        mol_type = protein
                        note = Modified light chain (substitution of glutamine at
                         position 1 with pyroglutamate)
                        organism = synthetic construct
SEQUENCE: 14
EIVLSQSPAI LSASPGEKVT MTCRASSSVS YMHWYQQKPG SSPKPWIYAT SNLASGVPAR          60
FSGSGSGTSY SFTISRVEAE DAATYYCQQW TFNPPTFGGG TRLEIKRTVA APSVFIFPPS         120
DEQLKSGTAS VVCLLNNFYP REAKVQWKVD NALQSGNSQE SVTEQDSKDS TYSLSSTLTL         180
SKADYEKHKV YACEVTHQGL SSPVTKSFNR GEC                                     213

SEQ ID NO: 15           moltype = AA  length = 447
FEATURE                 Location/Qualifiers
source                  1..447
                        mol_type = protein
                        organism = synthetic construct
```

```
SEQUENCE: 15
QAYLQQSGAE LVRPGASVKM SCKASGYTFT SYNMHWVKQT PRQGLEWIGG IYPGNGDTSY    60
NQKFKGKATL TVGKSSSTAY MQLSSLTSED SAVYFCARYD YNYAMDYWGQ GTSVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                       447

SEQ ID NO: 16            moltype = AA  length = 213
FEATURE                  Location/Qualifiers
source                   1..213
                         mol_type = protein
                         organism = synthetic construct
SEQUENCE: 16
QIVLSQSPAI LSASPGEKVT MTCRASSSVS YMHWYQQKPG SSPKPWIYAT SNLASGVPAR    60
FSGSGSGTSY SFTISRVEAE DAATYYCQQW TFNPPTFGGG TRLEINRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                 213

SEQ ID NO: 17            moltype = AA  length = 4
FEATURE                  Location/Qualifiers
source                   1..4
                         mol_type = protein
                         organism = synthetic construct
SEQUENCE: 17
MSCK                                                                   4

SEQ ID NO: 18            moltype = AA  length = 15
FEATURE                  Location/Qualifiers
source                   1..15
                         mol_type = protein
                         organism = synthetic construct
SEQUENCE: 18
ASGYTFTSYN MHWVK                                                     15

SEQ ID NO: 19            moltype = AA  length = 25
FEATURE                  Location/Qualifiers
source                   1..25
                         mol_type = protein
                         organism = synthetic construct
SEQUENCE: 19
QTPRQGLEWI GGIYPGNGDT SYNQK                                          25

SEQ ID NO: 20            moltype = AA  length = 9
FEATURE                  Location/Qualifiers
source                   1..9
                         mol_type = protein
                         organism = synthetic construct
SEQUENCE: 20
GKATLTVGK                                                              9

SEQ ID NO: 21            moltype = AA  length = 48
FEATURE                  Location/Qualifiers
source                   1..48
                         mol_type = protein
                         organism = synthetic construct
SEQUENCE: 21
SSSTAYMQLS SLTSEDSAVY FCARYDYNYA MDYWGQGTSV TVSSASTK                 48

SEQ ID NO: 22            moltype = AA  length = 58
FEATURE                  Location/Qualifiers
source                   1..58
                         mol_type = protein
                         organism = synthetic construct
SEQUENCE: 22
DYFPEPVTVS WNSGALTSGV HTFPAVLQSS GLYSLSSVVT VPSSSLGTQT YICNVNHK     58

SEQ ID NO: 23            moltype = AA  length = 28
FEATURE                  Location/Qualifiers
source                   1..28
                         mol_type = protein
                         organism = synthetic construct
SEQUENCE: 23
PKDTLMISRT PEVTCVVVDV SHEDPEVK                                       28

SEQ ID NO: 24            moltype = AA  length = 26
FEATURE                  Location/Qualifiers
```

-continued

```
source                  1..26
                        mol_type = protein
                        organism = synthetic construct
SEQUENCE: 24
DTLMISRTPE VTCVVVDVSH EDPEVK                                      26

SEQ ID NO: 25           moltype = AA  length = 14
FEATURE                 Location/Qualifiers
source                  1..14
                        mol_type = protein
                        organism = synthetic construct
SEQUENCE: 25
FNWYVDGVEV HNAK                                                   14

SEQ ID NO: 26           moltype = AA  length = 12
FEATURE                 Location/Qualifiers
source                  1..12
                        mol_type = protein
                        organism = synthetic construct
SEQUENCE: 26
VSNKALPAPI EK                                                     12

SEQ ID NO: 27           moltype = AA  length = 10
FEATURE                 Location/Qualifiers
source                  1..10
                        mol_type = protein
                        organism = synthetic construct
SEQUENCE: 27
NQVSLTCLVK                                                        10

SEQ ID NO: 28           moltype = AA  length = 22
FEATURE                 Location/Qualifiers
source                  1..22
                        mol_type = protein
                        organism = synthetic construct
SEQUENCE: 28
GFYPSDIAVE WESNGQPENN YK                                          22

SEQ ID NO: 29           moltype = AA  length = 25
FEATURE                 Location/Qualifiers
source                  1..25
                        mol_type = protein
                        organism = synthetic construct
SEQUENCE: 29
SRWQQGNVFS CSVMHEALHN HYTQK                                       25

SEQ ID NO: 30           moltype = AA  length = 20
FEATURE                 Location/Qualifiers
source                  1..20
                        mol_type = protein
                        organism = synthetic construct
SEQUENCE: 30
VTMTCRASSS VSYMHWYQQK                                             20

SEQ ID NO: 31           moltype = AA  length = 19
FEATURE                 Location/Qualifiers
source                  1..19
                        mol_type = protein
                        organism = synthetic construct
SEQUENCE: 31
SGTASVVCLL NNFYPREAK                                              19

SEQ ID NO: 32           moltype = AA  length = 20
FEATURE                 Location/Qualifiers
source                  1..20
                        mol_type = protein
                        organism = synthetic construct
SEQUENCE: 32
VDNALQSGNS QESVTEQDSK                                             20

SEQ ID NO: 33           moltype = AA  length = 29
FEATURE                 Location/Qualifiers
source                  1..29
                        mol_type = protein
                        organism = synthetic construct
SEQUENCE: 33
TKPREEQYNS TYRVVSVLTV LHQDWLNGK                                   29

SEQ ID NO: 34           moltype = AA  length = 23
```

```
FEATURE                 Location/Qualifiers
source                  1..23
                        mol_type = protein
                        organism = synthetic construct
SEQUENCE: 34
DIAVEWESNG QPENNYKTTP PVL                                           23

SEQ ID NO: 35           moltype = DNA  length = 1344
FEATURE                 Location/Qualifiers
source                  1..1344
                        mol_type = other DNA
                        organism = synthetic construct
SEQUENCE: 35
caggcttatc tacagcagtc tggggctgag ctggtgaggc ctggggcctc agtgaagatg    60
tcctgcaagg cttctggcta cacatttacc agttacaata tgcactgggt aaagcagaca   120
cctagacagg gcctggaatg gattggaggt atttatccag gaaatggtga tacttcctac   180
aatcagaagt tcaagggcaa ggccacactg actgtaggca aatcctccag cacagcctac   240
atgcagctca gcagcctgac atctgaagac tctgcggtct atttctgtgc aagatatgac   300
tacaactatg ctatggacta ctggggtcaa ggaacctcag tcaccgtctc ctcagcctcc   360
accaagggcc catcggtctt ccccctggca ccctcctcca agagcacctc tgggggcaca   420
gcggccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct tgggcaccca gacctacatc   600
tgcaacgtga atcacaagcc cagcaacacc aaggtggaca gaaagttga gcccaaatct    660
tgtgacaaaa ctcacacatg cccaccgtgc ccagcacctg aactcctggg gggaccgtca   720
gtcttcctct tccccccaaa acccaaggac accctcatga tctcccggac ccctgaggtc   780
acatgcgtgg tggtggacgt gagccacgaa gaccctgagg tcaagttcaa ctggtacgtg   840
gacggcgtgg aggtgcataa tgccaagaca aagccgcggg aggagcagta caacagcacg   900
taccgtgtgt tcagcgtcct caccgtcctg caccaggact ggctgaatgg caaggagtac   960
aagtgcaagg tctccaacaa agcccctccc gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
agcctctccc tgtctccggg taaa                                         1344

SEQ ID NO: 36           moltype = DNA  length = 639
FEATURE                 Location/Qualifiers
source                  1..639
                        mol_type = other DNA
                        organism = synthetic construct
SEQUENCE: 36
caaattgttc tctcccagtc tccagcaatc ctgtctgcat ctccagggga gaaggtcaca    60
atgacttgca gggccagctc aagtgtaagt tacatgcact ggtaccagca gaagccagga   120
tcctccccca aaccctggat ttatgccaca tccaacctgg cttctggagt ccctgctcgc   180
ttcagtggca gtgggtctgg gacctcttat tctttcacaa tcagcagagt ggctgaa     240
gatgctgcca cttattactg ccagcagtgg acttttaacc cacccacgtt cggaggggg   300
accaggctgg aaataaaacg gactgtggct gcaccaagtg tcttcatctt cccgccatct   360
gatgagcagt tgaaatctgg aactgcctct gttgtgtgcc tgctgaataa cttctatccc   420
agagaggcca aagtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgt                          639

SEQ ID NO: 37           moltype = AA  length = 5
FEATURE                 Location/Qualifiers
source                  1..5
                        mol_type = protein
                        organism = synthetic construct
SEQUENCE: 37
IRAHT                                                                5

SEQ ID NO: 38           moltype = AA  length = 4
FEATURE                 Location/Qualifiers
source                  1..4
                        mol_type = protein
                        organism = synthetic construct
SEQUENCE: 38
EPAN                                                                 4
```

What is claimed is:

1. A composition comprising a population of anti-CD20 antibody proteins, wherein the anti-CD20 antibody proteins in the population are expressed from one or more nucleic acid sequences encoding a heavy chain comprising the amino acid sequence of SEQ ID NO: 1 and a light chain comprising the amino acid sequence of SEQ ID NO: 2, and wherein the population of anti-CD20 antibody proteins has an N-glycan profile comprising 10 to 20% galactosylated glycans and 20 to 40% fucosylated glycans.

2. The composition of claim 1, wherein the N-glycan profile comprises 23% to 36% fucosylated glycans.

3. The composition of claim 1, wherein the N-glycan profile comprises 27% to 37% fucosylated glycans.

4. The composition of claim 1, wherein the N-glycan profile comprises 16 to 18% galactosylated glycans.

5. The composition of claim 1, wherein the N-glycan profile comprises 15% to 19% galactosylated glycans.

6. The composition of claim 1, wherein the N-glycan profile comprises 12% to 30% bisecting N-glycans.

7. The composition of claim 1, wherein the N-glycan profile comprises 16% to 20% bisecting N-glycans.

8. The composition of claim 6, wherein the bisecting N-glycans comprise one or more of G0B, G0FB, G1FB, G2FBS1, and G2FBS2.

9. The composition of claim 1, wherein the population of anti-CD20 antibody proteins further comprises at least two N-glycans within the following relative abundance ranges:
(a) 0.3% to 2% G0-GN;
(b) 0.1% to 2% G0F-GN;
(c) 30% to 60% G0;
(d) 0.1% to 1% G1-GN;
(e) 5% to 20% G0B;
(f) 5% to 30% G0F;
(g) 0.1% to 1.5% Man5;
(h) 1% to 15% G0FB;
(i) 1% to 13% G1;
(j) 0.5% to 10% G1';
(k) 0.5% to 6% G1B;
(l) 0.5% to 12% G1F;
(m) 0.1% to 3% G1F';
(n) 0.1% to 3% G1FB;
(o) 0.1% to 2% G2; and
(p) 0.1% to 2% G2F.

10. The composition of claim 9, wherein the population of anti-CD20 antibody proteins further comprises at least two N-glycans within the following relative abundance range:
(a) 0.8% to 1.1% G0-GN;
(b) 0.5% to 1.1% G0F-GN;
(c) 42.5% to 48.8% G0;
(d) 0.3% to 0.6% G1-GN;
(e) 9.5% to 14.1% G0B;
(f) 12.8% to 19.7% G0F;
(g) 0.4% to 0.7% Man5;
(h) 5.1% to 7.0% G0FB;
(i) 5.7% to 6.4% G1;
(j) 2.7% to 3.3% G1';
(k) 1.4% to 2.0% G1B;
(l) 2.6% to 4.2% G1F;
(m) 1.1% to 1.6% G1F';
(n) 1.1% to 1.8% G1FB;
(o) 0.5% to 0.7% G2; and
(p) 0.3% to 0.5% G2F.

11. The composition of claim 9, wherein the population of anti-CD20 antibody proteins further comprises at least two N-glycans in the following relative abundance:
(a) 0.9% G0-GN;
(b) 0.8% G0F-GN;
(c) 46.1% G0;
(d) 0.5% G1-GN;
(e) 10.9% G0B;
(f) 17.0% G0F;
(g) 0.6% Man5;
(h) 6.0% G0FB;
(i) 6.1% G1;
(J) 2.9% G1';
(k) 1.6% G1B;
(l) 3.2% G1F;
(m) 1.3% G1F';
(n) 1.3% G1 FB;
(o) 0.5% G2; and
(p) 0.3% G2F.

12. The composition of claim 9, wherein the population of anti-CD20 antibody proteins further comprises at least three, four or five N-glycans within the following relative abundance ranges:
(a) 0.3% to 2% G0-GN;
(b) 0.1% to 2% G0F-GN;
(c) 30% to 60% G0;
(d) 0.1% to 1% G1-GN;
(e) 5% to 20% G0B;
(f) 5% to 30% G0F;
(g) 0.1% to 1.5% Man5;
(h) 1% to 15% G0FB;
(i) 1% to 13% G1;
(j) 0.5% to 10% G1';
(k) 0.5% to 6% G1B;
(l) 0.5% to 12% G1F;
(m) 0.1% to 3% G1F';
(n) 0.1% to 3% G1FB;
(o) 0.1% to 2% G2; and
(p) 0.1% to 2% G2F.

13. The composition of claim 1, wherein less than 10% of the anti-CD20 antibody proteins in the population is non-glycosylated.

14. The composition of claim 13, wherein less than 5% of the anti-CD20 antibody proteins in the population is non-glycosylated.

15. The composition of claim 13, wherein less than 1% of the anti-CD20 antibody proteins in the population is non-glycosylated.

* * * * *